(12) United States Patent
Flynn et al.

(10) Patent No.: US 10,029,118 B2
(45) Date of Patent: Jul. 24, 2018

(54) ADVANCED ROTATING-SHIELD BRACHYTHERAPY AND PLANNING OF THE SAME

(71) Applicant: UNIVERSITY OF IOWA RESEARCH FOUNDATION, Iowa City, IA (US)

(72) Inventors: Ryan Flynn, Iowa City, IA (US); Hossein Dadkhah, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/803,427

(22) Filed: Jul. 20, 2015

(65) Prior Publication Data

US 2017/0165500 A1    Jun. 15, 2017

Related U.S. Application Data

(63) Continuation-in-part of application No. 14/418,274, filed as application No. PCT/US2013/032071 on Mar. 15, 2013.

(60) Provisional application No. 62/026,071, filed on Jul. 18, 2014, provisional application No. 61/678,802, filed on Jul. 31, 2012, provisional application No. 61/740,086, filed on Dec. 20, 2012, provisional application No. 61/678,080, filed on Jul. 31, 2012.

(51) Int. Cl.
*A61N 5/10*    (2006.01)

(52) U.S. Cl.
CPC ........... *A61N 5/1002* (2013.01); *A61N 5/103* (2013.01); *A61N 5/1007* (2013.01); *A61N 5/1027* (2013.01); *A61N 5/1044* (2013.01); *A61N 2005/1005* (2013.01); *A61N 2005/1094* (2013.01)

(58) Field of Classification Search
CPC .... A61N 5/1001; A61N 5/102; A61N 5/1007; A61N 5/1027; A61N 5/103; A61N 5/1044
USPC ........................................................ 600/1–8
See application file for complete search history.

(56) References Cited

U.S. PATENT DOCUMENTS

| 5,548,627 | A | * | 8/1996 | Swerdloff | A61B 6/00 378/19 |
|---|---|---|---|---|---|
| 7,686,755 | B2 | * | 3/2010 | Smith | A61N 5/1015 600/3 |
| 2009/0209805 | A1 | * | 8/2009 | Lubock | A61N 5/1015 600/7 |
| 2009/0216062 | A1 | * | 8/2009 | Axelrod | A61B 19/40 600/5 |
| 2010/0016649 | A1 | * | 1/2010 | Prionas | A61N 5/10 600/1 |
| 2017/0246476 | A1 | * | 8/2017 | Munro, III | A61N 5/1007 |

* cited by examiner

*Primary Examiner* — John Lacyk
(74) *Attorney, Agent, or Firm* — Smith, Gambrell & Russell, LLP

(57) ABSTRACT

Systems and methods for rotating shield brachytherapy. In an aspect, some of the systems and methods can be used to facilitate shield selection for use in rotating shield brachytherapy. In an aspect, the invention is a shielded needle or catheter system with a rotational controller for delivering radioisotope-based interstitial rotating shield brachytherapy (I-RSBT). In an aspect, the catheter system can utilize paddle-based RSBT. Further provided are methods and systems for helical RSBT.

10 Claims, 90 Drawing Sheets

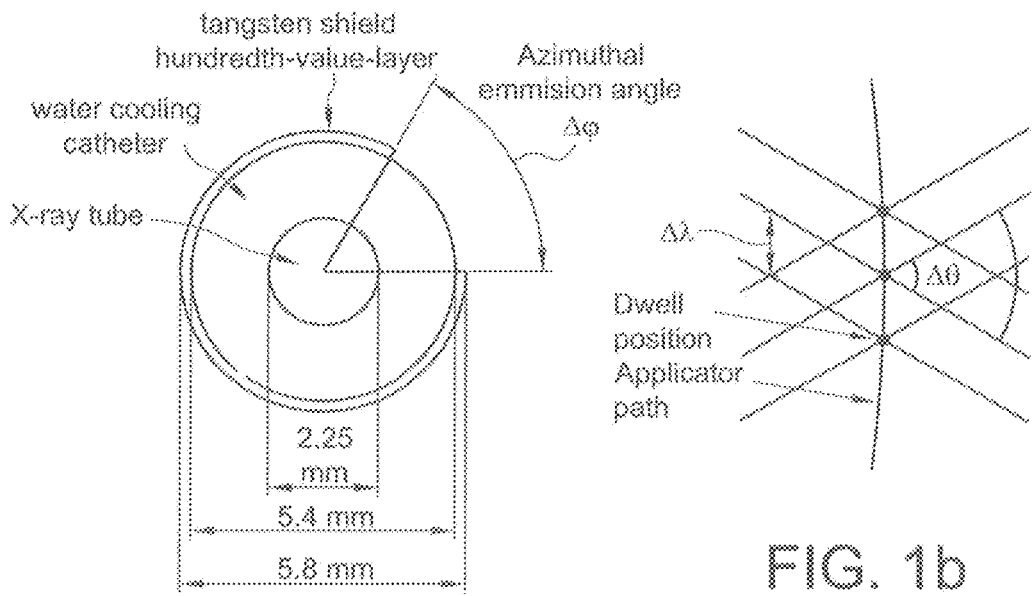
FIG. 1a
FIG. 1b
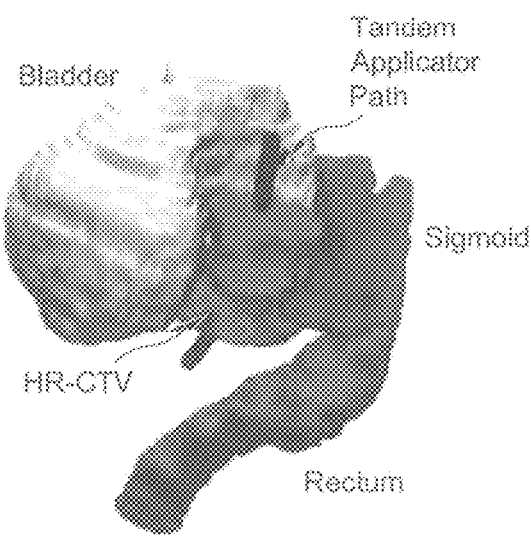
FIG. 2

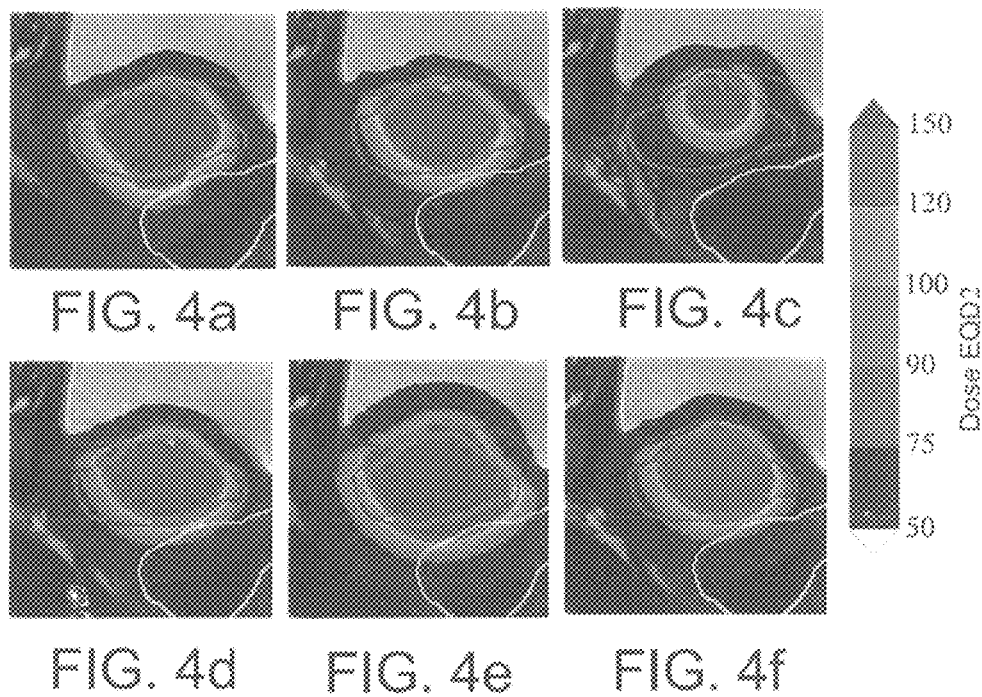
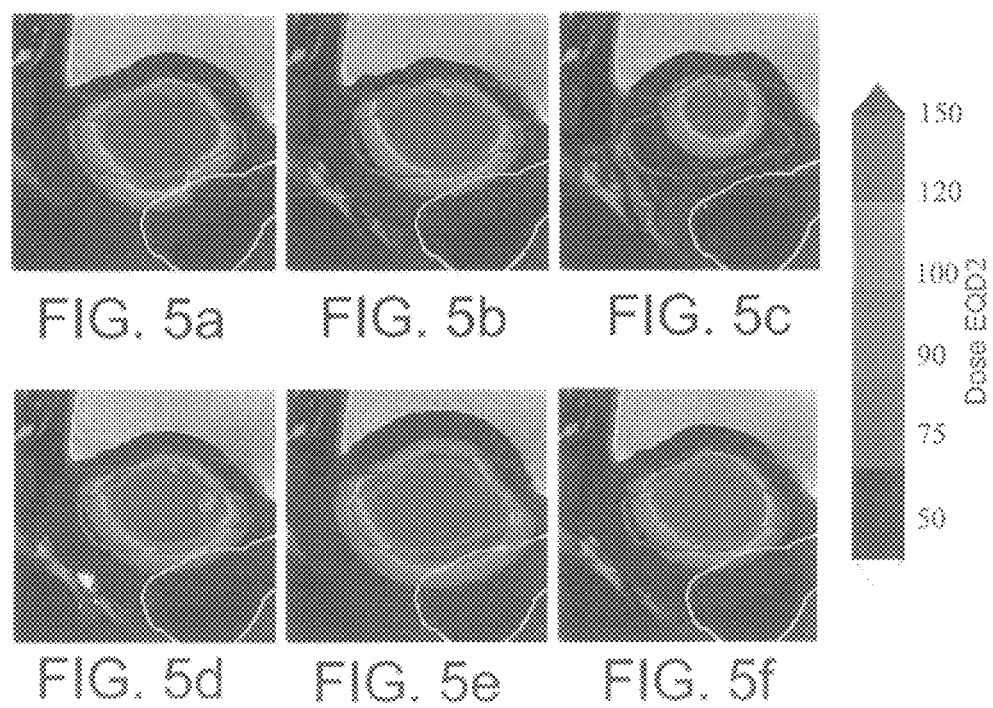

| Plans | $D_{90}$ $Gy_{10}$ | $D_{2cc}$ $Gy_3$ | | | Delivery time (min/fx) |
|---|---|---|---|---|---|
| | HR-CTV | Bladder | Rectum | Sigmoid | |
| (a) $\bar{P}^*$ | 100.6 | 90.0 | 56.0 | 75.0 | 19.2 |
| (b) $\hat{P}^{1*}$ | 93.4 | 90.0 | 58.3 | 75.0 | 9.3 |
| (c) $\hat{P}^{2*}$ | 94.5 | 90.0 | 56.2 | 74.8 | 6.2 |
| (d) $\hat{P}^{1*}$ | 97.3 | 90.0 | 57.9 | 75.0 | 7.9 |
| (e) $\hat{P}^{2*}$ | 93.6 | 90.0 | 56.1 | 74.8 | 6.2 |
| (f) $\hat{P}^{2*}$ | 94.5 | 90.0 | 56.2 | 74.8 | 6.2 |

FIG. 6

| Plans | $D_{90}$ $Gy_{10}$ | $D_{2cc}$ $Gy_3$ | | | Delivery time (min/fx) |
|---|---|---|---|---|---|
| | HR-CTV | Bladder | Rectum | Sigmoid | |
| (a) $\bar{P}^*$ | 99.1 | 89.9 | 75.0 | 53.4 | 27.0 |
| (b) $\hat{P}^{1*}$ | 82.9 | 90.0 | 69.9 | 57.5 | 11.0 |
| (c) $\hat{P}^{2*}$ | 55.8 | 90.0 | 50.6 | 51.2 | 4.3 |
| (d) $\hat{P}^{1*}$ | 84.0 | 83.7 | 69.7 | 54.0 | 11.8 |
| (e) $\hat{P}^{1*}$ | 84.0 | 88.6 | 68.4 | 53.3 | 12.7 |
| (f) $\hat{P}^{1*}$ | 84.0 | 89.4 | 70.7 | 57.5 | 11.7 |

FIG. 7

| Fan-angle | isotropic | 32 | 44 | 60 | 68 | 72 | 76 |
|---|---|---|---|---|---|---|---|
| PTV V100 | 67.2 | 90.1 | 90.1 | 90.1 | 90.0 | 90.0 | 90.1 |
| PTV V200 | 43.3 | 53.2 | 53.7 | 55.6 | 56.2 | 56.8 | 57.8 |
| Bladder D2CC | 71.4 | 42.3 | 43.1 | 42.6 | 41.3 | 42.5 | 43.2 |
| Mean dose to bladder | 14.3 | 8.3 | 8.4 | 8.4 | 8.1 | 8.2 | 8.3 |
| Rectum D2CC | 9.7 | 9.5 | 9.0 | 9.5 | 10.1 | 11.2 | 12.0 |
| Mean dose to rectum | 2.4 | 2.4 | 2.2 | 2.4 | 2.8 | 3.0 | 3.2 |
| D90 for tumor | 41.1 | 100.0 | 100.1 | 100.0 | 100.1 | 99.9 | 100.0 |
| Mean dose to tumor | 412.8 | 602.8 | 602.7 | 620.9 | 624.9 | 634.9 | 640.3 |
| CI | 0.86 | 0.98 | 0.97 | 0.93 | 0.91 | 0.90 | 0.89 |
| Delivery time | 16.4 | 242.6 | 161.1 | 137.9 | 113.1 | 110.4 | 108.1 |

FIG. 13

| Fan-angle | Isotropic | 32 | 48 | 60 | 68 | 72 | 76 |
|---|---|---|---|---|---|---|---|
| PTV V100 | 67.2 | 90.1 | 90.1 | 90.0 | 90.0 | 90.0 | 90.1 |
| PTV V200 | 43.3 | 52.3 | 52.7 | 55.2 | 55.8 | 56.2 | 57.3 |
| Bladder D2CC | 71.4 | 41.7 | 42.4 | 43.1 | 42.0 | 41.7 | 42.6 |
| Mean dose to bladder | 14.3 | 8.2 | 8.3 | 8.5 | 8.3 | 8.1 | 8.2 |
| Rectum D2CC | 9.7 | 8.0 | 7.9 | 8.9 | 8.5 | 10.2 | 11.3 |
| Mean dose to rectum | 2.4 | 2.0 | 2.0 | 2.3 | 2.3 | 2.7 | 3.0 |
| D90 for tumor | 41.1 | 100.1 | 100.1 | 100.0 | 100.0 | 100.0 | 100.0 |
| Mean dose to tumor | 412.8 | 595.4 | 602.8 | 620.5 | 627.4 | 623.0 | 634.3 |
| CI | 0.86 | 1.00 | 0.98 | 0.94 | 0.93 | 0.92 | 0.90 |
| Delivery time | 16.4 | 184.8 | 128.8 | 107.5 | 94.8 | 89.6 | 92.7 |

FIG. 14

|   |          | D90 (Gy10) HR-CTV | D2cc (Gy3) Bladder | Rectum | Sigmoid | Time (min/fx) |
|---|----------|-------------------|--------------------|--------|---------|---------------|
| #1 | baseline | 93.73 | 83.3  | 55.98 | 75    | 142.29 |
|    | full     | 95.58 | 83.03 | 56.43 | 75    | 21.48  |
|    | OSD      | 95.33 | 83.03 | 56.47 | 75    | 13.23  |
| #2 | baseline | 96.92 | 90    | 66.4  | 52.14 | 213.87 |
|    | full     | 98.54 | 90    | 66.43 | 52.02 | 48.12  |
|    | OSD      | 98.89 | 90    | 66.66 | 52.05 | 30.1   |
| #3 | baseline | 80.13 | 73.82 | 54.07 | 75    | 192.33 |
|    | full     | 80.64 | 74.03 | 54.29 | 75    | 29.43  |
|    | OSD      | 80.15 | 73.67 | 54.27 | 75    | 18     |
| #4 | baseline | 88.73 | 90    | 62.91 | 68.02 | 316.91 |
|    | full     | 89.22 | 90    | 63.03 | 70.33 | 69.73  |
|    | OSD      | 89    | 90    | 63.1  | 70.47 | 44.41  |
| #5 | baseline | 102.4 | 90    | 72.3  | 51    | 222.9  |
|    | full     | 103.1 | 90    | 72.6  | 51    | 45.3   |
|    | OSD      | 103.14| 90    | 72.76 | 51    | 27.72  |

FIG. 22

|    | Baseline    |             | OSD         |             |
|----|-------------|-------------|-------------|-------------|
|    | D90(Gy10)   | Time(min/fx)| D90(Gy10)   | Time(min/fx)|
| #1 | 101         | 151         | 100         | 20          |
| #1 | 107         | 234         | 91          | 20          |
| #1 | 92          | 260         | 81          | 19          |
| #1 | 91          | 369         | 84          | 30          |
| #1 | 95          | 205         | 95          | 20          |

| Shield-Sequencing Settings | Conventional, Point A-BT | DS-IMBT |
|---|---|---|
| Bladder $D_{2cc}$ [Gy] | 4.3 | 3.9 |
| Rectum $D_{2cc}$ [Gy] | 0.6 | 0.7 |
| HR-CTV $V_{100}$ [%] | 67.2 | 87.2 |
| $D_{90}$ for HR-CTV [Gy] | 2.5 | 5.7 |
| Delivery time increase factor | 0 | 1.2 |

FIG. 30

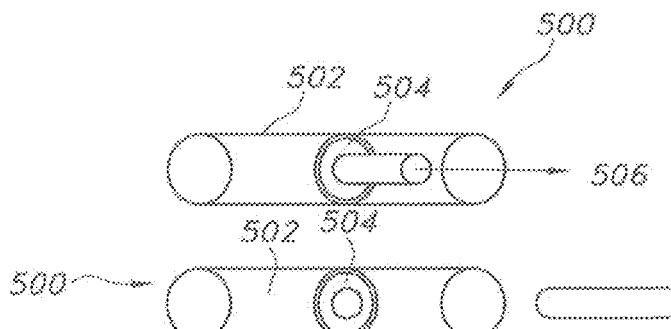
FIG. 44A
FIG. 44B
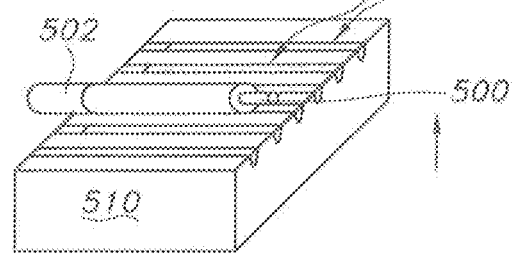
FIG. 44C
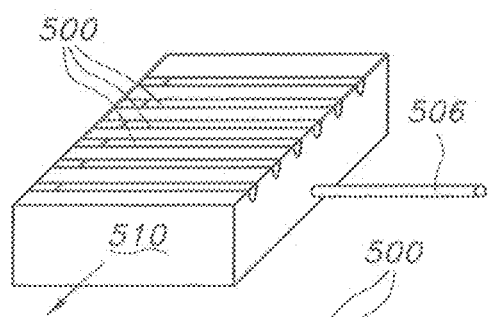
FIG. 44D
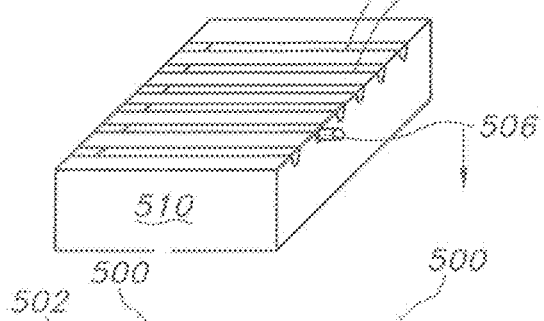
FIG. 44E
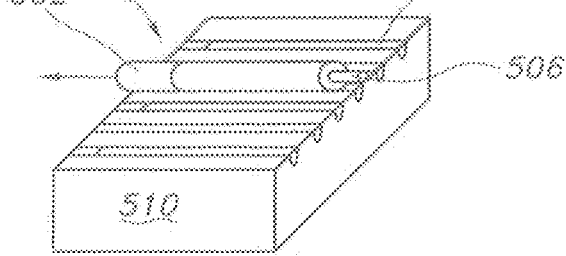
FIG. 44F

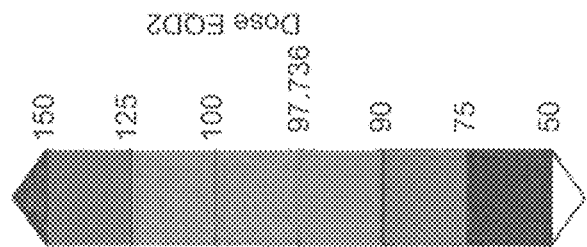
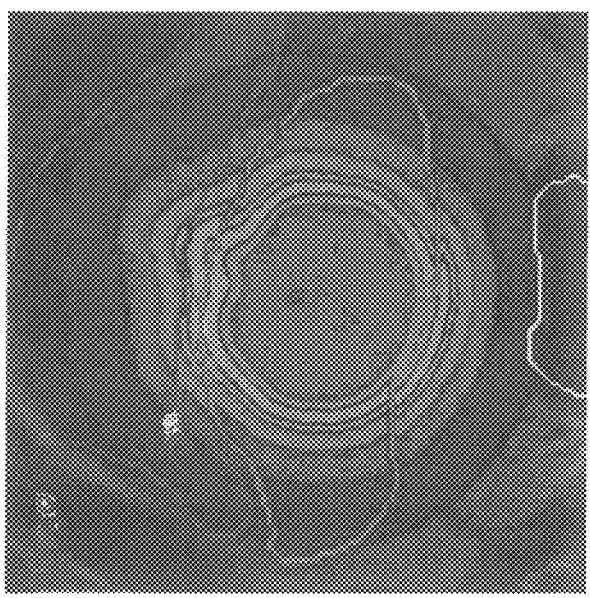
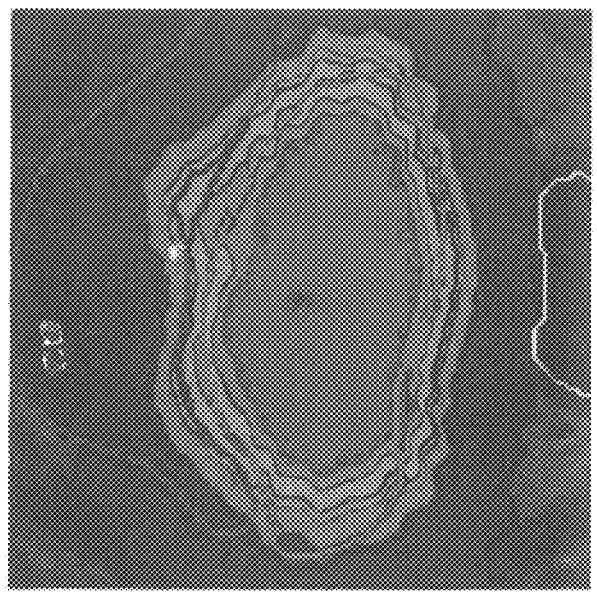
FIG. 46A  FIG. 46B

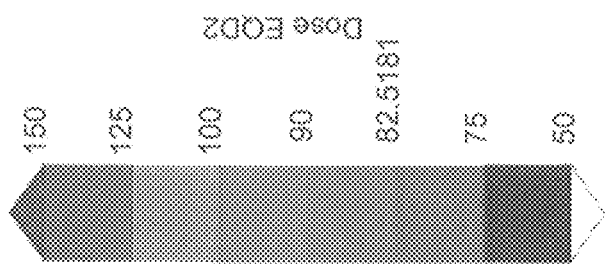
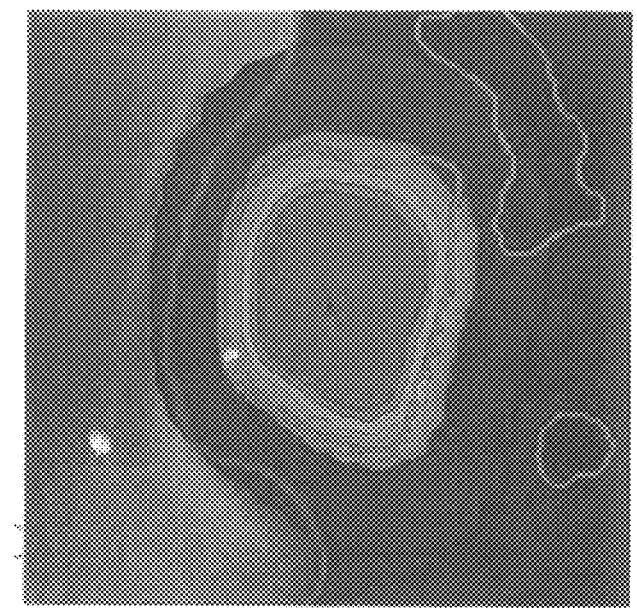
FIG. 48B
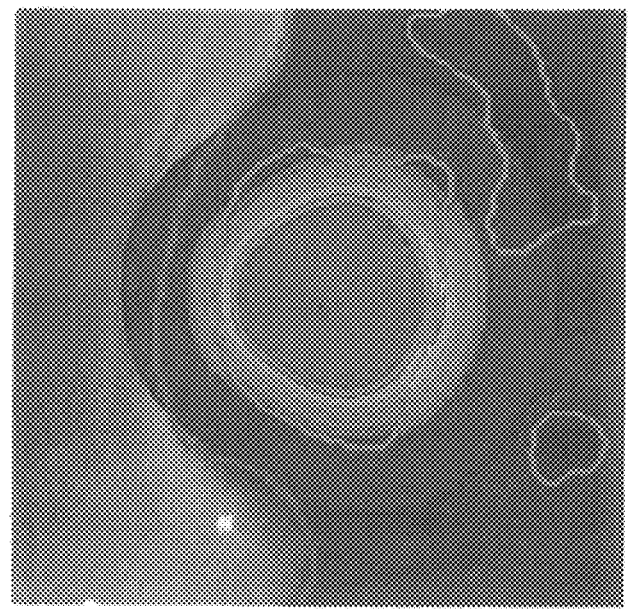
FIG. 48A

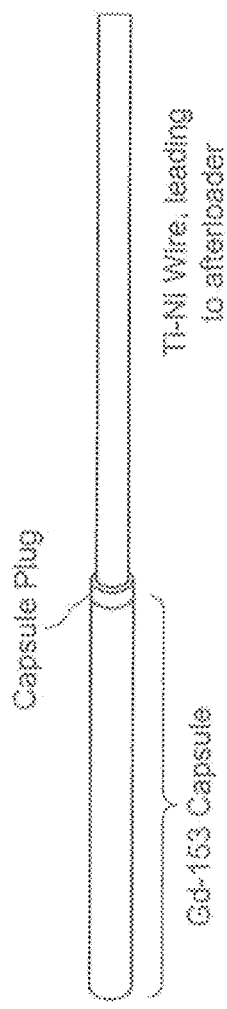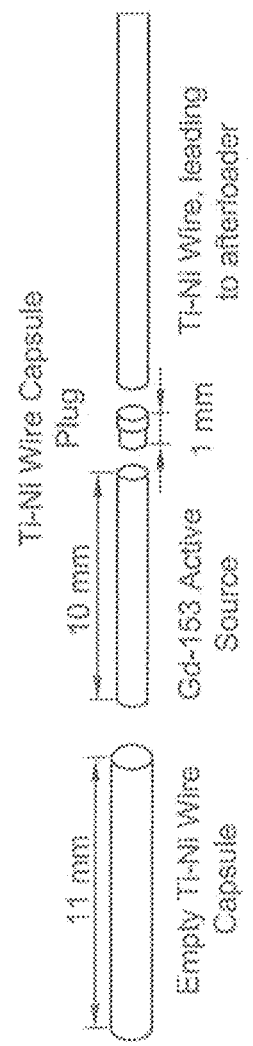
FIG. 52A
FIG. 52B

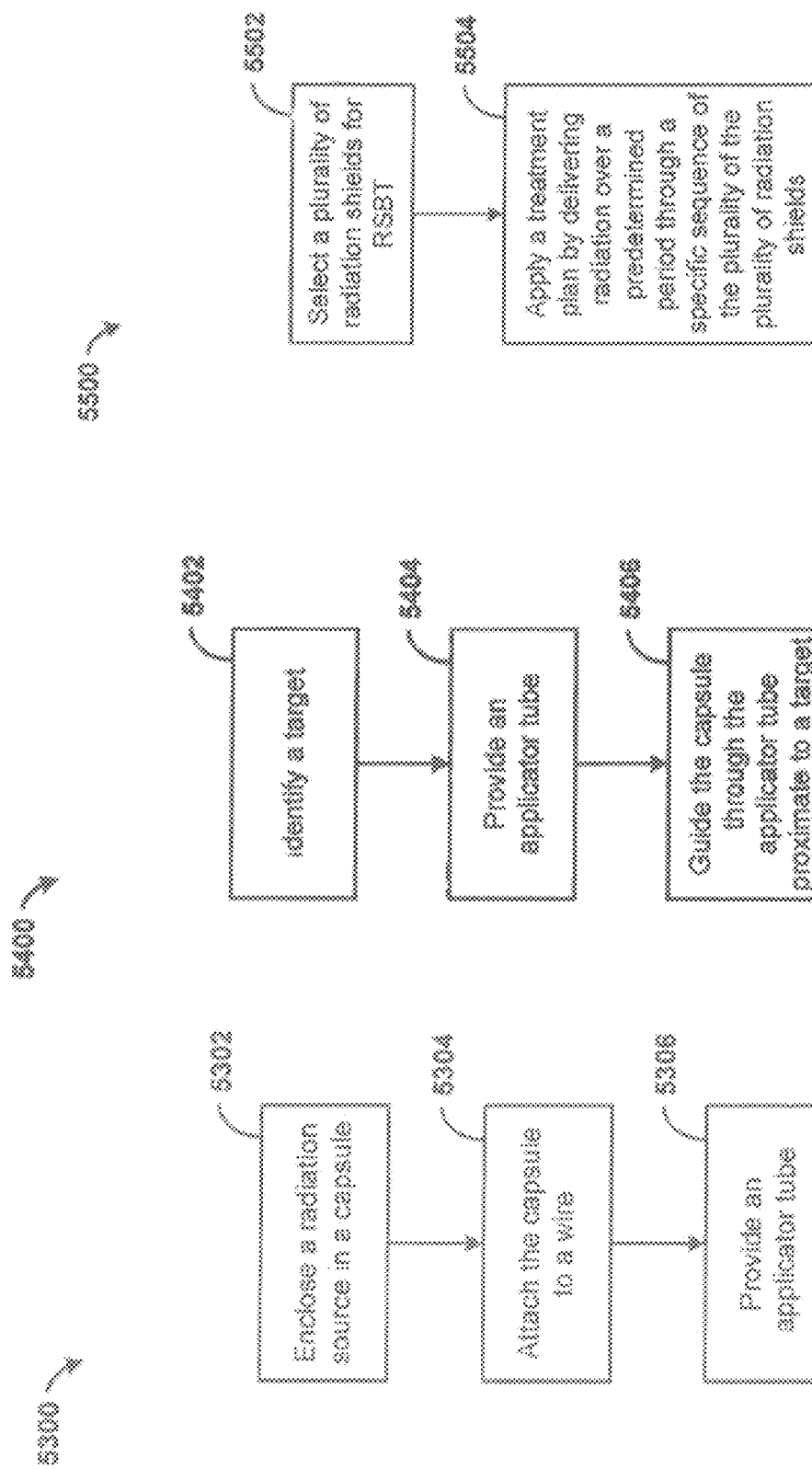

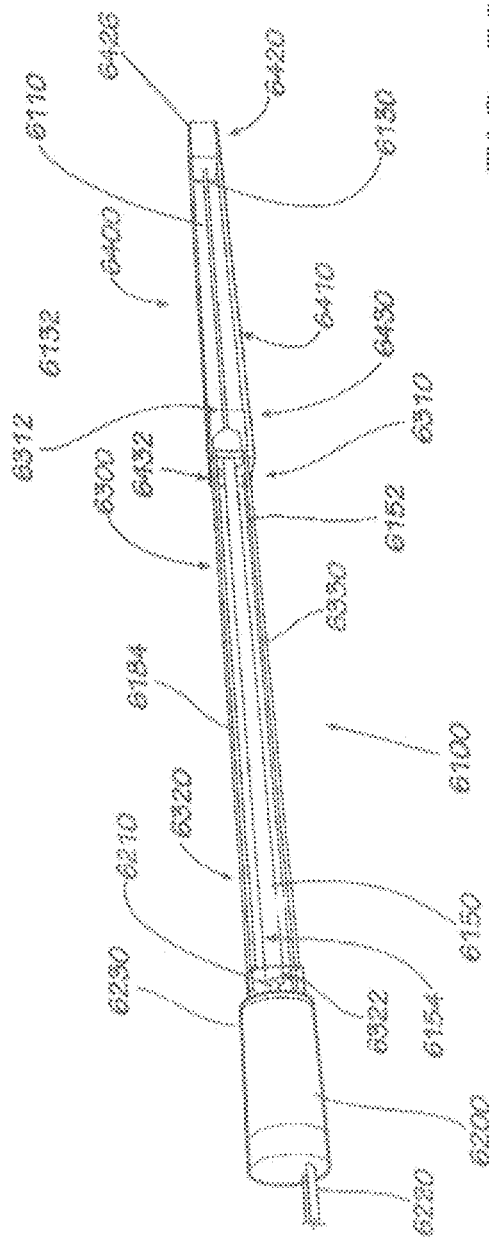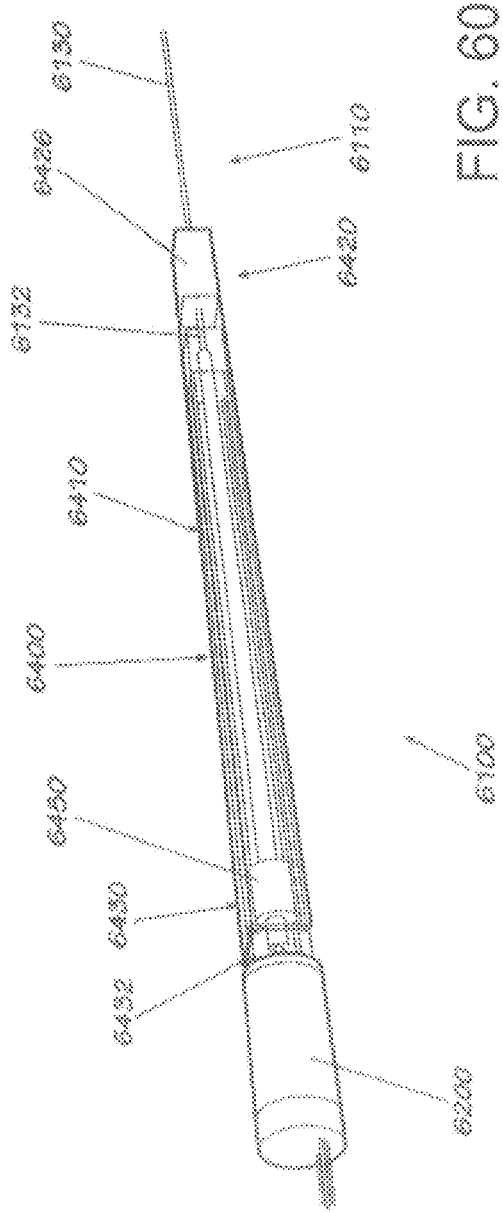

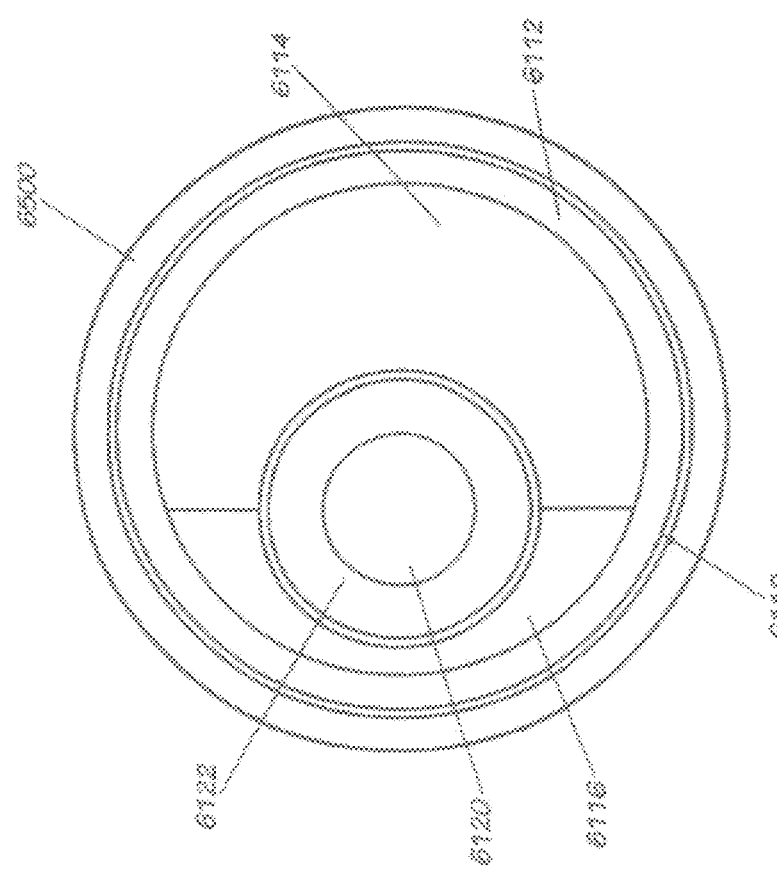

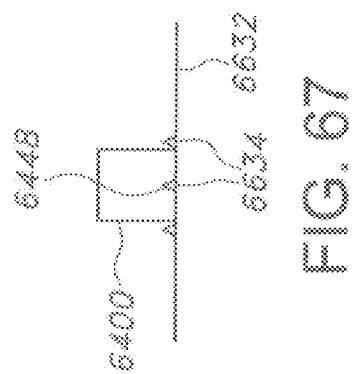
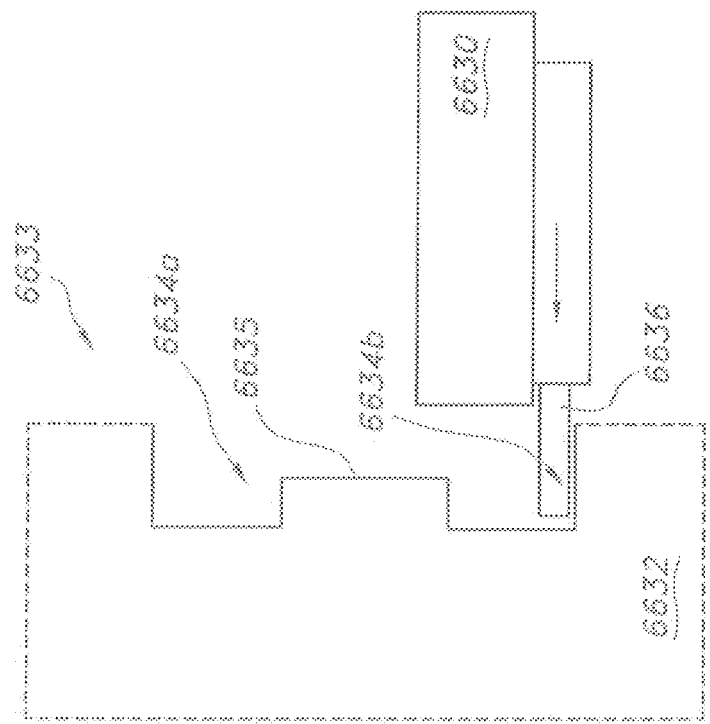

Delivery efficiency curve comparisons. P-RSBT with different paddle sizes was compared to S-RSBT and D-RSBT on 5 clinical cases. A point on a delivery efficiency curve stands for the maximal $D_{90}$ (y-axis) can be achieved with the corresponding delivery method for a given delivery time (x-axis). The rotation stride $r\delta\varphi$ for P-RSBT was 5°.

EQD2 dose distributions for Case #3 with a delivery time 15 min/fx using P-RSBT with different paddle sizes of 5°, 60°, 90° and 120°, and the rotation stride $r\delta\varphi = 5°$.

DVH plots for Case #3 (Table 1) with a delivery time 15 min/fx using P-RSBT with different paddle sizes of 5°, 60°, 90° and 120°, and the rotation stride $r \cdot \delta \varphi = 5°$.

EQD2 dose distributions of Case #3 with a delivery time 15 min/fx using S-RSBT, D-RSBT, P-RSBT90 and P-RSBT120. The rotation stride $r\delta\varphi$ for P-RSBT was 5°.

DVH plots for Case #3 with a delivery time 15 min/fx by S-RSBT, D-RSBT, P-RSBT60 and P-RSBT120. The rotation stride $r\delta\varphi$ for P-RSBT was 5°.

Comparisons of delivery efficiency curves for 5 clinical cases by P-RSBT with different combinations of the paddle size and the rotation stride. The efficiency curve (gray) by P-RSBT with a paddle size of 5° (no rotations) is referred as a reference, which serves as an upper bound of all other efficiency curves.

Delivery efficiency curves comparison between P-RSBT with different paddle sizes with different dose optimizer for 5 cases.

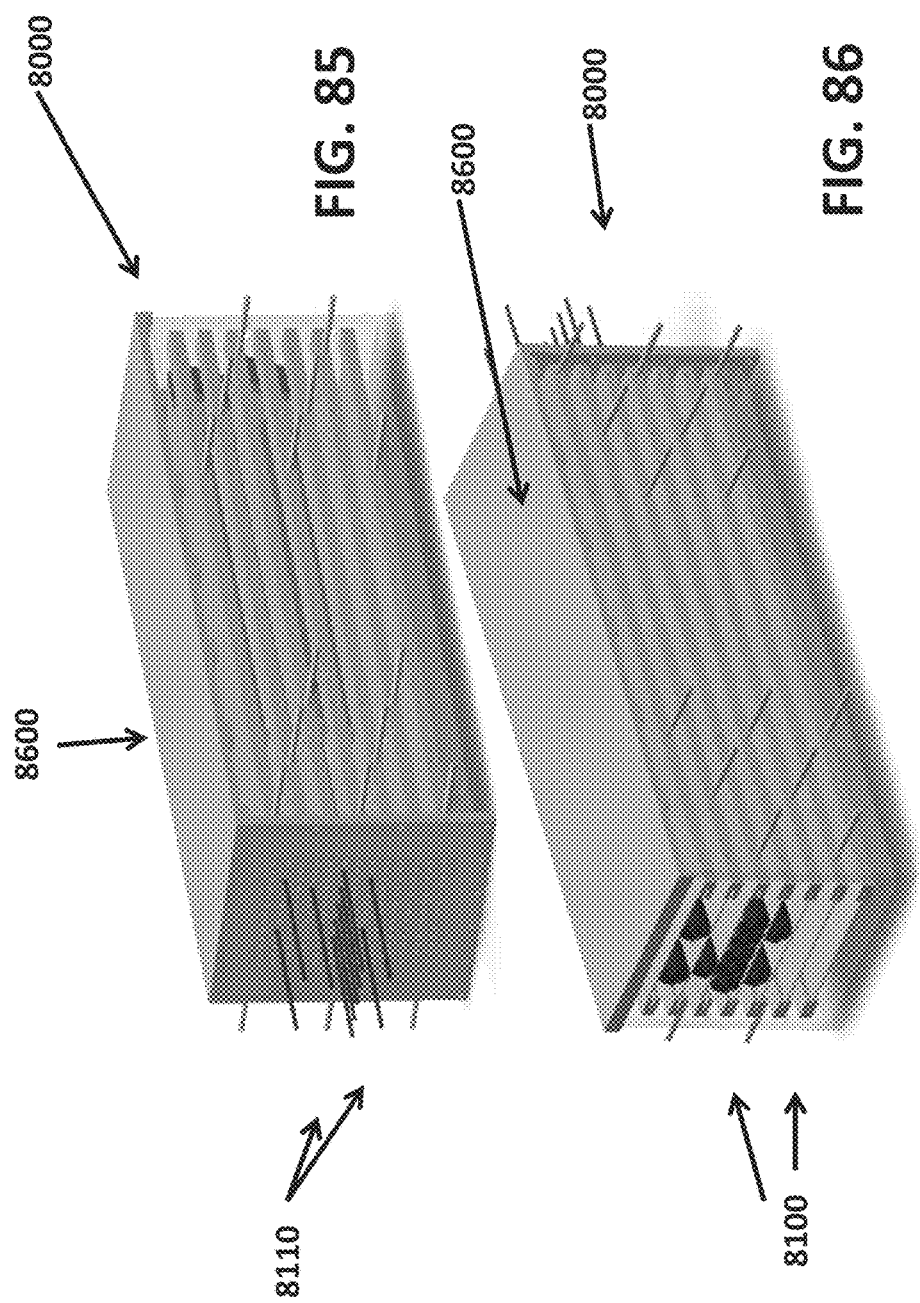

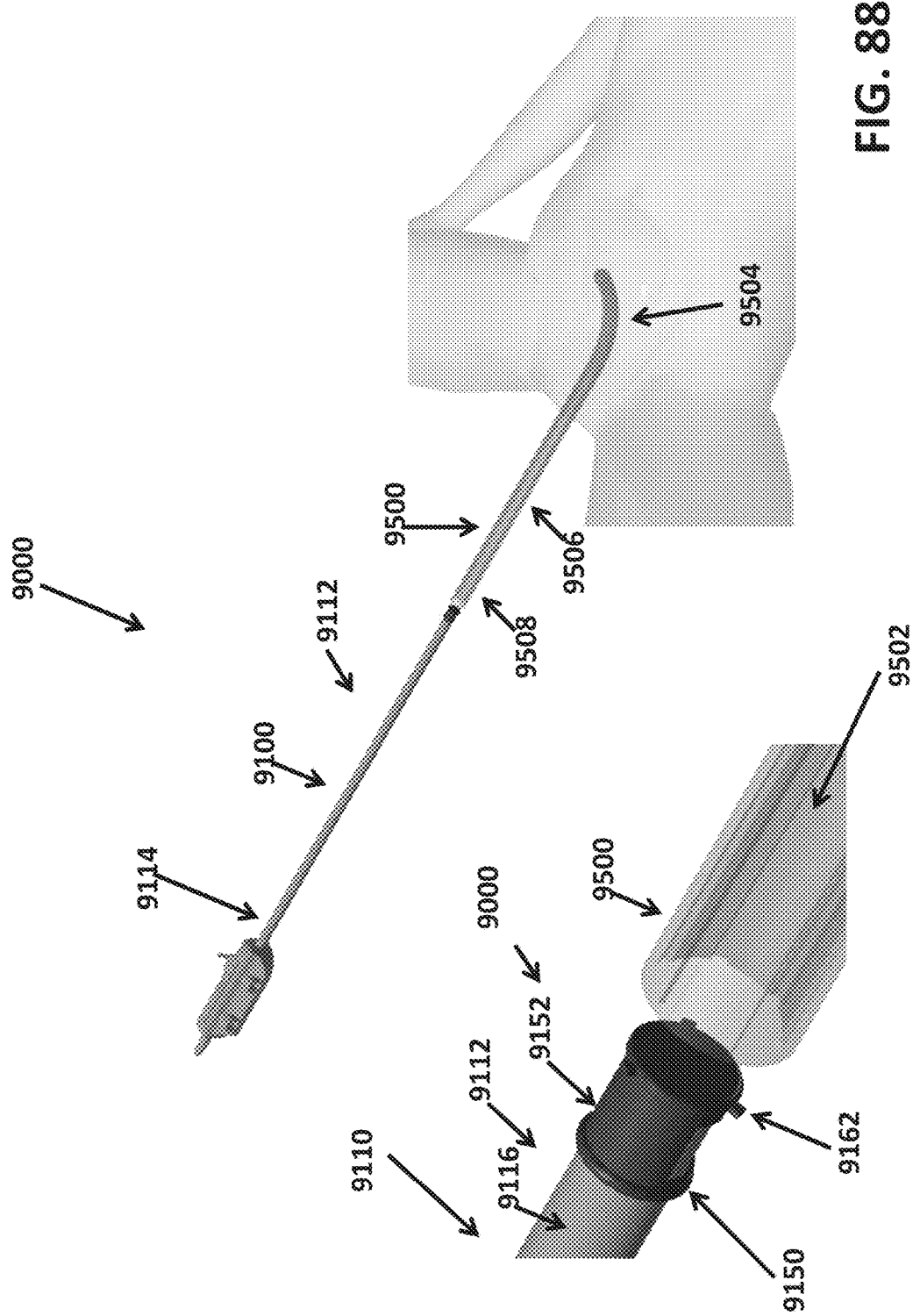

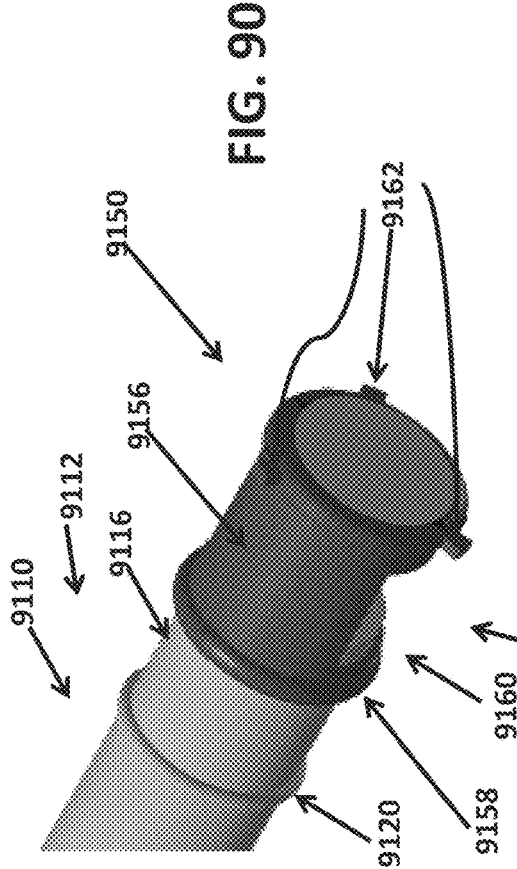
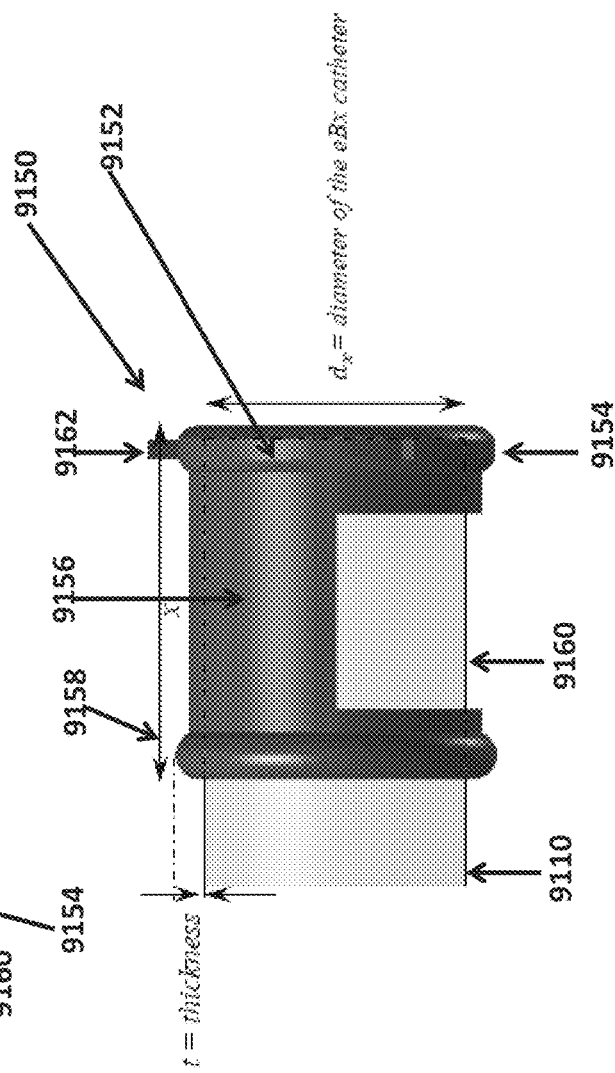
FIG. 90
FIG. 91

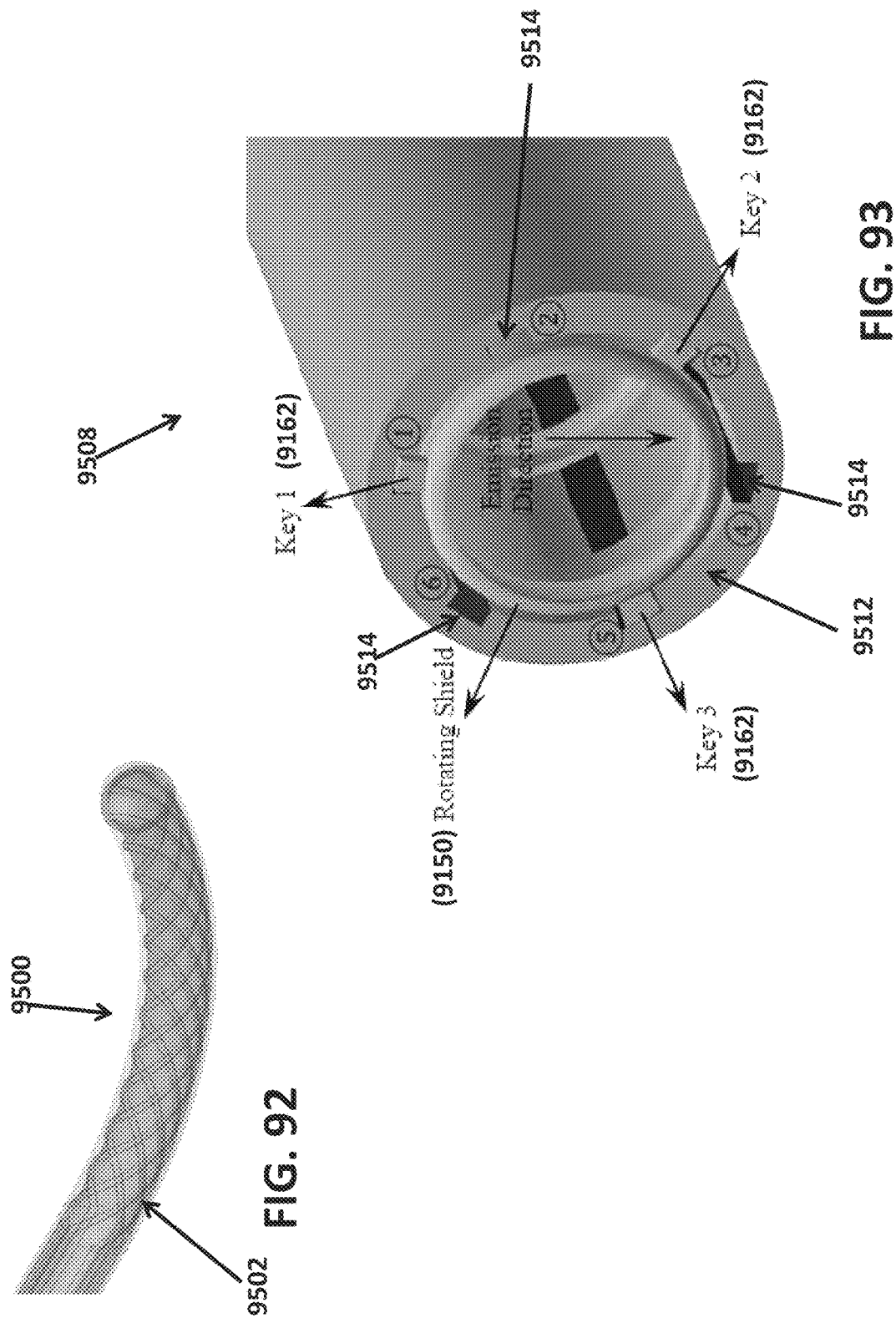

ADVANCED ROTATING-SHIELD BRACHYTHERAPY AND PLANNING OF THE SAME

CROSS-REFERENCE TO RELATED APPLICATIONS

This application claims priority in part from U.S. patent application Ser. No. 14/418,274, filed on Jan. 29, 2014, which claims priority to Patent Cooperation Treaty Application No. PCT/US13/32071, filed on Mar. 15, 2013, which claims priority to U.S. Provisional Patent Applications 61/678,080, filed on Jul. 31, 2012; 61/678,082, filed on Jul. 31, 2012; and 61/740,086 filed Dec. 20, 12012; and U.S. Provisional Application No. 62/026,071, filed Jul. 18, 2014. The contents of each of the foregoing documents are incorporated herein by reference.

BACKGROUND

High-dose-rate brachytherapy (HDR-BT) is a technique for treating cancerous tumors in which needles are inserted inside or close to the tumor. A radiation source travels inside each needle, depositing a radiation dose pattern inside the tumor over one or more treatment sessions, with the goal of killing all of the tumor cells and sparing radiation-sensitive normal tissue as much as possible. Brachytherapy enables the delivery of higher radiation doses than would be possible with external beam radiation therapy (EBRT), wherein radiation beams from outside the patient must pass through healthy tissues on the way to tumors. With brachytherapy, the radiation dose that can be delivered to tumors is still limited by the presence of adjacent healthy tissues. When treating cervical cancer, tumor dose limiting tissues are the rectum, bladder, and sigmoid colon. For breast cancer lumpectomy cavities treated with brachytherapy, the deliverable dose is limited by the skin on the surface of the breast, the ribs, and normal breast tissue. For prostate cancer, the urethra, rectum, and bladder limit tumor dose.

A major limitation of conventional brachytherapy is that the radiation dose distribution delivered with brachytherapy sources is radially symmetric about the source axis, which limits the tumor dose conformity achievable. Further, in the radiation oncology field, increased radiation doses delivered in fewer treatment fractions, or hypofractionation, is becoming increasingly important both for improving patient care and reducing treatment cost.

Conventional HDR-BT delivers radially-symmetric dose distributions in cervical cancer patients, which limits the radiation dose that can be delivered to tumor without exceeding the tolerance doses of the organs-at-risk (OARs) adjacent to or inside the tumor, especially in cases where the tumor is bulky (>40 cc), laterally-extended, or non-symmetric, thus comprising treatment effectiveness.

The use of interstitial brachytherapy is an option to overcome this drawback and is recommended by the American Brachytherapy Society (ABS). Large tumor can be conformally treated with needles. Another option recently introduced, is the use of supplementary needles along with intracavitary applicator (IS+ICBT), tandem and ring or tandem and ovoids plus needles have been introduced. These applicators enable the enhanced tumor coverage under magnetic resonance image (MRI)-guidance, yet, at the cost of more invasive treatment due to the presence of interstitial needles. In addition, even if the number of catheters, locations of catheters, and the source dwell times are computed in an optimized fashion, the resulting dose distributions may still be subject to the constraint that the source emits radially-symmetric dose distributions.

The rotating shield brachytherapy (RSBT) and dynamic modulated brachytherapy (DMBT) approaches have been introduced as a means to improve intracavitary brachytherapy dose distributions for rectal and cervical cancer. Dynamic-shield RSBT (D-RSBT) allows the use of different azimuthal emission angles during the delivery via a layered shielding apparatus with each layer independently rotatable to form different emission windows. The major drawback of D-RSBT lies on the limit of its maximal azimuthal emission angle that can be formed by the apparatus. With delivery times of 20-30 min per treatment fraction, D-RSBT can produce better delivery plans than S-RSBT, while S-RSBT may perform better when the delivery time is limited (e.g. <20 min/fx). Therefore, there is a need for a noninvasive, conformal brachytherapy treatment that can combine the power of S-RSBT and D-RSBT, thus performing better than both S-RSBT and D-RSBT in the sense of balancing the treatment time and dose quality.

In addition, certain forms of cancer need specialized application. For example, prostate cancer is the most common non-skin cancer in men, with 238,590 new diagnoses in 2013, a 9.5% increase over the 2010 estimate. Most prostate cancer patients have localized prostate cancer and a variety of treatment options including surgery, external beam radiotherapy (EBRT), low-dose-rate brachytherapy (LDR-BT), HDR-BT, and combinations thereof. Prostate cancer treatment cost is at least $19,901 per patient, and currently 82% of men diagnosed with prostate cancer receive surgery, brachytherapy or EBRT. If healthcare trends develop such that all low-risk prostate cancer patients (47.6% of patients) receive active surveillance and 30% of those patients receive treatment within 5 years of diagnosis, there will still be nearly 134,000 men who were diagnosed with prostate cancer in 2013 and who will receive treatment within the next five years.

Although long-term (10+ year) biochemical disease-free survival is high and tends to increase with radiation dose delivered, 29,720 men still died of prostate cancer in 2013. While achieving tumor control is paramount, prostate cancer patients may live with the side effects of their treatment for decades, and anticipated side effects play a strong role in treatment decisions. Treatment decisions are often based on anticipated side effects, such as urinary incontinence, urethral stricture, rectal bleeding, and sexual dysfunction. Existing treatments all have reducible incidences of side effects that can impact patients' quality of life for decades.

Existing brachytherapy techniques offer advantages over other treatments in both survival and side effects with the exception of increased urinary complications, highlighting a critical need for a lower-toxicity treatment technique. In a large-scale literature review (848 of 18,000 published abstracts), Grimm et al (2012) found that in low-risk patients brachytherapy provides superior long-term (10+ year) biochemical relapse-free survival to EBRT and surgery, in intermediate-risk patients brachytherapy alone is equivalent to EBRT in combination with brachytherapy and superior to surgery and EBRT alone, and in high-risk patients EBRT in combination with brachytherapy is superior to more localized treatments such as surgery alone, brachytherapy alone, or EBRT alone. The benefits of brachytherapy in obtaining long-term relapse-free survival are suspected to be due to the dose escalation achievable that would not be possible with EBRT alone. Surgery, even using the Da Vinci robot (Intuitive Surgical, Inc., Sunnyvale, Calif.), has been reported to have greater risks of urinary incontinence and sexual dysfunction than radiotherapy techniques, in that brachytherapy has a 3-fold higher rate of return than surgery to baseline urinary function at 36 months, and a 5-fold higher rate of return to baseline sexual function. HDR-BT and combined EBRT and HDR-BT have equivalent or lower sexual dysfunction and gastro-intestinal toxicity than EBRT alone, but greater late grade ≥3 urethral stricture rates at 5 years of 7-10% versus 1-2% for EBRT alone.

Therefore, there is thus a critical need in the urology and radiation oncology fields for prostate cancer treatment techniques with an equal or greater cancer control probability than current techniques, but with reduced toxicity.

SUMMARY OF THE INVENTION

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

Certain embodiments of the disclosure relate to methods for facilitating shield selection for use in single rotating shield brachytherapy. Such methods decouple the sequencing procedure from the dose optimization resulting in a reduction in treatment planning time as well as allow treatment providers to quickly select the optimal emission angle for a clinical case given the prescribed treatment time and dose. Certain other embodiments of the disclosure relate to methods for facilitating a method for sequencing the rotating shields in dynamic rotational shield brachytherapy. Such methods improve dose conformity without compromising adjacent healthy tissue within an acceptable delivery time relative to conventional techniques.

The invention is a shielded needle or catheter system with a rotational controller for delivering radioisotope-based interstitial rotating shield brachytherapy (I-RSBT). The I-RSBT system is applicable in the fields of radiation oncology and urology. The I-RSBT system overcomes the primary limitation of conventional interstitial HDR-BT, which is that individual needles can only deliver dose distributions that are radially symmetric about each needle. With I-RSBT, the shielded needles deliver dose distributions that are deliberately non-radially symmetric about each needle, enabling reduced doses to sensitive normal tissues. For prostate cancer patients, for example, a dose reduction to normal tissues enables reduced urethral (incontinence, urethral stricture) and rectal (bowel dysfunction) complications relative to conventional BT. In addition, reduced normal tissue doses could enable increased doses to the prostate cancer, potentially reducing the number of treatment sessions needed to deliver the therapy, which is typically two to four. In one aspect, I-RSBT is of significant commercial value because it could be the least expensive, lowest-complication-rate therapy for the nearly 180,000 patients who are diagnosed with localized prostate cancer per year in the U.S.

Embodiments of the invention can comprise an apparatus and method for modulating the intensity of x-rays or gamma-rays from a radiation source used to treat cancerous tumors, called multiple rotating shield brachytherapy (M-RSBT) and is applicable in the field of radiation oncology. Conventional brachytherapy (BT) entails the insertion of radioactive sources into tumors through interstitial needles or intracavitary applicators, and delivers very high radiation doses to tumors but often with poor tumor dose conformity, as conventional BT dose distributions are radially symmetric and tumors are usually not. This is of concern since tumor underdosage can lead to recurrence and tumor overdosage can damage nearby healthy tissue. Single rotating-shield brachytherapy (S-RSBT) uses a shielded BT source that emits more radiation at conventionally underdosed tumor regions and less radiation at conventionally overdosed tumor regions. However, the time necessary to treat a tumor with S-RSBT is inversely proportional to the shield emission angle, thus small emission angle shields produce long delivery times. M-RSBT significantly reduces intensity modulated brachytherapy (IMBT) treatment time by using intelligent combinations of varying emission angle shields. This invention is an apparatus that enables the fast, remote-controlled changing of radiation shields, and a method for rapidly determining which combination of radiation shields should be used for a given patient. The selection of shields is computer-optimized by specified source positions, tumor shape, and a desired dose distribution. The shields are composed of a high-density material such as tungsten, lead, gold, silver, or bismuth. M-RSBT is of commercial value because it is a method that provides a significant improvement over conventional BT and S-RSBT methods. Examples of cancers that we believe can be treated more effectively with M-RSBT include cervical, vaginal, endometrial, colorectal, prostate, and breast cancers.

Further provided are methods and systems for selecting an emission angle for use in S-RSBT. An example method can comprise calculating a dose, optimizing the calculated dose, generating a first treatment plan based on the optimized dose, generating a second treatment plan, and selecting one of the first treatment plan or the second treatment plan.

Further provided are methods and systems for sequencing the rotating shields. An exemplary method can comprise calculating a dose, optimizing the dose, and generating a treatment plan based on an optimal sequence of the dose. Further provided are methods and system for the multiple application of M-RSBT in a single setting.

In an aspect, the invention is an apparatus and method for using rotating shield brachytherapy (RSBT). In an aspect, RSBT can be used to maintain or increase tumor dose relative to conventional techniques, but with a dramatic reduction in radiation dose to the urethra, rectum, and bladder in the treatment of prostate cancer. In an aspect, with RSBT, partially shielded radiation sources can be placed in the prostate away from sensitive tissues.

In an aspect, the invention is an apparatus and method for the precise angular and linear positioning of a partial shield used for RSBT in a curved applicator. The system required only linear translational motion of the radiation source/shield combination. RSBT enables the delivery of deliberately non-symmetric, tumor-conformal, dose distributions that would be impossible to deliver with conventional, unshielded, radiation sources. The system could be used to treat rectal, cervical, vaginal, prostate, and breast cancers. Prior art exists for RSBT apparatus for straight, rigid, brachytherapy applicators (serial RSBT), but a simple, robust solution to the problem of delivering RSBT, especially in curved applications, does not currently exist. The wall of the applicator system contains a plurality of helical imprints, or keyways, that define the direction of the partial radiation shield as a function of depth. By including one or more protruding keys on the shield and attaching the shield to the source such that it rotates freely, longitudinal translational motion of the source is transferred to rotational motion of the shield. This novel applicator with spiral keyways is of commercial value because it enables clinical RSBT delivery, potentially improving tumor control probability and reducing complications, and could be accomplished by means of both electronic and isotope based brachytherapy sources.

Further provided are methods and systems for the use of paddle-based rotating shields for another form of brachytherapy called paddle-based rotating-shield brachytherapy (P-RSBT). In an aspect, multiple shield paddles can be oriented around a radiation source within an applicator. In another aspect, the multiple shield paddles can be independent of one another, and can be configured to apply the radiation dose in a helical pattern. This same approach can also be used for straight applicators and needles also, for both interstitial and intracavitary applications.

Additional aspects, features, or advantages of the subject disclosure will be set forth in part in the description which follows, and in part will be obvious from the description, or may be learned by practice of the subject disclosure. The advantages of the subject disclosure will be realized and attained by means of the elements and combinations particularly pointed out in the appended claims. It is to be understood that both the foregoing general description and the following detailed description are exemplary and explanatory only and are not restrictive of the subject disclosure. These and other objects and advantages of the invention will become apparent from the following detailed description of the preferred embodiment of the invention.

The accompanying drawings are included to provide a further understanding of the invention and are incorporated in and constitute part of this specification, illustrate several embodiments of the invention, and together with the description serve to explain the principles of the invention.

BRIEF DESCRIPTION OF THE DRAWINGS AND APPENDICES

The accompanying drawings are incorporated and illustrate exemplary embodiments of the disclosure and together with the description and claims appended hereto serve to explain various principles, features, or aspects of the subject disclosure.

FIG. 1A illustrates a cross-sectional view of an exemplary partially shielded BT source in RSBT. FIG. 1B illustrates a longitudinal-sectional view of the beamlets arrangement.

FIG. 2 illustrates a three dimensional view of an exemplary clinical cervical cancer case.

FIGS. 4a-f illustrate exemplary dose distributions of different RSBT treatment plans generated for Patient 1 on MRI scan slice 30.

FIGS. 5a-f illustrate exemplary dose distributions of different RSBT treatment plans generated for Patient 2 on MRI scan slice 30.

FIG. 6 is a table of an exemplary quantitative comparison between the dose quality of different delivery plans for Patient 1.

FIG. 7 is a table of an exemplary quantitative comparison between the dose quality of different delivery plans for Patient 2.

Figure 8:
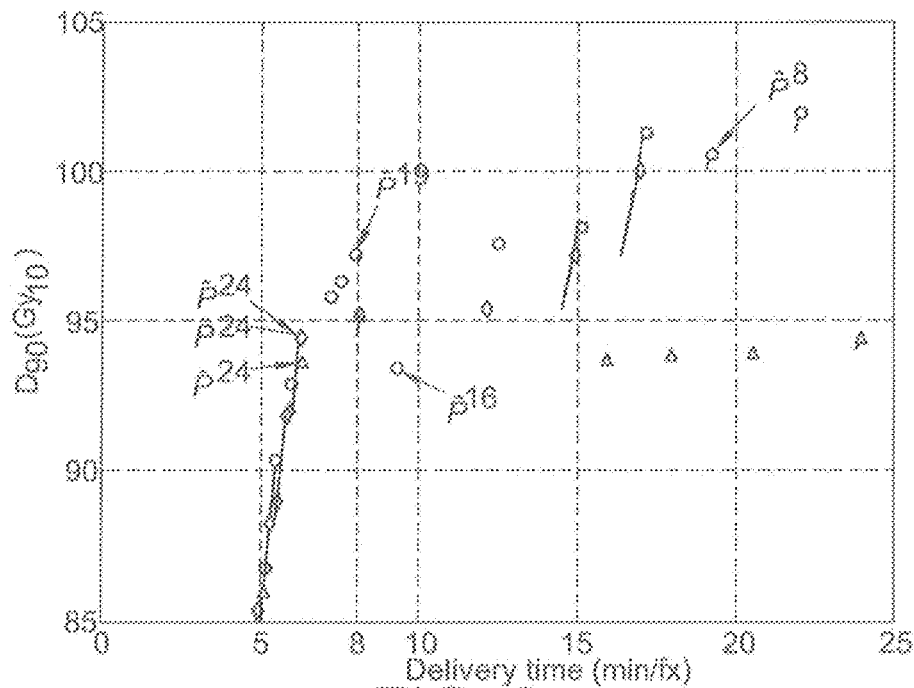

FIG. 8 is an exemplary Pareto plot generated using rapid emission angle selection (REAS) for Patient 1.

Figure 9:
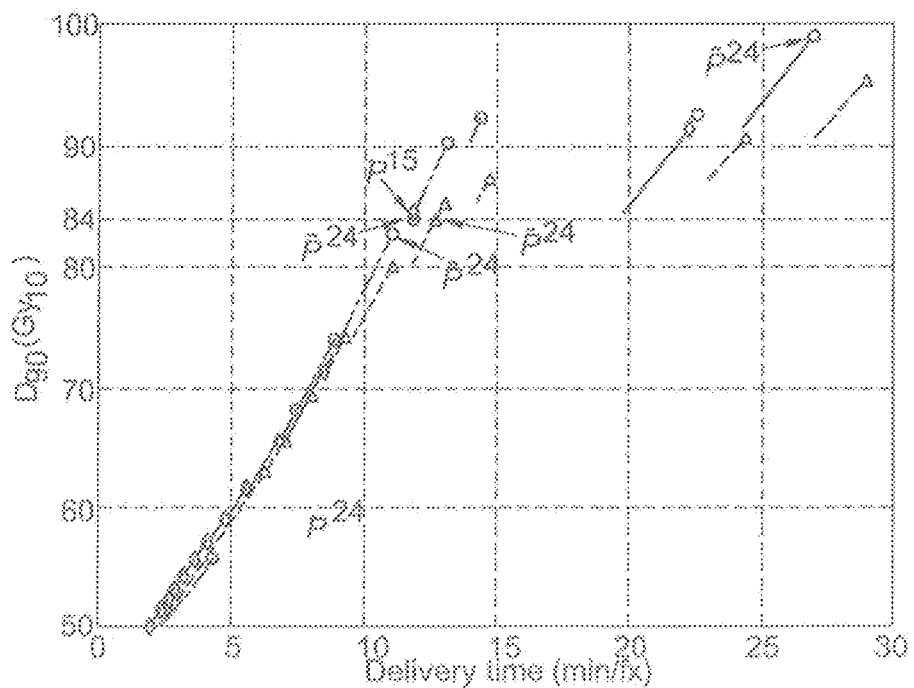

FIG. 9 is an exemplary Pareto plot generated using REAS for Patient 2.

Figure 10A:
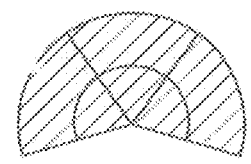
Figure 10B:
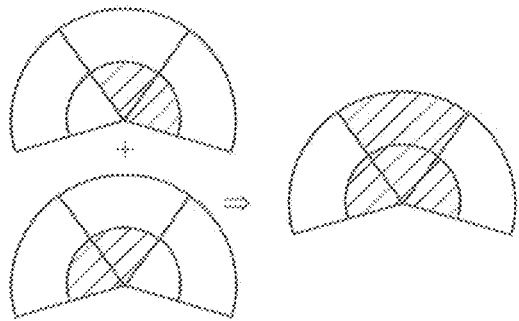

FIGS. 10(a-b) are schematic illustrations of emission angles according to an aspect.

FIGS. 11(a-d) illustrate a sequencing optimization model according to an aspect.

Figure 12:
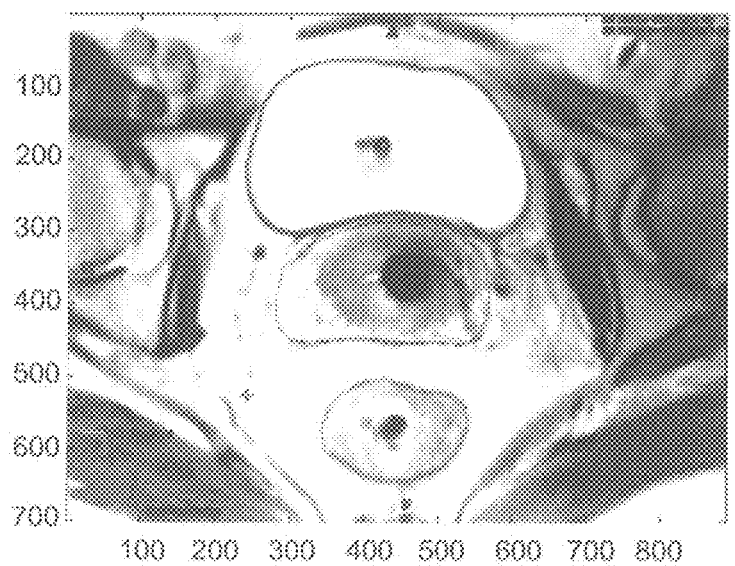

FIG. 12 illustrates an MRI 2D slice of a cervical cancer case used for verification in an aspect.

FIG. 13 is a table that compares plan quality and delivery times of the S-RSBT sequencing algorithm under different fan-angle and the conventional isotropic one according to an aspect. The prescription dose is normalized to 100, the volumes are also measured in percentage, and the delivery times are also listed with a relative time unit.

FIG. 14 is a table that compares plan quality and delivery times of the S-RSBT sequencing algorithm under different fan-angle with the maximum allowed combination of unshielded source and the conventional isotropic one. The prescription dose is normalized to 100, the volumes are also measured in percentage, and the delivery times are also listed with a relative time unit.

Figure 15:
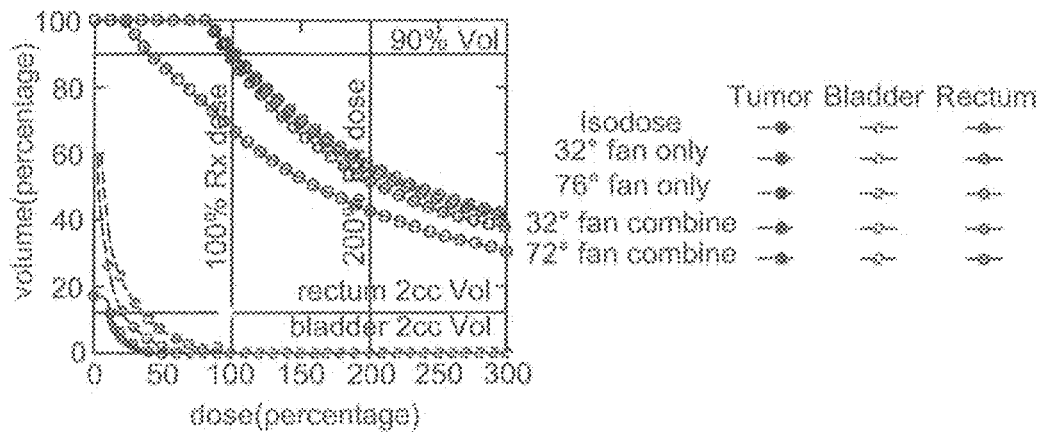

FIG. 15 shows a comparison of Dose-Volume Histogram (DVH) plots for IMBT with different settings and conventional BT.

Figure 16A:
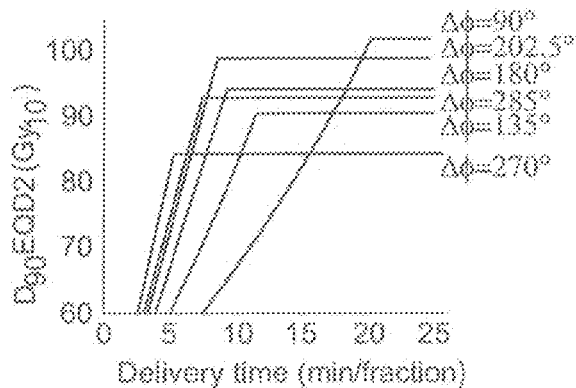
Figure 16B:
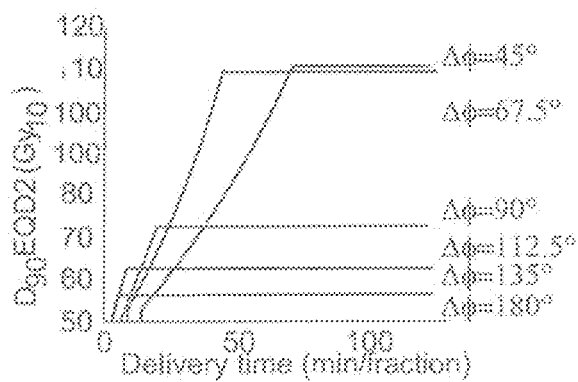

FIGS. 16(a)-16(b) show graphs of delivery time vs. D90 for every possible azimuthal emission angle and time bound for two exemplary clinical cases.

Figures 17, 18:
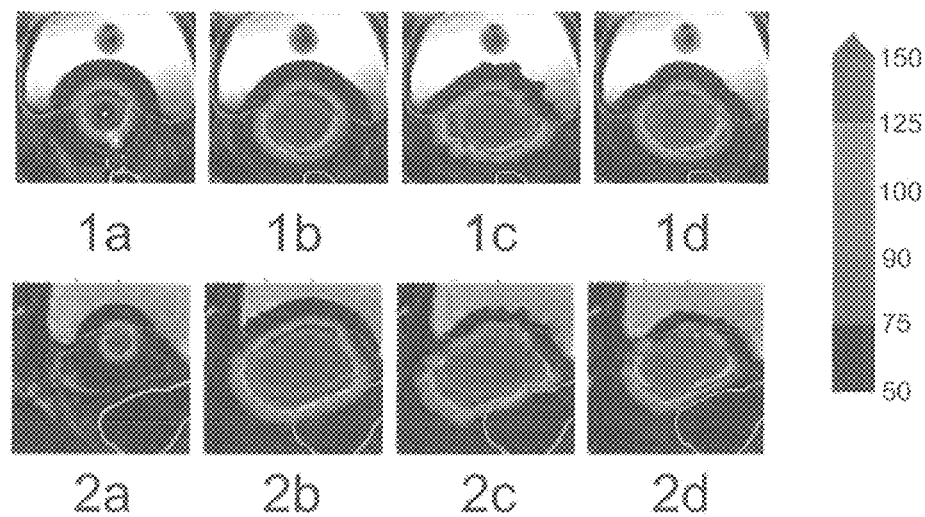

FIG. 17 illustrates exemplary dose distributions for selective delivery configurations for two exemplary clinical cases.

FIG. 18 is a table showing dose quality and delivery time comparison between different delivery configurations for two patients according to an aspect.

Figures 19, 20:
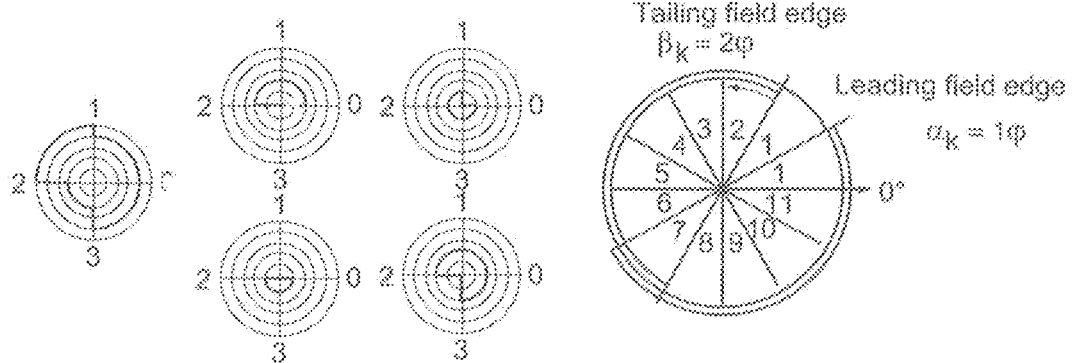

FIG. 19 illustrates a circular integral block decomposition (CIBD) problem according to an aspect.

FIG. 20 illustrates a cross-sectional view of an exemplary rotationally shielded source in D-RSBT according to an aspect.

Figure 21:
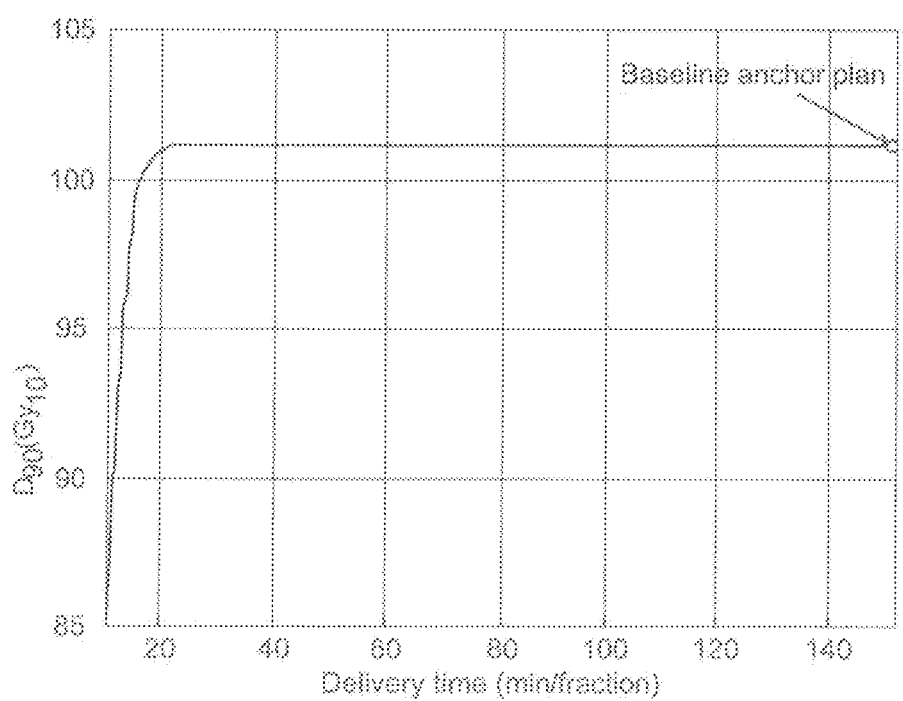

FIG. 21 is an exemplary optimal sequencing (OSD) generated Pareto plot.

FIG. 22 is a table comparing different delivery methods with OSD.

Figure 23:
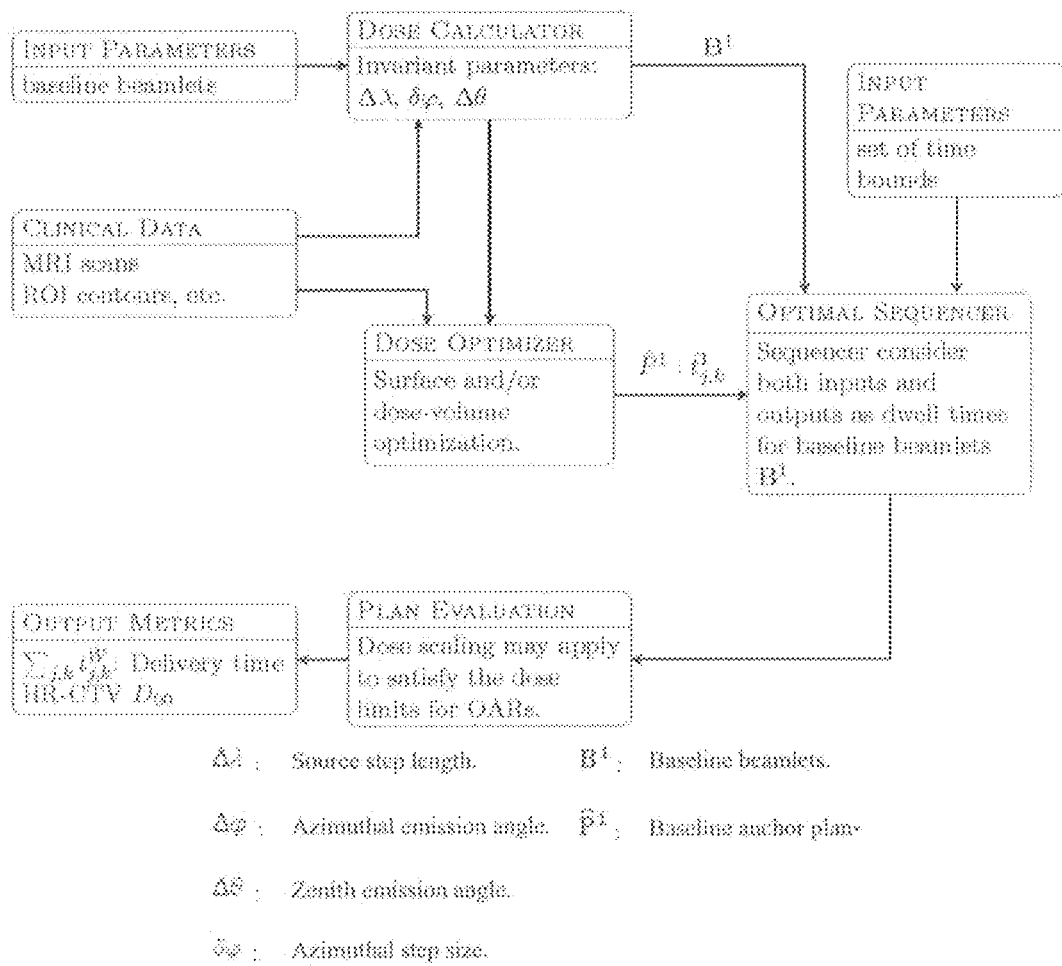

FIG. 23 is a flowchart showing the treatment planning steps of an exemplary method for treatment plan selection using optimal sequencing methods for D-RSBT.

Figure 24:
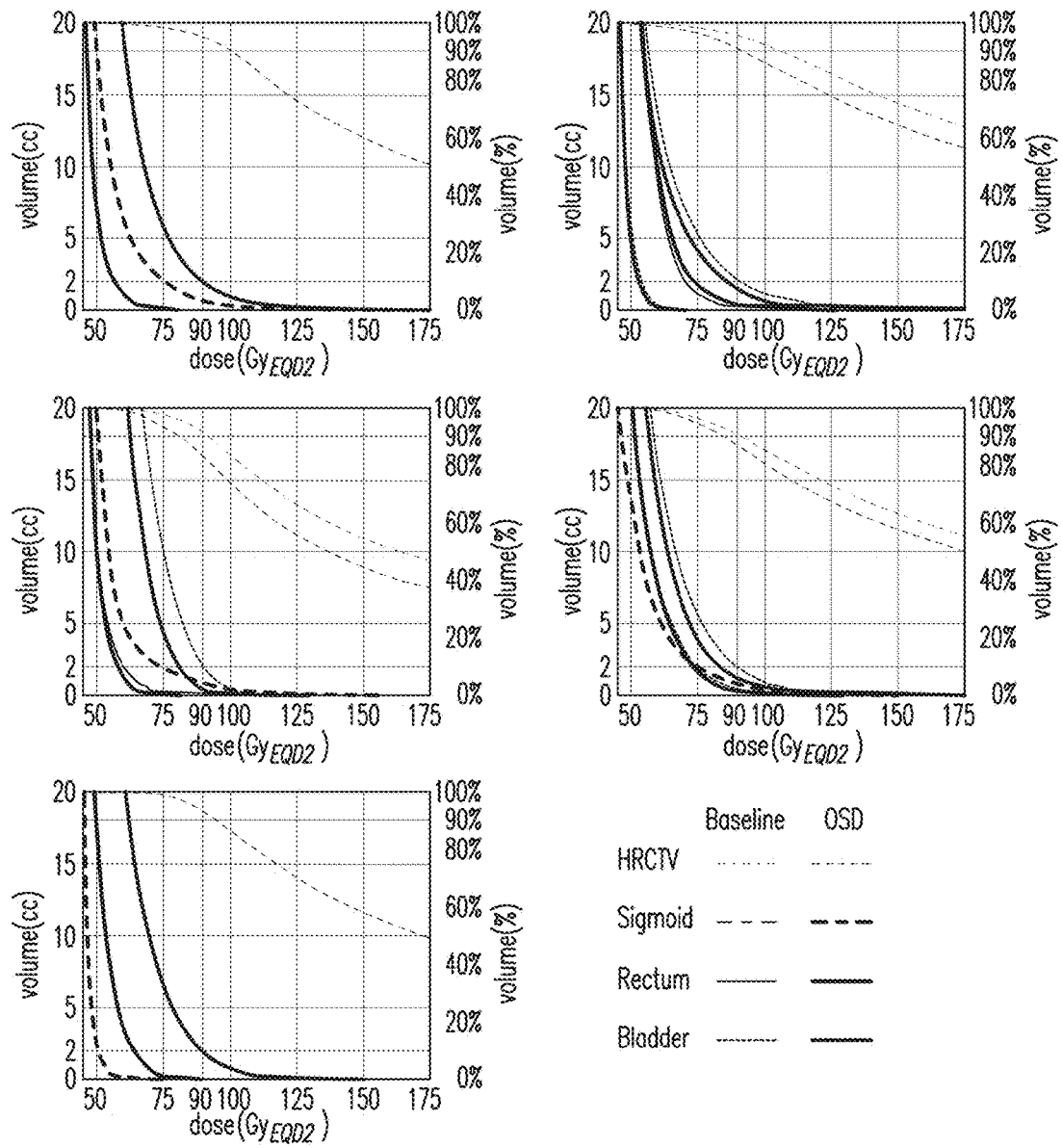

FIG. 24 shows a comparison of DVH plots for baseline anchor plans and selected OSD generated plans.

Figures 25, 26:
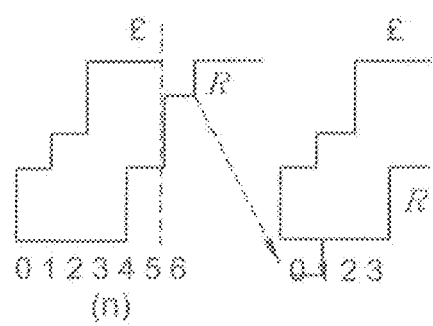

FIG. 25 is a table of an exemplary quantitative comparison between the dose quality between the baseline anchor plans and selected OSD generated plans.

FIG. 26 illustrates mapping from $(\mathcal{L},\mathcal{R})$ to $(\mathcal{L},\bar{\mathcal{R}})$.

Figure 27A:
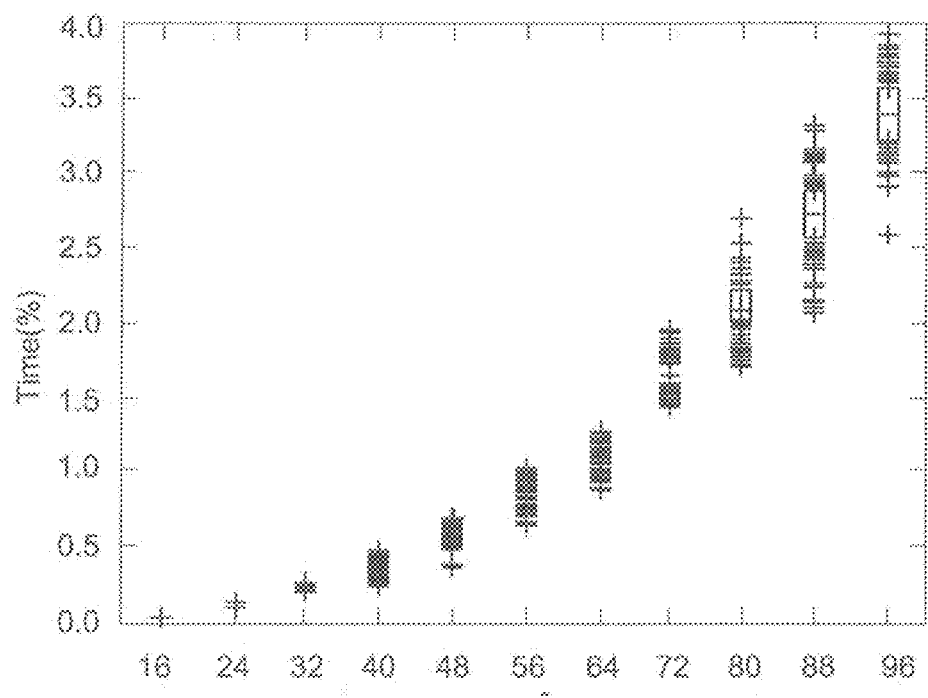

FIG. 27(a) illustrates the impact parameter n can have on the running time in the five exemplary clinical cases used.

Figure 27B:
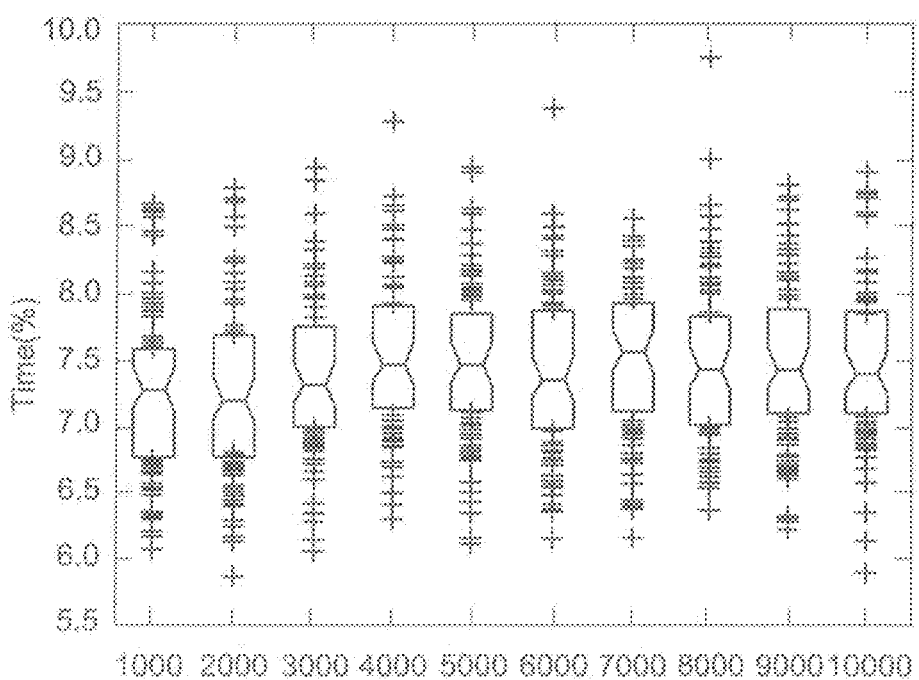

FIG. 27(b) illustrates the impact parameter H can have on the running time in the five exemplary clinical cases used.

Figures 28, 29:
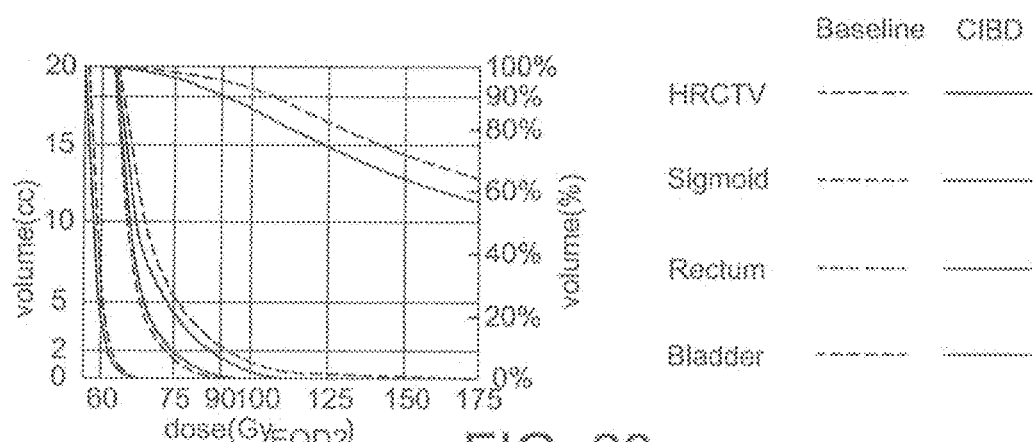

FIG. 28 is a table showing the plan quality comparisons for five exemplary clinical cases generated using the disclosed methods for optimizing treatment delivery of D-RSBT.

FIG. 29 illustrates one example of a DVH plot for one of the five exemplary clinical cases generated using the disclosed methods for optimizing treatment delivery of D-RSBT.

FIG. 30 illustrates a comparison of the results obtained by conventional BT versus using the disclosed methods for optimizing treatment delivery of D-RSBT for another exemplary clinical case.

Figure 31A:
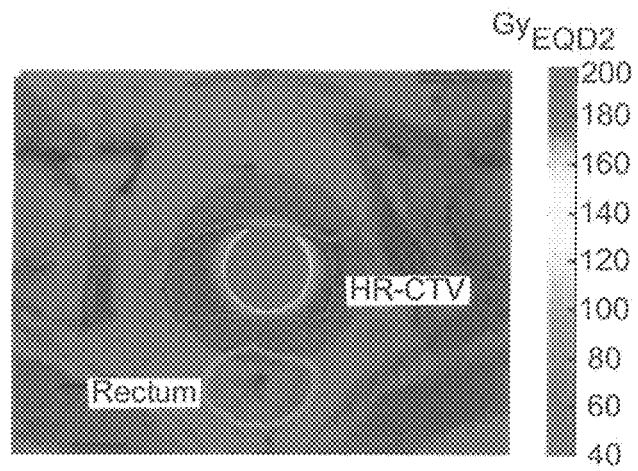
Figure 31B:
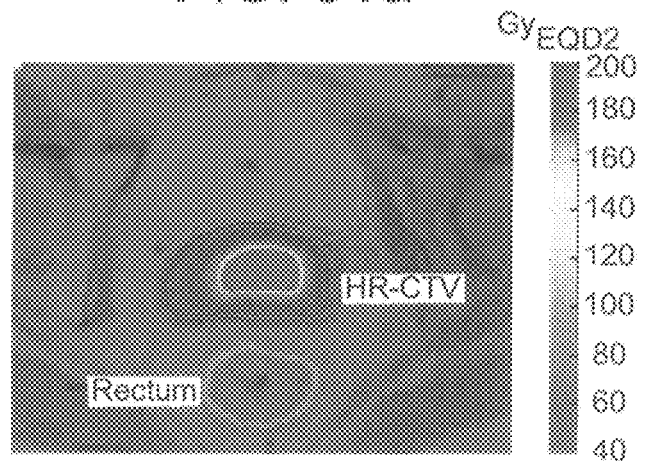
Figure 31C:
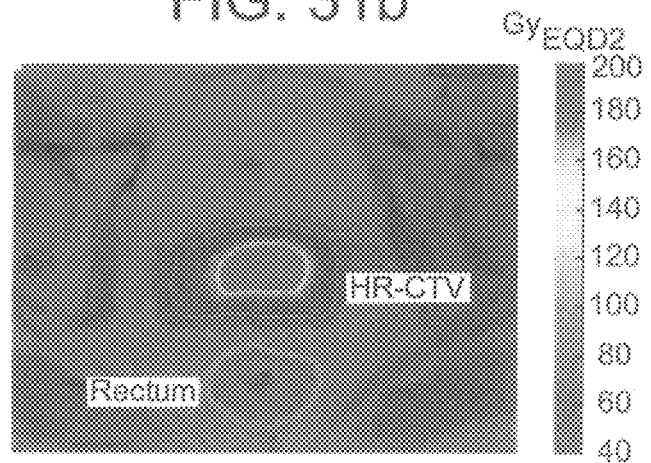

FIG. 31(a) shows one example of a dose distribution for conventional $^{192}$Ir unshielded source for an exemplary clinical case. FIG. 31(b) shows a dose distribution for IMBT using the Axxent Xoft eBT source configured with 60 divisions and no overlapping applied to the same exemplary clinical case. FIG. 31(c) shows a dose distribution for IMBT using the Axxent Xoft eBT source as well as the disclosed methods for optimizing treatment delivery of D-RSBT applied to the dame exemplary clinical case.

Figure 32:
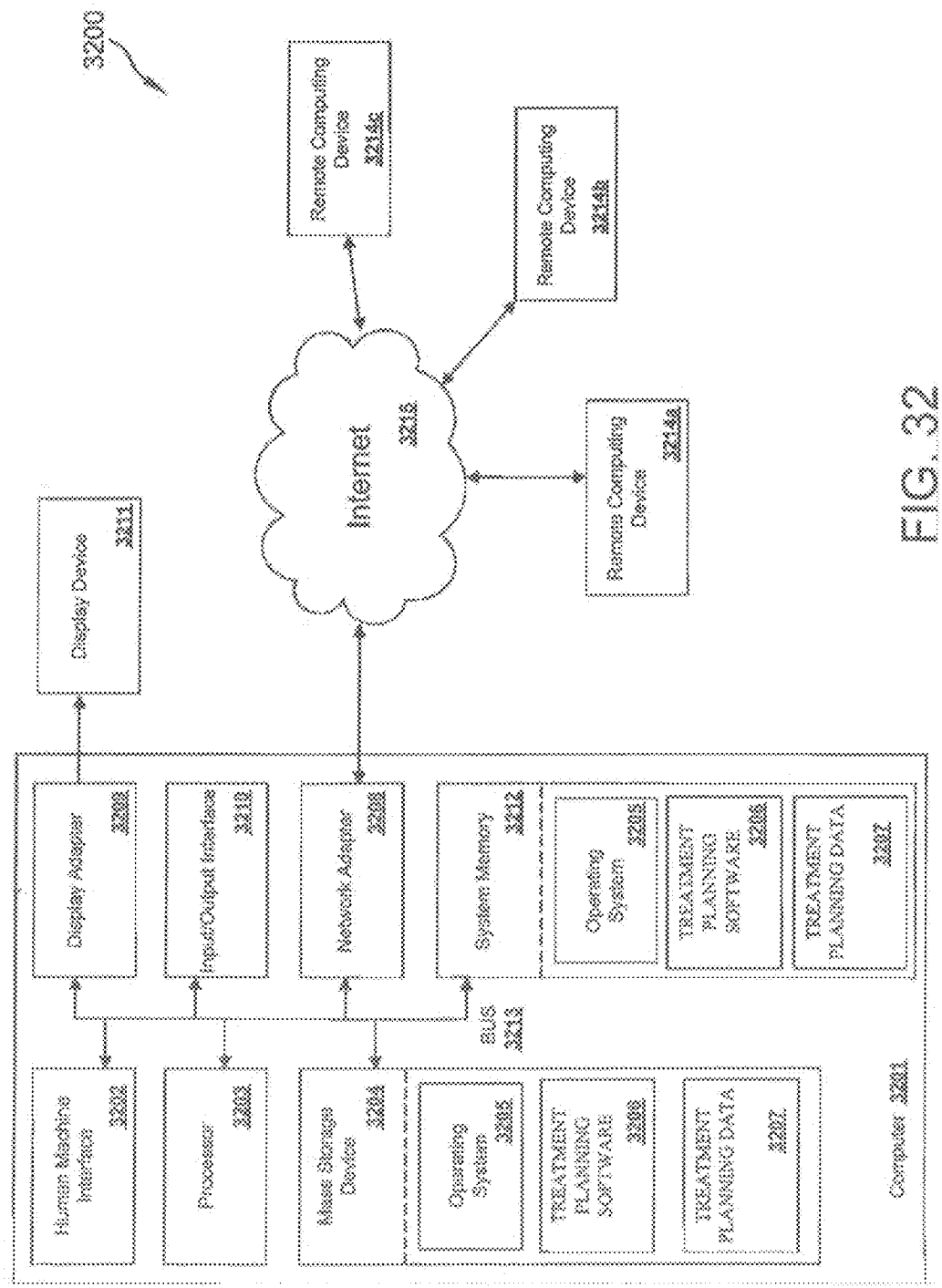

FIG. 32 illustrates a computing environment that enables various aspects of treatment planning and/or automation of treatment planning in accordance with aspects described herein.

Figure 33:
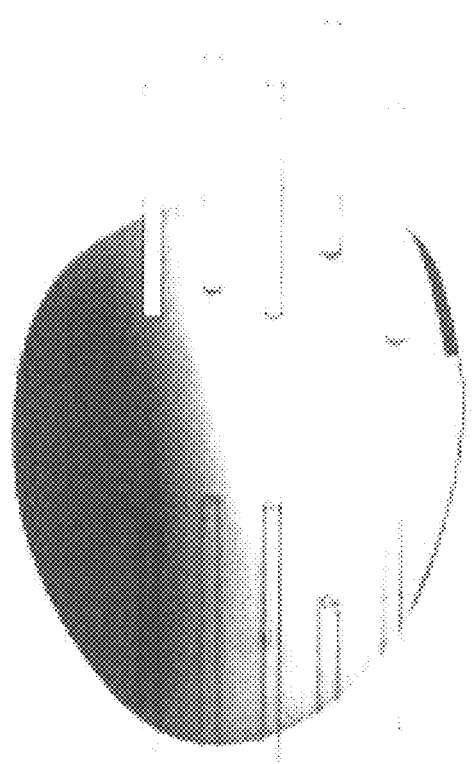

FIG. 33 illustrates example interstitial brachytherapy (BT) for localized prostate cancer.

Figure 34:
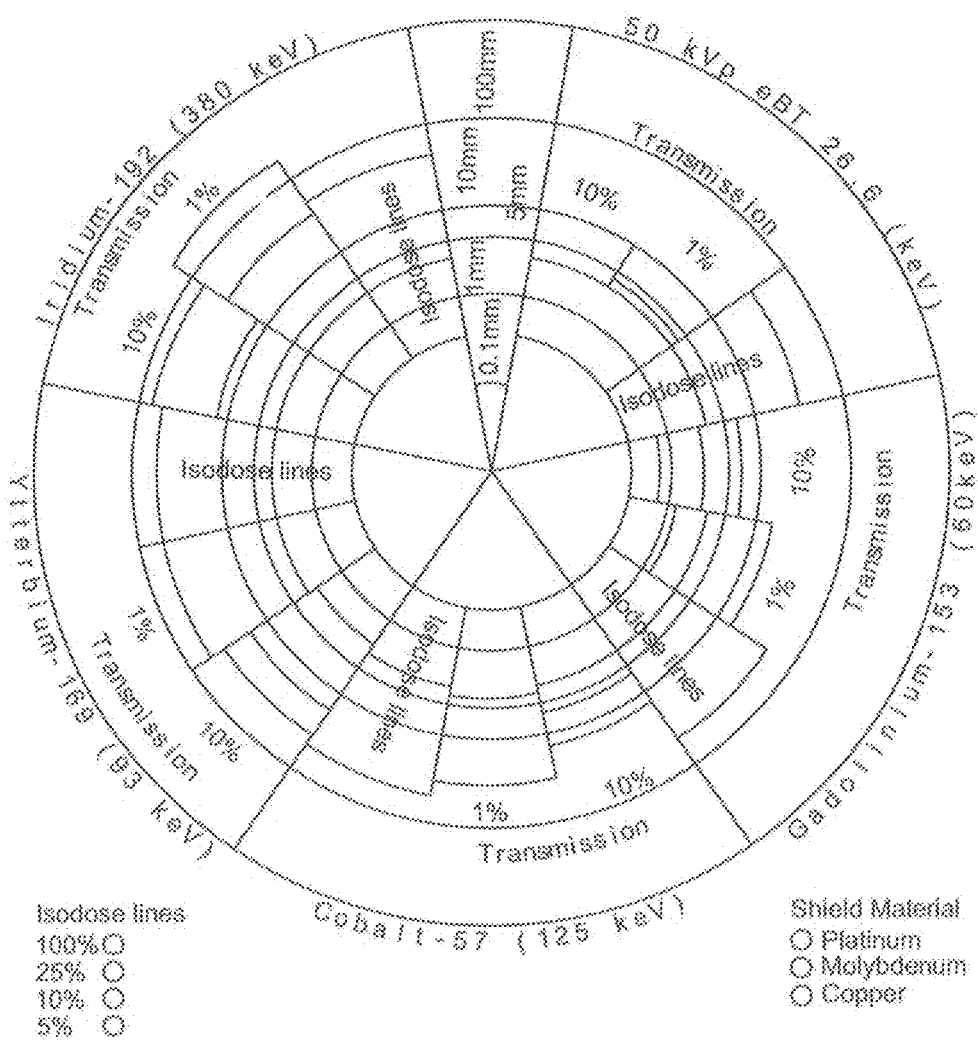

FIG. 34 illustrates radii of candidate source/shield combinations for RSBT, showing the different source sizes that would be required to produce the same dose rate in water at 1 cm lateral to the source axis as a 10 Curie $^{192}$Ir source.

Figure 35:
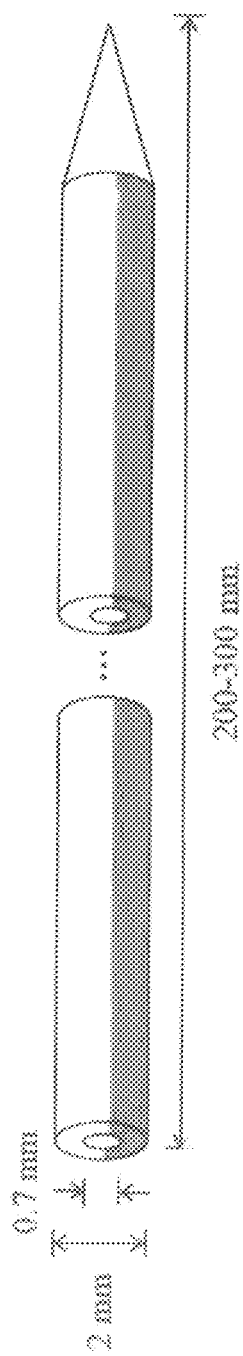

FIG. 35 illustrates an example embodiment of a shielded catheter for I-RSBT delivery with a sharp tip for use as a needle in accordance with one or more aspects of the disclosure. Blunt-tipped versions are also possible, which can be used as catheters.

Figure 36A:
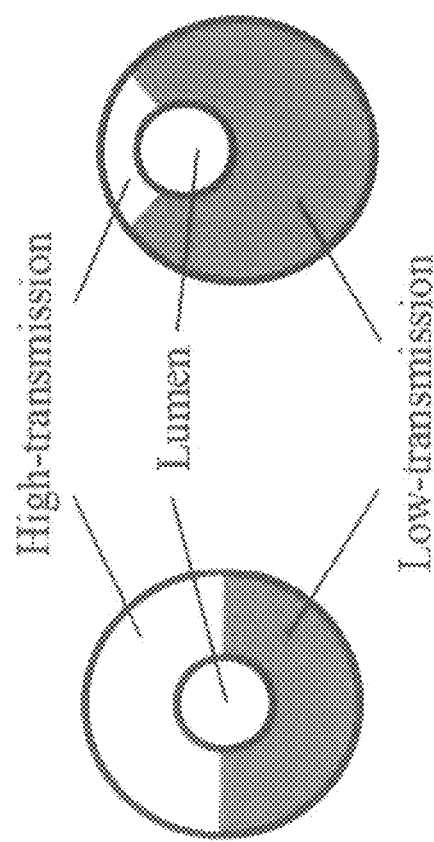
Figure 36B:
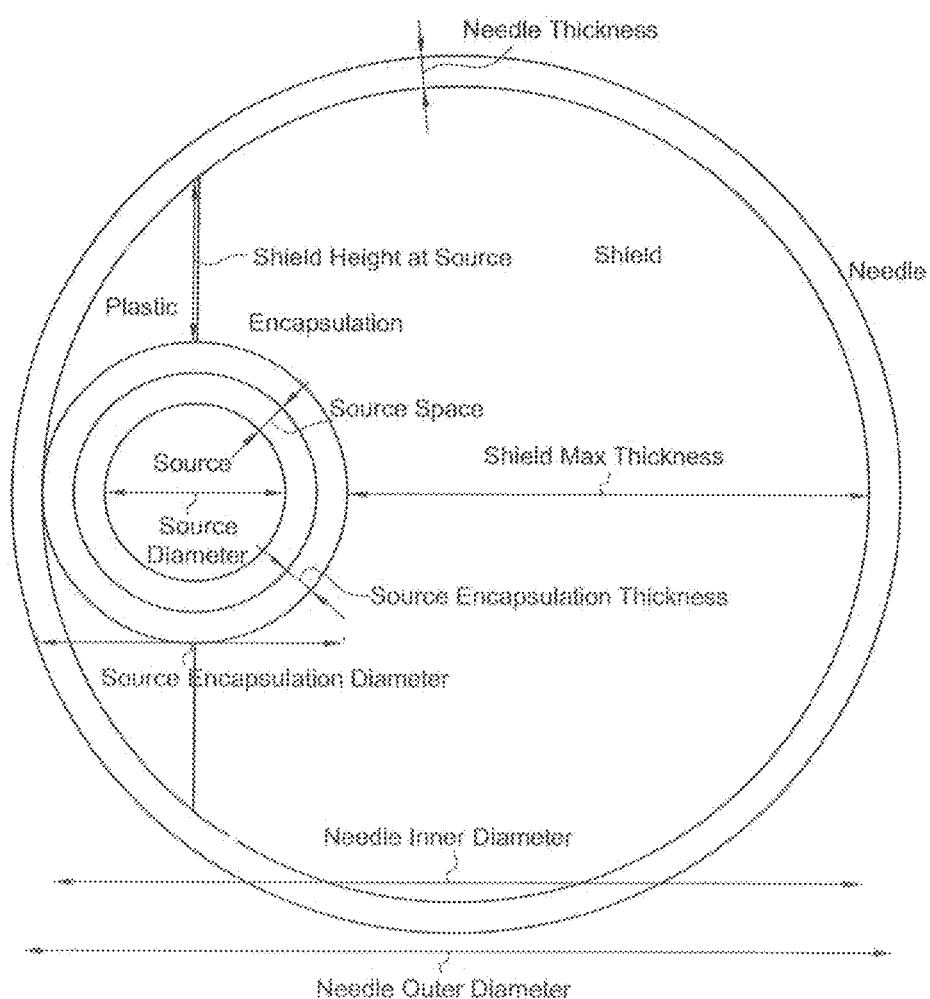
Figure 36C:
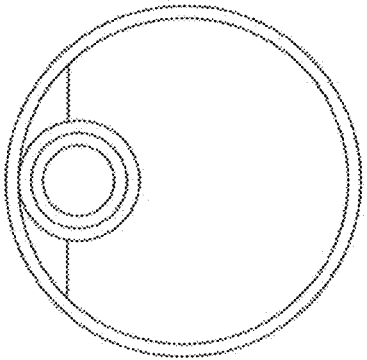
Figure 36D:
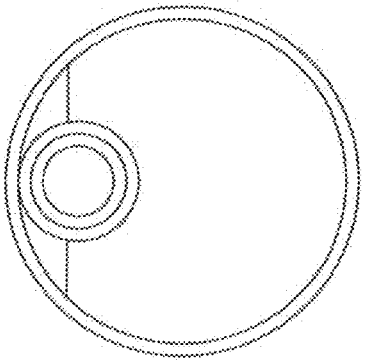
Figure 36E:
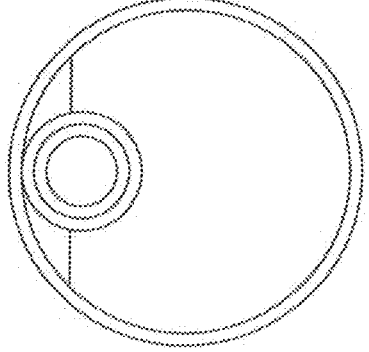
Figure 36F:
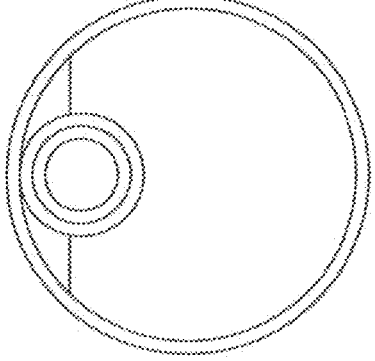
Figure 37A:
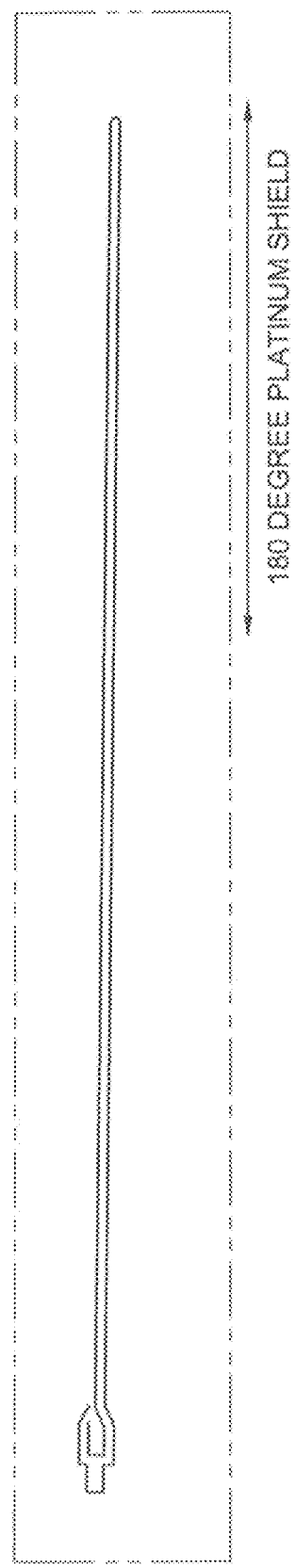
Figure 37B:
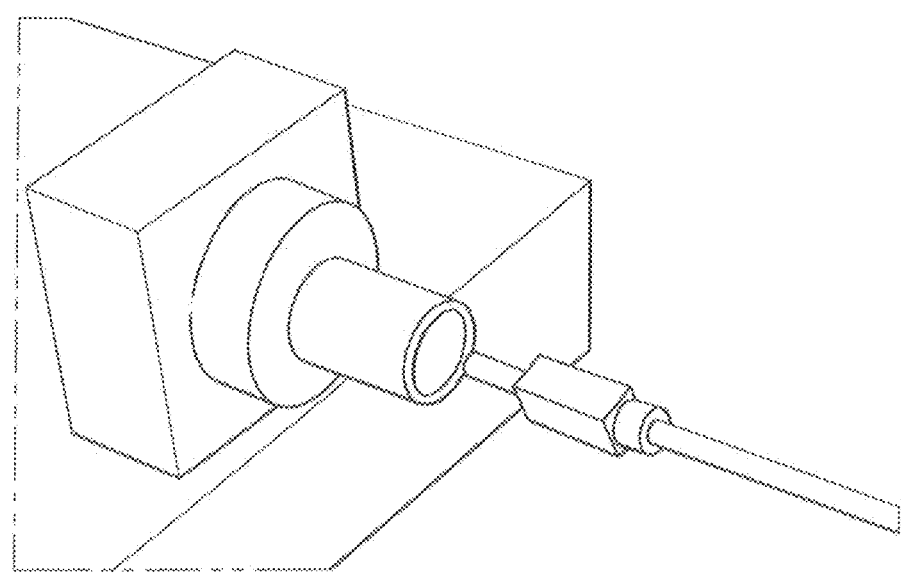

FIGS. 36A-F illustrate examples of I-RSBT catheter cross sections having a centered lumen and an off-center lumen according to aspects of the present invention FIGS. 37A-37B: Example prototypes of (a) 17 gauge stainless steel I-RSBT catheter with a 180° platinum shield and a plastic docking device (left). The grasping device mounts to a translating rotational motor and connects to each needle, enabling the delivery of I-RSBT plans in series, (b) needle grasping device and connector to permit rotation.

Figure 38A:
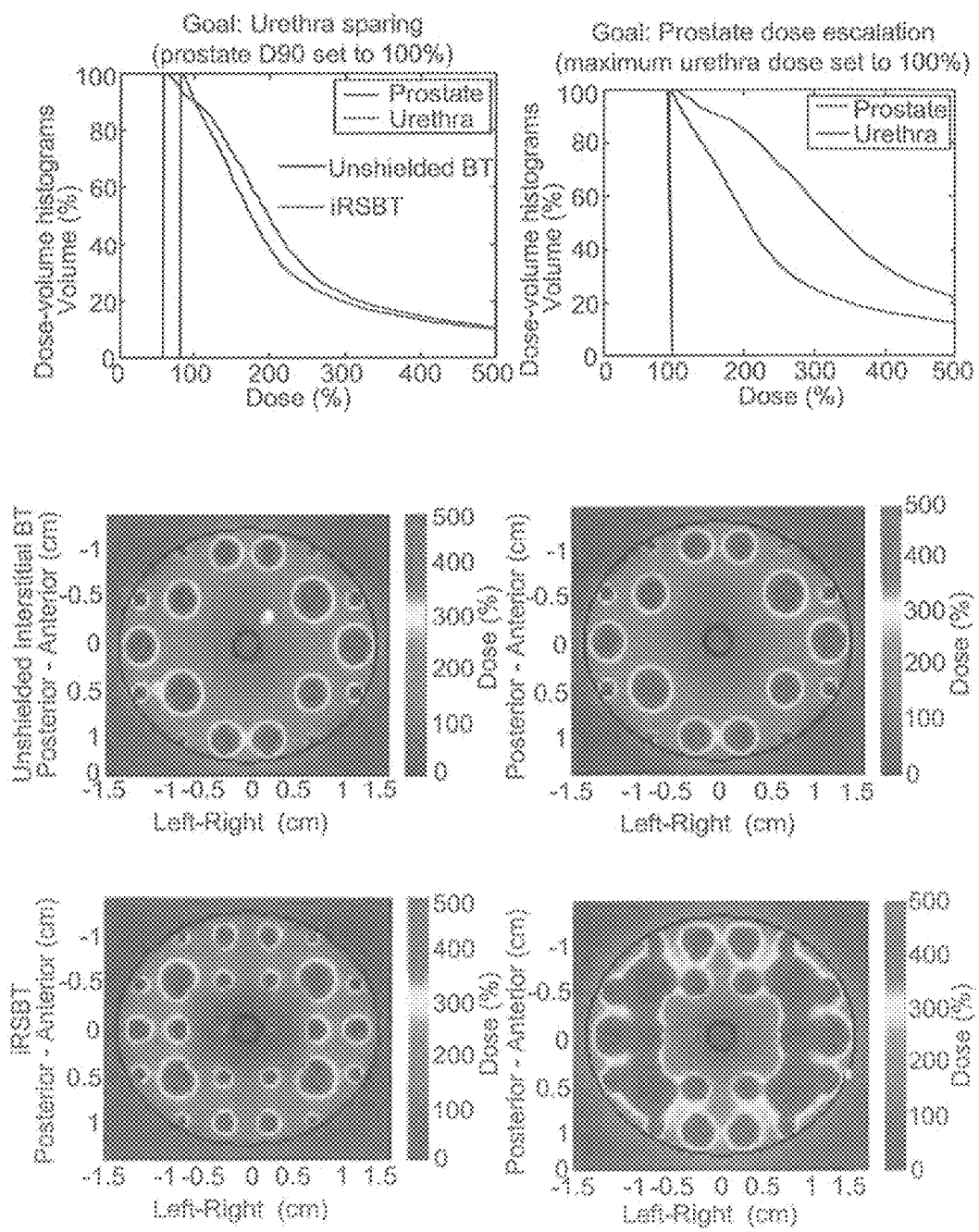
Figure 38B:
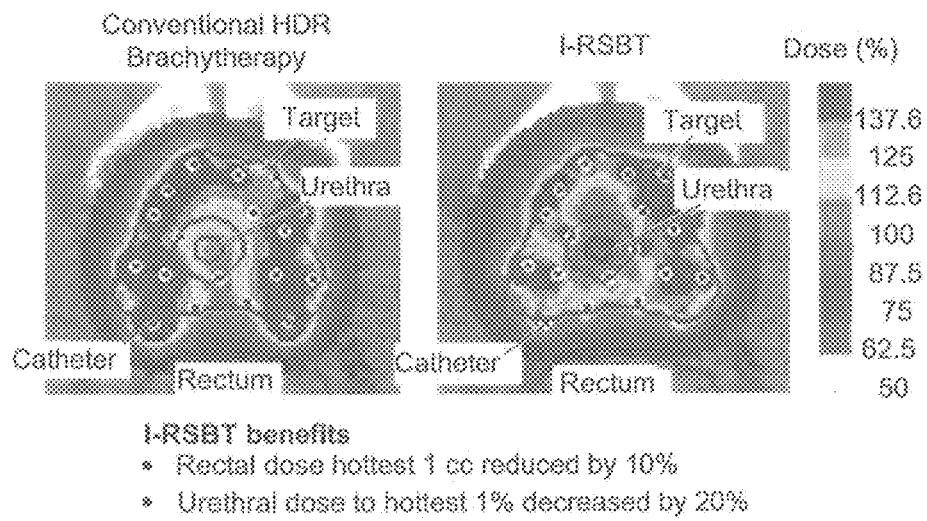

FIG. 38A illustrates examples of simulated localized prostate cancer treatments with unshielded BT and I-RSBT. The top row: dose-volume histograms (DVHs). Second row: conventional unshielded interstitial BT dose distributions. Bottom row: I-RSBT dose distributions. FIG. 38B illustrates another example of simulated localized prostate cancer treatments with unshielded BT and I-RSBT according to an aspect.

Figure 39A:
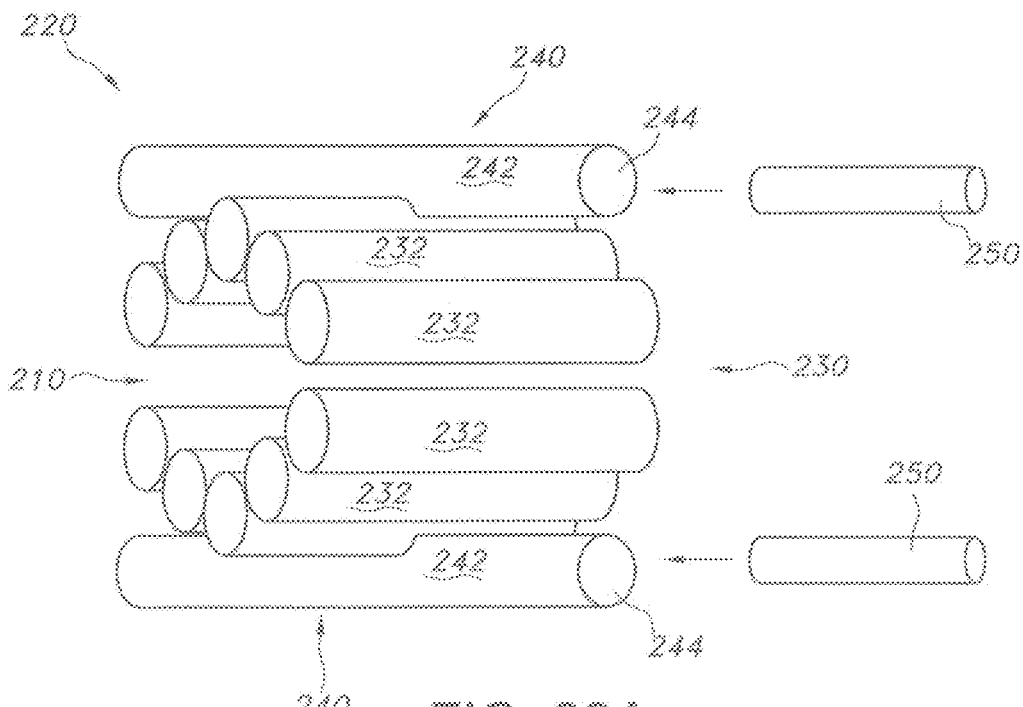
Figure 39B:
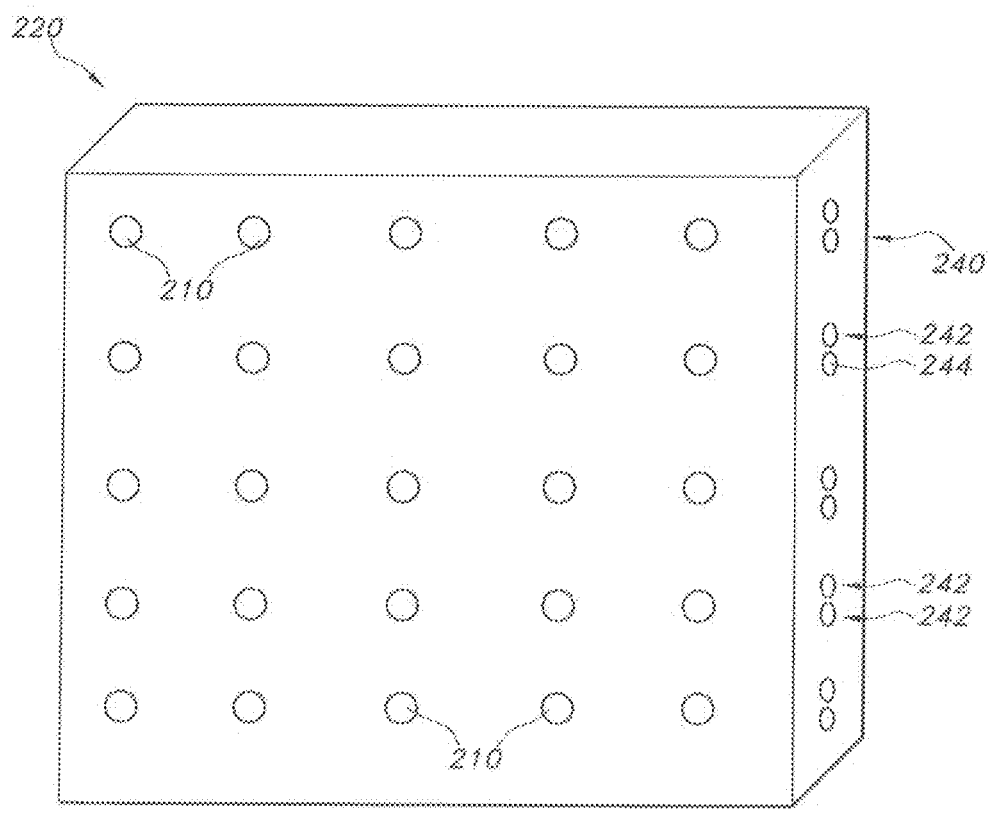
Figure 39C:
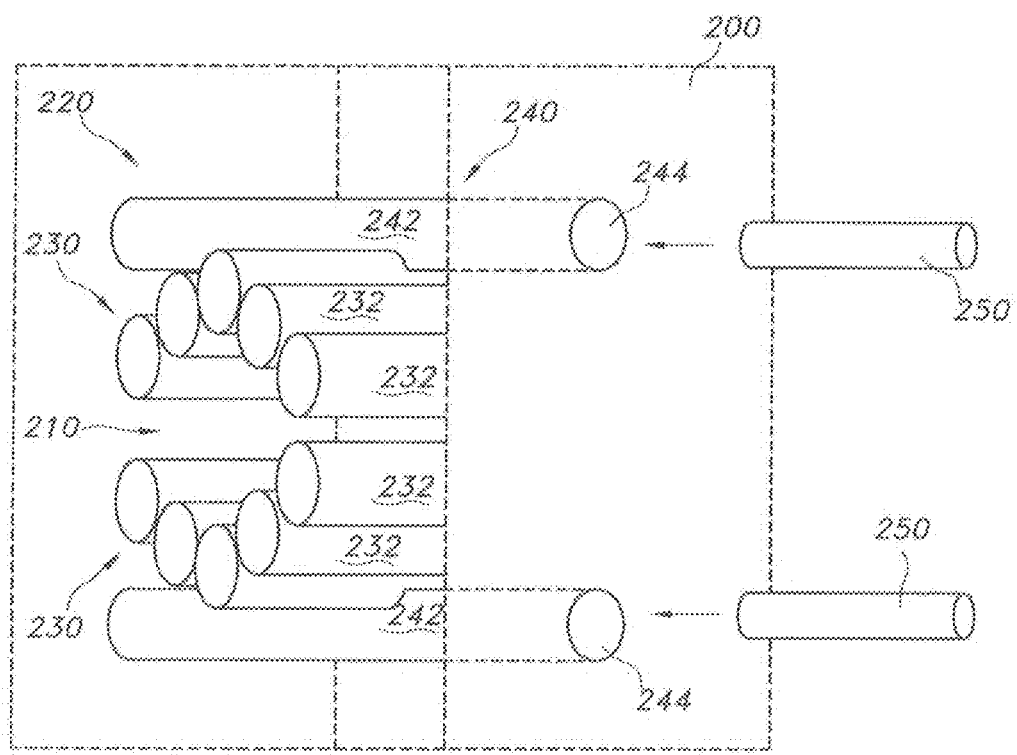

FIGS. 39A-39C illustrate example embodiments of docking devices in accordance with one or more aspects of the disclosure.

FIG. 40: (a) 3-D rendering of cervical cancer treatment geometry for T&O delivery. (b) The conventional BT dose distribution, underdoses the clinical target volume (CTV). (c) The IMBT dose distribution enhances CTV coverage and spares bladder/rectum.

Figure 41A:
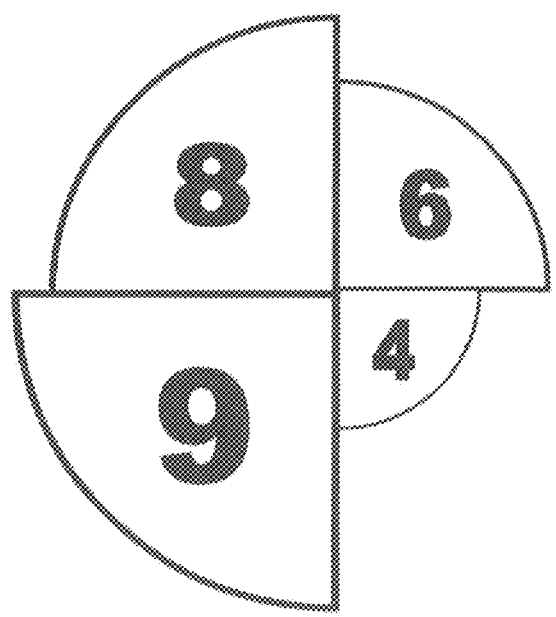
Figure 41B:
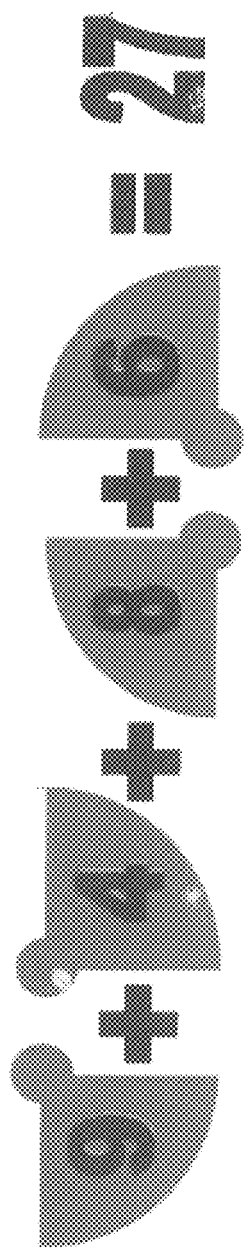
Figure 41C:
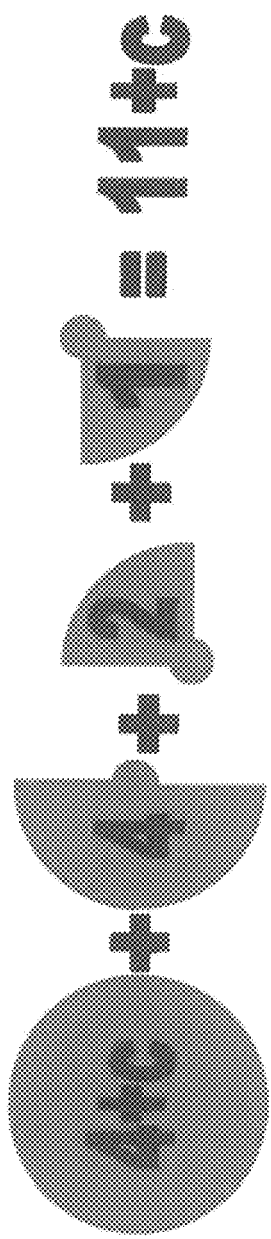

FIGS. 41A-C are schematic representations of dwell times for a 90° emission angle with four locations using S-RBST and M-RSBT according to an aspect.

FIGS. 42A-42D illustrate example cross sections of example intensity modulated brachytherapy (IMBT) insertion devices, which could be an intracavitary applicator of inner radius no and outer radius rot.

Figure 43:
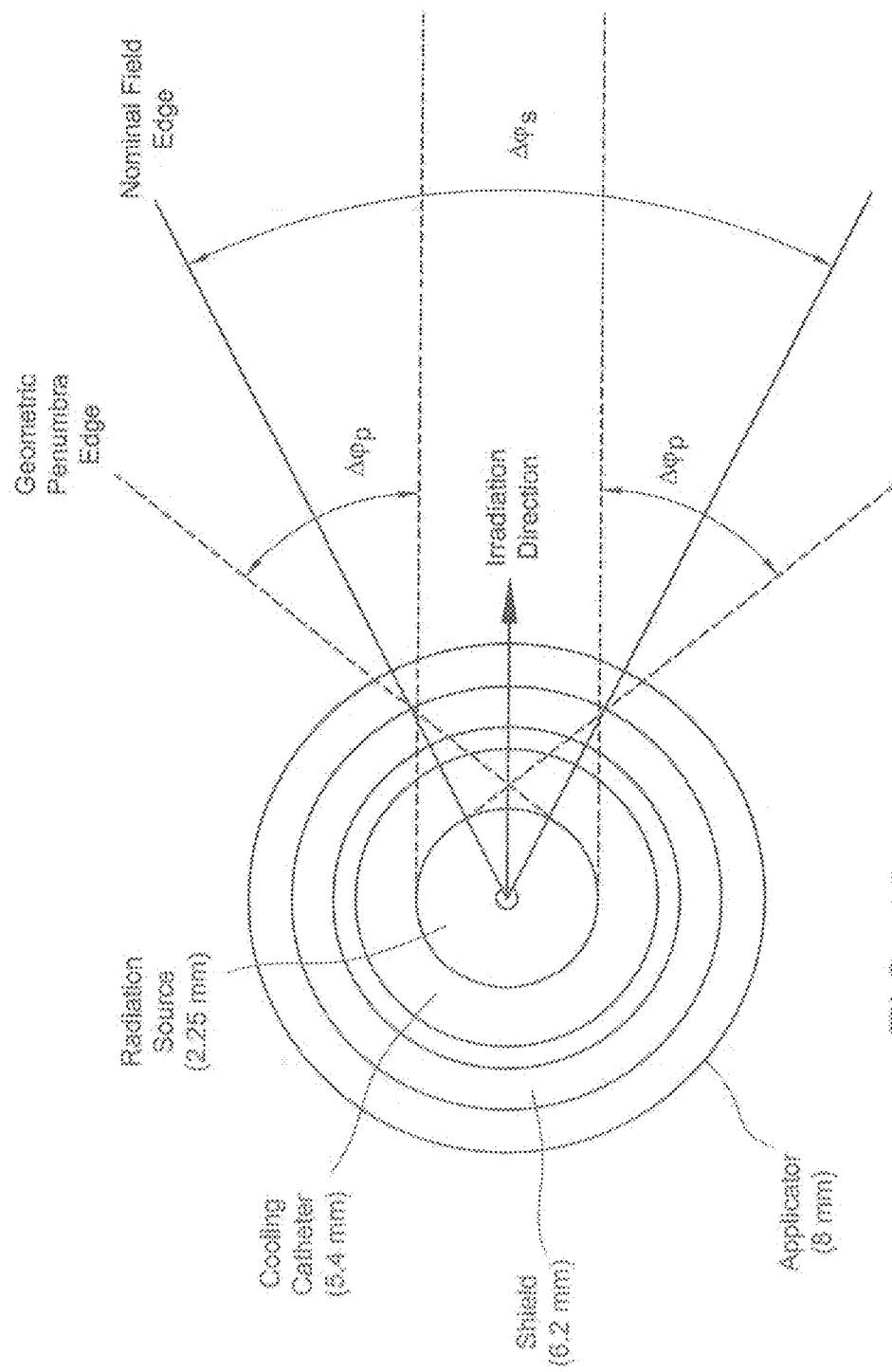

FIG. 43 illustrates an additional or alternative example cross section of the RS-IMBT delivery system.

FIG. 44 illustrates an example process that permits an M-RSBT apparatus to change radiation shields in order to deliver M-RSBT in accordance with one or more aspects of the disclosure.

Figure 45:
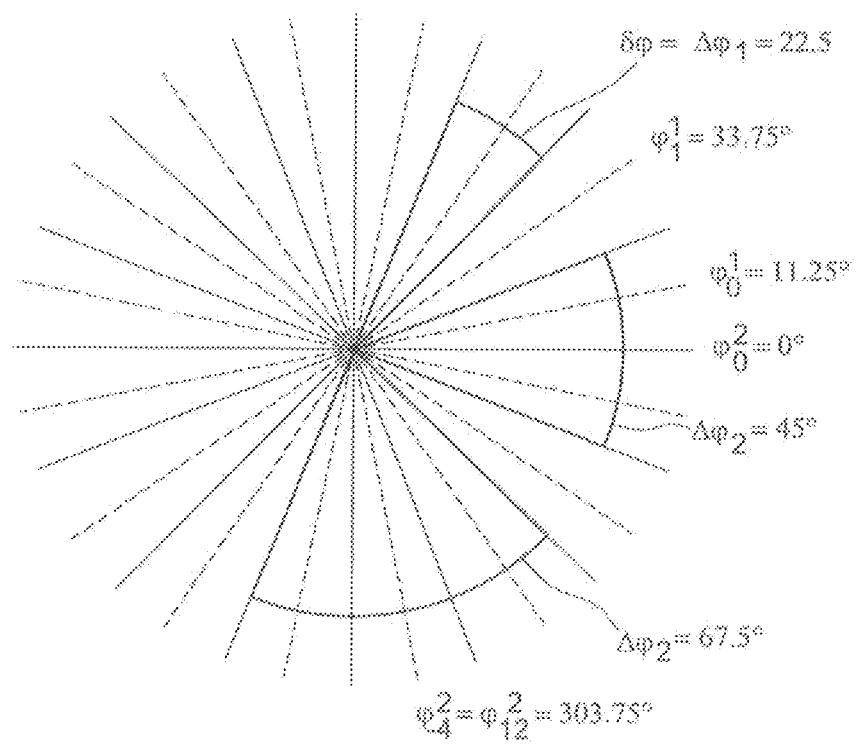

FIG. 45 presents definitions of shield emission angle, direction, and beamlet combination in accordance with one or more aspects of the subject disclosure.

FIGS. 46(a-b) present the dose distribution for a patient that would benefit less from M-RSBT using a minimum emission angle of 180° and the analogous distribution using a minimum emission angle of 22.5°.

Figure 47:
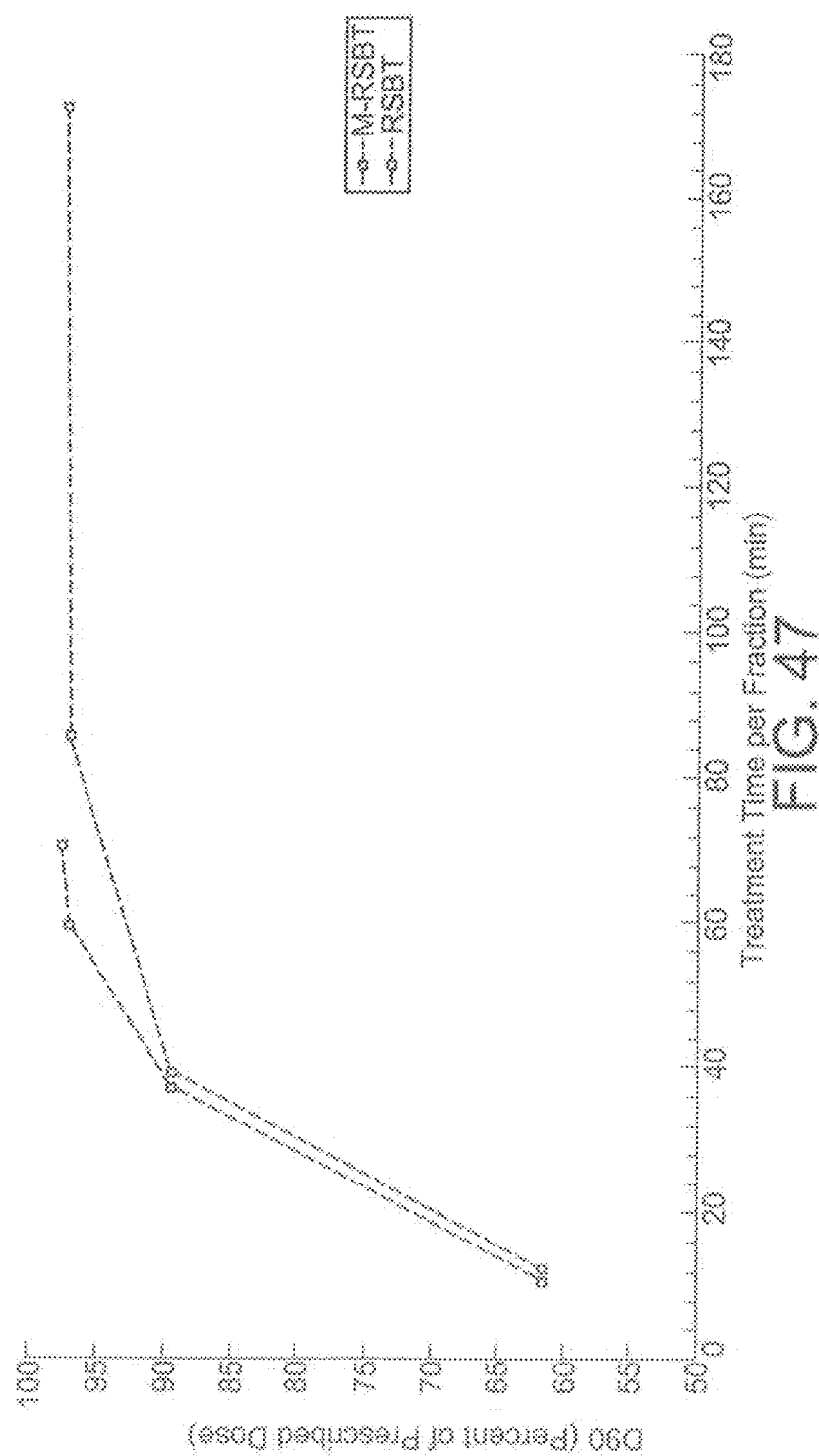

FIG. 47 presents a comparison of M-RSBT treatment times (green) and RSBT treatment times (blue) plotted against the $D_{90}$ for a tumor surface in accordance with one or more aspects of the disclosure.

FIG. 48: (a) The dose distribution for a patient that would benefit significantly from M-RSBT using a minimum emission angle of 180°. (b) The analogous distribution using a minimum emission angle of 22.5°.

Figure 49:
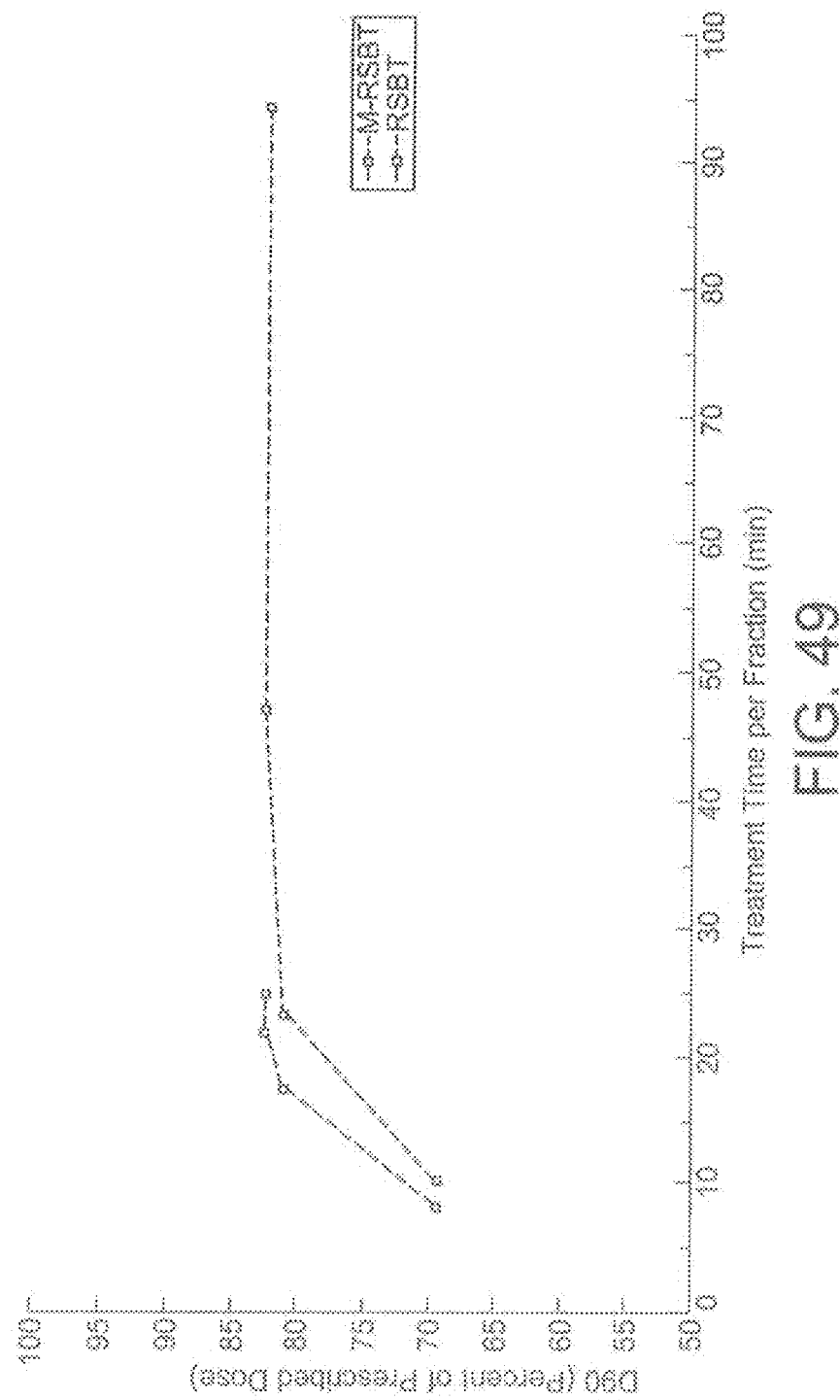

FIG. 49 presents a comparison of M-RSBT treatment times (green) and RSBT treatment times (blue) plotted against the $D_{90}$ for a tumor surface in accordance with one or more aspects of the disclosure.

Figure 50:
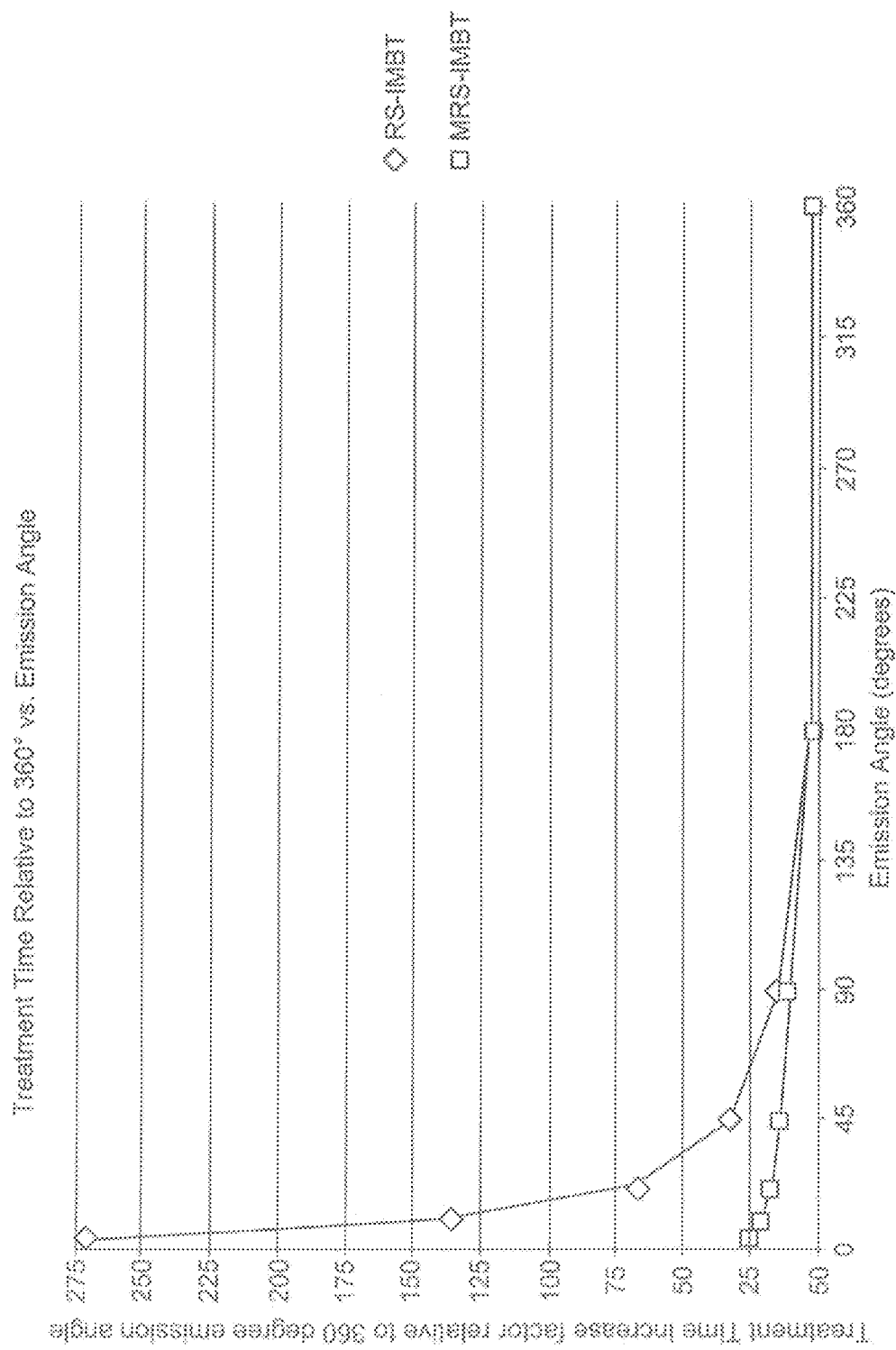

FIG. 50 illustrates an example comparison of treatment times for RSBT and M-RSBT (also referred to as MRS-IMBT) in accordance with one or more aspects of the disclosure.

Figure 51:
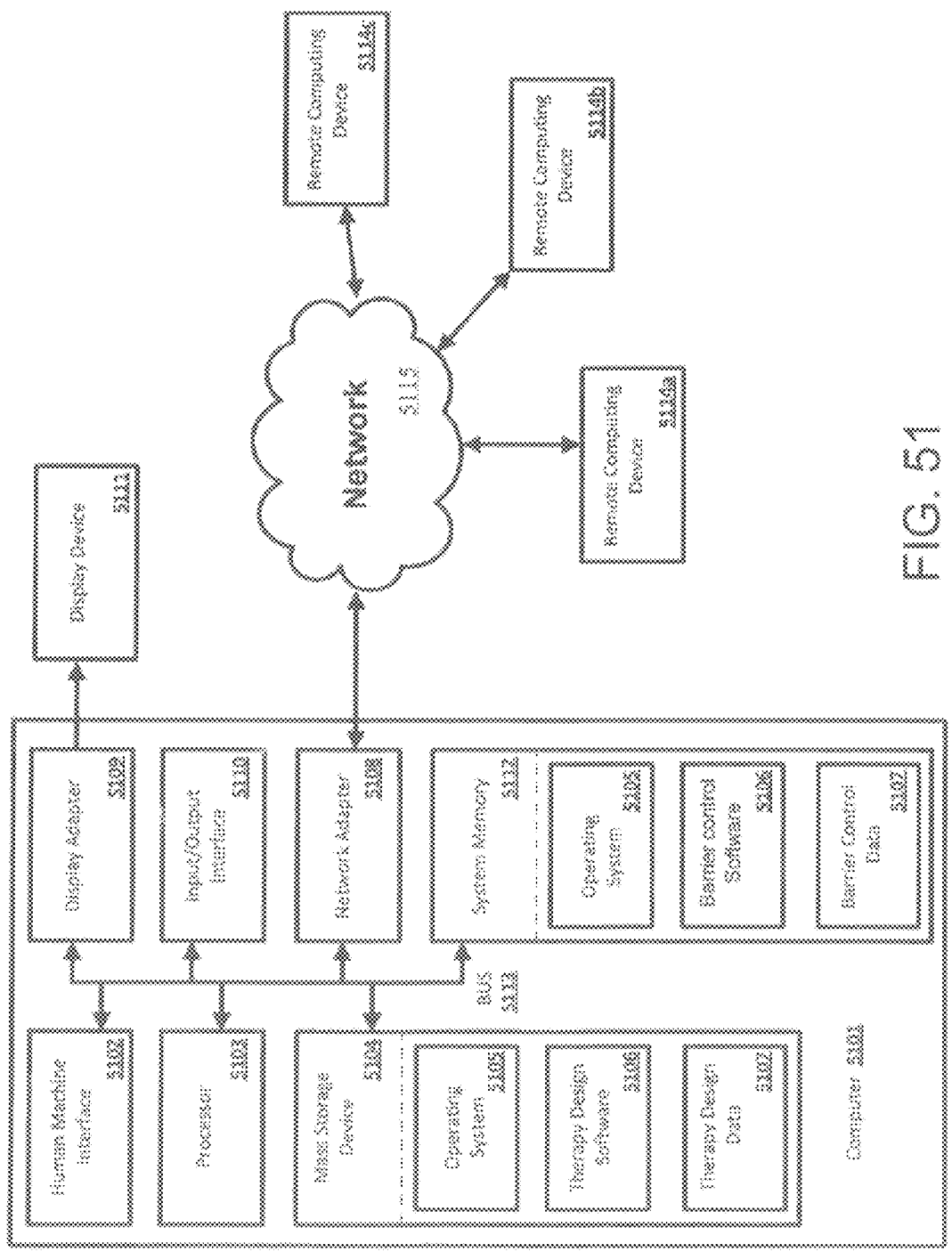

FIG. 51 illustrates an example computing environment that permits implementation of therapy design in accordance with one or more aspects of the disclosure.

FIGS. 52(a)-(b) illustrate an exemplary capsule, radiation source and wire.

FIG. 53 is a flowchart illustrating an exemplary method of forming a therapeutic radiation capsule.

FIG. 54 is a flowchart illustrating an exemplary method of providing therapeutic radiation.

FIG. 55 is a flowchart illustrating an exemplary method for rotating shield brachytherapy (RSBT).

Figures 56, 57:
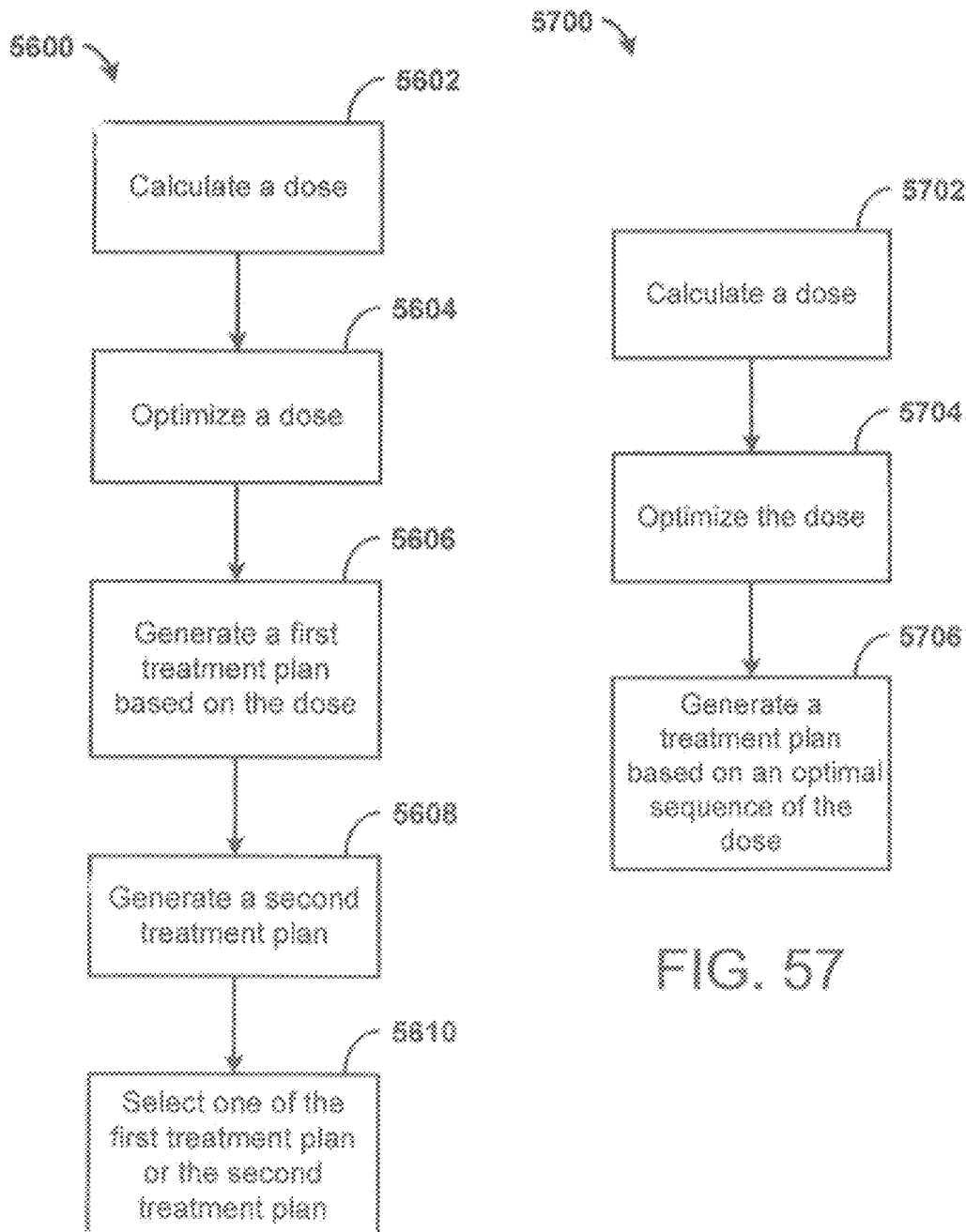

FIG. 56 is a flowchart illustrating an exemplary method for selecting an emission angle for use in single rotating-shield brachytherapy.

FIG. 57 is a flowchart illustrating an exemplary method for sequencing rotating shields.

Figure 58:
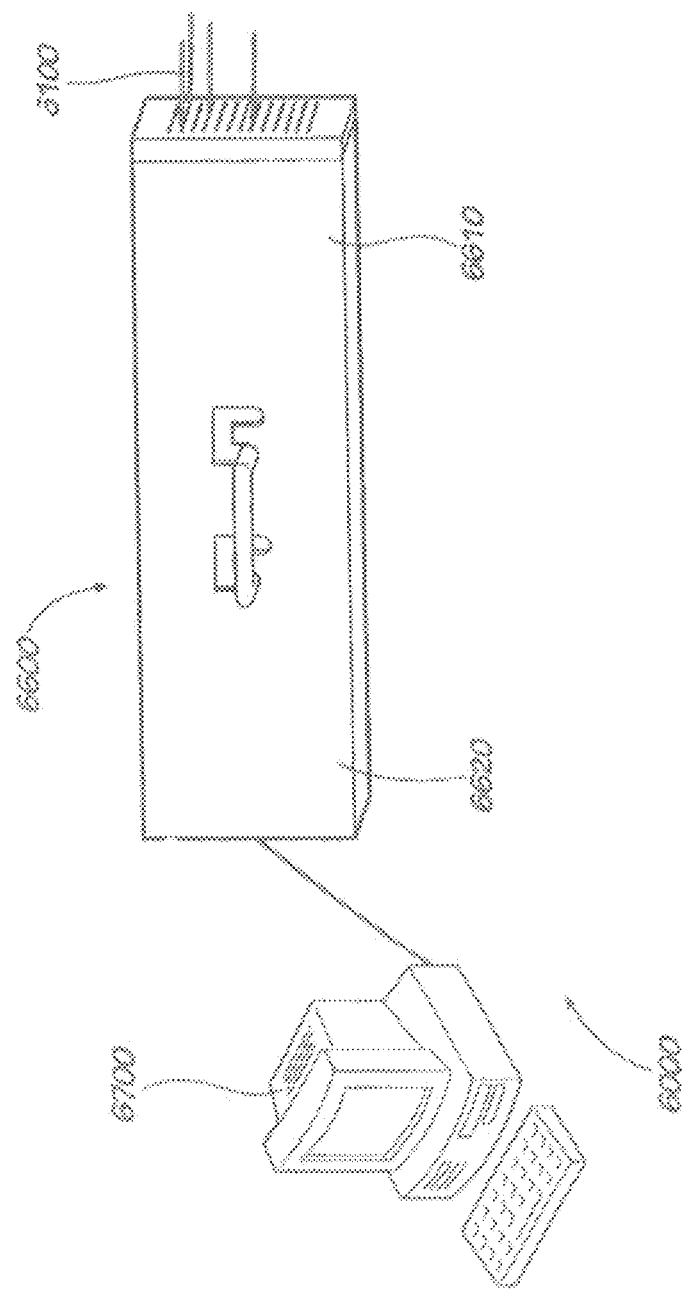

FIG. 58 is a schematic illustration of a RSBT application system according to an aspect.

FIGS. 59-60 are perspective see-through views of a catheter control cartridge of the RSBT application system according to an aspect.

FIG. 61 is a cross sectional view of at the distal end of a RSBT catheter of the RSBT application system according to an aspect.

Figure 62:
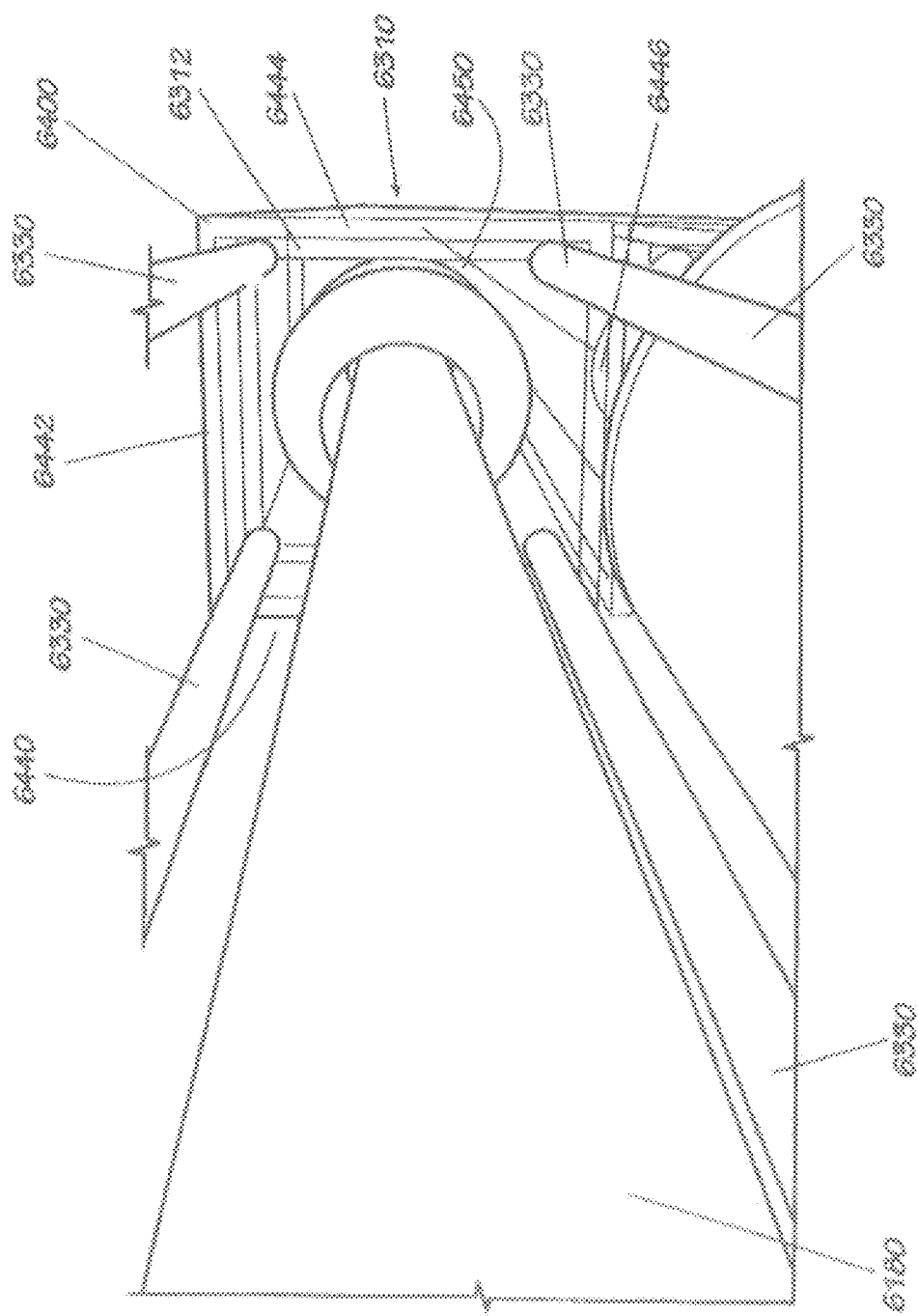

FIG. 62 is a partial bottom perspective view of a portion of the catheter control cartridge of FIGS. 59-60.

Figure 63:
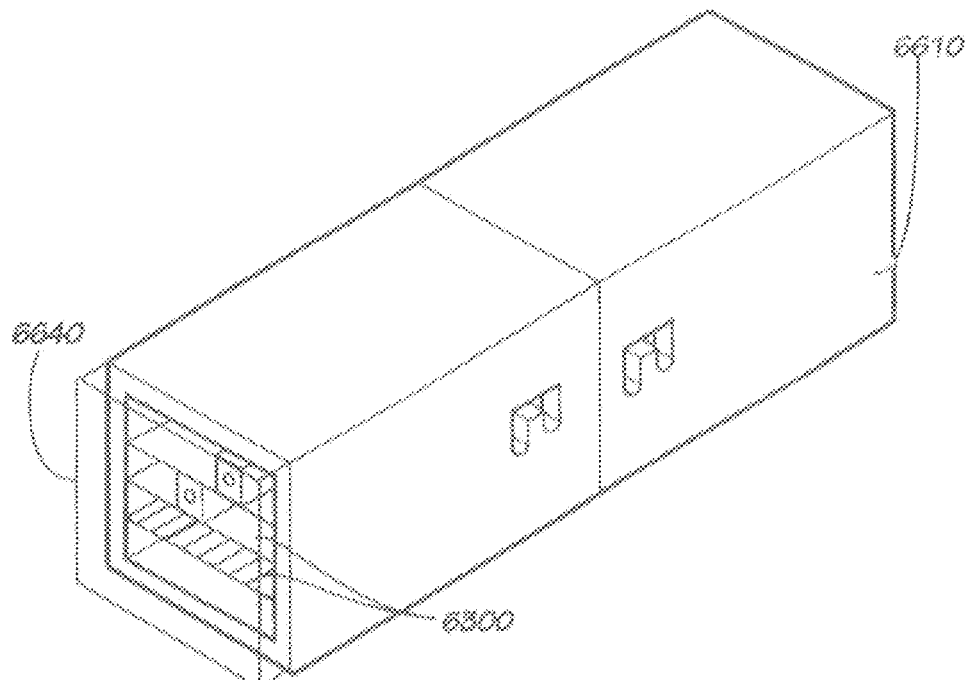

FIG. 63 is a top perspective view of a cartridge magazine of the RSBT application system according to an aspect.

Figure 64:
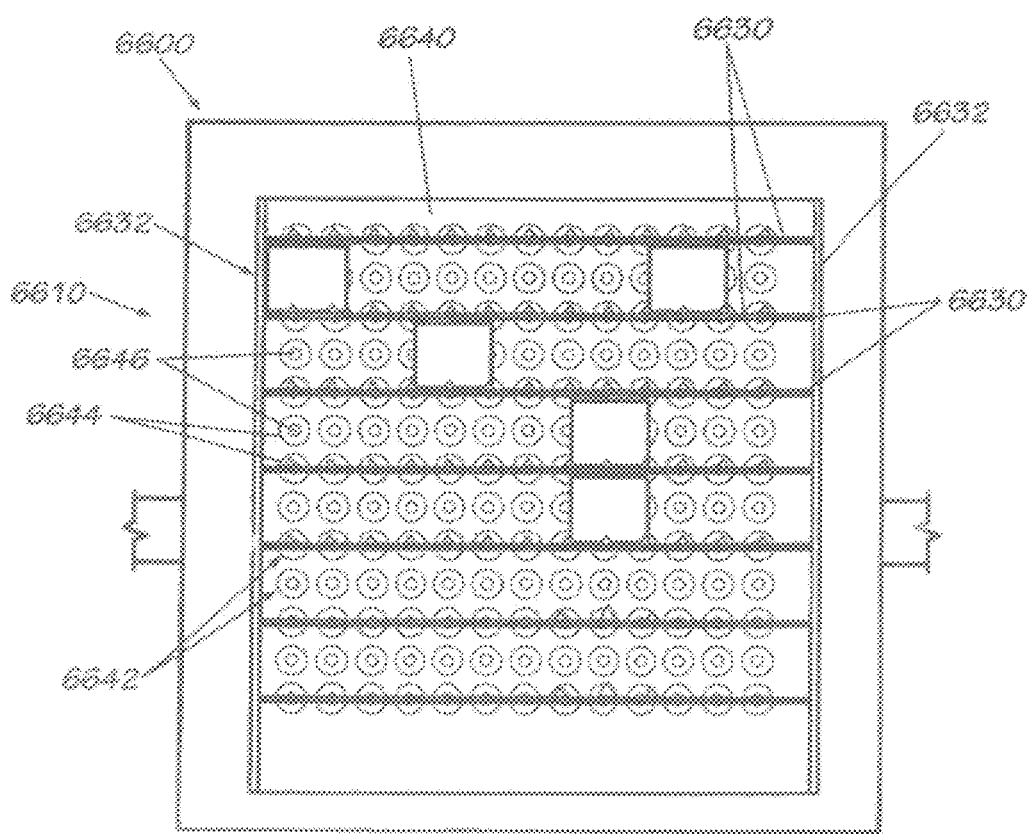

FIG. 64 is a back plane view of the proximal end of cartridge magazine of FIG. 63, seeing through the interior of the distal end.

Figure 65:
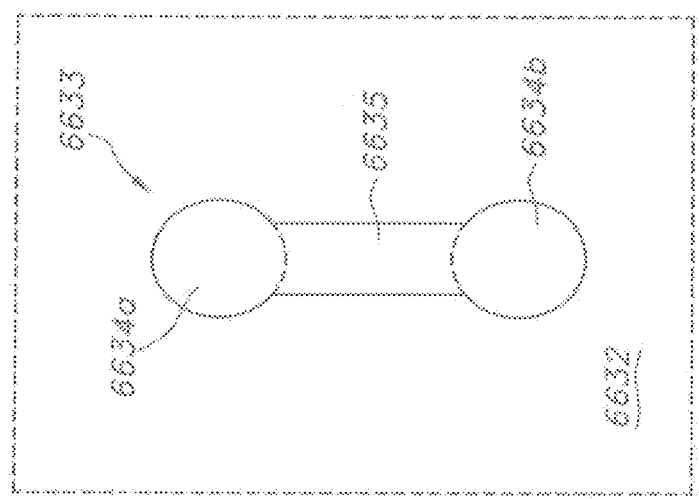
Figure 66C:
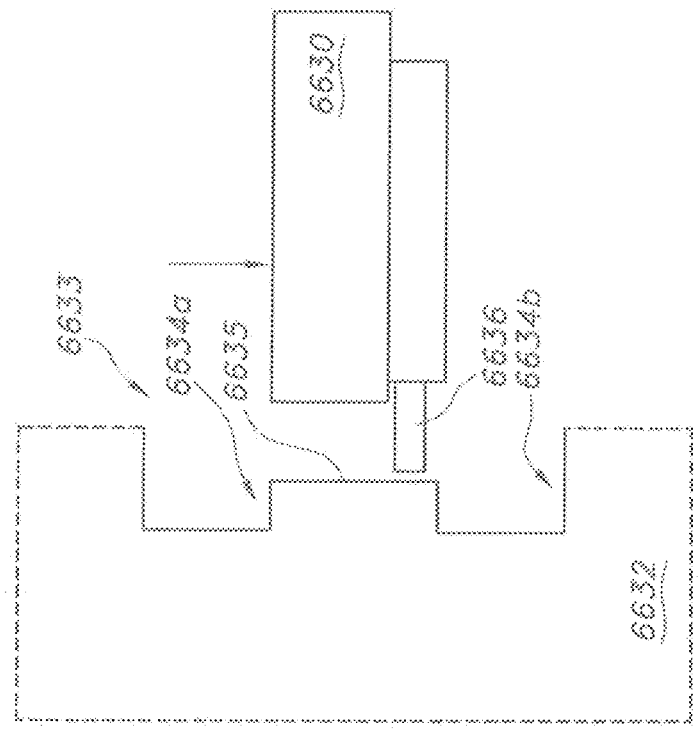
Figure 66B:
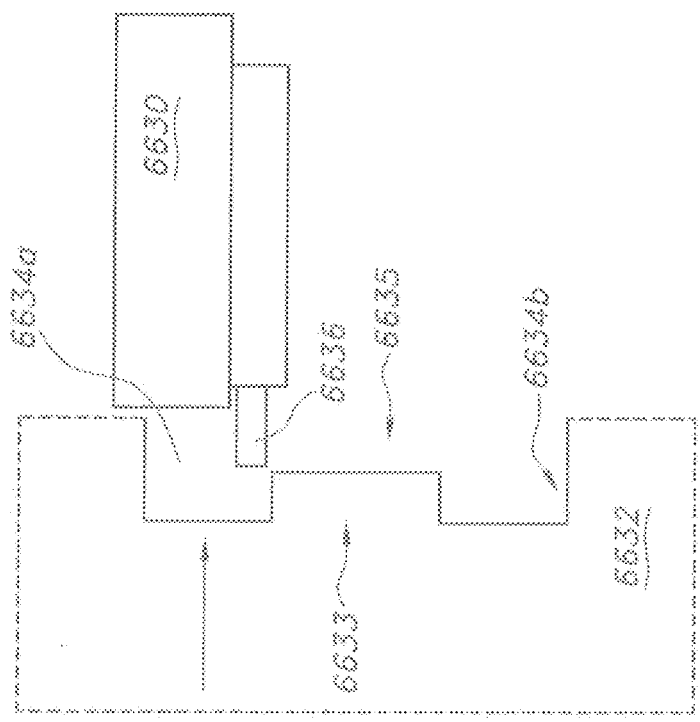

FIG. 65 is a front plane view of a mount of the RSBT application system according to an aspect.

FIG. 66a-66d are schematic representations of a mount of the RSBT application system according to an aspect.

FIG. 67 is a front plan view of a shelf and a cartridge of a RSBT application system according to an aspect.

Figure 68:
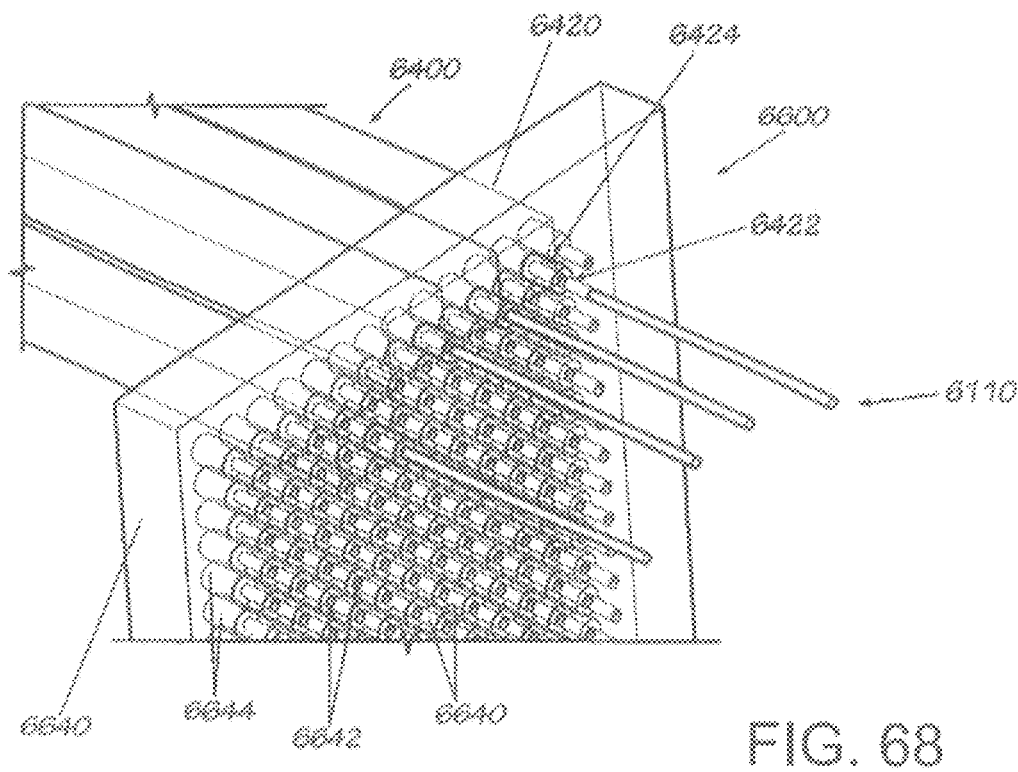

FIG. 68 is a partial top perspective see-through view of components of a RSBT application system according to an aspect.

Figure 69:
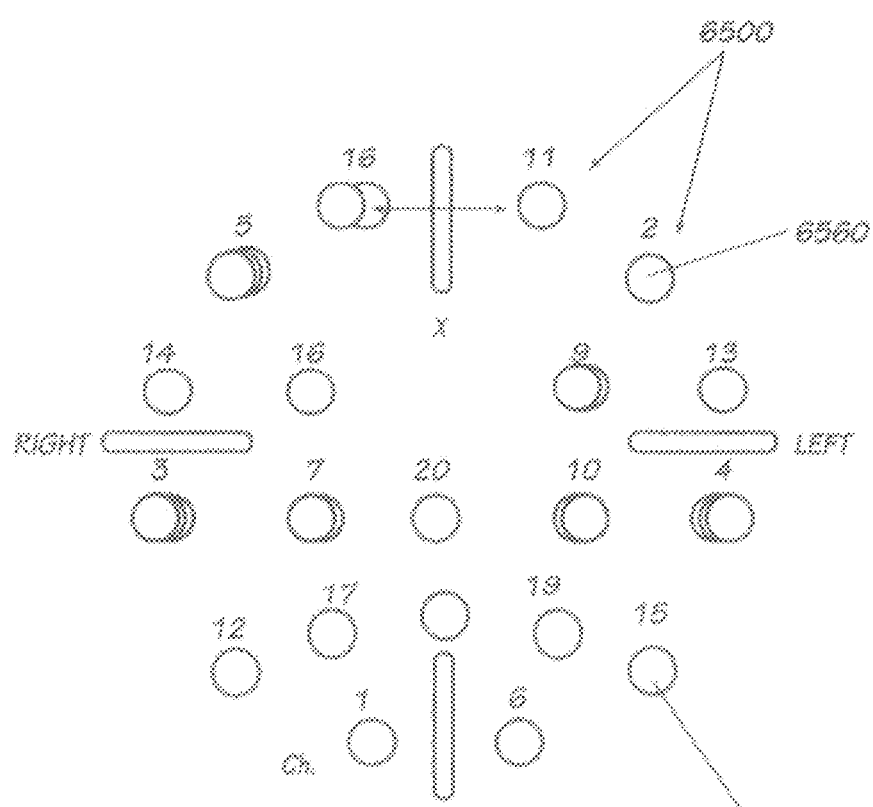

FIG. 69 is a schematic illustration of the orientation for needles within a subject according to an aspect.

Figure 70:
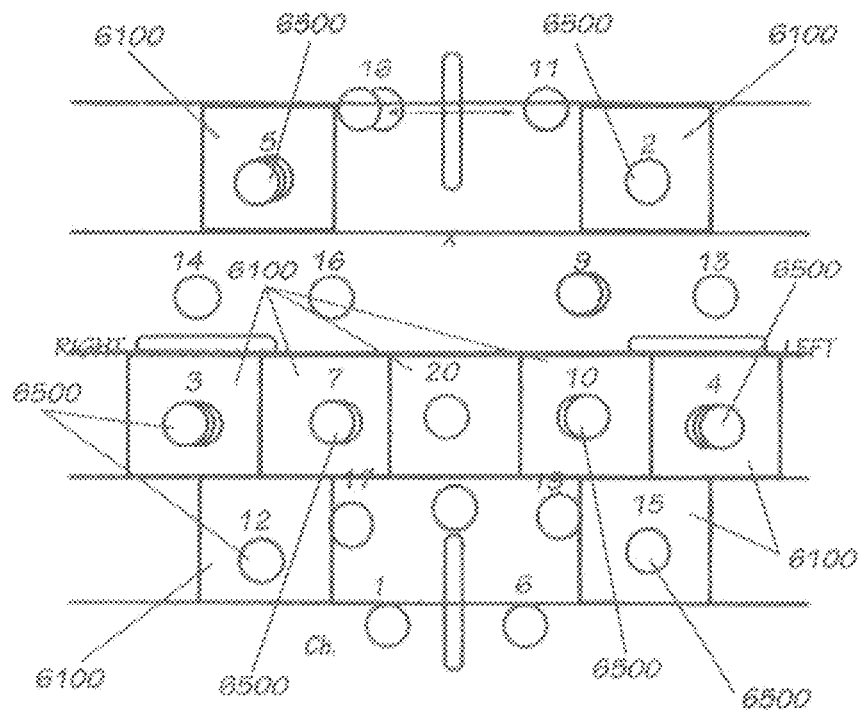
Figure 71:
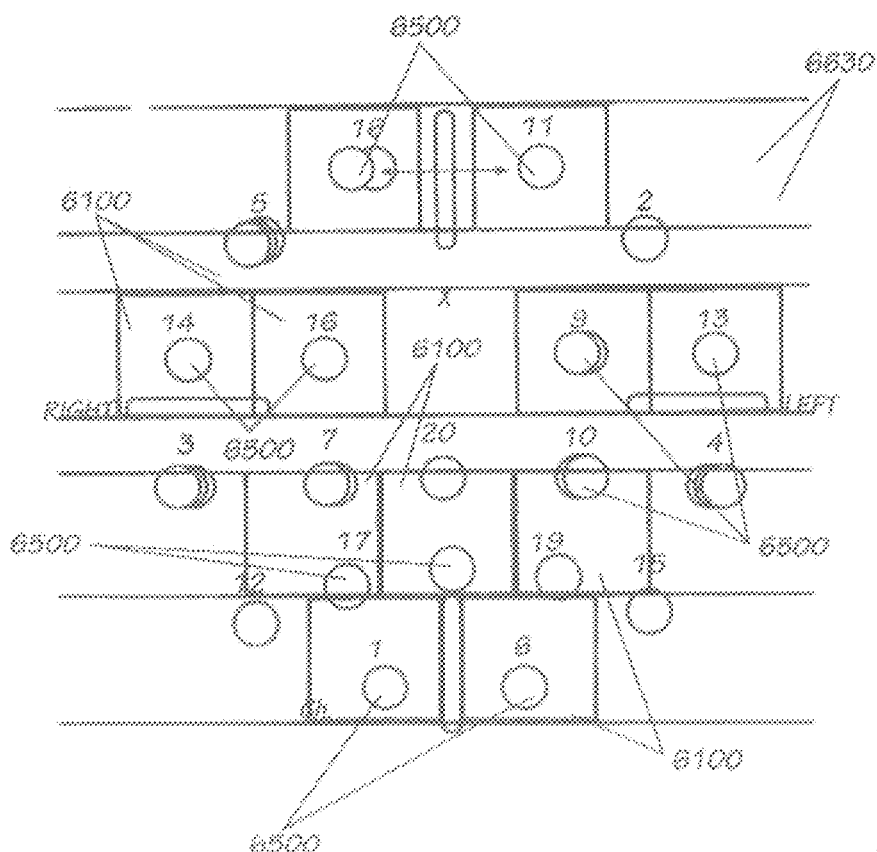

FIGS. 70-71 are schematic illustrations of the use of the RSBT application system according to an aspect.

Figure 72A:
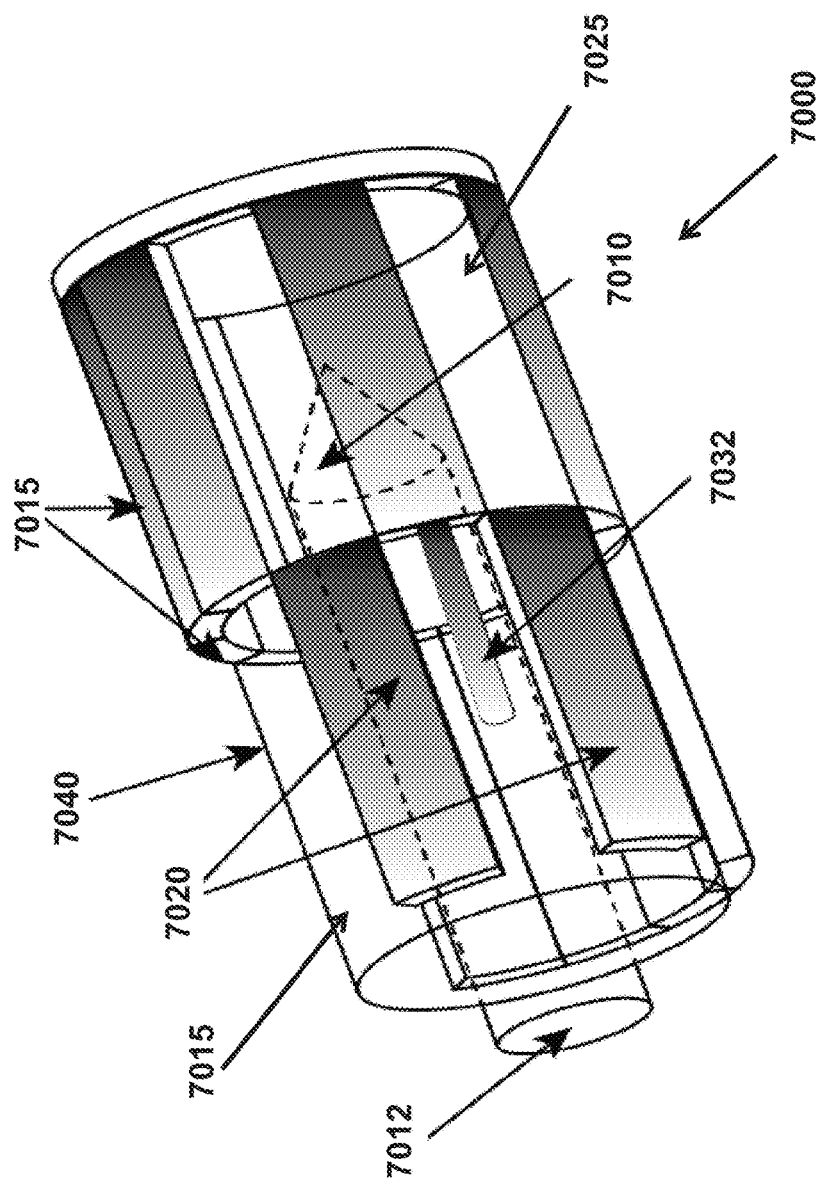

FIG. 72a is an illustration of a P-RSBT applicator according to embodiments of the present invention.

Figure 72B:
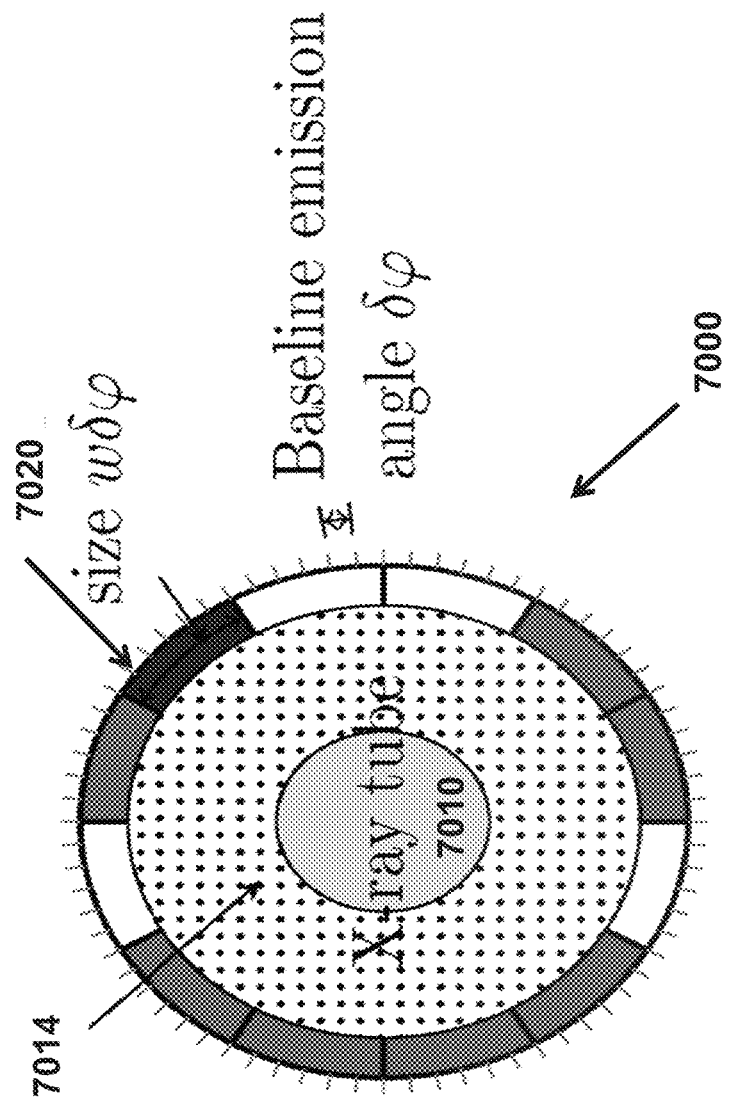

FIG. 72b depicts a cross-section view of a P-RSBT applicator according to embodiments of the present invention.

Figure 73A:
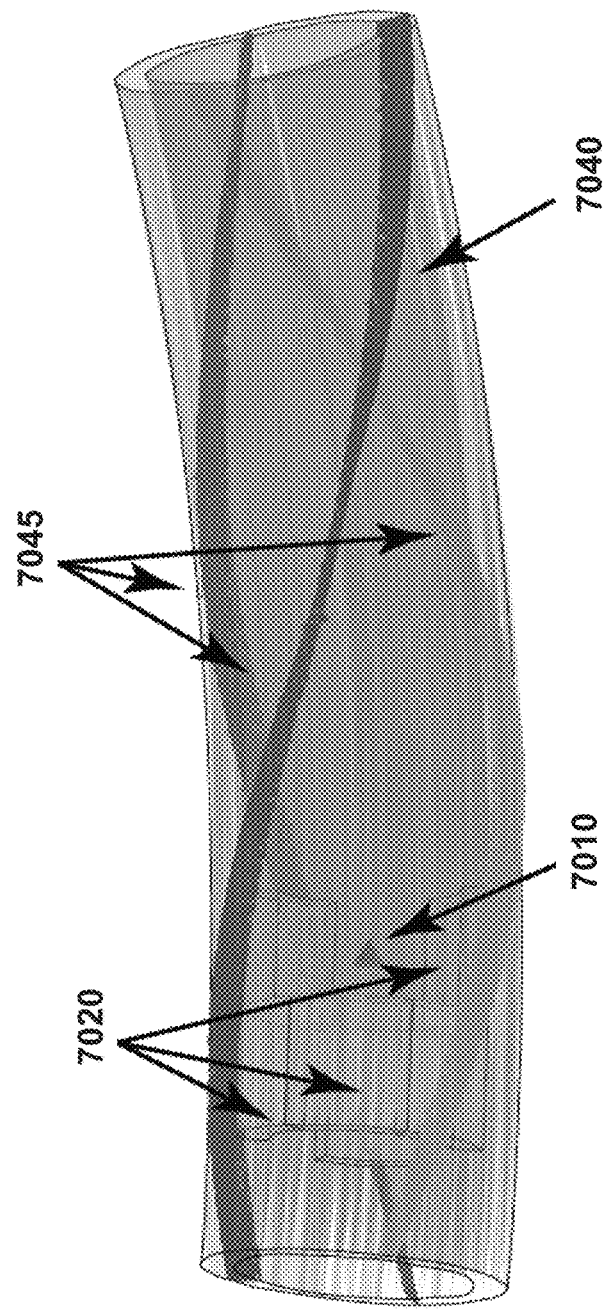

FIG. 73a depicts a P-RSBT applicator with a catheter according to embodiments of the present invention.

Figure 73B:
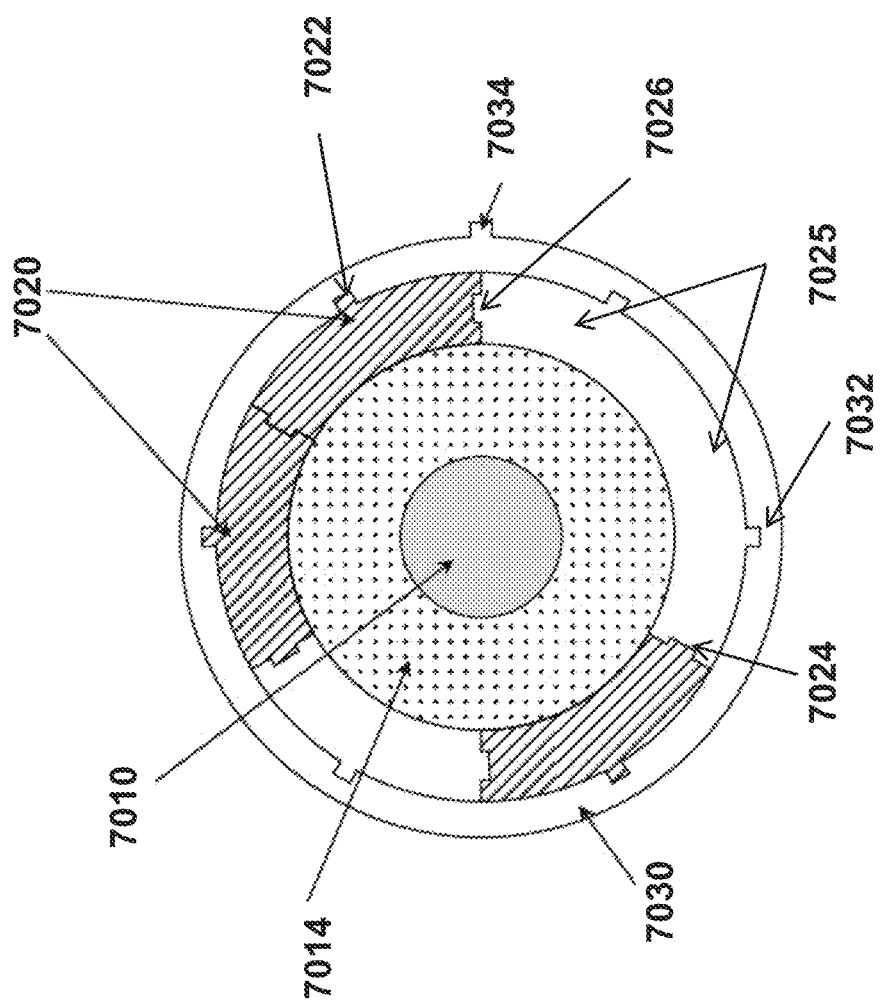

FIG. 73b depicts a cross-section view of a P-RSBT applicator according to embodiments of the present invention.

Figure 74:
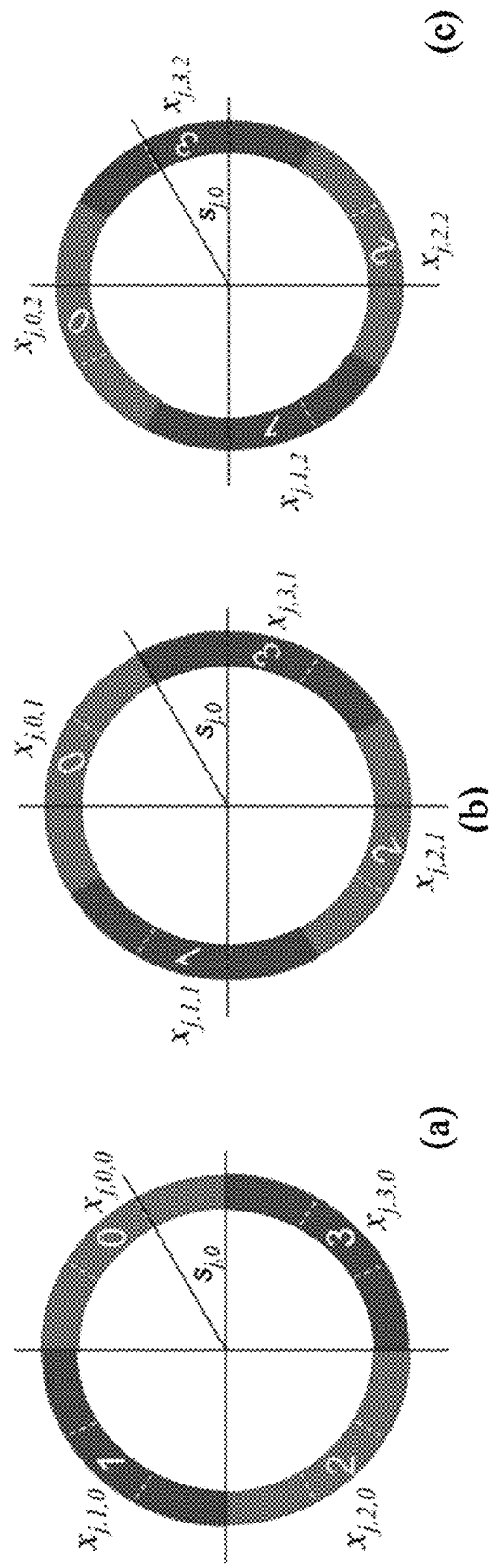

FIG. 74 depicts exemplary source emission beam coverage according to embodiments of the present invention.

Figure 75:
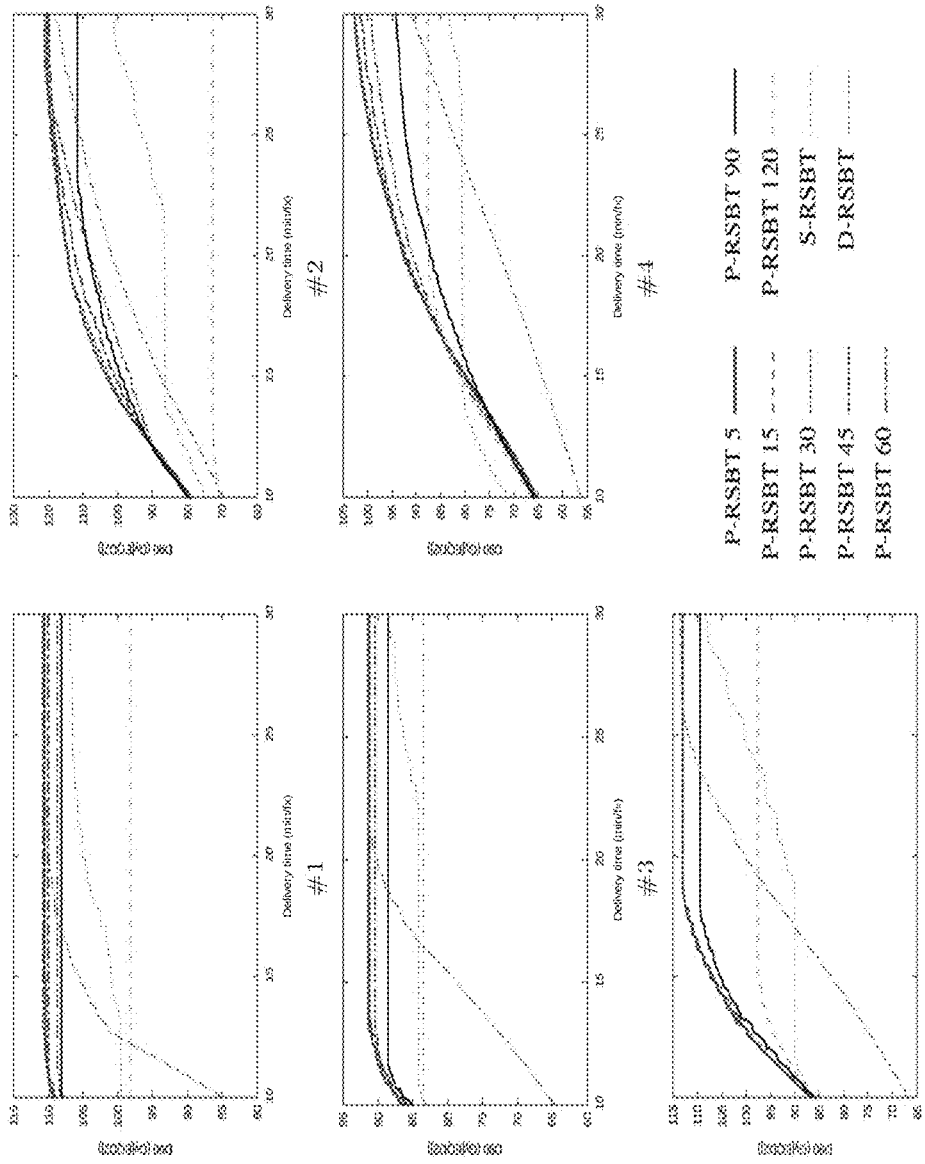

FIG. 75 illustrates plots of various source emission delivery efficiency curves according to embodiments of the present invention.

Figure 76:
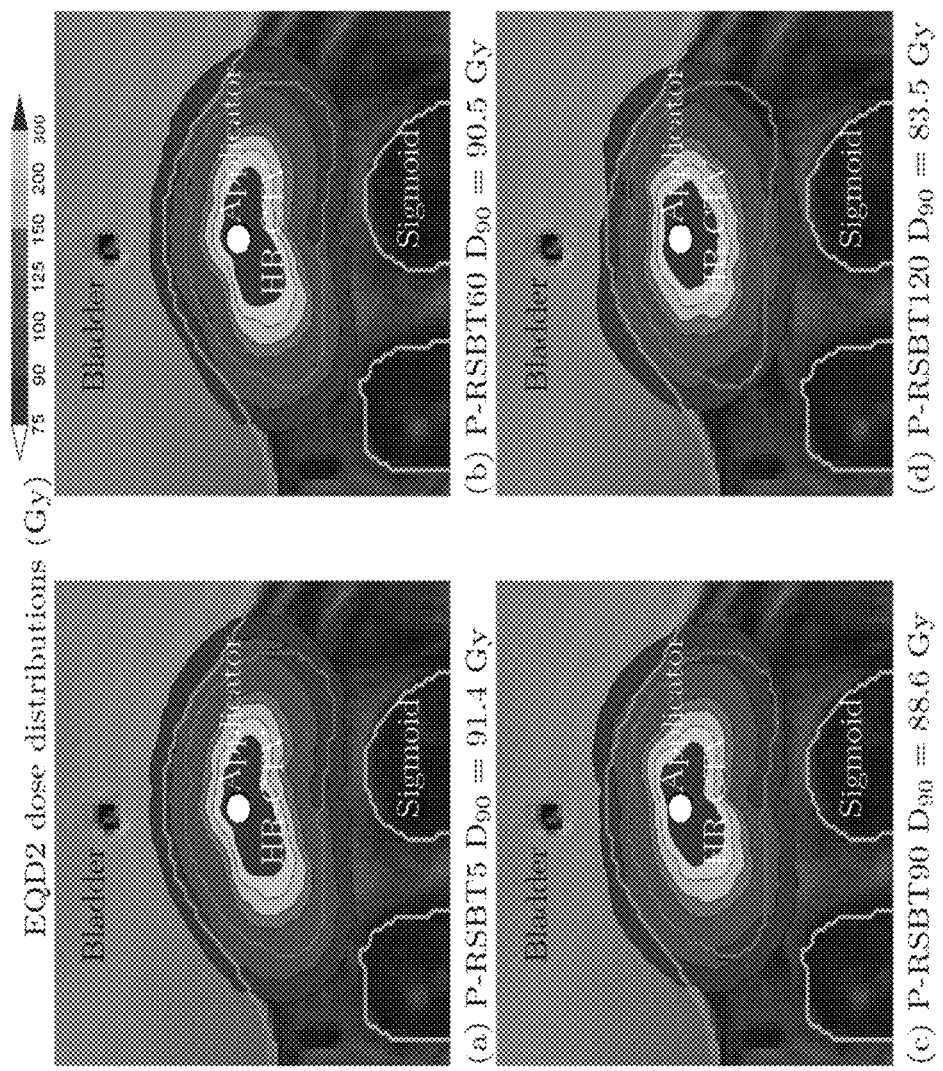

FIG. 76 depicts example EQD2 dose distributions (dose-volume histograms) for paddles of varying sizes according to embodiments of the present invention.

Figure 77:
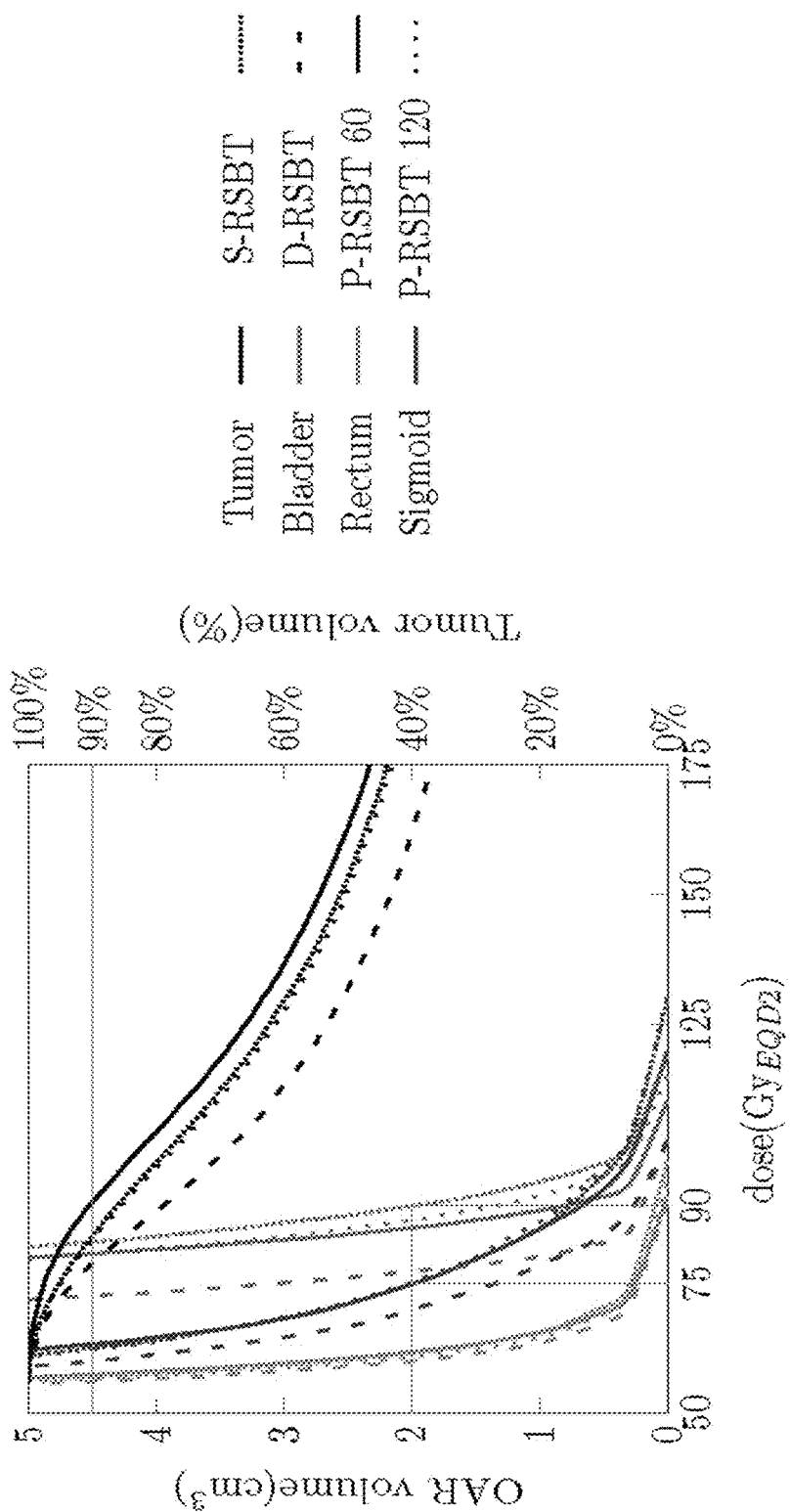

FIG. 77 provides DVH plots for an exemplary case (case #3; Table 1) with a delivery time 15 min/fx using P-RSBT with different paddle sizes of 5°, 60°, 90° and 120°, and the rotation stride r□δφ=5°.

Figure 78:
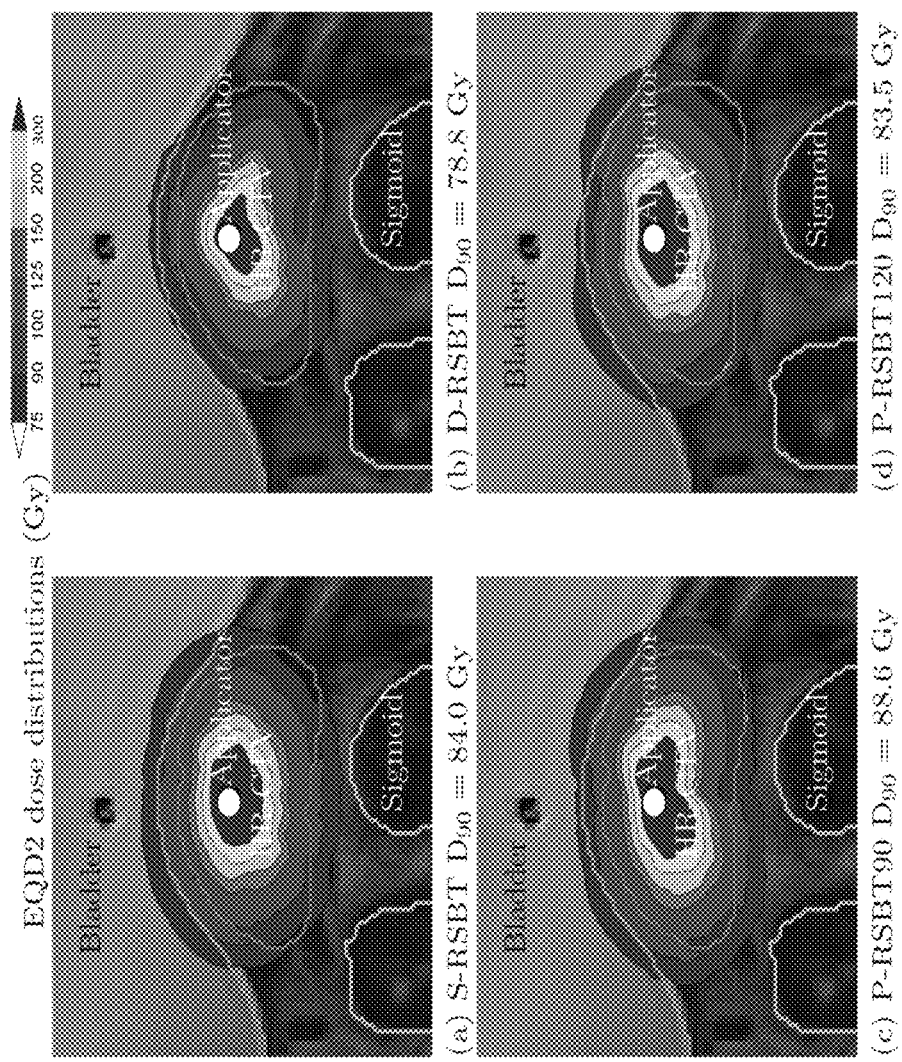

FIG. 78 is a chart comparing dose distributions and DVH's between P-RSBT, S-RSBT and D-RSBT according to embodiments of the present invention.

Figure 79:
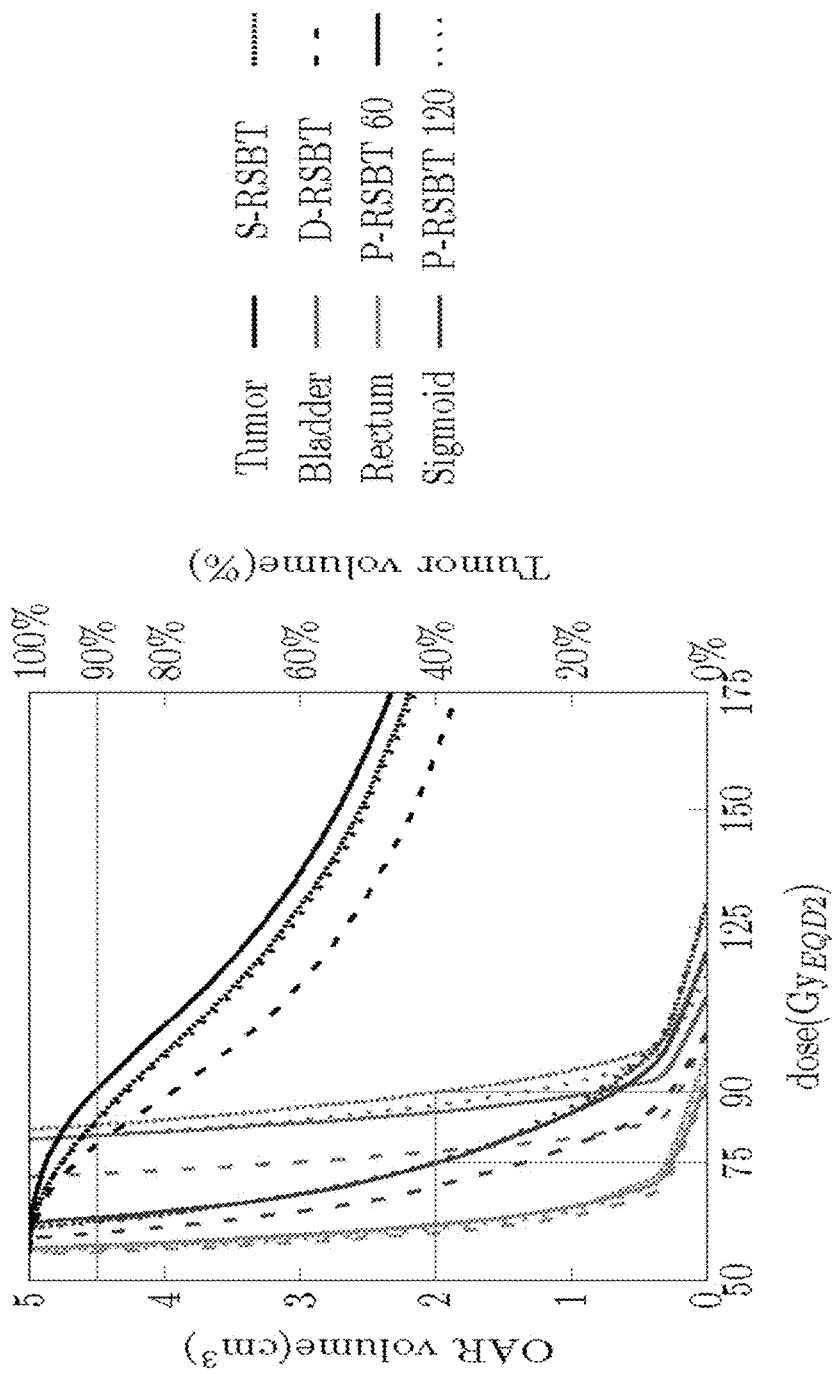

FIG. 79 provides DVH plots for an exemplary case (Case #3) with a delivery time 15 min/fx by S-RSBT, D-RSBT, P-RSBT60 and P-RSBT120, where the rotation stride r·δφ for P-RSBT is 5°.

Figure 80:
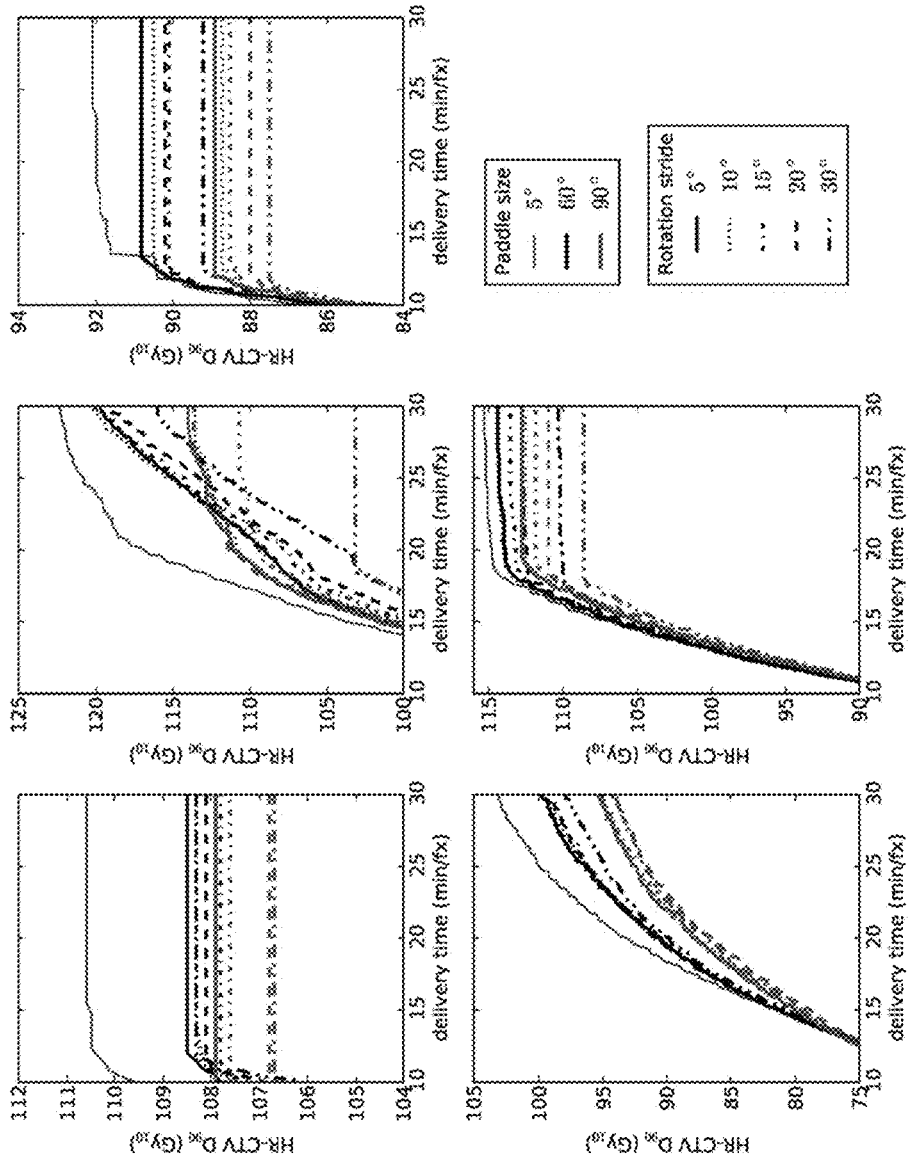

FIG. 80 provides comparisons of delivery efficiency curves for 5 clinical cases by P-RSBT with different combinations of the paddle size and the rotation stride.

Figure 81:
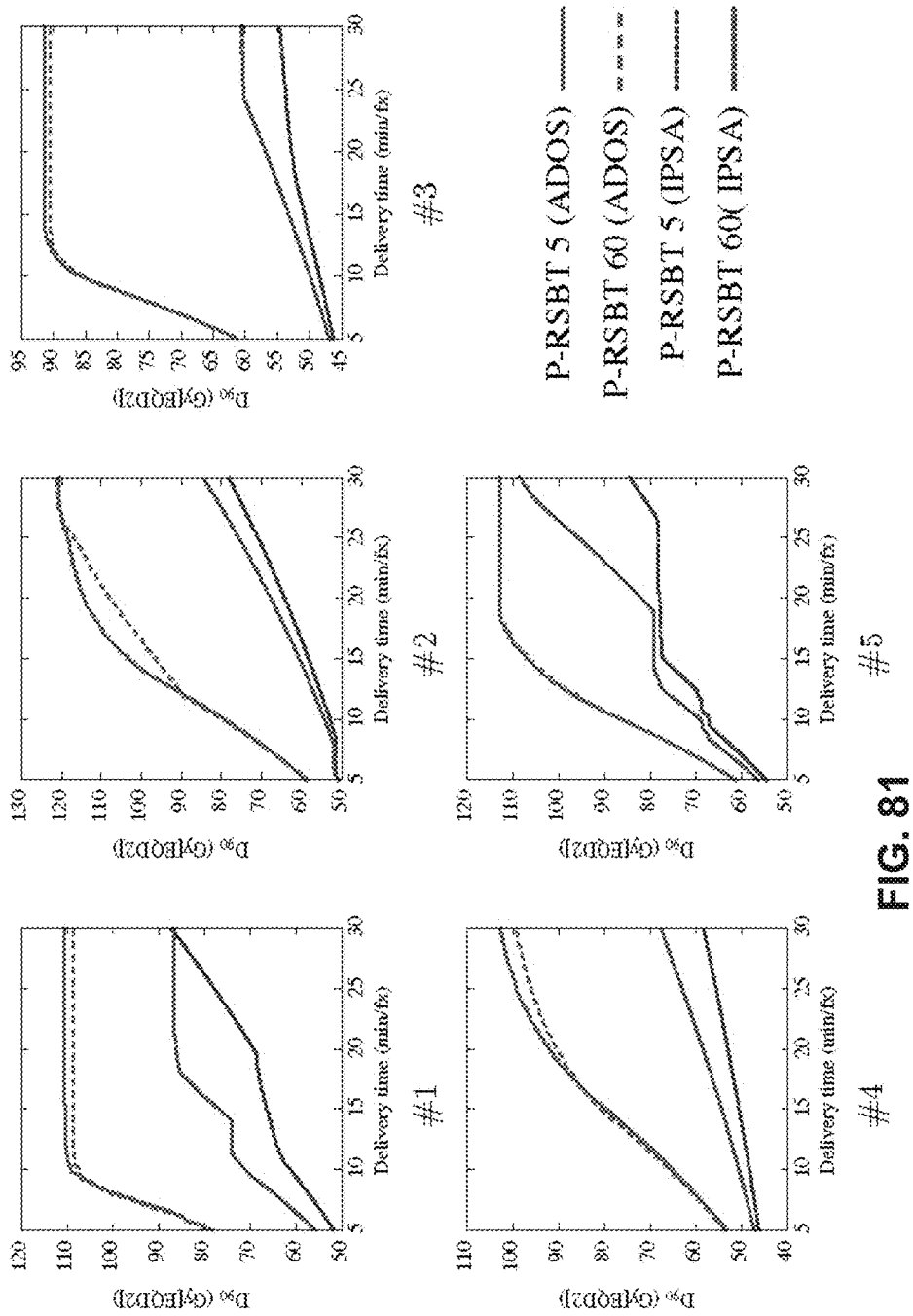

FIG. 81 depicts various delivery efficiency curves for P-RSBT with different paddle sizes and different dose optimizer for 5 cases.

Figure 82:
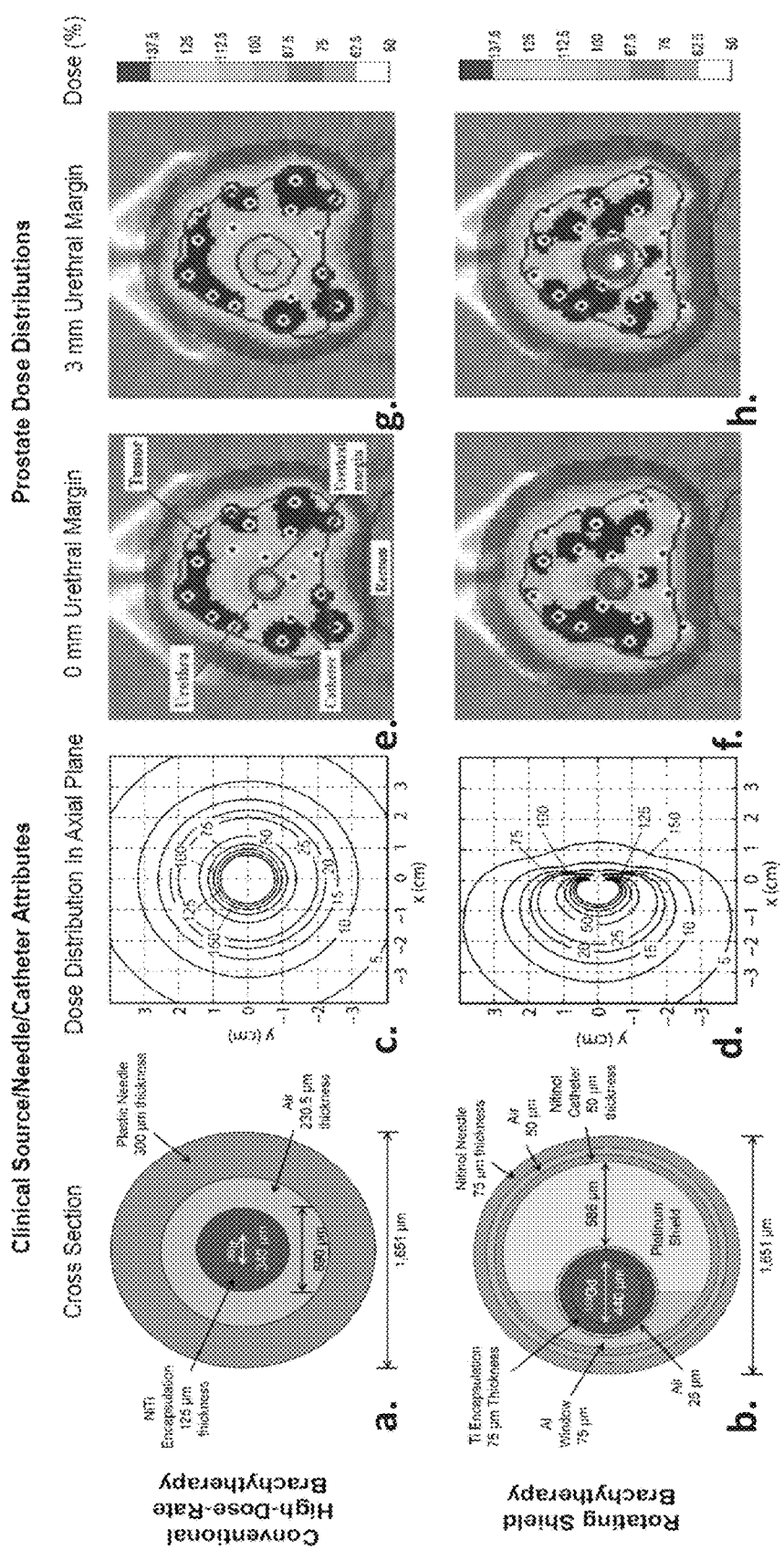

FIGS. 82a-b illustrate differences between conventional HDR-BT (top row) and $^{153}$Gd-based RSBT (bottom row). (a) Where a radially-symmetric applicator/source system is used for HDR-BT, (b) an applicator/source/catheter system with a spatially-offset $^{153}$Gd source and a platinum shield would be used for RSBT. The dose rate distributions from the sources, normalized to 100% at 1 cm off-axis, are radially-symmetric for (c) HDR-BT and (d) directionally-biased for RSBT. The resulting dose distributions have reduced doses to the urethra, rectum, and bladder, when the minimum dose delivered to the hottest 98% ($D_{98\%}$) of the prostate is held constant. For (e-f) 0 mm and (g-h) 3 mm urethral margins, RSBT reduced the minimum dose to the hottest 0.1 cm$^3$ of the urethra ($D_{0.1\ cc}$) by 29% and 38%, respectively. RSBT rectum and bladder $D_{1\ cc}$-values (complication predictors) were less than those for HDR-BT by 5-7%.

FIGS. 83a-b are schematic representations of a catheter according to aspects of the present invention.

Figure 83:
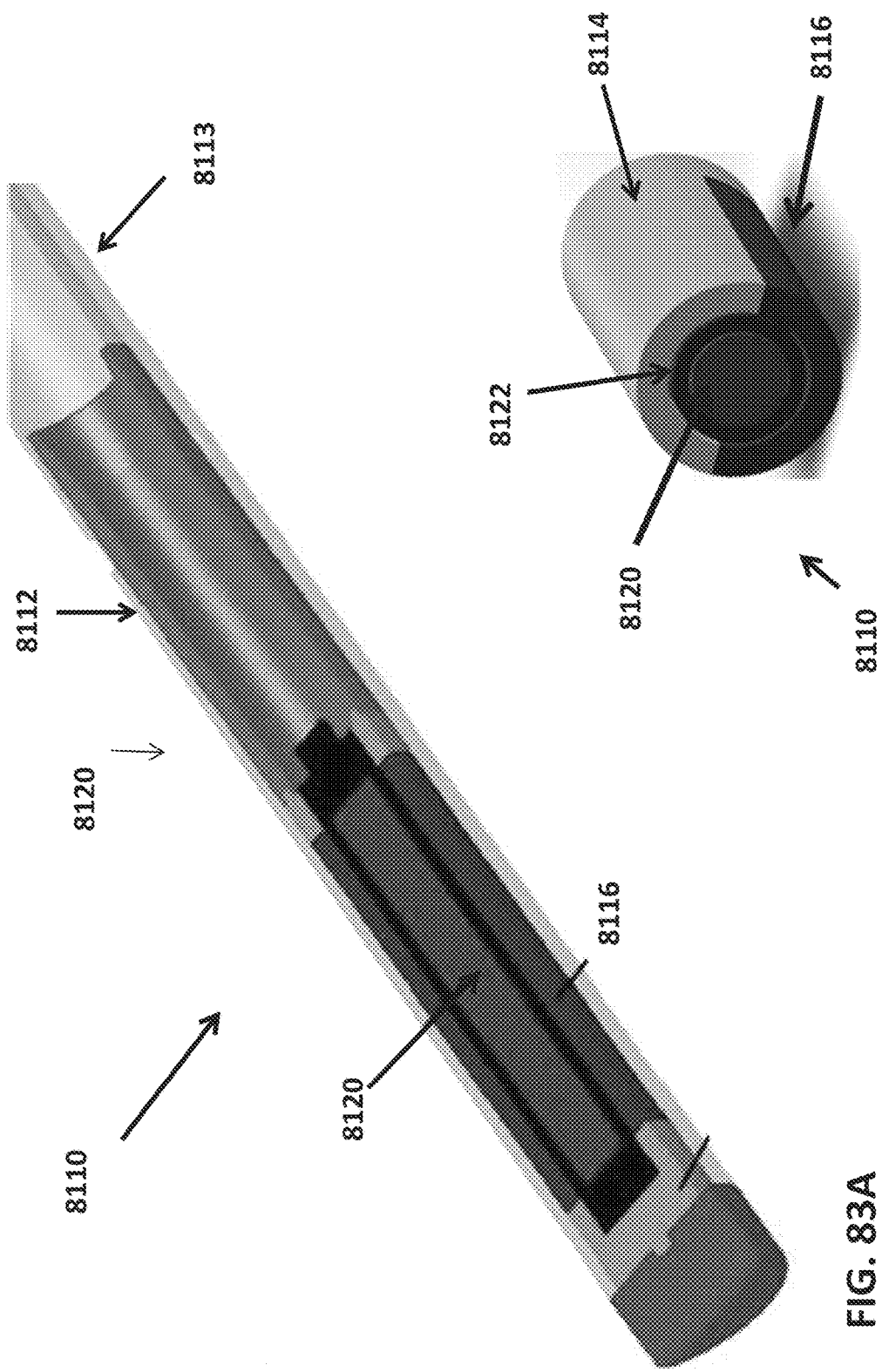
Figure 84:
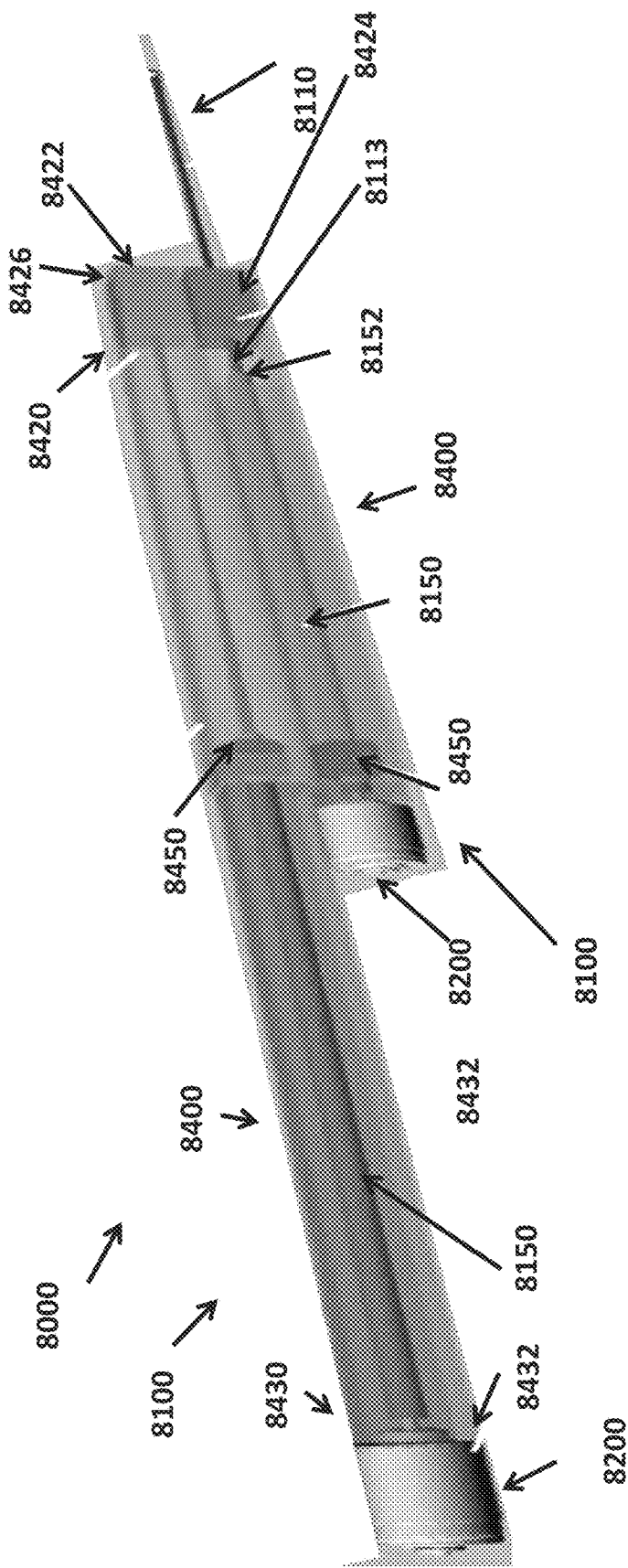

FIG. 84 illustrates side perspective views of catheter cartridges utilized for use with a catheter of FIGS. 83a-b.

FIGS. 85-86 illustrate a schematic representation of a cartridge magazine configured for use with the catheter cartridges of FIG. 84.

Figure 87:
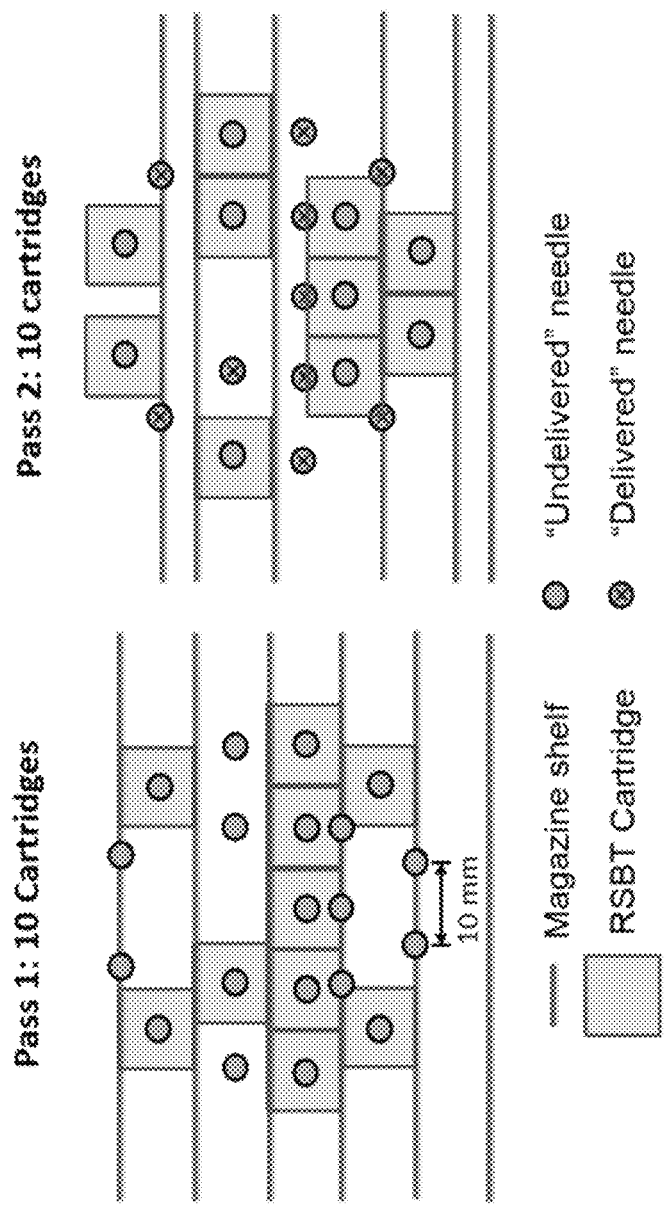

FIG. 87 illustrates an RSBT delivery technique in two "passes." First pass: cartridges are aligned with ten of the twenty needles and radiation is delivered through them; second pass: delivery through the other needles.

FIG. 88 is a schematic representation of a helical rotating shield brachytherapy (H-RSBT) system according to an aspect of the present invention.

FIG. 89 is a schematic representation of a catheter, shield, and applicator components of the system of FIG. 88.

FIG. 90 is a top perspective view of a shield and catheter combination FIG. 89.

FIG. 91 is a side view of the shield and catheter with geometrical parameters according to an aspect combination of FIG. 90.

FIG. 92 is a see-through representation of an applicator of the system of FIG. 88.

FIG. 93 is a cross sectional view of the applicator and shield of the system of FIG. 89.

Figure 94:
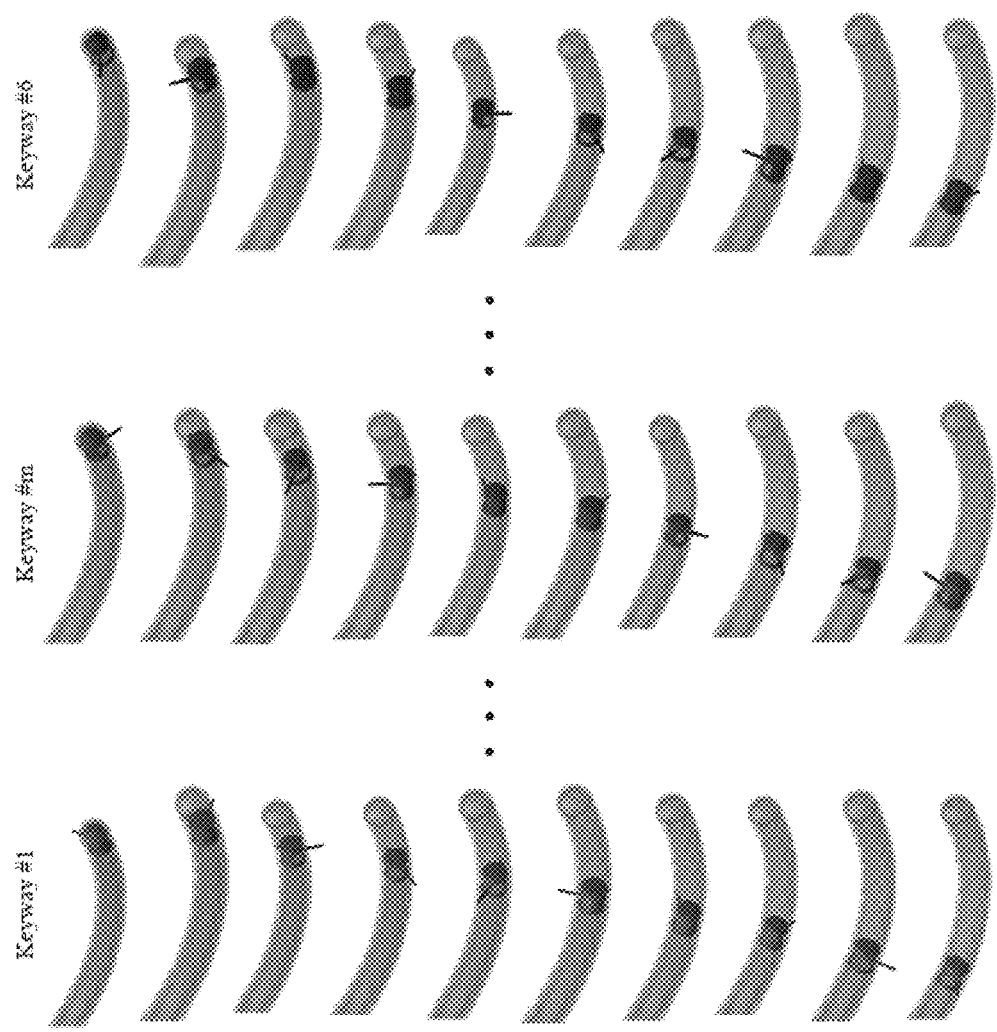

FIG. 94 is a representation of a trajectory sequence of a shield through motion into three of six spiral keyways according to an aspect of the present invention.

Figure 95:
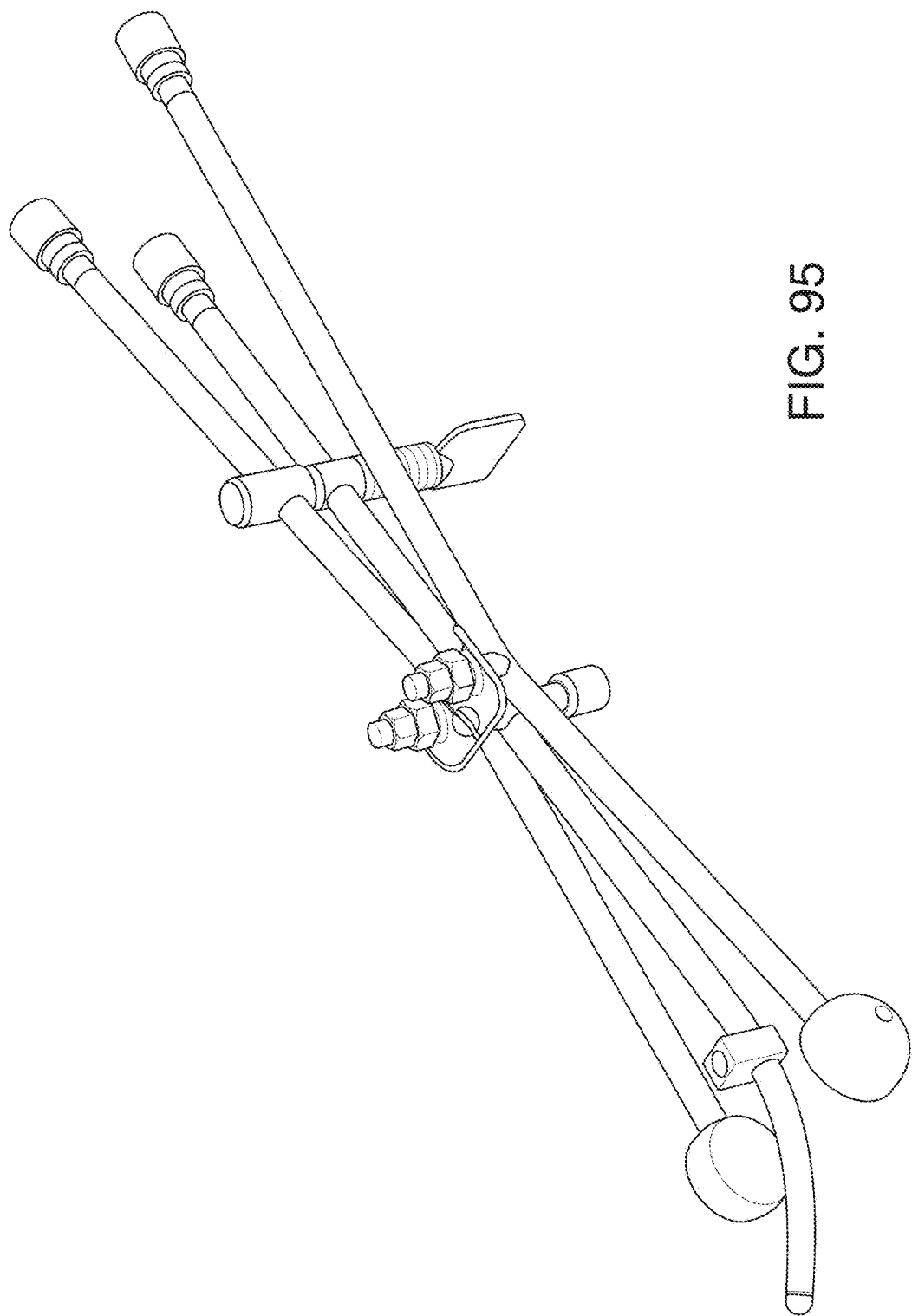

FIG. 95 is a known cervical applicator for which the system of the present invention can be used with according to an aspect.

Figure 96:
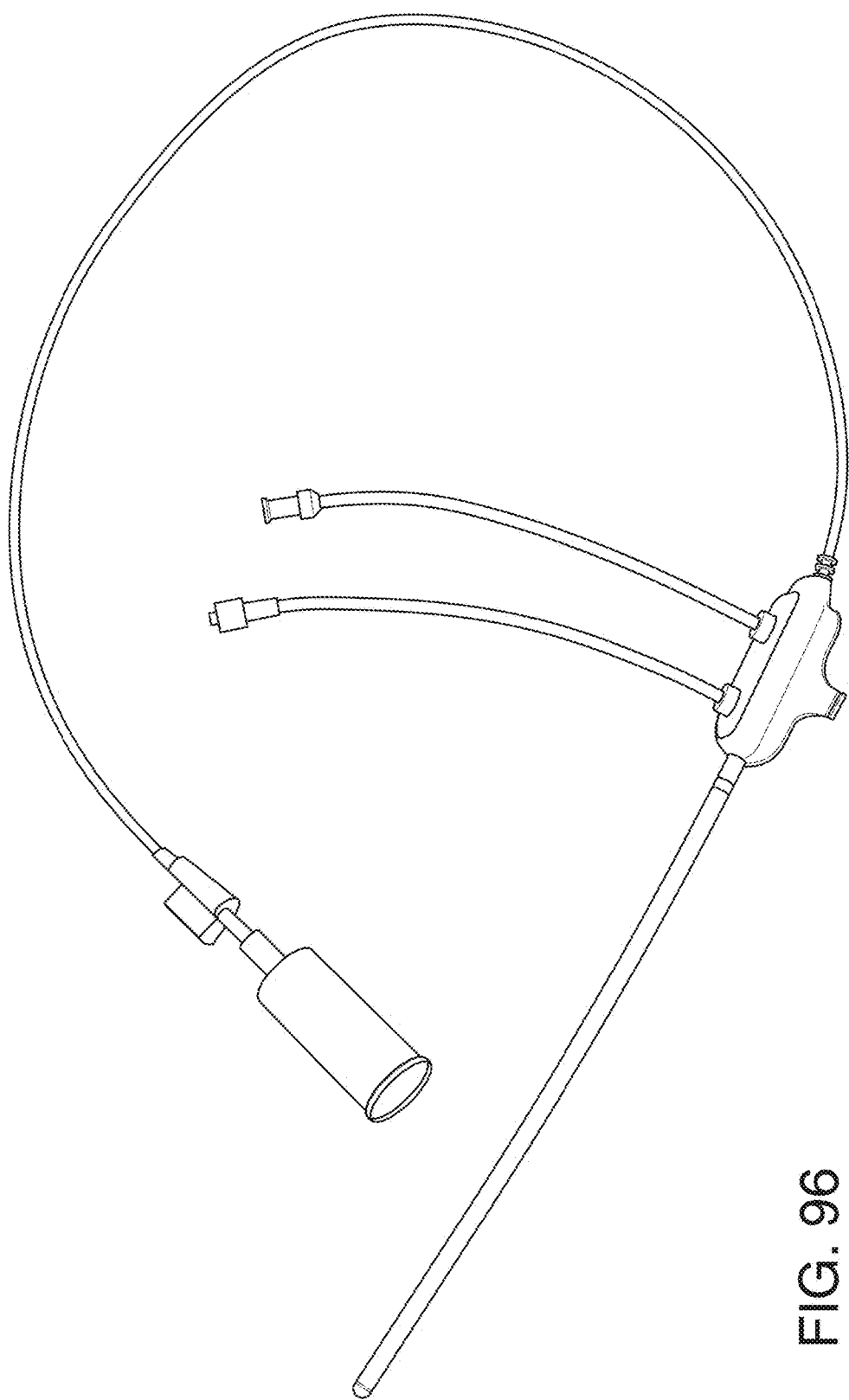

FIG. 96 is a Xoft Axxent Electronic Brachytherapy System.

Figure 97:
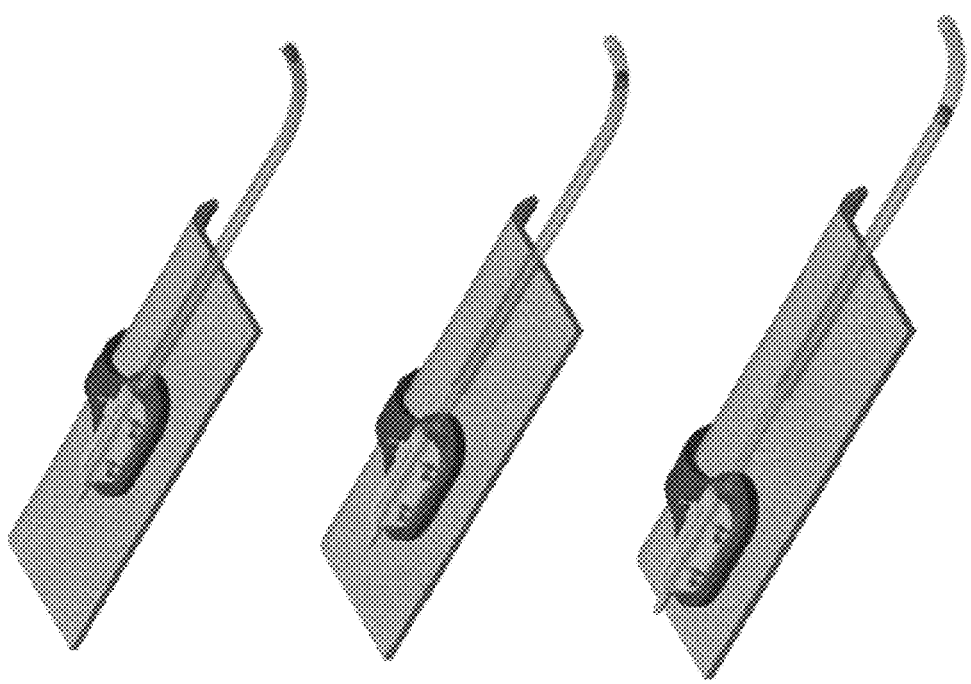

FIG. 97 is a representation of a series of motion and direction of a eBx source and shield within a H-RSBT applicator according to an aspect of the present invention.

Figure 98:
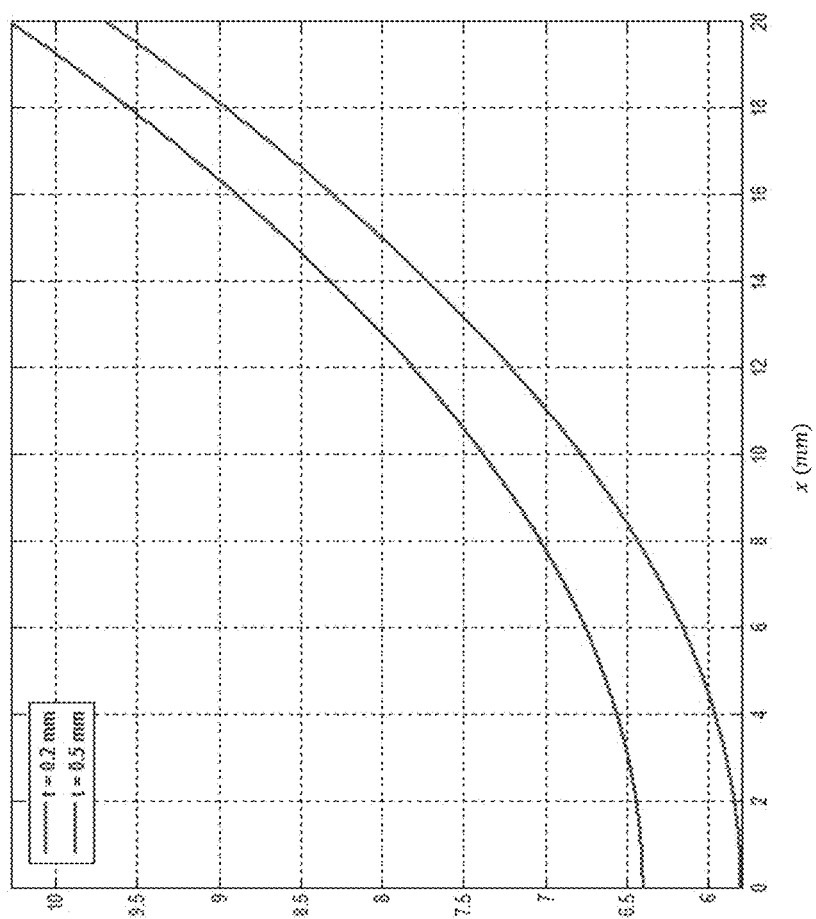

FIG. 98 is a graphical representation of the inner applicator diameter function: $D_i(R_c,x,t)$ according to an aspect.

Figure 99:
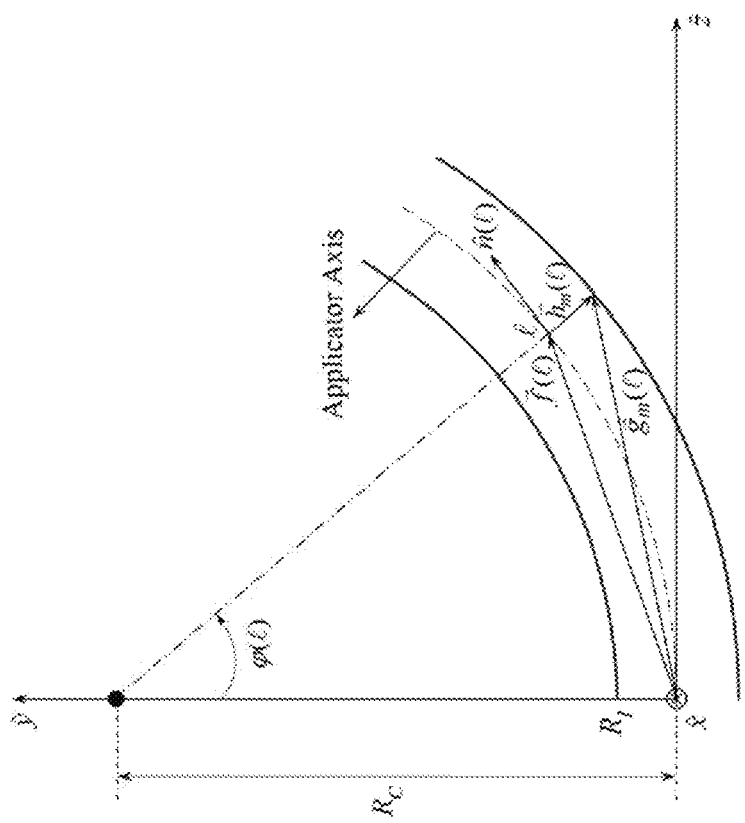

FIG. 99 is a graphical representation of a multi-helix RSB applicator trajectory on a circle according to an aspect.

Figure 100:
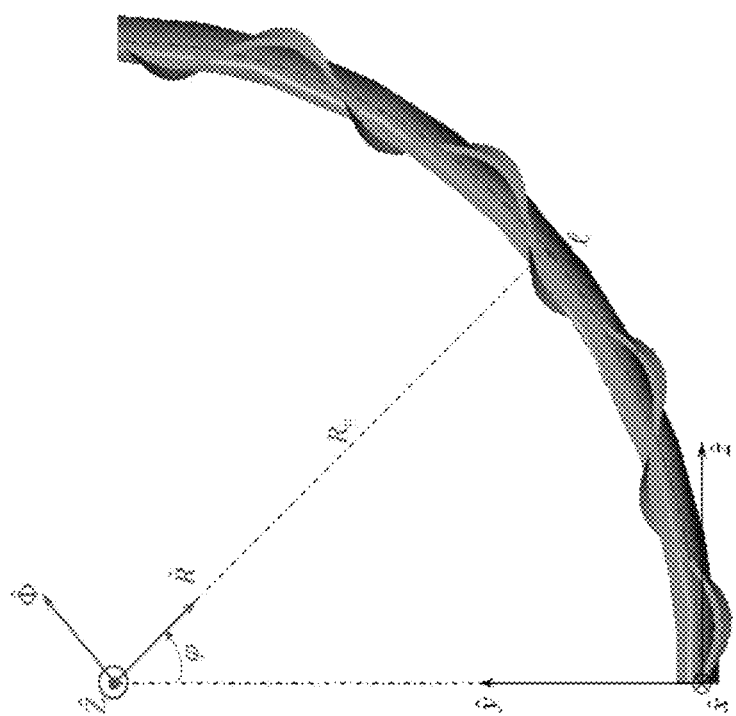

FIG. 100 is a graphical representation of a multi-helix applicator trajectory in cylindrical coordinate for the circular curvature according to an aspect.

Figure 101:
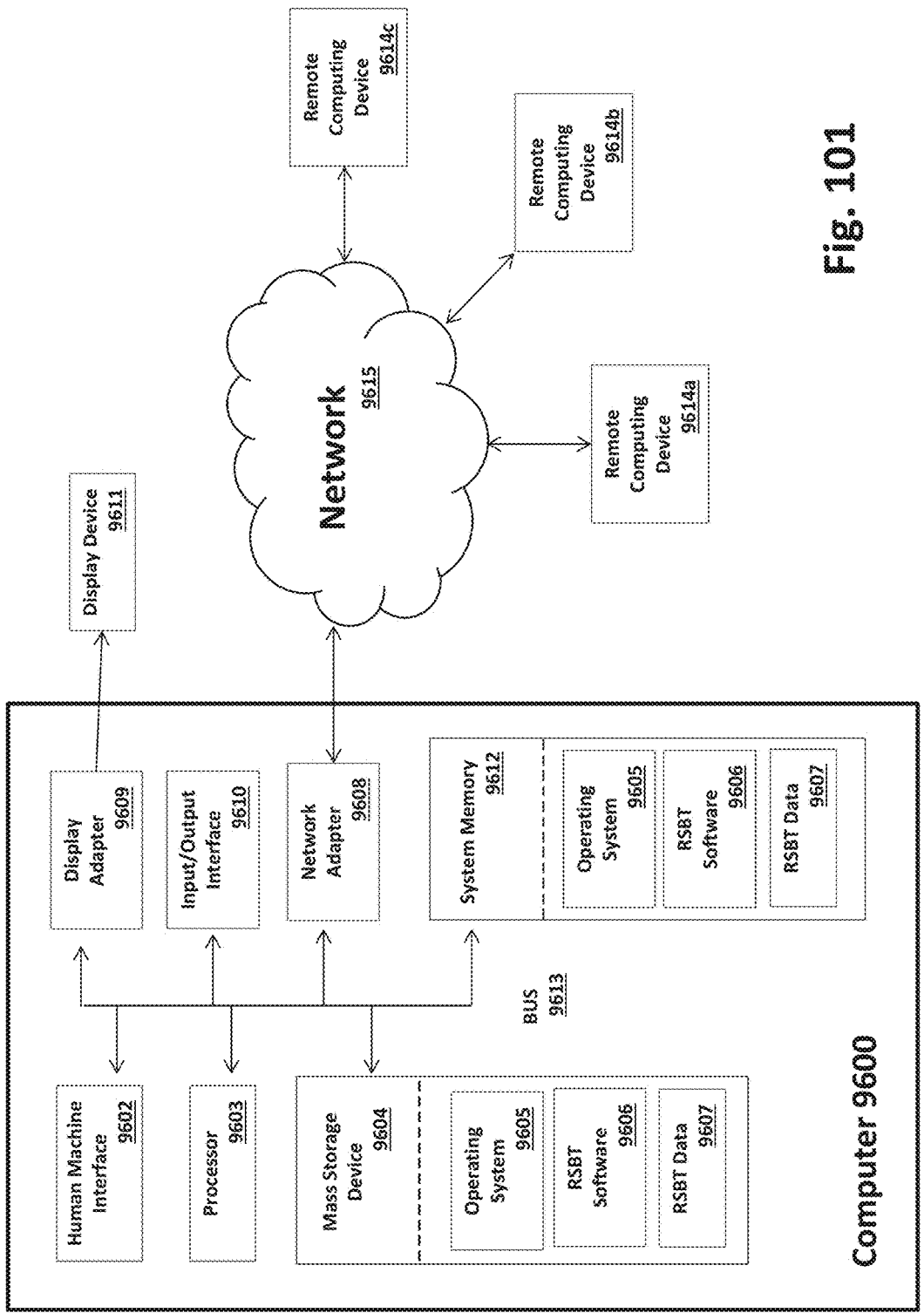

FIG. 101 illustrates a computing environment that enables various aspects of treatment planning and/or automation of treatment planning in accordance with aspects described herein.

DETAILED DESCRIPTION

The subject disclosure may be understood more readily by reference to the following detailed description of exemplary embodiments of the subject disclosure and to the Figures and their previous and following description.

Before the present compounds, compositions, articles, devices, and/or methods are disclosed and described, it is to be understood that the subject disclosure is not limited to specific systems and methods for shield-based brachytherapy and related devices. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In the subject specification and in the claims which follow, reference may be made to a number of terms which shall be defined to have the following meanings: "optional" or "optionally" means that the subsequently described event or circumstance may or may not occur, and that the description includes instances where said event or circumstance occurs and instances where it does not.

As employed in this specification and annexed drawings, the terms "unit," "component," "interface," "system," "platform," "stage," and the like are intended to include a computer-related entity or an entity related to an operational apparatus with one or more specific functionalities, wherein the computer-related entity or the entity related to the operational apparatus can be either hardware, a combination of hardware and software, software, or software in execution. One or more of such entities are also referred to as "functional elements." As an example, a unit may be, but is not limited to being, a process running on a processor, a processor, an object, an executable computer program, a thread of execution, a program, a memory (e.g., a hard disc drive), and/or a computer. As another example, a unit can be an apparatus with specific functionality provided by mechanical parts operated by electric or electronic circuitry which is operated by a software or a firmware application executed by a processor, wherein the processor can be internal or external to the apparatus and executes at least a part of the software or firmware application. In addition or in the alternative, a unit can provide specific functionality based on physical structure or specific arrangement of hardware elements. As yet another example, a unit can be an apparatus that provides specific functionality through electronic functional elements without mechanical parts, the electronic functional elements can include a processor therein to execute software or firmware that provides at least in part the functionality of the electronic functional elements. An illustration of such apparatus can be control circuitry, such as a programmable logic controller. The foregoing example and related illustrations are but a few examples and are not intended to be limiting. Moreover, while such illustrations are presented for a unit, the foregoing examples also apply to a component, a system, a platform, and the like. It is noted that in certain embodiments, or in connection with certain aspects or features thereof, the terms "unit," "component," "system," "interface," "platform" can be utilized interchangeably.

Throughout the description and claims of this specification, the words "comprise," "include," and "have" and variations of the word, such as "comprising," "comprises," "including," "includes," "has," and "having" mean "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Reference will now be made in detail to the various embodiment(s), aspects, and features of the subject disclosure, example(s) of which are illustrated in the accompanying drawings. Wherever possible, the same reference numbers are used throughout the drawings to refer to the same or like parts.

As described in greater detail below, this disclosure relates to methods for optimization of intensity modulated brachytherapy (IMBT). This disclosure relates, in one aspect, to a method for selecting the emission angle for use in single rotating-shield brachytherapy (S-RSBT) called rapid emission angle selection (REAS). In one aspect, REAS can enable a significant reduction in treatment time necessary to deliver an RSBT treatment by decoupling the planning and delivery of that treatment. In another aspect, decoupling the treatment planning and delivery can enable the treatment provider to quickly select a treatment plan that balances the delivery time and dose quality in RSBT based on the time budget for treatment and designated goal of the treatment plan. In yet another aspect, this disclosure relates to a method for sequencing the rotating shields with dynamic-sized opening in IMBT. In another aspect, this disclosure relates to a method for optimizing treatment delivery by approximating the dose distribution to the prescription within a given delivery time constraint.

Various aspects or features of the disclosure can be applied to the field of radiation oncology. Conventional brachytherapy entails the insertion of radioactive sources into tumors through interstitial needles or intracavitary applicators, and delivers very high radiation doses to tumors but often with poor tumor dose conformity. Without wishing to be bound by theory and/or simulation, such poor tumor dose conformity is due to the fact that conventional BT dose distributions typically are radially symmetric and tumors usually are not. It should be appreciated that poor dose conformity is of clinical concern since tumor underdosage leads to recurrence and tumor overdosage excessively damages nearby healthy tissue. One or more embodiments of the disclosure can rectify such deficiency by optimizing treatment delivery by at least one of approximating the dose distribution to the prescription within a given delivery time constraint and reducing the planning time cost while maintaining an acceptable approximation of the dose-volume optimization.

Brachytherapy, or "short-distance therapy," treats target tissues, such as cancerous tumors, with radiation sources that can be placed inside or directly adjacent to the target tissue using some applicator. Example target tissues include cervical, vaginal, endometrial, breast, and skin cancers. Brachytherapy can be delivered with both interstitial and intracavitary applicators The advantage of brachytherapy over external beam radiation therapy (EBRT) is that EBRT beams usually must pass through healthy tissue in order to reach their targets, while the radiation used in brachytherapy may not. As a result brachytherapy can be used to treat targets with very high radiation doses relative to those achievable with EBRT, with less concern for overdosing nearby healthy tissue. The application of 3-D imaging systems such as USI, CT, and MRI for brachytherapy guidance has revealed that the dose conformity to tumors is often poor. Without wishing to be bound by theory and/or simulation, it is believed that poor conformity of conventional brachytherapy (BT) typically is delivered with isotopes or electronic sources that emit radiation in a radially symmetric manner, yet tumors often are not radially symmetric. For example, FIG. 2 illustrates MRI-generated 3D renderings of the anatomy of a patient being treated for cervical cancer, including the tumor and nearby critical structures: bladder, rectum, and sigmoid colon. The radiation is delivered with an X-ray or gamma-ray emitting source that travels through a set of rigid tandem and ovoid (T&O) applicators inserted into the anesthetized patient. The radially symmetric dose distribution emitted by conventional BT sources, however, results in the poor tumor coverage as shown in FIG. 40. The desired radiation dose to the tumor, shown as the red outline, is 100% of the prescribed radiation dose, which is clearly not being achieved in a large fraction of the tumor. Improved tumor coverage can be achieved with intensity modulated brachytherapy (IMBT), which uses shielding of the radiation source to achieve a better dose distribution. Improved tumor coverage obtained with IMBT can be expected to increase local tumor control probability in any applicable tumor, improving patient outcomes.

The feasibility of IMBT has been investigated and it has been demonstrated that IMBT could be delivered using radioisotopes and the Xoft (Sunnyvale, Calif.) Axxent electronic brachytherapy source, respectively, by collimating the source with high-density shields that create fan beams. The fan beam source is rotated inside the patient in a manner such that the amount of time the source spends irradiating a given direction is optimized to ensure better tumor coverage and better critical structure avoidance than conventional brachytherapy. Although both approaches support the potential benefits of IMBT, there are two major challenges associated with the rotating shield approach to IMBT delivery. First, rotating and verifying the location of a moving shield inside a curved applicator is non-trivial. Second, the delivery times associated with IMBT are increased relative to conventional BT. This is due to the loss of emitted radiation in the rotating shield, which must remove a large fraction, possibly around 90%, of the radiation in order to achieve an advantage over conventional BT. If the rotating fan beam accounts for only 10% of the radiation emitted by the BT source, with the rest lost in the shield, then delivering the same dose distribution as conventional BT will require at least ten times as long with rotating-shield IMBT. This is because the fan will have to be pointed in 10 directions and stay pointed in each direction for the same amount of time necessary to deliver an entire conventional BT plan, which loses 0% of the radiation due to shielding.

In another aspect, of the nearly 11,000 annual cases of newly-diagnosed cervical cancer in the U.S., about 45% (5,000) are of stage IB2 or higher. Cervical cancer of stage IB2 or higher has 5-year survival rates of up to about 70%, and 5-year survival and local control ranges from 0-20% and 18-48%, respectively, for stage IVA tumors. Such cancers typically are treated with a combination of chemotherapy, EBRT, and an intracavitary BT boost to the tumor. The advent of MRI-guided BT has revealed that the close proximity of the bladder, rectum, and sigmoid to the tumor restrict the radiation dose that can be delivered to the non-symmetric extensions of bulky (e.g., greater than about 40 cc) tumors with conventional BT, likely reducing the chances of local control. Tumor dose conformity for such bulky tumors can be significantly improved through the use of supplementary BT through interstitial needles, which is more invasive than intracavitary BT, may cause complications, and can add 35-70 minutes to the BT procedure. As increasing tumor dose using supplementary interstitial BT has improved cervical cancer outcomes relative to intracavitary BT alone, it can be expected that RSBT based on eBT could be a less-invasive alternative to intracavitary plus interstitial BT, while still improving patient outcomes relative to intracavitary BT alone.

Rotating shield brachytherapy (RSBT) is one particular implementation of IMBT that can enable enhanced tumor conformity of the BT dose distribution through use of a partially-shielded radiation source. RSBT was first described theoretically as a means of improving tumor conformity of brachytherapy dose distributions for single-catheter and multi-catheter treatments. In early studies, RSBT dose distributions were modeled from a partially-shielded radiation source with the dosimetric characteristics of $^{192}$Ir, but shielded with an unknown material that provided a sufficient, hypothetically-low, transmission to enable RSBT to be beneficial. Although the ideal transmission for an RSBT shield is dependent on the clinical case and the emission angle, a shield transmission of 50% was shown to be unacceptable. Since the half-value layer of the gamma ray emissions from $^{192}$Ir is about 2.5 mm, relatively few cancer sites are treatable with $^{192}$Ir-based RSBT.

The advent of high-dose-rate electronic brachytherapy (eBT) sources such as the 40-50 kVp Xoft Axxent™ (Xoft Inc., Sunnyvale, Calif.) can enable RSBT in intracavitary applicators with diameters small enough to enable RSBT treatment of cervical cancer. The Xoft Axxent, shown in FIG. 1, is a 2.25 mm diameter x-ray tube, contained in a 5.4 mm diameter water cooling catheter, and emits x-rays with a hundredth-value-layer of 0.2 mm of tungsten. The Xoft Axxent, rotating shield, and applicator combination can provide an RSBT system with an overall diameter of less than 10 mm.

With RSBT, a shield partially-occludes the radiation source and rotates about the source in an optimized fashion, directing less radiation dose toward sensitive tissues than tumor tissues. However, for a given radiation source, single catheter RSBT treatment planning and delivery can be more costly and time consuming than conventional single-catheter BT treatment planning and delivery for multiple reasons. Since each source, e.g., a Xoft Axxent™ eBT source, has a finite lifetime, efficient usage of each source can be an important factor to ensure the treatment modality is cost-effective. Second, the treatment planning process for RSBT can be more time-consuming than that for conventional BT. Without wishing to be bound by theory and/or simulation, the number of optimization variables for RSBT is greater than that of conventional BT by a factor of K, where K is the number of allowed irradiation directions per dwell position. For example, it has been reported that multi-directional breast BT treatment planning and delivery times can take 120 minutes and 37 minutes, respectively, and conventional BT treatment planning and delivery times can both take only 5 minutes. Since patients tend to be under general or spinal anesthesia during BT treatment planning and delivery, prolonging any part of the treatment process is expensive and inefficient. Also, since BT radiation sources have a finite lifetime, efficient usage of each source is desirable to decrease the cost of BT therapy.

For patients treated with RSBT, it can be expected that treatment providers will have access to multiple shields with a range of emission angles. Without wishing to be bound by theory and/or simulation, the optimal emission angle for single-catheter, single-shield RSBT will be tumor-dependent, which can be illustrated clearly when a target with an ellipsoidal cross section and a catheter that passing through the center of mass of the target cross section is considered. For a target having an ellipsoidal cross section with a width of three times the height, an emission angle smaller than 180° will be desirable in order to treat the lateral tumor extensions without overdosing the normal tissue anterior and posterior to the tumor. For increasingly cylindrical targets, as the width and height of the tumor approach each other, larger emission angles become increasingly attractive, and the treatment times will decrease accordingly. For the limiting case of a target with a cylindrical cross section, the ideal source is an unshielded one, and the conventional BT case is desirable.

The choice of shield emission angle can be an important component in single-catheter, single-shield, RSBT planning. For difficult cases, determining the ideal shield angle for a given case by exhaustive treatment planning can be challenging due to the high computational cost, as the treatment planning time would scale with the number of available shields.

One or more embodiments of the disclosure can rectify such deficiencies by enabling a rapid RSBT emission angle selection method that can further enable the clinician to intuitively select an optimized balance between RSBT treatment time and dose distribution quality for a given clinical case. In one or more aspects, the shield angle selection method for several shield angles can require only half a minute of computational time beyond the time to generate a full RSBT treatment plan for a single shield angle. Other aspects, methods disclosed herein enable treatment providers to select the proper shield, balancing the delivery time and dose quality for each individual case, in a reasonable time with an REAS-generated Pareto plot as shown in FIG. 2. Each point on the Pareto plot represents the highest $D_{90}$ that can be achieved with the delivery time specified by its x-coordinate or the least delivery time required for achieving the $D_{90}$ specified by its y-coordinate. The emission angles for the delivery plans can also be indicated. Emission angles are invariant on the same curve segment, as plans located on the same curve segment are essentially the same plans with different scaling factors. In certain cases, the delivery time can be controlled below a certain time budget while minimizing the quality loss. In other cases, the dose quality (e.g., HR-CTV $D_{90}$) can be controlled above a certain goal while minimizing the delivery time. In one aspect, REAS can be of commercial value because it is a feasible method that can provide improvement over conventional S-RSBT treatment planning and delivery and can result in improved patient care. In another embodiment, the methods of the disclosure can enable shield selection methods requiring as little as about half of a minute of computational time beyond the time used to generate a full RSBT treatment plan for a single shield angle. Examples of cancers that can be treated more effectively with use of REAS in S-RSBT treatment comprise vaginal, cervical, endometrial, breast, lung, liver/bile duct, skin and/or prostate tumors.

One or more of the principles can be utilized in various therapeutic radiation treatments. In one aspect, an exemplary application of REAS is in the field of radiation oncology. More specifically, yet not exclusively, REAS can be utilized in conjunction with S-RSBT for the treatment of tumors that are not radially symmetric about a certain axis. In one example, REAS, in conjunction with S-RSBT, can overcome one or more limiting factors of treating cervical cancer tumors, which rarely are radially symmetric. In one embodiment, an electronic brachytherapy source, such as the Xoft Axxent™ can be inserted through a water cooling catheter and placed adjacent to or inside a target tissue using some applicator. Example applicators can include interstitial needles and intracavitary applicators. In S-RSBT as described herein, BT sources are not limited to electronic brachytherapy sources.

In one aspect, radiation source model and dose calculation can be accomplished by the following method. An RSBT beamlet, $\dot{D}_{i,j,k}(\Delta\varphi, \Delta\theta)$, can be defined as the dose rate at the point $\vec{r}_i$ due to a shielded radiation source at dwell position $\vec{s}_j (j=0, \ldots, J-1)$. As shown in FIG. 1(b), the shield has an azimuthal emission angle of $\Delta\varphi$ and a zenith emission angle of $\Delta\theta$. The irradiation direction of the beamlet is defined by $\varphi_k$, which is the lower of the two azimuthal angles defining the aperture: $\varphi_k=(k \mod K)\delta\varphi(k=0, \ldots, K-1)$, where $\delta\varphi=360°/K$ is the azimuthal step size between neighboring beamlets. The mod operation denotes modular arithmetic, enabling beamlet referencing with arbitrary integer k-values such that $\varphi_{k+K+1}=\varphi_{k+1}$. The upper azimuthal edge of beamlet k is located at angle $\varphi_k+\Delta\varphi$. The total dose delivered to point i from a shielded source with azimuthal and zenith emission angles of $\Delta\varphi$ and $\Delta\theta$, respectively, can be calculated, in one aspect, as a time-weighted sum of the appropriate beamlets over all dwell positions and emission angles:

$$d(\Delta\varphi, \Delta\theta) = \sum_{j=0}^{J-1} \sum_{K=0}^{K-1} \dot{D}_{i,j,k}(\Delta\varphi, \Delta\theta)\tau_{j,k}, \quad \text{Eq. (1)}$$

where $t_{j,k}$ is the dwell time, which is always greater than or equal to zero, for which the source is pointed in direction $\varphi_k$ while it is located at dwell position j. The source step length along the source trajectory, $\Delta j$, was set to 3 mm. As with $\varphi_k$, $\dot{D}_{i,j,k}(\Delta\varphi, \Delta\theta)$ and $\tau_{i,k}$ are periodic functions of the index k with a period of K.

For exemplary and illustrative purposes only, RSBT source was assumed to be a 50 kVp Xoft Axxent™ with a 0.5 mm tungsten shield providing less than 0.01%, or effectively zero, transmission. RSBT beamlets were obtained by multiplying unshielded 3-D dose rate distributions obtained using a TG-43 dose calculation model by a binary function that was zero at all points blocked by the shield and unity at all other points. Thus, the point source approximation was used and the effects of shield emission angle size on the x-ray scatter component of the Xoft Axxent™ dose distribution were neglected. These approximations for this example are suitable since the emission angle selection method can be applied regardless of the accuracy of the beamlet calculation technique. The exact result of the method can have a slight, although currently unknown, dependence on the beamlet calculation technique. Also, for illustrative purposes, the shield emission angle selection problem is limited to azimuthal angles, and the zenith angle is held constant throughout the current work at $\Delta\theta=120°$. Practically, the source emission direction would be controlled by rotating the shield about the source.

For exemplary and illustrative purposes only, two cervical cancer cases can be considered, and exemplary anatomy is shown in FIG. 2. The target region for each case is defined as the high-risk clinical target volume (HR-CTV), which was delineated by a radiation oncologist using the GEC-ESTRO recommendations and larger than 40 $cm^3$ for both cases considered. The organs at risk (OARs) were the rectum, sigmoid colon, and bladder. Prior external beam radiotherapy (EBRT) doses of 45 Gy in 25 fractions of 1.8 Gy were delivered to the HR-CTV and OARs for both patients, which was accounted for in the BT treatment planning. The BT delivery was assumed to take place over 5 treatment fractions. Doses to the HR-CTV and OARs were expressed as equivalent doses in 2 Gy fractions (EQD2) using $\alpha/\beta$ values of 10 Gy and 3 Gy, respectively.

The RSBT and conventional (unshielded) BT treatment goal was to escalate tumor dose without exceeding the OAR tolerances. Specifically, the minimum dose to the hottest 90% ($D_{90}$) of the HR-CTV was maximized under the constraint that the minimum doses to the hottest 2 $cm^3$ ($D_{2\ cc}$) of the rectum, sigmoid colon, and bladder could not exceed the tolerance doses of 75, 75, and 90 $Gy_3$, respectively. The $\Delta\varphi$-dependent treatment plan quality metrics were $D_{90}$ for the HR-CTV and the total delivery time.

In one aspect, the implementation of REAS can comprise the steps of generating beamlets by combining baseline beamlets, selecting a set of anchor plans, and generating a treatment plan.

In another aspect, generating beamlets can be accomplished by the following methods. The baseline beamlets can be defined as the beamlets generated using the baseline azimuthal angle, $\delta\varphi$. The baseline beamlets at a given dwell position j can be assumed to be non-overlapping, thus the shadows cast by the shields of neighboring beamlets (k and k+1 for a given dwell position j) do not overlap. An integer number, W (W>1), of neighboring baseline beamlets can be combined by superposition to produce a beamlet with a larger emission angle, $\Delta\varphi_W=W\delta\varphi$, in one aspect, as follows:

$$\dot{D}_{i,j,k}(\Delta\varphi, \Delta\theta) = \sum_{p=0}^{W-1} \dot{D}_{i,j,k+p}(\delta\varphi, \Delta\theta) \quad \text{Eq. (2)}$$

generating a set of "W-beamlets." Equation Eq. (2) is exact for the case of zero shield transmission, which is a safe assumption for the example of a Xoft Axxent™ shielded with 0.5 mm of tungsten.

In an example in which the W neighboring baseline beamlets, with indices from k to k+W−1, all share delivery times of $\dot{\tau}_{j,k} = \tau$, it follows from Equation Eq. (2) that the W neighboring beamlets can be replaced with a single beamlet with an emission angle $\Delta\varphi_W$ and a delivery time of $t_{j,k}^W = \tau$ where the t-superscript indicates that the delivery time is associated with a beamlet with an emission angle of $\Delta\varphi_W$. Conversely, a beamlet with an emission angle of $\Delta\varphi_W$ and a delivery time of T can be replaced with the baseline beamlets with indices between k and k+W−1, which will have delivery times of $t_{j,k}^1 = \tau$. Thus an entire set of dwell times associated with beamlets of emission angle $\Delta\varphi_W$ can be written as a set of baseline dwell times (W=1), in one aspect, as follows:

$$t_{j,k}^{W\to 1} = \sum_{k'=0}^{K-1} t_{j,k'}^W \prod\left(\frac{(k-k')\bmod K}{W}\right), \quad \text{Eq. (3)}$$

where $$\prod\left(\frac{a}{W}\right)$$

is unity when 0≤a≤W−1 (a is an integer) and zero otherwise. The purpose of the ⊓-function is to spread the dwell times from the $\Delta\varphi_W$ emission angle beamlets over multiple baseline beamlets. The modular arithmetic in its argument makes ⊓ a periodic function of k with period W. Equation Eq. (3) can, in one aspect, be simplified by changing summation indices for k' to p=k−k' as follows:

$$t_{j,k}^{W\to 1} = \sum_{p=0}^{K-1} t_{j,k-p}^W \prod\left(\frac{p \bmod K}{W}\right) = \sum_{p=0}^{W-1} t_{j,k-p}^W \quad \text{Eq. (4)}$$

Since the sum over k' in Equation Eq. (3) is over one period of a periodic function of k', the summation over p in the middle expression of Equation Eq. (4) can be done over the same range, even after changing variables.

In yet another aspect, a treatment plan can be generated from anchor plans using the following methods. A treatment plan generated using the W-beamlets (W>0) and an in-house dose-volume optimizer can be denoted as $\hat{P}^W$, which has dwell times of $\hat{t}_{j,k}^W$ and a dose distribution $\hat{d}_t^W$. The baseline equivalent plan of $\hat{P}^W$ is denoted as $\hat{P}^{W\to 1}$, which has dwell times of $\hat{t}_{j,k}^{W\to 1}$ for baseline beamlets and the same dose distribution $\hat{d}_t^W$. As the dose-volume optimization is a non-convex optimization problem and no polynomial algorithm exists, simulated annealing technique, in one aspect, can be applied to solve the dose-volume optimization. In order to make the simulated annealing efficient, initial solutions can be generated with a surface optimizer which uses a gradient-based least squares method to optimize the dose homogeneity on the HR-CTV surface. The simulated annealing can require 10-20 minutes to converge even with initial guesses from the surface optimizer. Therefore, it is not practical to generate plans with all possible W-values under the time requirement of clinical practices. In order to overcome this obstacle, RSBT plans can be used to limit the number of calls to the optimizer.

In one aspect, an anchor plan $\hat{P}^W$ for a given patient is the treatment plan generated with W-beamlets, by finding $\hat{t}_{j,k}^W$, which is the optimal $\hat{t}_{j,k}^W$ for (j=0, . . . , J−1, k 0, . . . , K−1). The baseline equivalent plan $\hat{P}^{W\to 1}$ can then be obtained directly from $\hat{P}^W$ without modifying the delivered dose distribution, $\hat{d}_t^W$. Then, an expedient treatment plan $\tilde{P}^{W'}$, which has dwell times $\tilde{t}_{j,k}^{W'}$, is rapidly generated from an anchor plan $\hat{P}^W$, in one aspect, by solving the following optimization problem:

$$\min \sum_{j=0}^{J-1}\sum_{k=0}^{K-1} \left(\hat{t}_{j,k}^{W\to 1} - \tilde{t}_{j,k}^{W'\to 1}\right)^2 \quad \text{Eq. (5)}$$

$$\text{s.t.} \quad \tilde{t}_{j,k}^{W'\to 1} = \sum_{p=0}^{W-1} \tilde{t}_{j,k-p}^{W'}$$

$$\sum_{j=0}^{J-1}\sum_{k=0}^{K-1} \tilde{t}_{j,k}^{W'} \leq T^{max}$$

However, due to the inevitable error between $\hat{t}_{j,k}^{W\to 1}$ and $\tilde{t}_{j,k}^{W\to 1}$ in most real-world cases, $\tilde{P}^{W'}$ may not be able to reproduce the dose distribution of $\hat{P}^W$ perfectly. The plan quality tends to degenerate as W increases. As a result, expedient plan $\tilde{P}^{W'}$ can be regarded as an approximation of dose-volume optimized plan $\hat{P}^W$, however, the approximation quality will decrease as W' increases.

With the solution to Equation Eq. (5), $\tilde{t}_{j,k}^{W'}$ is then escalated to maximize $D_{90}$ in the HR-CTV. $T_{max}$ is a constraint on the total delivery time of $\tilde{P}^{W'}$ which can be imposed to reduce treatment time at the expense of HR-CTV $D_{90}$. Obtaining $\tilde{P}^{W'}$ by solving the sequencing problem in Equation Eq. (5) enables a much faster result than by obtaining the full optimization needed to obtain $\hat{P}^{W'}$, since the problem concerns times only, rather than doses.

In one aspect, in order to balance the time cost spent on exhaustive re-optimization and the plan quality, a small set of anchor plans $\hat{P}^8$, $\hat{P}^{16}$ and $\hat{P}^{24}$ can be selected. The corresponding azimuthal emission angles are 90°, 180° and 240°. Since the emission angles selected are, evenly-spaced among all possible emission angles, they can be considered as a sampling of the full-set of simulated-annealing optimized plans. The optimal sequencing algorithm can then be applied for each anchor plan and a Pareto-front generated, showing the trade-off between $D_{90}$ and delivery times for all possible W' s.

Figure 3:
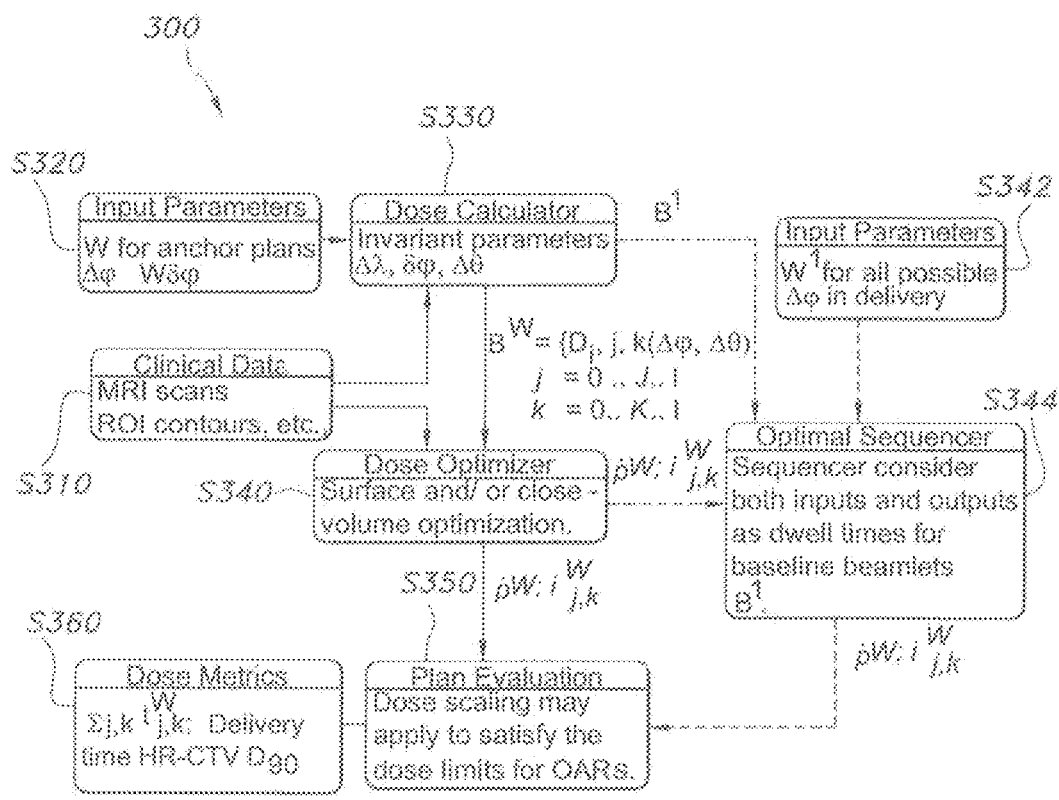
FIG. 3 is a flowchart showing the treatment planning steps of an exemplary method for treatment plan selection using exhaustive re-planning (either simulated or gradient-based) and using optimal sequencing with anchor plans.

In view of the aspects described hereinbefore, an exemplary method that can be implemented in accordance with the disclosed subject matter can be better appreciated with reference to the flowchart in FIG. 3. For purposes of simplicity of explanation, the exemplary method disclosed herein is presented and described as a series of acts; however, it is to be understood and appreciated that the claimed subject matter is not limited by the order of acts, as some acts may occur in different orders and/or concurrently with other acts from that shown and described herein. For example, the various methods or processes of the subject disclosure can alternatively be represented as a series of interrelated states or events, such as in a state diagram. Moreover, when disparate functional elements implement disparate portions of the methods or processes in the subject disclosure, an interaction diagram or a call flow can represent such methods or processes. Furthermore, not all illustrated acts may be required to implement a method in accordance with the subject disclosure. Further yet, two or more of the disclosed methods or processes can be implemented in combination with each other, to accomplish one or more features or advantages herein described. It should be further appreciated that the exemplary methods disclosed throughout the subject specification can be stored on an article of manufacture, or computer-readable medium, to facilitate transporting and transferring such methods to computers for execution, and thus implementation, by a processor or for storage in a memory.

FIG. 3 is a flowchart of an exemplary method 300 for selecting an emission angle for use in S-RSBT in accordance with aspects of the subject disclosure. Also shown in FIG. 3 is an exhaustive re-planning method (either simulated annealing or gradient-based) for comparison. A computer or computing device can implement (e.g., execute) exemplary method 300. In one aspect, a processor within or functionally coupled to the computer or computing device can be configured to execute computer-executable instructions and, in response to execution, the processor can carry out the various steps that comprise exemplary method 300. Similarly, yet not identically, the computer or computing device can execute the various methods, or portion(s) thereof, disclosed herein. The exemplary method 300 can comprise various steps. At step S310, receiving data indicative of a radiation treatment and topology of a region to be treated. At step S320, receiving input parameters for azimuthal emission angle and azimuthal emission step ratio for at least one and, preferably, three anchor plans. In an aspect, three anchor plans are needed to ensure that the generated plans are comparable to those that would be generated with less time-efficient planning methods. At step S330, calculating a dose. At step S340, optimizing the calculated dose using at least one of surface optimization and dose-volume optimization. At step S342, enumerating all possible input parameters. In an aspect, such a step can be done enumerating all possible positive integers that are less than or equal to 360°/βφ (the parameters supplied describe the azimuthal emission angles). At step S344, approximating the dose distribution of the anchor plan using beamlets from shields with azimuthal emission angle W'Δφ. At step S350, evaluating a treatment plan which may include dose scaling to satisfy dose limits for any organs at risk. At step S360, generating output metrics which may include generating a Pareto plot.

Steps S342 and S344 can be related to an optimal sequencing algorithm for REAS, which intends to reproduce the dose distribution of the anchor plan with beamlets that have larger azimuthal emission angles thus reduce the delivery time. The possible azimuthal emission angles were enumerated by step S342 to determine the best angle choice.

For further comparison, examples of three different planning methods are applied on two clinical cases for comparison. The two clinical cases are denoted Patient 1 and Patient 2, respectively. In FIG. 3, the exhaustive replanning method using a dose-volume optimizer, and the corresponding plans are denoted as $\hat{P}^W$; the exhaustive replanning using a surface optimizer, and the corresponding plans are denoted as $\hat{P}^W$, and the exemplary method 300 for selecting an emission angle for use in S-RSBT in accordance with aspects of the subject disclosure as $\tilde{P}^W$.

For the example of treatment plan generation by the exhaustive replanning method using a dose-volume optimizer, each additional optimization takes about 10 minutes. In one example where the computational budget is limited to about 10 minutes to avoid too much time cost, a planning procedure with 32 plans for W=1~32, takes about 7 hours to complete.

For the example of treatment plan generation by the exhaustive replanning method using a surface optimizer, the replanning procedure can take about 10 minutes to finish and the entire planning procedure can be completed in about 20 minutes.

For the example of treatment plan optimization via the exemplary method 300 for selecting an emission angle for use in S-RSBT in accordance with aspects of the subject disclosure, treatment plan generation requires about half of a minute beyond the generation of the anchor plans. Generating three anchor plans, in one aspect, takes about 40 minutes. In another aspect, the anchor plans can be generated in parallel and the entire planning procedure can be finished in about 20 minutes.

Visual comparisons of the dose distributions between the different plans described above are shown in FIG. 4 and FIG. 5. The corresponding quantitative comparisons are shown in FIG. 6 and FIG. 7 and the corresponding Pareto plots are shown in FIG. 8 and FIG. 9. For Patient 1, besides the anchor plans, the three additional plans (d)-(f) were selected as the optimal treatment plans to achieve minimal delivery time at the $D_{90}$ level 84 $Gy_{10}$. For Patient 2, the three additional plans (d)-(f) were selected as the optimal treatment plans to achieve the highest $D_{90}$ at the goal delivery time of 8 min/fx.

In certain embodiments, rapid emission angle selection can be achieved by combining dose-volume optimization and the sequencing algorithm, with setting either a goal for $D_{90}$ or a budget for the delivery time on the final Pareto plots. In one aspect, by selecting 3 anchor plans, sequenced plans can result in better approximations for dose-volume optimized plans compared with surface optimized plans, as shown in FIG. 8 and FIG. 9. In another aspect, the computational cost for sequencing algorithms can be negligible compared to the computational costs for dose calculations and optimizations. In another aspect, selection of the azimuthal emission angle Δφ can be case-dependent. In yet another aspect, smaller azimuthal emission angles do not necessarily result in a better dose distribution due to use of a fixed emission angle. If the larger emission angle is not a multiple of the smaller one, we cannot always expect getting a better dose distribution by using the smaller one. As illustrated by FIG. 10, suppose the ideal dose distribution is shown in (a), and it can be perfectly reproduce by set Δφ=3δφ. However, with a smaller emission angle Δφ=2δφ, it is impossible to perfectly reproduce the dose distribution, as shown in FIG. (b).

Figure 11A:
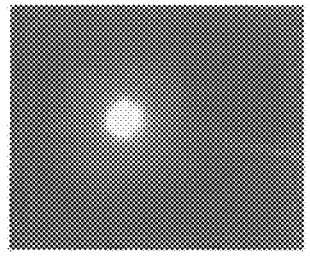
Figure 11B:
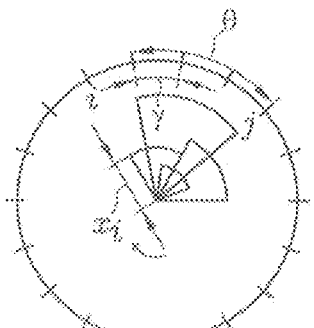
Figure 11C:
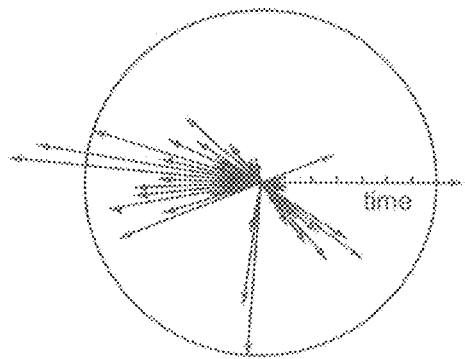
Figure 11D:
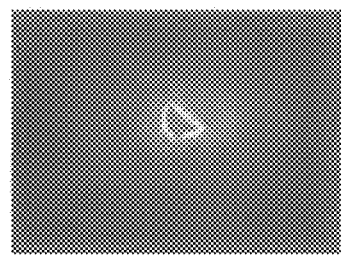

In yet another aspect, an Xoft Axxent electronic brachytherapy source shielded to less than about 1% transmission using less than about 0.2 mm of gold, tungsten, lead, or some other high-Z material is used. The shield design could, for example, be one of those shown in U.S. Pat. No. 7,686,755. The shield rotation can be accomplished by rotating the entire source wire inside the applicator, or rotating the shield about the source-containing catheter. In the present aspect, as illustrated in FIGS. 11(a-d), the source is partially shielded and the transmission rate at the shield is negligible or can be controlled at a low level. The dose distribution of a single beamlet through the shield is fan-like on a 2D slice with a certain thickness, as shown in FIG. 11(a). The color shows the difference of the dose contribution to different positions. The tumor surface can be equally divided into several divisions by angle in a polar system centering at the tandem point, with each division prescribed a desired dose, a maximum dose and a minimum dose it should receive. The shield can be rotated such that the fan-window opened in the shield can be selectively directed to any division or divisions. Typically, the fan window has an angle which can cover multiple adjacent divisions. Thus, each beamlet (corresponding to each direction the fan-window points to), will have a certain contribution to the surrounding tissues. FIGS. 11(b-c) illustrate an optimal dwelling time sequence for the fan-window to stop for the present aspect. As shown in FIG. 11(c), the case illustrated has 18 divisions, and the fan-window can cover 3 divisions at a time. The difference between the fans demonstrates the dwell-time difference for the fan-window when pointing to different divisions. The resulting dose distribution from FIG. 11(c) is illustrated in FIG. 11(d).

In an aspect, for the optimization objective, any of the following three options can be pursued: (i) minimizing the treatment time with all divisions receiving doses within the interval between the corresponding maximum and minimum (also referred to as the "MINTIME" problem); (ii) minimizing the total sum of errors within a given delivery time in addition to all constraints mentioned in (i) (also referred to as the "MINERR" problem); and (iii) minimizing the delivery time with the total sum of errors bounded in addition to all constraints mentioned in (i) (also called the "BALANCE" problem). It is a further aspect of this example to incorporate the combination of using an unshielded source together with the sequencing of the fan-window, which is equivalent with controlling the transmission rate through the shield, to gain further reduction of the delivery time.

A further feature of this example is the dual transformation. Although general integer programming problems are NP hard, which means that the global optimum cannot be guaranteed to be found in a short time, here the problems have a nice circular 1's property in the constraint matrix which enables them to be converted to network problems and then solved in polynomial time. After the dual transformation, in one aspect, the MINTIME problem can be solved by using a parametric shortest path algorithm reported by Dorit Hochbaum, et al. in 2005. The MINERR and BALANCE problems can also be solved by applying the net surface detection technique by Wu, et al. in 2002.

In one aspect, after the sequencing algorithm is completed, the outputs can be fed back to create new dose distributions and these new dose distributions are subjected to a dose rescale to ensure the tumor is not underdosed as long as the OARs are not overdosed according to GEC-ESTRO recommendations. The present method can be verified with a 2D slice from clinical cervical cancer case, as shown in FIG. 12. The tumor surface (contour) can be equally divided into 90 divisions by angle. The 3 contoured objects from top to bottom are bladder, tumor site and rectum. For the dose calculation, a single raytrace method that accounts for polyenergetic source model, attenuation in the patient, and inverse square law can be used. Scatter and anisotropy are not accounted for in this example.

The verification was performed by using a software implementation of the algorithms of this example with a computer workstation, and every single optimization procedure was performed within about 2 seconds. Testing of the software implementation of the algorithms can be under several different settings (varying fan angles, toggle between using combination with unshielded source or not) to see the impact of different parameters.

In order to simplify the verification process, all the doses were normalized such that the prescription dose is 100 units and, for simplicity in this 2-D example, it can also be assumed that each pixel in the image corresponds to 0.02 cc volume. Under this assumption, we will get 32.8 cc for the tumor, 59.98 cc for the bladder and 16.7 cc for the rectum. By following the GEC-ESTRO recommendations for DVH parameters, all the constraints for the dose rescaling procedure specifically for our test case are obtained:

1. At least 90% percent of the tumor should receive 100% prescription dose;
2. 2 cc of the bladder tissue should receive no more than 86% prescription dose;
3. 2 cc of the rectum tissue should receive no more than 58% prescription dose.

As presented in FIGS. 13-14, the results indicate that IMBT can noticeably increase the dose distribution quality compared with conventional isotropic radiation source, as the conventional method will inevitably underdose the tumor within the safety constraints. However, with IMBT, the price paid for increasing the dose distribution quality is a longer delivery time. The best result in FIG. 13 is that the IMBT delivery uses about 5.6 times more than conventional brachytherapy. It is also shown that, as the fan angle increases, both the delivery time and the conformity indices decrease. However, the treatment time cannot be decreased by increasing the fan-angle as it would lead to problems of feasibility. In the case we show in FIG. 15, a solution with all constraints satisfied cannot be determined when the fan-angle is 80° or more. This can be because the problem will degenerate to the conventional isotropic problem when the fan-angle increased to its maximum 360°. As shown in FIG. 15, the delivery time can be further reduced while suffering little from the dose distribution with the combination of using a unshielded source. Note that the maximum allowed percentage of dose from unshielded source while keeping the problem feasible is used here. Here, 4.46 times more delivery time compared to conventional isotropic source is achieved.

In yet another example, an efficient inverse planning system is need for making RSBT practical given the time constraints imposed by the anesthetized patient. Existing dose optimization methods can take a long time to reach a desired solution (e.g., simulated annealing), or can compromise the quality of the plan (e.g., using surface-based optimization instead of dose-volume based optimization). In this example, in order to optimize the balance between the dose quality and the delivery time, a rapid method for the dose quality for each possible delivery configuration is provided. However, the delivery configuration (i.e. azimuthal emission angle $\delta\varphi$ in this study) can vary significantly between cases, and dose-volume optimization with simulated annealing can take about 20 minutes for each delivery configuration. Therefore, it is unlikely to make repeated dose-volume optimization for each delivery configuration in clinical practices. In one aspect, this problem is addressed by decoupling the dose optimization and the plan delivery. For each of the two exemplary clinical cases used in this study, an anchor plan which maximizes the minimum dose received by the hottest 90% of the tumor ($D_{90}$) to the tumor but with infeasible delivery time can be generated. This anchor plan can utilize micro-azimuthal-angle $\delta\varphi$ as the azimuthal emission angle, and the dose-volume optimization can be accomplished with simulated annealing. Solutions generated from surface-based optimization can be used as initial solutions to speed up the optimization procedure. The whole optimization procedure can take about 20 minutes to finish. The RSBT emission angle selector can determine the optimal emission angle for a given clinical case by combining neighboring beamlets from the anchor plan to form the beamlets corresponding to larger emission angles $\Delta\varphi=W\delta\varphi$ (W>1). The delivery times for each beam direction for the larger emission angles can be determined by efficiently solving a globally-optimal quadratic programming problem that closely reproduces the angular distribution of beam intensities from the anchor plan. The dosimetric quality assessment for each emission angle $\Delta\varphi$ can take less than about one second.

In an aspect, a Pareto plot of the dosimetric plan quality metric, such as $D_{90}$ versus the delivery time, is generated for the treatment provider. Examples of such an aspect are shown in FIGS. 16(a-b). For each patient, points on a Pareto front (black curve) are generated for each available azimuthal emission angle. A subset of the emission angles is shown for the sake of clarity. Based on these Pareto plots, an appropriate azimuthal emission angle for patient 1 is $\Delta\alpha=202.5°$ and it is superior to the choice of 180° and 135°. For patient 2, $\Delta\varphi=67.5°$ would be a good choice for balancing the dose quality and delivery time in this example. It follows that, the treatment provider can determine the most appropriate emission angle for a given clinical case by considering the tradeoff between the dose quality and the delivery time. In this example, two cervical cancer cases were considered to test the emission angle selection algorithm and associated methods disclosed herein. The RSBT system can be a Xoft Axxent™ electronic brachytherapy source with a 0.2 mm tungsten shield. The goal of each treatment plan was to maximize tumor $D_{90}$ while respective the GEC-ESTRO recommended constraints on the $D_{2\,cc}$ values to the bladder, rectum, and sigmoid colon of 90, 75, and 75 $Gy_3$, respectively, which includes the dose from external beam radiotherapy (EBRT). For the purpose of comparison, the quantitative dosimetric plan qualities and delivery times for several different delivery configurations were calculated, including:

FIG. 17 illustrates exemplary dose distributions for selective delivery configurations for two exemplary clinical cases. FIG. 17(1a) and FIG. 17(2a) illustrate the delivery of doses with an unshielded eBT source, optimized with a surface-based optimizer for the two patients. A delivery using RSBT with all possible azimuthal emission angles, optimized with surface-based optimizer are shown for the two patients in FIG. 17(1b) and FIG. 17(2b). Patient 1 had the delivery applied at azimuthal emission angle $\Delta\varphi=202.50$ and Patient 2 at $\Delta\varphi=67.5°$.

FIG. 17(1c) and FIG. 17(2c) illustrate a delivery using RSBT with anchor plans optimized by both surface-based and dose-volume based optimizer, where azimuthal delivery angle $\Delta\varphi$ equals the micro-azimuthal-angle $\delta\varphi=11.25°$ in this study. FIG. 17(1d) and FIG. 17(2d) illustrate the delivery using RSBT with all possible azimuthal emission angles, using RSBT emission angle selector based on the dose-volume optimized anchor plan. (Patient 1 with $\Delta\varphi=202.5°$) and FIG. 17(2d) (Patient 2 with $\Delta\varphi=67.50$).

Appendix C illustrates yet another example of optimal emission angle selection in rotating shield BT illustrating another example of decoupling the sequencing procedure from dose optimization as described in the present disclosure.

Appendix D illustrates yet another example of a combinatorial optimization method for sequencing the rotating shields in IMBT described in the present disclosure.

Appendix E illustrates yet another example of a combinatorial optimization method for sequencing the rotating shields in IMBT described in the present disclosure.

In other embodiments of the disclosure, a method for facilitating the procedure of determining the delivery in dynamic rotating-shield brachytherapy (D-RSBT), called optimal sequencing for D-RSBT (OSD) is provided. D-RSBT, as an intensity modulation technique, can enable the delivery of deliberately non-symmetric, tumor-conformal, dose distributions that would be impossible to deliver with conventional radiation sources by using a source encapsulated by two partial shields. Using a small emission angle (referred as azimuthal step angle $\delta\varphi$), the dose optimizers can achieve high tumor dose conformity. However, the time necessary to treat a tumor with RSBT is inversely proportional to the shield emission angle, thus small emission angle shields increase delivery times. By decoupling the delivery step from the optimization step, OSD can enable treatment providers to make a quick decision on the trade-off between the dose quality and the delivery time based on the time budget for treatment and designated goal of plan quality. OSD is a method that can enable a reduction in the treatment time necessary to deliver an RSBT treatment.

Further, S-RSBT performs well in clinical cases where the targets are regularly shaped, however, when the shapes of targets become increasingly irregular, the REAS techniques applied to S-RSBT as described above may become less useful. Without wishing to be bound by theory and/or simulation, approximating a wavy curve is generally harder than approximating a smoother curve using the same window with fixed size. In one aspect, by using a coupled partial-shield, the D-RSBT applicator can enable adjustment of the emission angle even during the delivery, as shown in FIG. 20. Therefore, in those cases, D-RSBT can enable better delivery plans than S-RSBT as it can have a much wider selection of beams than S-RSBT.

Unlike S-RSBT, the delivery time is the primary factor influencing the dose quality in D-RSBT. As D-RSBT allows use of any azimuthal emission angle less than 180°, the OSD algorithm can enable improved reproduction of the dose distribution of anchor plans while reducing the delivery times to produce the dose distribution given an adequate delivery time budget. Even when presented with a suboptimal delivery time budget, the plan generated by OSD algorithm can be of comparable or improved quality compared to one generated using REAS as the set of beams used in S-RSBT (with azimuthal emission angle less than 180°) are a subset of the beams used in D-RSBT. Thus, in one aspect of the present disclosure, D-RSBT using OSD algorithm can enable the most accurate approximation of the anchor plans under any given delivery time budget.

One or more embodiments of the present disclosure provide for a method for optimal sequencing in D-RSBT that can enable a treatment provider to make a rapid and appropriate shield selection while (i) controlling the delivery time below a certain time budget to minimize loss of dose quality; or (ii) controlling the dose quality (e.g. HR-CTV $D_{90}$) above a certain goal while minimizing the delivery time. In another aspect, a treatment provider can balance the delivery time and the dose quality for each individual clinical case. Other aspects of the present methods enable treatment providers to select the proper shield, balancing the dose quality and the delivery time for each individual clinical case, in a reasonable time with an OAS-generated Pareto plot, an example of which is shown in FIG. 21. Each point on the Pareto plot represents the highest $D_{90}$ that can be achieved with the delivery time specified by its x-coordinate or the least delivery time required for achieving the $D_{90}$ specified by its y-coordinate.

In one aspect, radiation source model and dose calculation can be accomplished by the following method. An RSBT beamlet, $\dot{D}_{i,j,k}(\Delta\varphi,\Delta\theta)$, can be defined as the dose rate at the point $\vec{r}_i$ due to a shielded radiation source at dwell position $\vec{s}_j$ (j=0, . . . , J−1). As shown in FIG. 20, the shield has an azimuthal emission angle of $\Delta\varphi$ and a zenith emission angle of $\Delta\theta$. The irradiation direction of the beamlet is defined by $\varphi_k$, which is the lower of the two azimuthal angles defining the aperture: $\varphi_k$=(k mod K)$\delta\varphi$(k=0, . . . , K−1), where $\delta\varphi$=360° and K is the azimuthal step size between neighboring beamlets. The mod operation denotes modular arithmetic, enabling beamlet referencing with arbitrary integer k-values such that $\varphi_{k+K+1}=\varphi_{k+1}$. The upper azimuthal edge of beamlet k is located at angle $\varphi_k+\Delta\varphi$. The total dose delivered to point i from a shielded source with azimuthal and zenith emission angles of $\Delta\varphi$ and $\Delta\theta$, respectively, can be calculated, in one aspect, as a time-weighted sum of the appropriate beamlets over all dwell positions and emission angles:

$$d_i(\Delta\varphi, \Delta\theta) = \sum_{j=0}^{J-1}\sum_{k=0}^{K-1} \dot{D}_{i,j,k}(\Delta\varphi, \Delta\theta) t_{j,k}, \qquad \text{Eq. (6)}$$

where $t_{j,k}$ is the dwell time, which is always greater than or equal to zero, for which the source is pointed in direction $\varphi_k$ while it is located at dwell position j. The source step length along the source trajectory, $\Delta\lambda$, was set to 3 mm. As with $\varphi_k$, $\dot{D}_{i,j,k}(\Delta\varphi,\Delta\theta)$ and $t_{j,k}$ are periodic functions of the index k with a period of K.

In another aspect, generating beamlets can be accomplished by the following methods. The baseline beamlets can be defined as the beamlets generated using the baseline azimuthal angle, $\delta\varphi$. The baseline beamlets at a given dwell position j can be assumed to be non-overlapping, thus the shadows cast by the shields of neighboring beamlets (k and k+1 for a given dwell position j) do not overlap. An integer number, W (W≥1), of neighboring baseline beamlets can be combined by superposition to produce a beamlet with a larger emission angle, $\Delta\varphi_w=W\beta\varphi$, in one aspect, as follows:

$$\dot{D}_{t,j,k}(\Delta\varphi_W, \Delta\theta) = \sum_{p=0}^{W-1} \dot{D}_{i,j,k-p}(\delta\varphi, \Delta\theta), \qquad \text{Eq. (7)}$$

generating a set of "W-beamlets." Equation (7) is exact for the case of zero shield transmission, which is a safe assumption for the example of a Xoft Axxent™ shielded with 0.5 mm of tungsten.

In an example in which the W neighboring baseline beamlets, with indices from k to k+W−1, all share delivery times of $t_{j,k}=\tau$, it follows from Equation (7) that the W neighboring beamlets can be replaced with a single beamlet with an emission angle $\Delta\varphi w$ and a delivery time of $t_{j,k}^W=\tau$, where the t-superscript indicates that the delivery time is associated with a beamlet with an emission angle of $\Delta\varphi w$. Conversely, a beamlet with an emission angle of $\Delta\varphi w$ and a delivery time of r can be replaced with the baseline beamlets with indices between k and k+W−1, which will have delivery times of $t_{j,k}^1=\tau$. Thus an entire set of dwell times associated with beamlets of emission angle $\Delta\varphi w$ can be written as a set of baseline dwell times (W=1), in one aspect, as follows:

$$t_{j,k}^{W\to 1} = \sum_{k'=0}^{K-1} t_{j,k'}^{W} \prod\left(\frac{(k-k')\bmod K}{W}\right), \qquad \text{Eq. (8)}$$

where $$\prod\left(\frac{a}{W}\right)$$

is unity when 0≤a≤W−1 (a is an integer) and zero otherwise. The purpose of the $\prod$-function is to spread the dwell times from the $\Delta\varphi_W$ emission angle beamlets over multiple baseline beamlets. The modular arithmetic in its argument makes $\prod$ a periodic function of k' with period W. Equation (8) can, in one aspect, be simplified by changing summation indices for k' to p=k−k' as follows:

$$t_{j,k}^{W\to 1} = \sum_{p=0}^{K-1} t_{j,k-p}^{W} \prod\left(\frac{p \bmod K}{W}\right) = \sum_{p=0}^{W-1} t_{j,k-p}^{W'}, \qquad \text{Eq. (9)}$$

Since the sum over k' in Equation (8) is over one period of a periodic function of k', the summation over p in the middle expression of Equation (9) can be done over the same range, even after changing variables.

In yet another aspect, a treatment plan can be generated from anchor plans using the following methods. A treatment plan generated using the W-beamlets (W>0) and in-house dose-volume optimizer can be denoted as $\hat{P}^1$ (also referred as the "baseline anchor plan"), which has dwell times of $\hat{t}_{j,k}^1$ and a dose distribution $\hat{d}_t^1$. As the dose-volume optimization is a non-convex optimization problem and no polynomial algorithm exists, simulated annealing techniques, in one aspect, can be applied to solve the dose-volume optimization. In order to make simulated annealing efficient, initial solutions can be generated with a surface optimizer which uses a gradient-based least squares method to optimize the dose homogeneity on the HR-CTV surface. The simulated annealing can require about 10-20 minutes to converge, even with initial guesses from the surface optimizer.

In another aspect, baseline anchor plans can have a high dose quality due to their small emission angle; however, they also have impractical delivery times as the plans only utilize the W-beamlets.

In other aspects, in order to utilize the full range of possible W-beamlets, there are two different options: First, delivery plans for D-RSBT can be generated directly by using the union of all W-beamlets that satisfies W$\delta\varphi$≤180° in the dose optimizer. However, that this option can place high demand on available computational resources (e.g., memory and CPU time) and the simulated annealing optimizer can, in one aspect, be rendered unable to compute due memory overflow (e.g., on a 4 GB workstation); the computational time for the gradient method can increase by about 5 times; and, meanwhile, delivery time can be decreased. Second, delivery plans for D-RSBT can be generated using the baseline anchor plan and applying OSD which can access all possible W-beamlets to reproduce the dose distribution of the baseline anchor plan within a given delivery time. This option places less demand on available computational resources. In another aspect, as shown in FIG. 22, using the full range of W-beamlets in the optimizer can enable achievement of approximately the same quality as the baseline anchor plans with a shorter delivery time; and the OSD algorithm can enable further reductions of about 40% in the delivery time. Five exemplary clinical cases are used for this comparison. For each exemplary clinical case, a baseline anchor plan was first computed (using gradient-based optimizer as the simulated annealing optimizer cannot finish for the latter optimization with a full range of beamlets) and is referred to as "baseline" in the table. Next, another delivery plan with full range of beamlets was computed with the same gradient-based optimizer and is referred to as "full" in the table. Then, an OSD algorithm is applied to the plan generated from the full delivery and is referred to as "OSD" in the table.

The OSD algorithm, in one aspect, can be formulated through Equation (10).

$$\min \sum_{j=0}^{J-1} \sum_{k=0}^{K-1} \left( \tilde{t}_{j,k}^1 - \vec{t}_{j,k}^{\,1} \right)^2 \quad \text{Eq. (10)}$$

$$\text{s.t. } \vec{t}_{j,k}^{\,1} = a_{j,k} - b_{j,k} + a_{j,K-1}, \ 0 \le k < W_{max}$$

$$\vec{t}_{j,k}^{\,1} = a_{j,k} - b_{j,k}, \ W_{max} \le k \le K$$

$$a_{j,k} \le a_{j,k-1}, \ b_{j,k} \le b_{j,k-1}, \ a_{j,k} \le a_{j,k-1}, \ a_{j,0} \ge 0$$

$$\sum_{j=0}^{J-1} a_{j,k-1} \le T^{max}$$

In Equation (10), $\tilde{t}_{j,k}^{\,1}$ stands for the dwell time of the baseline equivalent of the OSD generated plan, $a_{j,k}$ and $b_{j,k}$ are related to the time point when the tailing and leading field edges pass the direction $k\delta\varphi$ at dwell position j. $T^{max}$ stands for the delivery time budget and can be used to control the balance between dose quality and the delivery time.

With the solution to Equation (10), $\tilde{t}_{j,k}^{\,1}$ is then scaled to ensure that the constraints on the minimum doses to the hottest 2 cm³ ($D_{2\ cc}$) of OARs do not exceed the tolerance. Obtaining the OSD sequenced plan by solving the sequencing problem in Equation (10) can require less computational resources than all the dose optimization problems above, since the problem concerns times only, rather than doses.

FIG. 23 is a flowchart of an exemplary method 2300 for using OSD in D-RSBT treatment planning. Also shown in FIG. 23 is an exhaustive replanning method (either simulated annealing or gradient-based) for comparison. A computer or computing device can implement (e.g., execute) exemplary method 2300. In one aspect, a processor within or functionally coupled to the computer or computing device can be configured to execute computer-executable instructions and, in response to execution, the processor can carry out the various steps that comprise exemplary method 2300. Similarly, yet not identically, the computer or computing device can execute the various methods, or portion(s) thereof, disclosed herein. The exemplary method 2300 can comprise various steps. At step S2310, receiving data indicative of a radiation treatment and topology of a region to be treated. At step S2320, receiving input parameters for azimuthal emission angle and azimuthal emission step ratio for at least one anchor plan. At step S2330, calculating a dose. At step S2340, optimizing the calculated dose using at least one of surface optimization and dose-volume optimization.

At step S2342, enumerating all possible input parameters, which are a set of time bounds. In an aspect, such parameters are the delivery time budgets. At step S2344, approximating the dose distribution created from S2340, which is made subject to a delivery time constraint or budget from S2342. To find a balance between the dose quality and the delivery time, S2342 enumerates a set of different time budges, and the delivery efficiency curve is generated accordingly. At step S2350, evaluating a treatment plan which may include dose scaling to satisfy dose limits for any organs at risk. At step S2360, generating output metrics which may include generating a Pareto plot.

In one aspect, use of the OSD technique can result in significant reductions in delivery time relative to the baseline anchor plans without significantly impacting dose quality. In another aspect, the time cost of OSD can be negligible (e.g., a few seconds). In another aspect, compared to S-RSBT, OSD generated plans can have improved quality for cases with irregular geometries.

In another example of the methods of this disclosure, beamlets can be generated using a dose calculator and the anchor plans can be computed using a dose-volume based optimizer (using simulated annealing). The optimizer can maximize the $D_{90}$ to HR-CTV while keep the $D_{2\ cc}$ of the rectum, sigmoid colon, and bladder below 75, 75, and 90 $Gy_3$, respectively. A surface based optimizer (using gradient method) can be applied first to obtain an initial solution in order to speed up the subsequent dose-volume optimization. In this aspect, it can be shown that: (i) dose-volume optimization can increase the $D_{90}$ for about 10 $Gy_{10}$ compared to surface optimization with an extra computation time of about 10-20 min.; and (ii) without the initial solutions from the surface optimization, the dose-volume optimization can take over 5 hours to converge.

The OSD algorithm of the present disclosure can also be referred to as circular integral block decomposition (CIBD). Exemplary results of OSD are shown in FIG. 24 and FIG. 25.

In an aspect, a globally-optimal algorithm based on combinatorial optimization technique that balances the trade-off between treatment plan quality and delivery time is presented and can enable efficient D-RSBT delivery. In another embodiment, a CIBD problem can be configured to seek for an optimal set of circular blocks that stacks up to approximate a given reference integral function defined on a circular interval. This problem can be an effective model of the radiation dose delivery in D-RSBT. One challenge can lie in the circularity of the problem domain and the maximum length constraint of the circular blocks. In one aspect, an efficient polynomial time algorithm for solving the CIBD problem can be provided, enabling formulation of the CIBD problem as a convex cost integer dual network flow. In another aspect, implementation of the CIBD algorithm can run relatively fast and can produce promising D-RSBT treatment plans.

In one aspect, a CIBD problem can be provided and two integer parameters w>0 and H>0, and a non-negative integral function t that can be defined on a circular interval C=[0, n−1]. A circular window function $f_k(x)$, with $$f_k(x) = \begin{cases} h_k, & \text{if } x \in I_k \subset C, \\ 0, & \text{otherwise,} \end{cases}$$

where $h_k$>0 is an integer constant and $|I_k| \le w$. can be provided. In one aspect, the CIBD problem can be utilized to find a set of circular window functions $f_k(x)$ that approximates the given function t by tiling them up and the total height of the window functions $\Sigma h_k \leq H$.

As shown by FIG. 19, a function t can be defined on a circular interval with n=4, namely $x \in \{0, 1, 2, 3\}$ (CCW) and $t(x)=\{4, 5, 2, 4\}$. In one aspect, the function can then be perfectly decomposed (error-free) to a set of 4 circular window functions, denoted as $\mathbf{B} =\{\langle\ 0, 2, 2\rangle\ , \langle\ 1, 0, 1\rangle\ , \langle\ 2, 0, 1\rangle\ , \langle\ 3, 2, 2\rangle\ \}$, where each triplet $\langle\ a_k, b_k, h_k\rangle$ represents a circular window function, with $$f_k(x) = \begin{cases} h_k, & \text{if } a_k < b_k, x \in I_k = [a_k, b_k - 1] \\ h_k, & \text{if } a_k \geq b_k, x \in I_k = [a_k, n-1] \cup [0, b_k - 1] \\ 0, & \text{otherwise} \end{cases} \quad (1)$$

Throughout this disclosure, circular window functions can also be referred to as a "block." In one aspect, the maximal window size w among those blocks is 3 and the total height of all window functions is $\Sigma h_k = 6$. In yet another aspect, function yield by tiling up all window functions in $\mathbf{B}$ can be defined as $$\mathcal{F}_B(x) = \sum_{f_k \in B, x \in I_k} h_k \quad (2)$$

and $\forall x \in [0, n-1]$. $\mathcal{F}_B(x)=t(x)$.

In certain aspects, due to the constraint $\Sigma h_k \leq H$, an exact decomposition of t may not be found. In one aspect, the CIBD problem can be defined as the following optimization problem:

$$\min \mathcal{E}(B) = \sum_{x=0}^{n-1} (\mathcal{F}_B(x) - t(x))^2$$

s.t. $1 \leq b_k - a_k \leq \omega$ or $1 \leq b_k + n - a_k \leq \omega$, $k \in [1, |B|]$ $$\sum_{k=1}^{|B|} h_k \leq H$$

$a_k, b_k \in [0, n-1], h_k > 0, a_k, b_k, h_k \in \mathbb{Z}$, $k \in [1, |B|]$ Such CIBD problems can arise in the state-of-the-art Dynamic Rotating-Shield Brachytherapy (D-RSBT), which is another intensity-modulation technology for delivering radiation dose in brachytherapy.

In D-RSBT, the radiation source is partially-covered by a multi-layered radiation-attenuating shield, forming directed apertures called beamlets by rotating the field edges as illustrated in FIG. 20. The leading and tailing field edge can rotate independently, stopping at n discrete positions that can be distributed evenly along the circle. Each beamlet can be defined by the directions of the leading and tailing field edges with their rotation angles relative to some reference angle 0°.

In one aspect, for any known set of beamlets, a dose optimizer can assign emission times for those beamlets to optimize the dose distribution. However, as the quality of a dose distribution can be evaluated based on dose-volume metrics, such as the $D_{90}$: minimum dose that covers 90% of the high risk clinical tumor volume; and the $D_{2\,cc}$: minimum dose that is absorbed in the most irradiated 2 cm³ of each individual organ at risk, and these metrics can be non-convex. Due to the non-convex nature of these metrics, optimizing the dose distribution regarding the emission times can be time consuming. In one aspect, instead of using $\mathcal{O}(n^2)$ possible beamlets, the optimization can be accomplished with a set of n beamlets with a fine azimuthal emission angle $\varphi$, which are called baseline beamlets. Dose optimization with baseline beamlets can yield high-quality dose distributions, but the delivery is typically impractical as it can require a long time to finish. The output of dose optimization, in one aspect, defines an integral function t assigning each baseline beamlet an integral emission time. The delivery time can be the total emission time of all n baseline beamlets, which can be impractical from a clinical standpoint. RSBT can be time-critical since the process should occur rapidly in order to ensure effective utilization of clinical resources, as the patient is typically under general, epidural, or spinal anesthesia throughout the process. It follows that an additional sequencing step configured to make a trade-off between the delivery time and the dose quality could be beneficial. In one aspect, to reduce the delivery time, several consecutive baseline beamlets can be combined into a larger deliverable beamlet $B_k$, denoted by $\langle a_k, b_k, h_k\rangle$ with the leading field edge pointing to $a_k=a_k\varphi'$ and the tailing field edge pointing to $B_k=b_k\varphi$ with an emission time $h_k$. The delivery time can then be the total sum of $h_k$ of all those deliverable beamlets used. Given a delivery time threshold H, the sequencing problem can be to find a set B of deliverable beamlets whose total delivery time is no larger than H and well approximates the dose distribution output by the dose optimization with minimum dose errors, that is, $\Sigma_{x=0}^{n-1}(\mathcal{F}_B(x)-t(x))^2$ is minimized. In another aspect, due to the physical constraint of the shielding device illustrated in FIG. 20, there is a maximum opening w of the deliverable beamlets. Hence, the D-RSBT sequencing problem can be modeled as a CIBD problem.

It should be appreciated that the CIBD problem arises from D-RSBT. In certain scenarios, the CIBD problem can have similarities to the Generalized Shape Rectangularization (GSR) problems and the Coupled Path Planning (CPP) problems for Intensity-Modulated Radiation Therapy. In one aspect, one significant difference between the CIBD problem and GSR/CPP is that the CIBD problem is defined on a circular interval with the maximum window constraint; whereas the GSR/CPP problem is defined on a linear interval. The circularity of the problem domain and the maximum window constraint introduce complexity into the CIBD problem. In another aspect, the CIBD problem is also closely related to the $DCCF_0$ problem, in which the energy function $\varepsilon_0(y)=\Sigma_{(u,v)\in E}V_{uv}(x_v-x_u)$ is minimized subject to $y\in\mathbb{Z}^V$, where $V_{uv}$ are convex functions. $DCCF_0$ can be solved by the algorithm proposed by Ahuja, et al. (Management Science 49(7), 950964 (2003)) with time $\mathcal{O}(nm \log (n^2/m)\log(nK))$, which is the best known algorithm on this problem. Other differences between the CIBD problem and the $DCCF_0$ problem include: (i) CIBD is not $L_\natural$-convex due to the maximal window constraints and the circular domain constraint; and (ii) the number of functions $V_{uv}$ is bounded by $\mathcal{O}(n)$.

In one aspect, the challenges arising from the maximal window constraint and the circularity of the CIBD problem when formulated as a convex cost integer dual network flow problem can be dealt with to enable a solution to the CIBD problem in $\mathcal{O}(n^2 \log nH)$ time. Due to the space limit, the details on the proofs of lemmas, theorems and the algorithmic details are found in the Appendix A.

In one aspect, the CIBD problem can be defined on a circular interval C=[0, n−1], and a window function (a block) can be defined on a sub-interval $[a_k, b_k] \subset C$ with $a_k$, $b_k \in [0, n-1]$. Without loss of generality, a block is a feasible if and only if $\langle (a_k, b_k, h_k) \rangle$ with $b_k > a_k \geq 0$, $(b_k - a_k) \leq w$, $a_k < n$ and $h_k > 0$. Thus, $a_k \in [0, n-1]$ and $b_k \in [0, n+w-1]$.

Definition 1.

A blockset B is feasible if and only if $\forall \mathbf{B}_k = \langle a_k, b_k, h_k \rangle \in B$, $a_k \in [0, n-1]$, $b_k \in [0, n+w-1]$, $1 \leq b_k - a_k \leq w$ and $h_k > 0$.

Definition 2.

Two blockset B and B' are equivalent if and only if $\mathcal{F}_B = \mathcal{F}_{B'}$, and $H_B = H_{B'}$, where $\mathcal{F}_B = \mathcal{F}_{B'}$ stands for a function equivalence:

$\forall x \in [0, n-1]$, $\mathcal{F}_B(x) = \mathcal{F}_{B'}(x)$; and $H_B = \Sigma_k h_k$ stands for the total height of blocks in a blockset B.

Definition 3.

A feasible blockset $B = \{\langle a_k, b_k, h_k \rangle | k \in [1, K]\}$ is canonical if and only if B satisfies the following properties:

CB1. $\forall k \in [1, K-1]$, $a_k \leq a_{k+1}$, $b_k \leq b_{k+1}$;
CB2. $b_K - n \leq b_1$;

Lemma 1.

For any feasible blockset B, there exists a canonical blockset $\overline{B} = \{\langle \overline{a}_k, \overline{b}_k, \overline{h}_k \rangle | k \in [1, \overline{K}]\}$ such that $\overline{B}$ and B are equivalent.

According to Lemma 1, the CIBD problem can be solved by considering canonical blocksets only.

In one aspect, a pair of functions $(\mathcal{L}, \mathcal{R})$ for a canonical blockset $B = \{B_1, B_2, \ldots, B_K\}$, can be defined as follows.

$$\mathcal{L}(x) = \sum_{B_k \in B, a_k \leq x} h_k, \forall x \in [0, n-1]$$

$$\mathcal{R}(x) = \sum_{B_k \in B, b_k \leq x} h_k, \forall x \in [0, n+\omega-1]$$

$$\mathcal{F}_{(\mathcal{L},\mathcal{R})}(x) = \begin{cases} \mathcal{L}(x) - \mathcal{R}(x) + \mathcal{L}(n-1) - \mathcal{R}(n+x), & \forall x < \omega \\ \mathcal{L}(x) - \mathcal{R}(x), & \forall x \geq \omega \end{cases}$$

Notice that $\mathcal{L}(n-1) = \Sigma_{k, a_k \leq n-1} h_k = \Sigma_{k=1}^K h_k = H_B$.

Lemma 2.

If $(\mathcal{L}, \mathcal{R})$ is defined with a canonical blockset B, then $\mathcal{F}_{(\mathcal{L},\mathcal{R})}(x) = \mathcal{F}_B(x)$ for any $x \in [0, n+w-1]$.

Definition 4.

A function pair $(\mathcal{L}, \mathcal{R})$ with $\mathcal{L}: [0, n-1] \to \mathbb{Z}$ and $\mathcal{R}: [0, n+w-1] \to \mathbb{Z}$ is admissible if and only if $(\mathcal{L}, \mathcal{R})$ satisfies the following properties;

AD1: $\mathcal{L}$ and $\mathcal{R}$ are non-negative, $\mathcal{L}(0)=0$:
AD2: $\mathcal{L}$ and $\mathcal{R}$ are monotonically non-decreasing. i.e. $\forall x \in [0, n-2]$, $\mathcal{L}(x) \leq \mathcal{L}(x+1)$; $\forall x \in [0, n+w-2]$, $\mathcal{R}(x) \leq \mathcal{R}(x+1)$;
AD3: $\forall x \in [0, n-1]$, $\mathcal{L}(x) \geq \mathcal{R}(x)$; $\forall x \in [n, n+w-1]$, $\mathcal{L}(n-1) \geq \mathcal{R}(x)$; particularly, $\mathcal{L}(n+w-1) = \mathcal{L}(n-1)$:
AD4: $\forall x \in [0, n-1]$, $\mathcal{L}(x) \leq \mathcal{R}(x+w)$:
AD5: $\forall x \in [0, n-1]$, $\mathcal{L}(x) \geq \mathcal{R}(x+1)$;
AD6: $\forall x \geq b_1 + n$, $\mathcal{R}(x) = \mathcal{L}(n-1)$, where $b_1 = \min \arg (\mathcal{R}(x) > 0)$.

Lemma 3.

If a function pair $(\mathcal{L}, \mathcal{R})$ is defined with a canonical blockset B, then it is admissible.

Lemma 4.

If a function pair $(\mathcal{L}, \mathcal{R})$ is admissible, then there exists a canonical blockset B, with $\mathcal{F}_B(x) = \mathcal{F}_{(\mathcal{L},\mathcal{R})}(x)$ for any $x \in [0, n+w-1]$, and $\mathcal{L}(n-1) = H_B$.

Theorem 1.

For any canonical blockset B, we can find an admissible function pair $(\mathcal{L}, \mathcal{R})$ with $\mathcal{F}_B(x) = \mathcal{F}_{(\mathcal{L},\mathcal{R})}(x)$, $H_B = \mathcal{L}(n-1)$, and vice versa.

In one aspect, according to Theorem 1, the objective of the CIBD problem can be formulated as:

$$\min \mathcal{E}(\mathcal{L}, \mathcal{R}) = \sum_{x=0}^{\omega-1} (\mathcal{L}(x) - \mathcal{R}(x) + \mathcal{L}(n-1) - \mathcal{R}(n+x) - f(x))^2 + \sum_{x=\omega}^{n-1} (\mathcal{L}(x) - \mathcal{R}(x) - f(x))^2 \quad \text{Eq. (11)}$$

However, not all properties can be expressed with linear constraints defined with $(\mathcal{L}, \mathcal{R})$ since $b_1$ in (AD6) remains unknown until $(\mathcal{L}(x), \mathcal{R}(x))$ is known. In one aspect, moreover, Equation (6) is not sub-modular since the off-diagonal non-positivity cannot stand with more than 2 variables in a single term of the quadratic objective function, and lacking of sub-modularity can make this problem hard to solve.

In one aspect, the following transformation for admissible function pairs $(\mathcal{L}, \mathcal{R})$ can be introduced.

$$\overline{\mathcal{R}}(x) = \begin{cases} \mathcal{R}(n+x) - \mathcal{L}(n-1), & \forall x \in [0, b_1 - 1] \\ \mathcal{R}(x), & \forall x \in [b_1, n-1] \end{cases} \quad \text{Eq. (12)}$$

In a further aspect, the CIBD problem can then be formulated, as follows.

$$\min \mathcal{E}(\mathcal{L}, \overline{\mathcal{R}}) = \sum_{x=0}^{n-1} (\mathcal{L}(x) - \overline{\mathcal{R}}(x) - f(x))^2 \quad \text{Eq. (13)}$$

s.t. $\mathcal{L}(x) \leq \mathcal{L}(x+1), \forall x \in [0, n-2]$ (13a)

$\overline{\mathcal{R}}(x) \leq \overline{\mathcal{R}}(x+1), \forall x \in [0, n-2]$ (13b)

$\mathcal{L}(x) \leq \overline{\mathcal{R}}(x+\omega), \forall x \in [0, n-\omega-1]$ (13c)

$\mathcal{L}(x) \leq \overline{\mathcal{R}}(x+\omega-n) + \mathcal{L}(n-1), \forall x \in [n-\omega, n-1]$ (13d)

$\overline{\mathcal{R}}(x) \leq \mathcal{L}(x-1), \forall x \in [1, n-1]$ (13e)

$\overline{\mathcal{R}}(0) \leq 0, \mathcal{L}(0) \geq 0, \mathcal{L}(n-1) \leq H$ (13f)

Lemma 5.

For any admissible function pair $(\mathcal{L}, \mathcal{R})$, $(\mathcal{L}, \overline{\mathcal{R}})$ is feasible to Equation (8) with $\varepsilon(\mathcal{L}, \mathcal{R}) = \varepsilon(\mathcal{L}, \overline{\mathcal{R}})$ and for any feasible solution $(\mathcal{L}, \overline{\mathcal{R}})$, to Equation (13), there exist an admissible function pair $(\mathcal{L}, \mathcal{R})$, such that $\varepsilon(\mathcal{L}, \mathcal{R}) = \varepsilon(\mathcal{L}, \overline{\mathcal{R}})$;

Proof.

As illustrated in FIG. 26, to illustrate the correctness of Lemma 5, first, the one-to-one correspondence between admissible function pairs $(\mathcal{L}, \mathcal{R})$, and feasible solutions $(\mathcal{L}, \overline{\mathcal{R}})$, to Equation (12) can be shown.

According to Equation (12), in one aspect, any admissible function pairs $(\mathcal{L}, \mathcal{R})$, can be uniquely mapped to a solution $(\mathcal{L}, \overline{\mathcal{R}})$ by shifting $\mathcal{R}$ ($x \in [n, n+w-1])$n units leftwards and $\mathcal{L}(n-1)$ units downwards, as illustrated by FIG. 26. Notice that, the domain of $\overline{\mathcal{R}}$ is reduced from [0, n+w-1] to [0, n+w−1] compared to $\overline{\mathcal{R}}$ as the shifting operation overlapped the intervals [0, w−1] and [n, n+w−1]. According to (AD6), $\forall x \in [0b_1]$, $\overline{\mathcal{R}}(x)=0$, and $\forall x \in [b_1, w-1]$, $\overline{\mathcal{R}}(n+x)=\mathcal{L}(n-1)$; I.e. $\forall x \in [0, w-1]$ either $\overline{\mathcal{R}}(x)=0$ or $\overline{\mathcal{R}}(n+x)=\mathcal{L}(n-1)$ or both. That can serve to enable a unique mapping from $(\mathcal{L}, \overline{\mathcal{R}})$ back to $(\mathcal{L}, \mathcal{R})$ with, in one example, the following equation:

$$\mathcal{R}(x) = \begin{cases} \overline{\mathcal{R}}(x), & x \in [w, n-1] \text{ or } (x<w, \overline{\mathcal{R}}(x) \geq 0) \\ 0, & x < w, \overline{\mathcal{R}}(x) < 0 \\ \mathcal{L}(n-1), & x \geq n, \overline{\mathcal{R}}(x-n) \geq 0 \\ \mathcal{L}(n-1)+\overline{\mathcal{R}}(x-n), & \geq n\overline{\mathcal{R}}(x-n) < 0 \end{cases} \quad \text{Eq. (14)}$$

Together with Equation (14), Equations (13a) and (13b) can be used to enforce the non-decreasing property AD2; Equations (13c) and (13d) can enforce the maximal window constraint AD4; Equation (13e) can encode AD5 which can exclude infeasible blocks with 0 width; AD6 can be enforced by $\overline{\mathcal{R}}(0) \leq 0$ based on Equations (12) and (14); the non-negativity AD1 can be inferred from $\mathcal{L}(0) \geq 0$. Equations (13a) and (13b); and $\mathcal{L}(n-1) \leq H$ can be used to enforce the constraint on total height of blocks. AD3 is inferred by AD2 and AD5.

In one aspect, the optimization problem in Equation (13) can be solved in $O(n^2 \log(nH))$ time with Ahuja's algorithm $f\mathcal{L}^{(n-1)}$ is known. Thus, it can be solved in $O(n^2 \log(nH))$ time. In another aspect, discovering the following property of the problem enables an improved method for optimization.

Theorem 2.

If there exist some feasible solution to Equation (13), i.e. dom $\varepsilon \neq \emptyset$, and $H \leq \Sigma_{x=0}^{n-1} f(x)$, then there exist a solution $y^* = (\mathcal{L}^*, \overline{\mathcal{R}}^*)$ such that $\mathcal{L}^*(n-1)=H$ and $\forall y \in$ dom $\varepsilon$, $\varepsilon(y^*) \leq \varepsilon(y)$.

Proof.

Theorem 2 can be proved in a constructive way, i.e. suppose there exists some other optimal solution $y'=(\mathcal{L}', \overline{\mathcal{R}}')$ such that $H'=L'(n-1) \leq H$ and $\forall y \in$ dom $\varepsilon$, $\varepsilon(y') \leq \varepsilon(y)$, then another solution can be $y^* = (\mathcal{L}^*, \overline{\mathcal{R}}^*)$ with $\mathcal{L}'(n-1)=H$ and $\varepsilon(y^*) \leq \varepsilon(y')$.

The construction of $y^*$ differs in two different cases. For the first case, if $H \leq \Sigma_{x=0}^{n-1} (\mathcal{L}'(x) - \overline{R}'(x))$, set $y^* = (\mathcal{L}' + \delta, \overline{\mathcal{R}}' + \delta)$, where $$\delta(x) = \begin{cases} \min\{\overline{\mathcal{R}}'(0), H-H'\} & x=0 \\ \min\{\mathcal{L}'(x-1)-\overline{\mathcal{R}}'(x)+\delta(x-1), H-H'\} & x>0 \end{cases} \quad \text{Eq. (15)}$$

In one aspect, the function $\delta$ can be applied to $y'$ in order to make the new solution $y^*=(\mathcal{L}^*, \overline{\mathcal{R}}^*)$ can satisfy $\mathcal{L}^*(n-1)=H$ without changing the objective value while preserving all the constraints.

For the second case, where $H>\Sigma_{x=0}^{n-1}(\mathcal{L}'(x)-\overline{\mathcal{R}}'(x))$, let $y''=(\mathcal{L}'', \overline{\mathcal{R}}'')=(\mathcal{L}'+\delta, \overline{\mathcal{R}}'+\delta)$, where $\delta$ can be the same as defined in Equation (15). As same as the previous case $y''$ can be feasible to Equation (13) and $\varepsilon(y'')=\varepsilon(y')$, however, $\mathcal{L}''(n-1)<H$. But, in one aspect, $y''$ has its specialties: $\overline{\mathcal{R}}''(0)=0$ and $\forall x \in [0,n-1]$, $\overline{\mathcal{R}}''(x)=\mathcal{L}''(x-1)$ (define $\mathcal{L}''(-1)=0$). By enforcing these two specialties into Equation (13), Equation (13b)-(13e) becomes redundant, and Equation (13f) can be rewritten to $\mathcal{L}(n-1) \leq H$, $\mathcal{L}(0)=0$. In one aspect, the constraint $\mathcal{L}(0)=0$ as CIBD" can be relaxed. Assuming $\mathcal{L}^o(n-1)=H$, finding the solution $y^o=\mathcal{L}^o$ with $\varepsilon''(\mathcal{L}^o)=0$ to CIBD" can be done in linear time (the objective function of CIBD" is defined as $\varepsilon''(\mathcal{L})=\Sigma_{x=0}^{n-1}(\mathcal{L}(x)-\mathcal{L}(x-1)-f(x))^2$, the $\overline{\mathcal{R}}$ part of the solution is omitted since it can be determined by $(\mathcal{L})$.

Then, $y^*=(\mathcal{L}^*, \overline{\mathcal{R}}^*)$ can be assigned with $\forall x \in [0,n-1]$, $\mathcal{L}^*(x)=(\mathcal{L} \wedge \mathcal{L}^o)(x)$, $\overline{\mathcal{R}}^*(x)=(\mathcal{L}'' \wedge \mathcal{L}^o)(x-1)$. According to the L$^\natural$-convexity of CIBD", $\varepsilon(y^*)=\varepsilon^*(\mathcal{L}'' \vee \mathcal{L}^o) \leq \varepsilon'(\mathcal{L}'')=\varepsilon(y')$. By further showing $(\mathcal{L}'' \vee \mathcal{L}^o)(-1)=\mathcal{L}''(-1)=0$, $(\mathcal{L}'' \vee \mathcal{L}^o)(n-1)=\mathcal{L}^o(n-1)=H$, it can be shown that $y^*$ is feasible to Equation (13) and it can also be a global optimizer.

According to Theorem 2, whenever $H \leq \Sigma_{x=0}^{n-1} f(x)$, Equation (13) can be solved by setting $\mathcal{L}(n-1)=H$. Setting $\mathcal{L}(n-1)=H$ makes Equation (13) a convex cost integer dual network flow problem, which can be solved in time $O(n^2 \log(nH))$ for this case. In another aspect, if $H>\Sigma_{x=0}^{n-1} f(x)$, it can be solved in linear time.

Although Ahuja's algorithm has the best know theoretical complexity, Kolmogorov et al. (Mathematical Programming (2007)) found that their algorithm runs better in practice. We implemented our CIBD algorithm using C++ base on Kolmogorov's framework with a specialized local search step (see Appendix B) and the total time complexity is $O(n^3 \log n \log H)$. In one example, for the combinations of parameters n and H, 100 computer-generated exemplary cases were used to test the efficiency of the disclosed methods for optimizing treatment delivery of D-RSBT.

FIG. 27(a) and FIG. 27(b) show the impact parameters n and H can have on the running time, respectively. In one aspect, based on exemplary results, the running time can quadratically increase with n but is not noticeably impacted by H.

In another example, the disclosed methods for optimizing treatment delivery of D-RSBT were applied to 5 distinct clinical cases. One example of a DVH (Dose-Volume Histogram) plot for one of the 5 cases is shown in FIG. 29. In a DVH plot, each point on the curve represents the volume of structure (y-axis) receiving greater than or equal to that dose (x-axis). The delivery plans were evaluated with HR-CTV (High Risk Clinical Tumor Volume) $D_{90}$ and the delivery time (minutes per fraction). In one aspect, all of the clinical cases completed optimization with the disclosed methods within about 1 second. The plan quality comparisons are shown in FIG. 28.

In another example, a partially-shielded electronic BT source with an azimuthally-adjustable shield aperture was employed and treatment plans for a bulky cervical cancer tumor (>40 cc) were generated using the present methods. In shielding-sequencing optimization, a non-trivial network transformation scheme was utilized to efficiently find the global optimum with network flow algorithms. The treatment plan goals of MRI-guided, volume-optimization BT per GEC-ESTRO recommendations were utilized. $D_{90}$ of the HR-CTV receives a prescription dose (Rx) while OAR (rectum & sigmoid (bladder)) $D_{2\ cc} \leq 75(90)$ Gy$_3$ EQD2 (equivalent dose in 2Gy fraction) from external beam radiotherapy and BT. The feasibility was tested using the metric of plan conformality ($D_{90}$ in HR-CTV and $D_{2\ cc}$ in OAR) and treatment delivery time. Here, the shield-sequencing algorithm described in this disclosure can improve tumor coverage ($D_{90}$) with favorable OAR sparing with an acceptable increase in delivery time. The $D_{90}$ (100% Rx) was improved from 41% Rx from conventional, Point-A plan. $D_{2 cc}$ of OAR can be kept under the recommended limits. The increase of delivery time was recorded as less than about 4.2 times higher compared with conventional BT, or less than about 1.2 times higher with $D_{90}$ improved to 94% Rx. The total optimization time was around 10 minutes. FIG. 30 presents a comparison of the results obtained by conventional BT versus D-RSBT.

In a further example, FIGS. 31(a)-(c) illustrate treatment planning and results that can be achieved using the disclosed methods for optimizing treatment delivery of D-RSBT. FIG. 31(a) shows a dose distribution for conventional $^{192}$Ir unshielded source with a $D_{90}$ of 44.6 $Gy_{10}$ and a time of 22.4 units. FIG. 31(b) shows a dose distribution for IMBT using the Axxent Xoft eBT source configured with 60 divisions and no overlapping with a $D_{90}$ of 89.5 $Gy_{10}$ and a time of 450.6 units. FIG. 31(c) shows a dose distribution for IMBT using the Axxent Xoft eBT source as well as the disclosed methods for optimizing treatment delivery of D-RSBT with a $D_{90}$ of 82.9 $Gy_{10}$ and a time of 36.34 units. The conventional approach results in a poor quality while the IMBT approach alone results in a planning time that is not practical. However, using an IMBT in conjunction with the disclosed methods for optimizing treatment delivery, a 38 $Gy_{10}$ increase over conventional BT and a 6 $Gy_{10}$ decrease over non-overlapping fine resolution IMBT alone is achieved. Additionally, this is accomplished within only about 1.6 times the conventional $^{192}$Ir delivery time.

Appendix F illustrates yet another example of dynamic rotating-shield intensity modulated brachytherapy using the combinatorial optimization model for sequencing the rotating shields with dynamic-sized opening described in this disclosure used in the treatment of cervical cancer.

In another aspect, the disclosed methods for optimizing treatment delivery of D-RSBT also provide a means for computing the tradeoff between the delivery time and $D_{90}$ such that a treatment provider may optimize treatment for a given clinical case by selecting different time budgets or quality goals.

FIG. 32 illustrates a block diagram of an exemplary operating environment 3200 that enables various features of the subject disclosure and performance of the various methods disclosed herein. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The various embodiments of the subject disclosure can be operational with numerous other general purpose or special purpose computing system environments or configurations. Examples of well known computing systems, environments, and/or configurations that can be suitable for use with the systems and methods comprise, but are not limited to, personal computers, server computers, laptop devices or handheld devices, and multiprocessor systems. Additional examples comprise wearable devices, mobile devices, set top boxes, programmable consumer electronics, network PCs, minicomputers, mainframe computers, distributed computing environments that comprise any of the above systems or devices, and the like.

The processing effected in the disclosed systems and methods can be performed by software components. The disclosed systems and methods can be described in the general context of computer-executable instructions, such as program modules, being executed by one or more computers or other computing devices. Generally, program modules comprise computer code, routines, programs, objects, components, data structures, etc. that perform particular tasks or implement particular abstract data types. The disclosed methods also can be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 3201. The components of the computer 3201 can comprise, but are not limited to, one or more processors 3203, or processing units 3203, a system memory 3212, and a system bus 3213 that couples various system components including the processor 3203 to the system memory 3212. In the case of multiple processing units 3203, the system can utilize parallel computing.

In general, a processor 3203 or a processing unit 3203 refers to any computing processing unit or processing device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally or alternatively, a processor 3203 or processing unit 3203 can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors or processing units referred to herein can exploit nano-scale architectures such as, molecular and quantum-dot based transistors, switches and gates, in order to optimize space usage or enhance performance of the computing devices that can implement the various aspects of the subject disclosure. Processor 3203 or processing unit 3203 also can be implemented as a combination of computing processing units.

The system bus 3213 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 3213, and all buses specified in this description also can be implemented over a wired or wireless network connection and each of the subsystems, including the processor 3203, a mass storage device 3204, an operating system 3205, treatment planning software 3206, treatment planning data 3207, a network adapter 3208, system memory 3212, an Input/Output Interface 3210, a display adapter 3209, a display device 3211, and a human machine interface 3202, can be contained within one or more remote computing devices 3214a,b,c at physically separate locations, connected through buses of this form, in effect implementing a fully distributed system.

In one aspect, treatment planning software 3206 can comprise computer-executable instructions for implementing the various methods described herein, such as exemplary method 2300. In another aspect, treatment planning software 3206 can include software to control various aspects of manufacturing of the radiation shield and, as part of manufacturing, treating a surface in accordance with aspects described herein in order to attain a desired thickness profile for the surface of the radiation shield. In certain embodiments, treatment planning software 3206 also can include computer-executable instruction for selecting radio-opaque materials for manufacturing the radiation shield. Treatment planning software 3206 and treatment planning data 3207 configure processor 3203 to perform the one or more steps of the methods described herein. In addition or in the alternative, treatment planning software 3206 and treatment planning data 3207 can configure processor 3203 to operate in accordance with various aspects of the subject disclosure.

The computer 3201 typically comprises a variety of computer readable media. Exemplary readable media can be any available media that is accessible by the computer 3201 and comprises, for example and not meant to be limiting, both volatile and non-volatile media, removable and non-removable media. The system memory 3212 comprises computer readable media in the form of volatile memory, such as random access memory (RAM), and/or non-volatile memory, such as read only memory (ROM). The system memory 3212 typically contains data and/or program modules such as operating system 3205 and treatment planning software 3206 that are immediately accessible to and/or are presently operated on by the processing unit 3203. Operating system 2405 can comprise OSs such as Windows operating system, Unix, Linux, Symbian, Android, iOS, Chromium, and substantially any operating system for wireless computing devices or tethered computing devices.

In another aspect, the computer 3201 also can comprise other removable/non-removable, volatile/non-volatile computer storage media. By way of example, FIG. 32 illustrates a mass storage device 3204 which can provide non-volatile storage of computer code, computer readable instructions, data structures, program modules, and other data for the computer 3201. For example and not meant to be limiting, a mass storage device 3204 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 3204, including by way of example, an operating system 3205, and treatment planning software 3206. Each of the operating system 3205 and treatment planning software 3206 (or some combination thereof) can comprise elements of the programming and the treatment planning software 3206. Data and code (e.g., computer-executable instruction(s)) can be retained as part of treatment planning software 3206 and can be stored on the mass storage device 3204. Treatment planning software 3206, and related data and code, can be stored in any of one or more databases known in the art. Examples of such databases comprise, DB2®, Microsoft® Access, Microsoft® SQL Server, Oracle®, mySQL, PostgreSQL, and the like. Further examples include membase databases and flat file databases. The databases can be centralized or distributed across multiple systems.

In another aspect, the user can enter commands and information into the computer 3201 via an input device (not shown). Examples of such input devices comprise, but are not limited to, a camera; a keyboard; a pointing device (e.g., a "mouse"); a microphone; a joystick; a scanner (e.g., barcode scanner); a reader device such as a radiofrequency identification (RFID) readers or magnetic stripe readers; gesture-based input devices such as tactile input devices (e.g., touch screens, gloves and other body coverings or wearable devices), speech recognition devices, or natural interfaces; and the like. These and other input devices can be connected to the processing unit 3203 via a human machine interface 3202 that is coupled to the system bus 3213, but can be connected by other interface and bus structures, such as a parallel port, game port, an IEEE 1394 Port (also known as a Firewire port), a serial port, or a universal serial bus (USB).

In yet another aspect, a display device 3211 also can be connected to the system bus 3213 via an interface, such as a display adapter 3209. It is contemplated that the computer 3201 can have more than one display adapter 3209 and the computer 3201 can have more than one display device 3211. For example, a display device can be a monitor, an LCD (Liquid Crystal Display), or a projector. In addition to the display device 3211, other output peripheral devices can comprise components such as speakers (not shown) and a printer (not shown) which can be connected to the computer 3201 via Input/Output Interface 3210. Any step and/or result of the methods can be output in any form to an output device. Such output can be any form of visual representation, including, but not limited to, textual, graphical, animation, audio, tactile, and the like.

The computer 3201 can operate in a networked environment using logical connections to one or more remote computing devices 3214a,b,c. By way of example, a remote computing device can be a personal computer, portable computer, a mobile telephone, a server, a router, a network computer, a peer device or other common network node, and so on. Logical connections between the computer 3201 and a remote computing device 3214a,b,c can be made via a local area network (LAN) and a general wide area network (WAN). Such network connections can be through a network adapter 3208. A network adapter 3208 can be implemented in both wired and wireless environments. Such networking environments are conventional and commonplace in offices, enterprise-wide computer networks, intranets, and the Internet. Networking environments are referred to as network(s) 3215 and generally can be embodied in wireline networks or wireless networks (e.g., cellular networks, such as Third Generation (3G) and Fourth Generation (4G) cellular networks, facility-based networks (femtocell, picocell, Wi-Fi networks, etc.).

As an illustration, application programs and other executable program components such as the operating system 3205 are illustrated herein as discrete blocks, although it is recognized that such programs and components reside at various times in different storage components of the computing device 3201, and are executed by the data processor(s) of the computer. An implementation of treatment planning software 3206 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer-readable media can comprise "computer storage media," or "computer-readable storage media," and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

In various embodiments, the disclosed systems and methods for CBT can employ artificial intelligence (AI) techniques such as machine learning and iterative learning for identifying patient-specific, treatment-specific shields. Examples of such techniques include, but are not limited to, expert systems, case based reasoning, Bayesian networks, behavior based AI, neural networks, fuzzy systems, evolutionary computation (e.g., genetic algorithms), swarm intelligence (e.g., ant algorithms), and hybrid intelligent systems (e.g., Expert inference rules generated through a neural network or production rules from statistical learning).

As described in greater detail below, the subject disclosure relates to advanced intensity-modulated brachytherapy. In one aspect, the disclosure recognizes and overcomes the issue of treating tumors (such as cervical cancer tumors) that non-radially symmetric cancer tumors due to one or more of the shape of the tumor or the location of an intracavitary applicator utilized for treatment. In one scenario, as described herein, M-RSBT can be used to deliver highly patient specific doses to cervical cancer tumors that are impossible to deliver with conventional BT. In another aspect, the disclosure recognizes and overcomes the issue of the treatment time for S-RSBT increasing nonlinearly as a radiation shield emission angle decreases, which can cause treatment times for S-RSBT to be infeasible to implement into the clinic. In one scenario, M-RSBT utilizes a judicious combination of several different shield emission angles to reduce the treatment time of S-RSBT by a significant factor while duplicating the dose distribution exactly. It should be appreciated that the therapy advantages (such as reduced treatment time) of M-RSBT with respect to other RSBT techniques can offset the complexity associated with changing the size of the radiation shield during delivery.

In one aspect, the fields of application of I-RSBT can comprise radiation oncology and urology. In various scenarios, it is anticipated that I-RSBT can be the treatment of choice for patients with localized prostate cancer who are willing and able to undergo 2-4 general anesthesia sessions for the delivery of the therapy.

In one aspect, I-RSBT provides the opportunity for reduced complications and dose escalation for prostate cancer patients, which we expect to result in improved outcomes with reduced toxicity. Urethral dose in HDR-BT has been shown to be closely associated with the incidence of Grade 2 or higher acute genitourinary (GU) toxicity. We expect I-RSBT will have lower urinary complications than radical prostatectomy (RP), external beam radiotherapy (EBRT), low-dose-rate brachytherapy (LDR-BT), and conventional HDR-BT, and will be the preferable approach to treating localized prostate cancers. It is also expected that I-RSBT can reduce rectal toxicity associated with HDR-BT treatments of prostate cancer.

The shielded needle device and automation of its rotation system and software enable the delivery of radiation dose distributions that are non-radially-symmetric about the needle by rotating the needle inside the tumor while it contains a radiation source. This allows the clinician to tailor the radiation dose delivered to a tumor in a manner that significantly reduces the dose delivered to sensitive normal tissue that is inside or adjacent to the tumor, which is the I-RSBT technique. Multiple shielded needles can be used to deliver I-RSBT, which is an HDR-BT technique that entails rotating a radiation-attenuating shield about a BT source in an optimized fashion. In an aspect, the multiple shielded needles used to deliver I-RSBT can comprise shielded needles with different azimuthal shield emission angles. I-RSBT is a type of intensity modulated brachytherapy (IMBT) technique. While IMBT techniques have been introduced in the literature, practical implementation of I-RSBT with radioisotopes remains largely untapped because radioisotopes for I-RSBT delivery may be difficult to obtain or need further development.

Five-year relative survival rates for the nearly 180,000 patients annually diagnosed with localized prostate cancer in the U.S. are almost 100%, independent of the three most common treatment methods used: radical prostatectomy (RP), external beam radiation therapy (EBRT), low-dose-rate brachytherapy (LDR-BT) with permanent $^{125}$I or $^{103}$Pd implants. Treatment decisions for localized prostate cancer thus depend strongly on anticipated morbidity, and convenience for the patient.

EBRT and LDR-BT are associated with greater bowel toxicity than RP, but lower urinary incontinence rates. Urinary obstruction/irritation rates are similar for all three therapies, and sexual dysfunction rates are lowest for LDR-BT. HDR-BT is an increasingly popular option for treating localized prostate cancer as a monotherapy, as a single-fraction boost to EBRT, or as a multi-fraction boost to EBRT. Prostate HDR-BT entails ultrasound, computed tomography (CT), or magnetic resonance (MR) image-guided $^{192}$Ir-BT using at least 14 plastic catheters. The therapy is typically delivered in 2-4 fractions over 1-2 days, and consensus has not been reached on an HDR-BT fractionation scheme for prostate cancer. HDR-BT deliveries are more geometrically stable than those of EBRT in that they are not influenced by inter- or intra-fraction patient motion. With HDR-BT, all radiation delivered to the prostate is tailored to the shape of the prostate, bladder, rectum, and urethra, on the day of treatment. Thus changes in the shape, size, and location of the prostate due to bladder filling and edema can be accounted for in each delivery session. In EBRT, the urethra is typically not spared and is delivered the same dose as the prostate.

HDR-BT is advantageous over LDR-BT in that no radioactive seeds are implanted, eliminating dosimetric uncertainty due to seed migration. In addition, LDR-BT does not exploit the late-responding characteristics of prostate cancer as HDR-BT does. HDR-BT monotherapy has been shown to decrease toxicity rates relative to LDR-BT for grade 1-3 acute dysuria (36% vs. 67%, p<0.001), acute urinary frequency/urgency (54% vs. 92%, p<0.001), acute rectal pain (6% vs. 20%, p<0.017), chronic urinary frequency (54% vs. 92%, p<0.004), and actuarial impotence at 36 months (16% vs. 45%, p<0.062). As LDR-BT is the localized prostate therapy typically associated with lower toxicity rates than RP and EBRT, the lower toxicity of HDR-BT relative to LDR-BT makes HDR-BT the therapy of choice for localized prostate cancer. Typically, HDR-BT is delivered over a fractionated schedule which can require in-patient hospital visits.

The standard-of-care HDR-BT isotope, $^{192}$Ir, is suboptimal for I-RSBT of any site in which the needle or catheters used must be 2 mm in diameter or smaller. Data and simulations indicate that I-RSBT can be effective, in certain scenarios, if the shield transmission is 10% or less, and $^{192}$Ir shielded with a 5 mm of tungsten results in a suboptimal 30% transmission.

In an aspect, breast and rectal cancers can be treated with $^{192}$Ir-RSBT using a 1 cm radius tungsten shield. In another aspect, cervical or prostate cancer RSBT can use applicators of less than 5 mm radius and interstitial needles of less than 1 mm radius, respectively. Therefore, the different radiation source/shield combinations for RSBT (FIG. 34) are necessary.

In one aspect, as illustrated in FIG. 34, platinum-shielded $^{153}$Gd and $^{57}$Co sources were feasible for interstitial RSBT.

Some aspects provide a catheter for interstitial brachytherapy comprising at least two or more materials that transmit varying quantities of the radiation source used to deliver I-RSBT, and aligned such that their interfaces extend longitudinally along the catheter shaft (see, e.g., FIG. 35). The catheter is encased with a non-toxic material to enable its safe insertion into patient tissue. The materials composing the catheter can extend the entire distance of the catheter shaft, or only along a fraction of the shaft. The catheter lumen can be located at the center of the catheter cross section or off center, as illustrated in FIG. 36A. The emission angles subtended by the materials composing the catheter can vary between 0° and 360°. In certain embodiments, the catheter could also be in the form of a needle with a sharp tip, as shown in FIG. 35.

FIG. 36B illustrates an example cross-section of shaft suitable for application in I-RSBT in accordance with one or more aspects of the subject disclosure. Various embodiments of such shaft can be implemented, as shown in FIGS. 36B-F (the color scheme introduced in FIG. 36B indicates the portions of the shaft, and is consistent throughout FIGS. 36B-F).

In certain treatment scenarios, I-RSBT can be delivered with a number of different catheters or needles that will inserted into the patient's tissue through a template consisting of a number of holes through which the catheters or needles pass. An example of a template 200 is shown in FIG. 39B. For HDR-BT, delivery templates are often sutured to the patient's perineum during delivery in order to ensure its stability throughout the catheter placement and delivery processes. The I-RSBT template can include an automated mechanism that locks or unlocks a given needle or catheter, enabling independent rotation, discussed in more detail below. The radiation source may be inserted into each needle or catheter individually, and, during delivery, the needle or catheter must be rotated in a manner that is independent of its neighbors.

In an aspect, the proximal ends of the shaft (embodying or comprising a catheter and/or needle, for example) for I-RSBT can be fitted with a docking device that can be inserted into a grasping mechanism, or control unit, that can rotate the shaft (e.g., a needle or a catheter). Examples of catheter docking and grasping devices are shown in FIGS. 37A-B.

FIGS. 39A-39C illustrate example embodiments of docking devices in accordance with one or more aspects of the disclosure. As shown in FIGS. 39A-C, the docking device can include a template 200 (FIGS. 39B-C) that contains a clamp 220 (FIGS. 39A & B) around the openings 210 of the template 200. The clamp 220 (FIG. 39A) includes a first series 230 of individual tubes 232. The individual tubes 232 of the first series 230 are positioned around the opening 210 of the template 200 that is configured to receive an I-RSBT needle. The first series 230 of tubes 232 are arranged in parallel with the opening 210. In some instances, the tubes 232 of the first series 230 can form the boundaries of the openings 210. The clamp 220 includes a second set 240 of tubes 242. The second set 240 of tubes 242 can run perpendicularly to the first set 230 of tubes 232. In an aspect, the second set 240 of tubes 242 includes two tubes 242, with one tube 242 abutting a tube 232 of the first series 230 that is positioned on one side of the opening 210, and the other tube 242 abutting a different tube 232 of the first series 230 found on the opposite side of the opening 210. In an aspect, the tubes 242 of the second series 240 can be positioned at the top and the bottom of the opening 210. The tubes 242 of the second series 240 can include an opening 244 that runs the length of the tube 242. The openings 244 can be configured to receive an engaging pin 250.

When an I-RSBT needle is received within an opening 210 of the template 200, an engaging pin 250 can be inserted into the openings 244 of the tubes 242 of the second series 240. The engaging pin 250 applies pressure to the adjacent tube 232 of the first series 230, which prevents the needle from moving inwardly or outwardly of the opening 210 surrounded by the clamp 220. The parallel arrangement of the tubes 232 of the first series 230 allows for the rotational movement of the needle within the opening 210. As shown, the openings 210 of the template 200 can be placed in parallel lines, allowing the tubes 242 of the second series 240 to run the length of the template 200. However, in other aspects, the arrangement of the openings 210 and clamps 220, and the components of the clamps 220, can vary.

In an aspect, the I-RSBT system is not necessarily limited to $^{57}$Co and $^{153}$Gd for radiation delivery, although those isotopes are considered to be the most optimal. Other radioisotopes could be used for I-RSBT delivery, including $^{192}$Ir, $^{131}$Cs, $^{125}$I, $^{103}$Pd, $^{198}$Au, $^{187}$W, $^{169}$Yb, $^{145}$Sm, $^{137}$Cs, $^{109}$Cd, $^{65}$Zn, $^{56}$Co, and $^{58}$Co.

It should be appreciated that the presence of the shielded needles or catheters in the patient's tumor may make imaging of the tumor difficult, with possible introduction of artifacts. In one aspect, a technique (e.g., system, method, etc.) for mitigating or avoiding such difficulty can comprise an I-RSBT system with plastic needles that can be placed in the tumor first for initial positioning and shielded catheters that can then be placed inside the plastic needles after a final, artifact-free, image is acquired to confirm the locations of the catheters. In an aspect, the plastic needles can be placed in the targeted area using known imaging navigation techniques. Such a system is discussed in more detail below.

In addition to the prototypes shown in FIGS. 37A-37B and 39A-C, preliminary simulated prostate results shown in FIG. 38A-B demonstrate that I-RSBT is effective in reducing the doses to untargeted areas when compared to conventional HDR-BT. For example, FIG. 38A shows that a shield transmission for the I-RSBT plans was assumed to be 10%, which can be achieved for $^{153}$Gd and $^{57}$Co sources using platinum shields with 0.37 mm and 0.71 mm thicknesses, respectively. For the goal of urethral sparing with a prostate $D_{90}$ (minimum dose to the hottest 90% of the prostate) of 100%, then the maximum urethral dose is reduced from 84% for unshielded BT to 60% for I-RSBT, a 38.5% drop. If the goal is prostate dose escalation while holding maximum urethral dose constant at 100%, then the prostate Do is increased from 119% for unshielded BT to 167% for I-RSBT, a 40% increase.

FIG. 38B shows that I-RSBT can reduce the rectal dose to the hottest 1 cc by 10% and the urethal dose to the hottest 1% by 20% when compared to conventional HDR-BT. In another aspect, utilizing I-RSBT for treating a prostate tumor can allow for prostate tumor dose escalation, in which the dose to the prostate tumor is increased as much as possible until the urethral tolerance dose is reached. For dose escalation, tumor $D_{90}$ can be increased by 40% above the previous limits without increasing urethral toxicity above standard HDR-BT levels. Dose escalation can enable a reduction in the number of treatment fractions needed for I-RSBT relative to HDR-BT (currently 2-4), as well as enable a more aggressive treatment regimens for advanced prostate cancer, which has been demonstrated to respond favorably to dose escalation.

In another aspect, various embodiments of RSBT can be applied to in the field of radiation oncology, specifically for the treatment of tumors that are not radially symmetric about some axis. In particular, embodiments related to M-RSBT can be suitable for such application. Several aspects utilizing various embodiments of RSBT are disclosed in Appendices G-H.

Figure 40A:
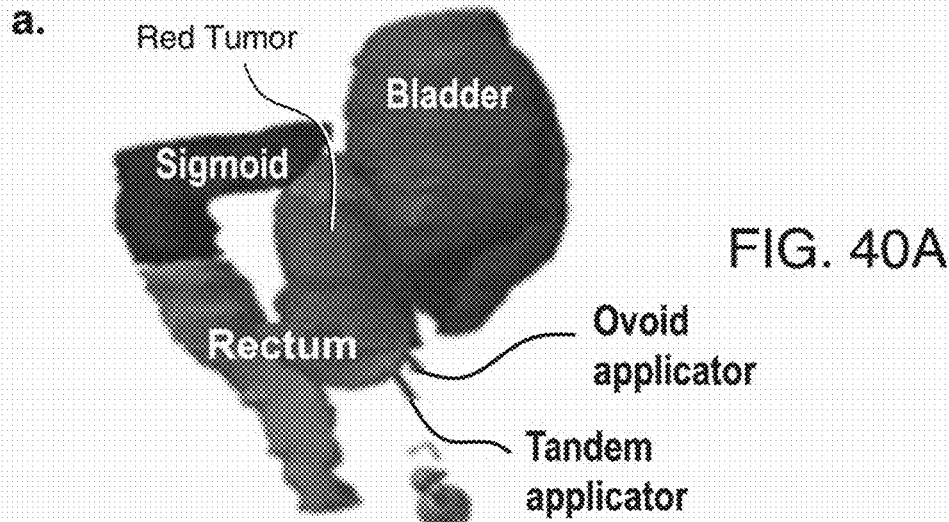
Figure 40B:
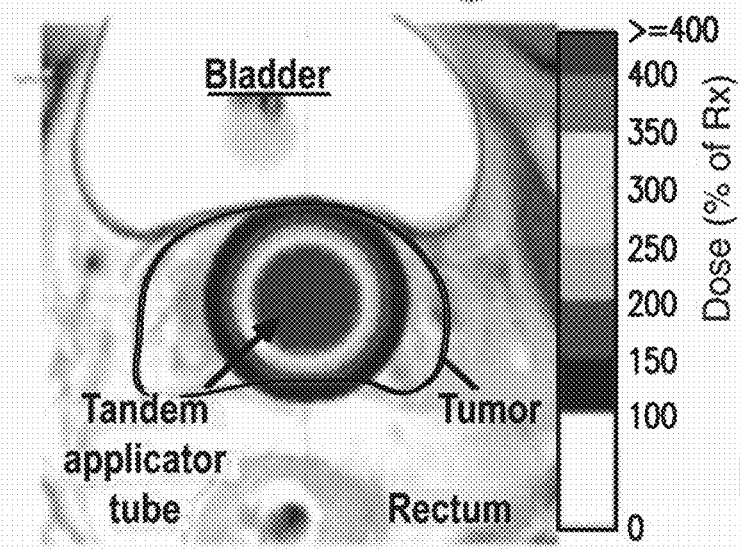

FIG. 40a shows MRI-generated 3-D renderings of the anatomy of a patient being treated for cervical cancer, including the tumor and nearby critical structures: bladder, rectum, and sigmoid colon. Typical conventional brachytherapy delivers radiation with an x- or gamma-ray emitting source that travels through a set of rigid tandem-and-ovoid (T&O) applicators inserted into the anesthetized patient. The radially symmetric dose distribution emitted by conventional brachytherapy (BT) sources, however, results in the poor tumor coverage, as shown in FIG. 40b. The desired radiation dose to the tumor, shown as the red outline, is 100% of the prescribed radiation dose, which is clearly not being achieved in a large fraction of the tumor. Improved tumor coverage can be achieved with rotating shield intensity modulated brachytherapy (S-RSBT), which uses shielding of the radiation source to achieve the dose distribution shown in FIG. 40c. It is expected that the improved tumor coverage obtained with S-RSBT to increase local tumor control probability in any applicable tumor, improving patient outcomes.

Figure 40C:
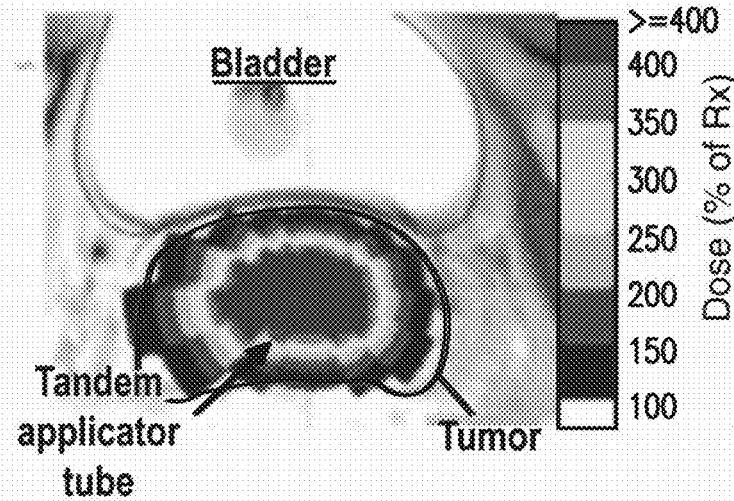

S-RSBT can be delivered using radioisotopes and the Xoft Axxent electronic brachytherapy source, respectively, by collimating the source with high-density shields that create fan beams. The fan beam source is rotated inside the patient in a manner such that the amount of time the source spends irradiating in a given direction is optimized to ensure better tumor coverage and better critical structure avoidance than conventional brachytherapy (FIG. 40c). Although both works demonstrate the potential benefits of S-RSBT, there is a crippling challenge associated with the single rotating shield approach: the delivery times associated with IMBT are increased relative to conventional BT. This is due to the loss of emitted radiation in the rotating shield, which must remove a large fraction, possibly around 90%, of the radiation in order to achieve an advantage over conventional BT. If the rotating fan beam accounts for only 10% of the radiation emitted by the BT source, with the rest is lost in the shield, then delivering the same dose distribution as conventional BT will require at least ten times as long with rotating-shield IMBT. This is because the fan will have to be pointed in 10 directions and stay pointed in each direction for the same amount of time necessary to deliver an entire conventional BT plan, which loses 0% of the radiation due to shielding.

In one aspect, the disclosed apparatus for Multiple Rotating-Shield IMBT (M-RSBT) can permit the delivery of radiation does distributions with the advantages of S-RSBT, but with substantially lower treatment times. With one or more embodiments of the disclosure, a patient-specific combination of shield emission angles is chosen intelligently to reduce the treatment times while exactly duplicating the dose distribution of S-RSBT. In one aspect, the combination favors large emission angles, so that as little of the emitted radiation is lost as possible, and is determined by computer-based optimization following determination of the tumor shape and applicator by imaging, an example of which is shown in FIG. 40a.

Delivery Apparatus Description

In an aspect, the principle of M-RSBT can be described with reference to FIGS. 41A-41C, which illustrate how the intelligent use of multiple shields can dramatically reduce the treatment time of S-RSBT, while exhibiting the exact same dose distribution. In general, a brachytherapy source is inserted into a source catheter and allowed to dwell at a number of positions within a tumor to apply the treatment. Radiation is emitted by the source in all directions from each dwell positions (i.e., a position in which the BT source stays to apply BT). Using S-RSBT, each direction of the emission angle is required to have a specific dwell time (e.g, FIG. 41B), increasing the specificity of the tumor but drastically increasing treatment time. However, FIGS. 41B-C shows that M-RSBT can achieve tumor specificity with a lower treatment time than S-RSBT.

FIG. 41A-B show a schematic representation of the dwell times according to an example of an application of S-RSBT to a tumor. As shown in FIG. 41A, the S-RSBT utilizes a 90° emission angle in four discrete locations. The four locations are exposed to the S-RSBT (i.e., dwell time), starting at the bottom left and traveling clockwise, for: 9 units, 8 units, 6 units, and 4 units. FIG. 41B shows the total amount of the treatment time using the S-RBST application shown in FIG. 41A: the treatment time equals of 27 units. FIG. 41C illustrates the total time units when M-RSBT is used to treat the same dose distribution. The total treatment time is 11 units plus an extremely small factor "c", which is less than half the time it takes to treat the same distribution with S-RSBT. "c" is a correction term for the transmission differences, and is described herein. In an aspect, c is equal to $4T_{shield}$, where $T_{shield}$ is the radiation transmission through the shield.

A cross sectional view of an intensity modulated brachytherapy (IMBT) insertion device 301 is shown in FIGS. 42A-42D and FIG. 43, which more comprehensively illustrates the relative locations of a BT source 310, a BT source catheter 320, a shield 315 (or space 330 for one), and applicator 340. In an aspect, the BT source catheter 320 is configured to contain the BT source 310. In an aspect, the shield 315 can include a shield with an emission angle filed with a window, or just the shield with an emission angle. In another aspect, the applicator 340 can be an insertion device that encloses the BT source 310, the BT source catheter 320, and a shield 315. In an aspect, the applicator 340 can already be positioned within a body of a subject. In general, the BT source 310 is inserted in the catheter 320 and allowed to dwell at a number of positions along the axis of the applicator 340. The exemplary aspect of the IMBT insertion device 301 of FIGS. 42A-42D illustrate an intracavitary applicator 340 of inner radius $r_{ID}$ and outer radius $r_{tot}$. The BT/radiation source 310 has an outer radius of $r_s$. A BT source catheter tube 320 of outer radius $r_c$ may be present, through which the radiation from the BT source 310 travels. The shield may fit in the space 330 between the catheter 320 and insertion device, or, if no BT catheter 320 is used, between the source 310 and surface of the inner applicator 340.

Figure 42A:
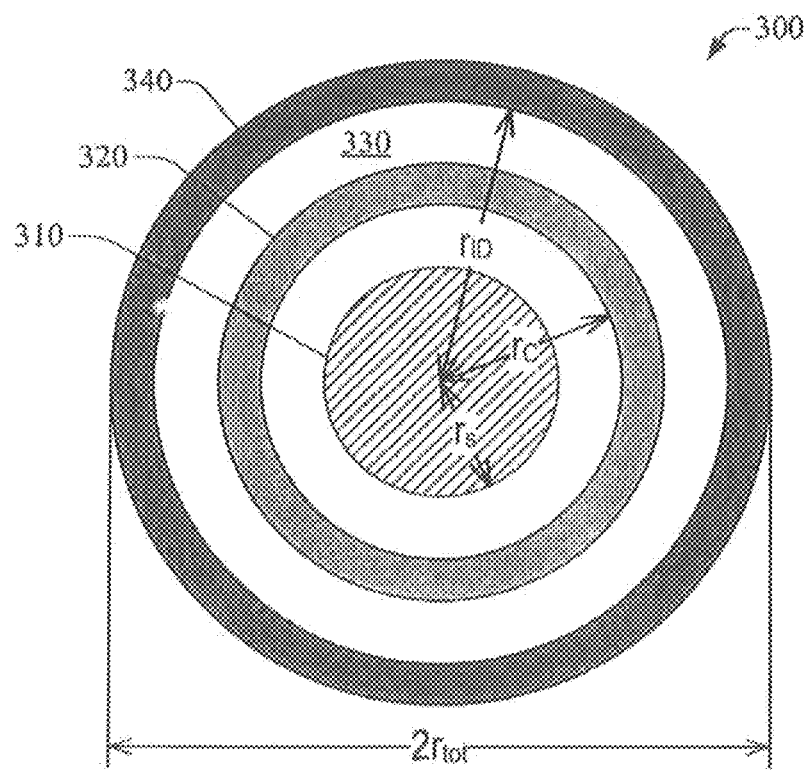
Figure 42B:
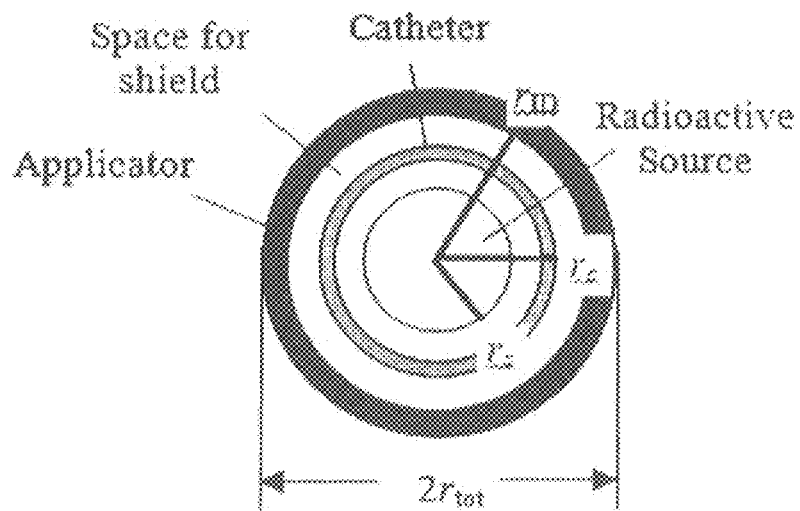
Figure 42C:
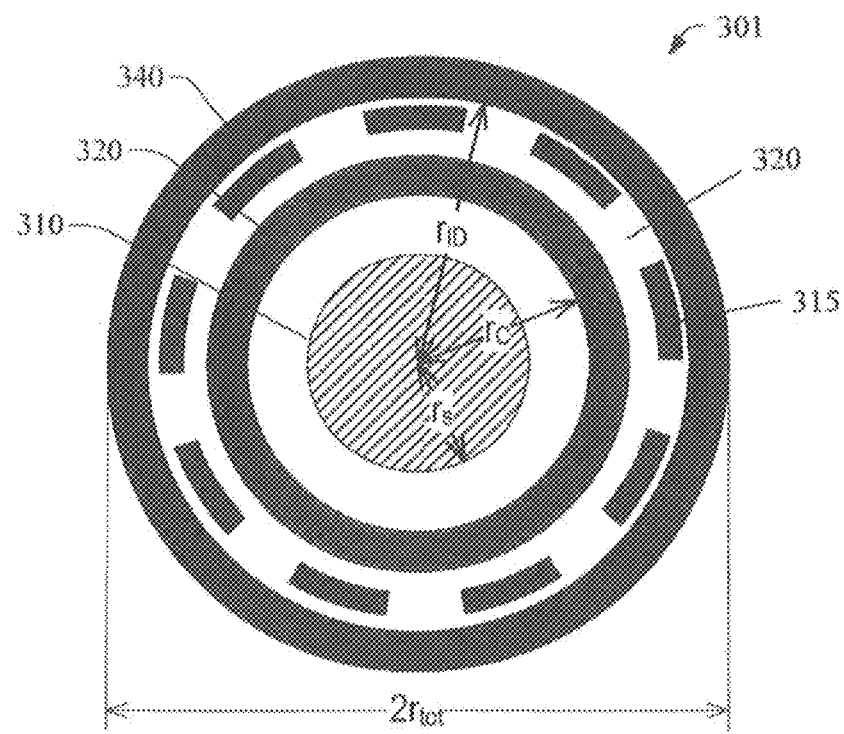

A cross sectional view of an IMBT insertion device 301 is illustrated in FIG. 42A, which depicts the relative locations of the BT source 310, a catheter tube 320 (or catheter 320), a space 330 for a shield in accordance with one or more aspects described herein, and applicator 340. The IMBT insertion device 301 may be embodied in a needle or an intracavitary applicator 340 of inner radius $r_{ID}$ and outer radius rot. In one aspect, the radiation source 310 can have an outer radius $r_s$. The radiation source 310 can move through the catheter tube 320, which can have an outer radius $r_c$. In one aspect, the catheter tube 320 forms, at least in part, a first enclosure into which the radiation source 310 can be inserted. In embodiments, such as illustrated in FIG. 42C. a shield 315 (indicated with a thick dashed line) fits in the space 330 between the catheter tube 320 and the applicator 340. More generally, other embodiments of IMBTs can be implemented with ample or sufficient space between $r_c$ and $r_{ID}$ for insertion of the shield. It is noted that CBT also can be implemented in embodiments in which no catheter tube 320 is used between the BT source 310 and the inner surface of the applicator 340.

Figure 42D:
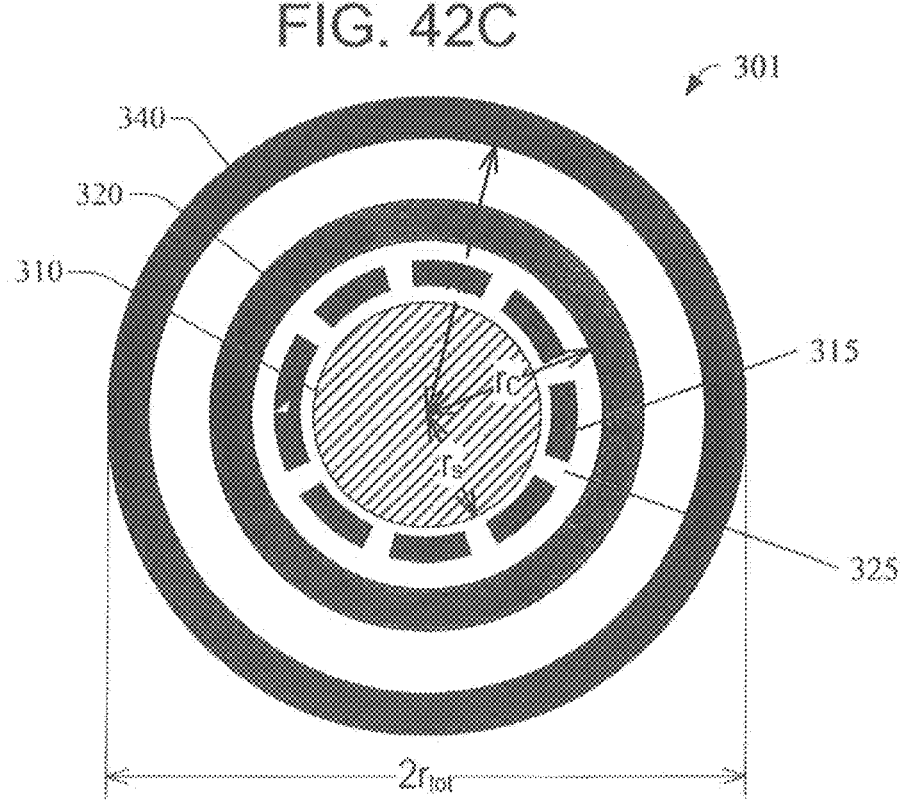

In an aspect, the radiation shield 315 can be coupled to the first enclosure 325 formed by the catheter tube 320 around the source 310, as shown in FIG. 42D. In another aspect, the space 330 is bound by the applicator 340 and the catheter tube 320 and forms a second enclosure that encompasses the first enclosure. As described herein, the catheter 320, which can form the first enclosure, can be adapted to move relative to the second enclosure, defined in part by the applicator 340. As described herein, in one embodiment, the applicator 340 and thus the second enclosure 325, can be coupled to alignment means for positioning the first enclosure (e.g., the catheter tube 320) relative to the second enclosure 325 (e.g., the applicator 340).

FIG. 43 illustrates an additional or alternative example cross section of the RS-IMBT delivery system, with diameters of each component listed. The geometric penumbra edges are shown as dotted lines. The azimuthal shield emission angle is $\Delta\varphi_s=45°$; the geometric penumbra angle is $\Delta\varphi_p$.

FIG. 44(a-f) illustrate an example apparatus 500 that can be utilized to deliver M-RSBT. The apparatus 500, a combination of a sheath 502 and a shield 504 contained therein, permits changing of sheaths 502 (and therefore shields 504) either automatically (e.g., mechanically, electromechanically, or the like) or manually, especially if electronic radiation sources 506 are being used. A holding block 510 can hold multiple apparatuses 500, with each shield 504 having a different emission angle. The holding block 510, in combination with the apparatuses 500 (already containing different shields 504 within a sheath 502 for easy application of the source 506), allows for the efficient switching between shields 504 and a source 506. In one aspect, the same set of apparatuses 500 can be used for every patient (as shown in FIGS. 44(a-b)), yet the use of the apparatuses 500 would differ allowing each treatment to be highly specific to each patient.

In one aspect, a process by which an individual can change shields 504, by using different apparatuses 500, in order to deliver M-RSBT can comprise the following stages (or actions). As illustrated in FIG. 44(a) during delivery, the source 506 will be inside the sheath 502 and shield 504 of one apparatus 500, and together they will go into the applicator (not shown). As illustrated in FIG. 44(b), during the switching of the source 506, the first apparatus 500 will have the source 506 removed from the sheath 502 and the shield 504. The apparatus 500 with the next appropriate shield 504 will replace it. As illustrated in FIG. 44(c), when the shield 504 needs to be switched, the apparatus 500 will be placed into the holding block 510. In an aspect, the holding block 510 can hold a plurality of apparatuses 500 waiting for use. As shown in FIG. 44(d), the block 510 is then shifted horizontally (shown in the direction of the arrow) so that the next appropriate apparatus 500 aligns with the source 506. As illustration in FIG. 44(e), the source 506 is then inserted into the shield 504 and sheath 502 of the new apparatus 500. As shown in FIG. 44(f), the holding block 510 can be lowered, allowing the new apparatus 500, with the source 506 within it, to be inserted back into the applicator.

RSBT Treatment Planning

In an aspect, a RSBT treatment plan can be determined. Define a beamlet, $\dot{D}_{i,j,k}(\Delta\varphi,\Delta\theta)$, as the dose rate, in Gy/min, at point at $\vec{r}_i$ due to a shielded radiation source at dwell position $\vec{s}_j$. The shield has an azimuthal emission angle of $\Delta\varphi$, a zenith emission angle of $\Delta\theta$. The beamlet direction, $\varphi_k$, is the azimuthal direction of the center of the emission aperture. Beamlets are patient-dependent in general and can be calculated using techniques such as analytical methods, Monte Carlo methods, solving the radiation transport equation, and interpolation based on pre-calculated or measured dose rate distributions. The beamlet direction is defined as:

$$\varphi_k=[\mod(k,K)+\tfrac{1}{2}]\delta\varphi, \ k\in Z, \quad (16)$$

where $\delta\varphi=360°/K$ is the azimuthal spacing between beamlet emission angles, K is the total number of azimuthal emission angles per shield rotation considered in the treatment planning problem, and Z is the set of all integers. The modular arithmetic (mod) operator in Equation (16) enables the use of negative k-indices.

For S-RSBT, the total dose delivered to point i is calculated as a time-weighted sum of the beamlets over all dwell positions, indexed by $j=0, \ldots, J-1$ and emission angles:

$$d_i = \sum_{j=0}^{J-1}\sum_{k=0}^{K-1} t_{j,k} \dot{D}_{i,j,k}(\Delta\varphi,\Delta\theta), \quad (17)$$

where $t_{j,k}$ is the time the source is pointed in direction $\varphi_k$ while it is located at dwell position $\vec{s}_j$. The $t_{j,k}$ values are determined using a treatment planning system that optimizes the radiation dose distribution to meet the clinical goal as closely as possible. An example clinical goal is to maximize the minimum dose received by the 90% of the tumor volume receiving the highest dose under the constraint that none of the tolerance doses for any of the radiation-sensitive normal tissues are exceeded.

In certain implementations, it is straightforward to use deterministic (gradient-based, for example) or stochastic (simulated annealing, for example) optimization algorithms to determine $t_{j,k}$ values that produce to a superior dose distribution to that of the unshielded BT case, as long as effective $\Delta\theta$ and $\Delta\varphi$ parameters are selected. The total delivery time for the S-RSBT case, $t_{tot}^{RSBT}$, will be strongly influenced by the shield angles selected, and is approximately related to the total delivery time for an unshielded BT source, $t_{tot}^{BT}$, as:

$$t_{tot}^{RSBT} = \sum_j \sum_k t_{j,k} \propto t_{tot}^{BT} \frac{180°}{\Delta\theta} \frac{360°}{\Delta\varphi}. \quad (18)$$

Thus an azimuthal shielding angle of $\Delta\varphi=45°$ would be expected to result in an S-RSBT delivery time of at least eight-fold that of the unshielded case, even if the zenith emission angle is 180°. For non-radially-symmetric targets, S-RSBT dose distributions will be superior to those of conventional BT, and may be worth some increased cost in delivery time. Multiple rotating shield brachytherapy (M-RSBT), which uses a combination of multiple shields rather than just a single shield, can significantly reduce treatment times below those of S-RSBT. Such a reduction in treatment time can reduce clinical resources by reducing the staffing requirements per patient. For brachytherapy sources such as the Xoft Axxent, which have a finite lifetimes, maximizing delivery efficiency can significantly reduce equipment costs as well.

Method for M-RSBT Shield Angle and Dwell Time Combinations

With M-RSBT, the radiation dose is delivered with a combination of M different shield emission angles in series. Each shield used in the delivery, indexed by m(m=1, ..., M), has azimuthal and zenith emission angles of $\Delta\varphi_m$ and $\Delta\theta_m$, respectively, and the total dose distribution is the following:

$$d_i = \sum_{m=1}^{M} \sum_{j=0}^{J-1} \sum_{k=0}^{K-1} \dot{D}_{i,j,k}(\Delta\varphi_m, \Delta\theta_m) t_{j,k,m}, \quad (19)$$

which is a generalized version of Equation (17) that includes a sum over all shield angles considered. An m-index is present on the M-RSBT dwell times, $t_{j,k,m}$, since each shield used in the delivery will have its own set of dwell times for all dwell positions and emission directions. By convention, shield angle increases with shield index m=1, and m=M corresponds to the unshielded case, thus $\Delta\varphi_M=360°$. The beamlets corresponding to the shielding hardware shown in FIG. 44 can be used in Equation (19) for M-RSBT treatment planning with standard deterministic or stochastic optimization methods that minimize delivery time without reducing plan quality significantly below that of S-RSBT. The resulting M-RSBT treatment plans will have lower total delivery times, $t_{tot}^{MRSBT}$, than S-RSBT, and comparable dose distributions to S-RSBT.

Rapid M-RSBT Planning by Combining Neighboring Baseline Beamlets

Suppose a set of baseline beamlets is available for a baseline emission angle, $\Delta\varphi$, and $\Delta\varphi=\delta\varphi$. The M-RSBT treatment plan optimization process can be accomplished approximately M-times faster than optimizing Equation (19) directly, based on the recognition that beamlets with emission angles that are integer multiples of $\Delta\varphi$ can be constructed by superposing neighboring baseline beamlets. In this section we describe a rapid M-RSBT technique that is based on combining neighboring baseline beamlets into larger beamlets by superposition.

Summing m neighboring baseline beamlets results in a new beamlet with an azimuthal emission angle of m-times $\Delta\varphi$, and an emission direction that is the average of the emission directions of the m combined beamlets. Superposing an odd and even number of neighboring baseline beamlets produces a larger beamlet with a direction that is and is not shared with one of the baseline beamlets, respectively. In order to differentiate between beamlet angles different m-values, we define $\varphi_k^m$ as the emission angle for beamlet k. $\varphi_k^m$ has an azimuthal emission angle of $\Delta\varphi_m=m\Delta\varphi$, which can be calculated in general as:

$$\varphi_k^m = \left[\text{mod}(k, N) + \frac{1}{2}\text{mod}(m, 2)\right]\delta\varphi, \quad (20)$$

FIG. 45 illustrates examples for the case in which the baseline azimuthal emission angle, $\Delta\varphi$, is equal to the azimuthal emission direction separation, $\delta\varphi$. The figure shows neighboring beamlet superpositions for the cases in which m is 1 and 2, which correspond to superposing 2 and 3 neighboring beamlets, respectively.

In the disclosed approach, the key relationship enabling the construction of beamlets with emission angles larger than the finest angle is the following:

$$\sum_{k'=-\lfloor m/2 \rfloor}^{\lceil m/2 \rceil - 1} \dot{D}_{i,j,k+k'}(\Delta\varphi, \Delta\theta) = \dot{D}_{i,j,k}(m\Delta\varphi, \Delta\theta) + (m-1)\dot{D}_{i,j}(0°, \Delta\theta), \quad (21)$$

where $\dot{D}_{i,j}(0°, \Delta\theta)$ is the dose rate at point i when the radiation source is located at dwell position j and completely surrounded by the shield. The $\lceil \; \rceil$ and $\lfloor \; \rfloor$ operators denote ceiling (round-up) and floor (round-down) operations, respectively. Equation (21) holds regardless of the methodology used for calculating $\dot{D}_{i,j,k}(\Delta\varphi,\Delta\theta)$, which could vary widely depending on the application. The practical implication of Equation (21) is that m neighboring beamlets with emission angles of $\Delta\varphi$ can be superposed and replaced with a single beamlet with an emission angle of $\varphi_m=m\Delta\varphi$, plus a transmission term. The transmission term is equal to (m−1) times the dose rate at all voxels due to transmission through a completely-shielded source, since adding kernel beamlets (emission angles of $\Delta\varphi$) also adds the radiation transmission values of the kernel beamlets. Shield transmission cannot be neglected in general, but, if the shield is thick enough for transmission to be negligible, then the transmission term vanishes.

The goal of the M-RSBT method is to enable the user to conduct a single optimization with the kernel beamlets, then determine a new set of delivery times using a combination of shielded sources. Producing a set of delivery times that applies to all desired shield emission angles without the need to re-calculate the beamlets or dose distributions for all of the different shield angles is desirable in order to ensure that the algorithm is efficient. The following approximation enables the problem to be solved completely in the space of delivery times:

$$\dot{D}_{i,j}(0°,\Delta\theta) \cong T_{shield}\dot{D}_{i,j}(360°,\Delta\theta), \quad (22)$$

which enables us to rewrite Equation ( ).

Assume for a given dwell position j that there are m kernel directions, centered on direction k, that have dwell times of at least τ. Mathematically, this can be written as:

$$\min_{k-\lfloor m/2 \rfloor \leq k' \leq k+\lceil m/2 \rceil - 1} t_{j,k'} = \tau, \quad (23)$$

The m neighboring kernel beamlets can then be superposed into a single beamlet centered on emission direction $\varphi_k$ and with an emission angle of $\Delta\varphi_m = m\Delta\varphi$, plus a transmission term, as follows:

$$\tau \sum_{k'=-\lfloor m/2 \rfloor}^{\lceil m/2 \rceil - 1} \dot{D}_{i,j,k+k'}(\Delta\varphi, \Delta\theta) = \tau[\dot{D}_{i,j,k}(m\Delta\varphi, \Delta\theta) + (m-1)T_{shield}\dot{D}_{i,j}(0°, \Delta\theta)]. \quad (24)$$

Thus the dwell times for M-RSBT can be determined as:

$$t_{j,k,m} = t_{j,k,m} + \tau \text{ and}$$
$$t_j^{360°} = t_j^{360°} + \tau(m-1)T_{shield}, \quad (25)$$

where $t_j^{360°}$ is the dwell time for the unshielded beamlet at dwell position j. The original times $t_{j,k}$ are then decremented as:

$$t_{j,k'} = t_{j,k} - \tau \text{ for } k - \lfloor m/2 \rfloor \leq k' \leq k - \lceil m/2 \rceil - 1, \quad (26)$$

and the process repeats for any m-values corresponding to shield emission angles the user has access to. At the end of the dwell time reassignment process for emission angles larger than $\Delta\varphi$, the remaining $t_{j,k}$ values are added to $t_{j,k,1}$, ensuring all $t_{j,k}$ values are reassigned to $t_{j,k,m}$.

Circumstances exist for which it is preferable to redistribute the dwell times due to transmission terms amongst the baseline beamlet times rather than directly into the unshielded beamlet. An approximate $\dot{D}_{i,j}(360°, \Delta\theta)$ can now be calculated, the dose rate delivered to all voxels from a shield with a zenith emission angle of $\Delta\theta$ and a 360° azimuthal emission angle by combining kernel beamlets as follows:

$$\sum_{k=0}^{K-1} \dot{D}_{i,j,k}(\Delta\varphi, \Delta\theta) = \dot{D}_{i,j}(360°, \Delta\theta) + (K-1)\dot{D}_{i,j}(0°, \Delta\theta) \quad (27)$$
$$\cong \dot{D}_{i,j}(360°, \Delta\theta) + (K-1)T_{shield}\dot{D}_{i,j}(360°, \Delta\theta)$$
$$= [1 + (K-1)T_{shield}]\dot{D}_{i,j}(360°, \Delta\theta),$$

therefore:

$$\dot{D}_{i,j}(360°, \Delta\theta) \cong \frac{1}{1 + (K-1)T_{shield}} \sum_{k=0}^{K-1} \dot{D}_{i,j,k}(\Delta\varphi, \Delta\theta). \quad (28)$$

It follows from Equation (28) that the shielded dose can be calculated using the kernel beamlets as:

$$\dot{D}_{i,j}(0°, \Delta\theta) \cong \frac{T_{shield}}{1 + (K-1)T_{shield}} \sum_{k=0}^{K-1} \dot{D}_{i,j,k}(\Delta\varphi, \Delta\theta). \quad (29)$$

Equation (29) can be substituted into the first line of Equation (24) to obtain:

$$\tau \sum_{k'=-\lfloor m/2 \rfloor}^{\lceil m/2 \rceil - 1} \dot{D}_{i,j,k+k'}(\Delta\varphi, \Delta\theta) = \quad (30)$$
$$\tau \dot{D}_{i,j,k}(m\Delta\varphi, \Delta\theta) + \sum_{k=0}^{K-1} \left[ \frac{\tau(m-1)T_{shield}}{1+(K-1)T_{shield}} \right] \dot{D}_{i,j,k}(\Delta\varphi, \Delta\theta).$$

Thus the dwell times for M-RSBT can be to account for the reassignment to a larger emission angle beamlet and radiation transmission from the baseline beamlets as follows:

$$t_{j,k,m} = t_{j,k,m} + \tau \quad (31)$$
$$t_{j,k,1} = t_{j,k,1} + \tau \frac{(m-1)T_{shield}}{1+(K-1)T_{shield}} \text{ for all } k'$$

The original times $t_{j,k}$ are then decremented as:

$$t_{j,k'} = t_{j,k} - \tau \text{ for } k - \lfloor m/2 \rfloor \leq k' \leq k - \lceil m/2 \rceil - 1, \quad (32)$$

Data and/or simulation demonstrate, in one aspect, that the treatment time using the M-RSBT delivery method will always be as short as or shorter than could be obtained using S-RSBT. In one aspect, the radiation source was modeled as a Xoft Axxent electronic brachytherapy (eBT) source and assumed the system of shields allowed 0% transmission. The RSBT treatment plans were generated using a dose calculator developed at the University of Iowa Hospital & Clinics' Radiation Oncology Department using MATLAB (2009b, The MathWorks, Natick, Mass.). The prescription was set to 100% for all voxels on the tumor surface, and restrictions were set such that the maximum dose for any voxel on the surface of the bladder, sigmoid, and rectum were 90%, 75%, and 75% respectively. Only the surface voxels were considered in the optimization since the source position ensures that the dose inside the tumor will always be greater than the dose delivered at the surface. Similarly, it should be appreciated that the inside of the Organs at Risk (OARs) can always be less than at the surface due to the source position. It also should be appreciated that the therapy advantages (such as reduced treatment time) of M-RSBT with respect to other RSBT techniques can offset the complexity associated with changing the size of the radiation shield during delivery.

The dose distributions for the patient that would benefit least from M-RSBT out of all the patients tested using a minimum emission angle of 180° and 22.5° are shown in FIG. 46(a) and FIG. 46(b), respectively. Tumor coverage is much better using the smaller emission angle, but but treatment time increased. This patient is not the ideal candidate for M-RSBT because less recombination into the larger emission is possible, yet still consistently yields a shorter treatment time when the M-RSBT method is used.

It is observed that the treatment times for this patient, though not the ideal for M-RSBT are always shorter than when using RSBT, as demonstrated in FIG. 47. In addition, as the minimum emission angle gets smaller, M-RSBT increasingly outperforms RSBT. M-RSBT treatment times (green) and RSBT treatment times (blue) plotted against the $D_{90}$ for the tumor surface. The figure shows that as the $D_{90}$ gets closer to 100% for the tumor surface (a result of lowering the emission angle) M-RSBT has significantly shorter treatment times than RSBT. However, even at large emission angles M-RSBT outperforms RSBT because some recombination is still possible. The emission angles used for this figure were 180°, 90°, 45°, and 22.5°.

Similar performance is readily available for a patient with a tumor with a high potential for recombination, such as the tumor shown in FIG. 48(a) and FIG. 48(b). FIG. 48(a) shows a dose distribution for a patient that would benefit significantly from M-RSBT using a minimum emission angle of 180°. FIG. 48(b) illustrates the analogous distribution using a minimum emission angle of 22.5°. Tumor coverage is much better using the smaller emission angle.

FIG. 49 shows the treatment times for the patient from FIG. 48(a-b), with M-RSBT treatment times (green) and RSBT treatment times (blue) plotted against the $D_{90}$ for the tumor surface. The figure shows that M-RSBT is substantially more efficient for all emission angles. The emission angles used for this figure were 180°, 90°, 45°, and 22.5°.

As disclosed herein, in one aspect, for every patient and every emission angle, M-RSBT had a shorter treatment time than when using the RSBT method, especially when the emission angle is small enough to provide a satisfactory Do for the tumor surface.

FIG. 50 illustrates an example comparison of treatment times for RSBT and M-RSBT (also referred to as MRS-IMBT) in accordance with one or more aspects of the disclosure.

FIG. 51 illustrates a block diagram of an exemplary operating environment 5100 that enables the implementation of therapy design (e.g., treatment plan, beamlet selection construction, radiation shield design, optimization of treatment plan, etc.) and other various features of the subject disclosure and performance of the various methods disclosed herein. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The various embodiments of the subject disclosure can be operational with numerous other general purpose or special purpose computing system environments or configurations. Examples of well-known computing systems, environments, and/or configurations that can be suitable for use with the systems and methods comprise, but are not limited to, personal computers, server computers, laptop devices or handheld devices, and multiprocessor systems. Additional examples comprise wearable devices, mobile devices, set top boxes, programmable consumer electronics, network PCs, minicomputers, mainframe computers, distributed computing environments that comprise any of the above systems or devices, and the like.

The processing effected in the disclosed systems and methods can be performed by software components. The disclosed systems and methods can be described in the general context of computer-executable instructions, such as program modules, being executed by one or more computers or other computing devices. Generally, program modules comprise computer code, routines, programs, objects, components, data structures, etc. that perform particular tasks or implement particular abstract data types. The disclosed methods also can be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 5101. The components of the computer 5101 can comprise, but are not limited to, one or more processors 5103, or processing units 5103, a system memory 5112, and a system bus 5113 that couples various system components including the processor 5103 to the system memory 5112. In the case of multiple processing units 5103, the system can utilize parallel computing.

In general, a processor 5103 or a processing unit 5103 refers to any computing processing unit or processing device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally or alternatively, a processor 5103 or processing unit 5103 can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors or processing units referred to herein can exploit nano-scale architectures such as, molecular and quantum-dot based transistors, switches and gates, in order to optimize space usage or enhance performance of the computing devices that can implement the various aspects of the subject disclosure. Processor 5103 or processing unit 5103 also can be implemented as a combination of computing processing units.

The system bus 5113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 5113, and all buses specified in this description also can be implemented over a wired or wireless network connection and each of the subsystems, including the processor 5103, a mass storage device 5104, an operating system 5105, therapy design software 5106, therapy design data 5107, a network adapter 5108, system memory 5112, an Input/Output Interface 5110, a display adapter 5109, a display device 5111, and a human machine interface 5102, can be contained within one or more remote computing devices 5114a,b,c at physically separate locations, connected through buses of this form, in effect implementing a fully distributed system.

In one aspect, therapy design software 5106 can comprise computer-executable instructions for implementing the various methods described herein; in particular, yet not exclusively, the various methods described herein. In another aspect, therapy design software 1706 can include software to control various aspects of manufacturing of the shield and, as part of manufacturing, treating a surface in accordance with aspects described herein in order to attain a desired thickness profile for the surface of the shield. In certain embodiments, therapy design software 5106 also can include computer-executable instruction for selecting radio-opaque materials for manufacturing the shield. Therapy design software 5106 and therapy design data 5107 (which can comprise radiation shield data) can configure processor 5103 to perform the one or more steps (or stages or actions) of the methods described herein. In addition or in the alternative, therapy design software 5106 and therapy design data 5107 can configure processor 5103 to operate in accordance with various aspects of the subject disclosure.

The computer 5101 typically comprises a variety of computer readable media. Exemplary readable media can be any available media that is accessible by the computer 5101 and comprises, for example and not meant to be limiting, both volatile and non-volatile media, removable and non-removable media. The system memory 5112 comprises computer readable media in the form of volatile memory, such as random access memory (RAM), and/or non-volatile memory, such as read only memory (ROM). The system memory 5112 typically contains data and/or program modules such as operating system 5105 and therapy design software 5106 that are immediately accessible to and/or are presently operated on by the processing unit 5103. Operating system 5105 can comprise OSs such as Windows operating system, Unix, Linux, Symbian, Android, iOS, Chromium, and substantially any operating system for wireless computing devices or tethered computing devices.

In another aspect, the computer 5101 also can comprise other removable/non-removable, volatile/non-volatile computer storage media. By way of example, FIG. 51 illustrates a mass storage device 5104 which can provide non-volatile storage of computer code, computer readable instructions, data structures, program modules, and other data for the computer 5101. For example and not meant to be limiting, a mass storage device 5104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 5104, including by way of example, an operating system 5105, and therapy design software 5106. Each of the operating system 5105 and therapy design software 5106 (or some combination thereof) can comprise elements of the programming and the therapy design software 5106. Data and code (e.g., computer-executable instruction(s)) can be retained as part of therapy design software 5106 and can be stored on the mass storage device 5104. Therapy design software 5106, and related data and code, can be stored in any of one or more databases known in the art. Examples of such databases comprise, DB2®, Microsoft® Access, Microsoft® SQL Server, Oracle®, mySQL, PostgreSQL, and the like. Further examples include membase databases and flat file databases. The databases can be centralized or distributed across multiple systems.

In another aspect, the user can enter commands and information into the computer 5101 via an input device (not shown). Examples of such input devices comprise, but are not limited to, a camera; a keyboard; a pointing device (e.g., a "mouse"); a microphone; a joystick; a scanner (e.g., barcode scanner); a reader device such as a radiofrequency identification (RFID) readers or magnetic stripe readers; gesture-based input devices such as tactile input devices (e.g., touch screens, gloves and other body coverings or wearable devices), speech recognition devices, or natural interfaces, and the like. These and other input devices can be connected to the processing unit 5103 via a human machine interface 5102 that is coupled to the system bus 5113, but can be connected by other interface and bus structures, such as a parallel port, game port, an IEEE 1394 Port (also known as a Firewire port), a serial port, or a universal serial bus (USB).

In yet another aspect, a display device 5111 also can be connected to the system bus 5113 via an interface, such as a display adapter 5109. It is contemplated that the computer 5101 can have more than one display adapter 5109 and the computer 5101 can have more than one display device 5111. For example, a display device can be a monitor, an LCD (Liquid Crystal Display), or a projector. In addition to the display device 5111, other output peripheral devices can comprise components such as speakers (not shown) and a printer (not shown) which can be connected to the computer 5101 via Input/Output Interface 5110. Any step and/or result of the methods can be output in any form to an output device. Such output can be any form of visual representation, including, but not limited to, textual, graphical, animation, audio, tactile, and the like.

The computer 5101 can operate in a networked environment using logical connections to one or more remote computing devices 5114*a,b,c*. By way of example, a remote computing device can be a personal computer, portable computer, a mobile telephone, a server, a router, a network computer, a peer device or other common network node, and so on. Logical connections between the computer 5101 and a remote computing device 5114*a,b,c* can be made via a local area network (LAN) and a general wide area network (WAN). Such network connections can be through a network adapter 5108. A network adapter 5108 can be implemented in both wired and wireless environments. Such networking environments are conventional and commonplace in offices, enterprise-wide computer networks, intranets, and the Internet. Networking environments are referred to as network(s) 5115 and generally can be embodied in wireline networks or wireless networks (e.g., cellular networks, such as Third Generation (3G) and Fourth Generation (4G) cellular networks, facility-based networks (femtocell, picocell, Wi-Fi networks, etc.).

As an illustration, application programs and other executable program components such as the operating system 5105 are illustrated herein as discrete blocks, although it is recognized that such programs and components reside at various times in different storage components of the computing device 5101, and are executed by the data processor(s) of the computer. An implementation of therapy design software 5106 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer-readable media can comprise "computer storage media," or "computer-readable storage media," and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

In various embodiments, the systems and methods of the subject disclosure for implementation of advanced rotating-shield brachytherapy can employ artificial intelligence (AI) techniques such as machine learning and iterative learning. Examples of such techniques include, but are not limited to, expert systems, case based reasoning, Bayesian networks, behavior based AI, neural networks, fuzzy systems, evolutionary computation (e.g., genetic algorithms), swarm intelligence (e.g., ant algorithms), and hybrid intelligent systems (e.g., Expert inference rules generated through a neural network or production rules from statistical learning).

In an aspect, exemplary systems and methods can comprise a radiation source wire designed to contain a sufficient quantity of the gadolinium-153 ($^{153}$Gd) radioisotope for high-dose-rate brachytherapy of cancerous tumors. The distal portion of the source wire can comprise a plugged capsule containing the $^{153}$Gd, which is welded to a wire having a length between 20 cm and 2 m, and which can be controlled with a remote afterloading system. In one example, the wire can be 30 cm and can be administered by manually or robotically inserting it into a shielded or unshielded catheter. As $^{153}$Gd sources will have a lower dose rate than $^{192}$Ir high-dose-rate sources, a radiation plan can be administered by inserting a plurality of $^{153}$Gd source wires into a plurality of shielded catheters, each of which can be individually controlled by a rotating, translating, motor. All of the metals associated with the wire besides the $^{153}$Gd can comprise NiTi (nitinol), for strength and flexibility, or stainless steel. In order to construct a source wire, the open $^{153}$Gd capsule can be filled with the radioactive material and then sealed with a NiTi (or stainless steel) plug, for example, by laser-welding to the capsule opening. The invention can be useful in the fields of Radiation Oncology and Urology, and can be described as a new form of Brachytherapy called Intensity Modulated Brachytherapy (IMBT), rotating shield brachytherapy (RSBT), or dynamically modulated brachytherapy (DMBT). Intensity modulated Brachytherapy can significantly improve radiation dose distribution for brachytherapy patients, especially those with cervical cancer, colorectal cancer, liver cancer, lung cancer, and prostate cancer. The systems and methods can be of commercial value because the systems and methods provide a novel radiation source with an ideal gamma ray energy spectrum that enables patient-specific shielding and similar penetration in tissue to the gamma rays of the $^{192}$Ir isotope, and these properties are ideal for IMBT. The $^{153}$Gd isotope emits radiation with an optimal energy spectrum, at an acceptable dose rate, and with a half-life of 240 days. Existing Iridium-192 ($^{192}$Ir) source wires have sub-optimal energy spectra for IMBT.

In an aspect, the methods and systems can be applied to Radiation Oncology, and, when applied for prostate cancer treatment, Urology. An exemplary system can comprise a source wire apparatus containing $^{153}$Gd, shown in FIG. 52. FIG. 52(a) is an exemplary apparatus. The apparatus can comprise an assembled source wire. The assembled source wire can comprise a capsule. In an aspect, the capsule can comprise a radiation source. An example radiation source is $^{153}$Gd. The assembled source wire can also comprise a plug. The assembled source wire can further comprise a wire attached to the capsule. FIG. 52(b) is an exploded view of source wire. In an aspect, laser welding can be used to connect the Ti—Ni parts together, which encapsulates the $^{153}$Gd active source. The diameter of the active $^{153}$Gd source can be 0.3-0.9 mm, and the diameter of the capsule, thick part of the plug, and wire can be 0.5-1.0 mm. The space between the active source and the outer source capsule consists of encapsulation material, which can be NiTi or stainless steel, for example. Encapsulation thicknesses range from 0.05 mm to 0.125 mm. Active source lengths can range from 5 mm to 30 mm. The diameter can be configured for compatibility with an afterloader system such as the GammaMed Plus afterloader system, currently sold by Varian. It should be noted that though FIGS. 52(a)-(b) illustrate particular dimensions and materials, other dimensions and materials can be used.

The wire can be used to deliver high-dose-rate Brachytherapy using a remote afterloading system, which can mechanically control the location of the radiation source wire inside of catheters or applicators that are inserted into a patient. The invention is novel because it is the first such source wire to use the $^{153}$Gd radioisotope to deliver the radiation dose.

Single or multiple $^{153}$Gd wires can be used simultaneously with rotating shielded catheters to deliver low-dose-rate (0.4-2 Gy/h), medium-dose-rate (2-12 Gy/h), and high-dose-rate (>12 Gy/h) I-RSBT.

The specific problem the invention can overcome is that of delivering intensity modulated Brachytherapy (I-RSBT) with a radiation source that emits gamma rays in the 100 keV energy range. $^{153}$Gd emits primarily gamma rays between 40 and 100 keV, which are ideal for enabling the construction of novel shielding systems that can be built into Brachytherapy catheters. The tenth-value-layer, which is the thickness of a shielding material to reduce the radiation dose to 10% of it sun shielded value, is only 0.37 mm of platinum for $^{153}$Gd, and over 11 mm for $^{192}$Ir, which is the conventional high-dose-rate brachytherapy isotope. In an aspect, the systems and methods can comprise fitting at least one tenth-value-layer of shielding material inside the catheters through which the source wire will travel in order to deliver I-RSBT effectively. Since $^{192}$Ir, the conventional high-dose-rate brachytherapy isotope, has such a large tenth-value-layer, it is infeasible to construct shielded catheters that are small enough to treat cancers such as prostate cancer, which involve catheters of 2 mm in diameter or less.

Determining an isotope that is acceptable for I-RSBT has historically been a difficult problem. The concept of single-catheter I-RSBT was proposed in 2002, and multiple catheter I-RSBT was proposed in 2006, yet it was never made clear what isotope could be used to best enable I-RSBT. Low-energy isotopes have been considered for I-RSBT, but the sources have been electronic brachytherapy sources with diameters too large for interstitial applications, which has a relatively short half-life of 59.4 days. Low energy sources also can have the disadvantage of more rapid dose fall-off with distance from the source than higher energy sources, which can increase the magnitude of radiation dose hotspots in the patient. We propose using $^{153}$Gd for I-RSBT due to its ideal gamma ray energy emission spectrum, long half-life, and recently developed potential for mass production.

Gadolinium-153 ($^{153}$Gd) is not the only isotope that emits gamma rays in the energy range of interest, and it is not obvious that it would be the ideal radioisotope for I-RSBT. According to a previous analysis by Oak Ridge National Laboratory for a very different purpose (atmospheric density measurements), there are several other candidate isotopes, including $^{57}$Co, $^{91m}$Nb, $^{101}$Rh, $^{151}$Gd, $^{168}$Tm, $^{173}$Lu, $^{174}$Lu, $^{195}$Au, $^{97m}$Tc, $^{99m}$Tc, $^{93}$Mo, $^{113m}$Cd, $^{188}$W, $^{139}$Ce, $^{123m}$Te, $^{125}$Te, $^{127m}$Te, $^{170}$Tm, $^{155}$Eu, and $^{109}$Cd. Through scientific research, $^{153}$Gd is discovered to be an ideal radiation source for I-RSBT. For example, other candidates can be too costly to produce ($^{91m}$Nb, $^{101}$Rb, $^{151}$Gd, $^{168}$Tm, $^{173}$Lu, $^{174}$Lu, and $^{195}$Au), can have too low specific activities or gamma ray yield ($^{97m}$Tc,$^{93}$Mo,$^{109}$Cd,$^{113m}$Cd, and $^{170}$Tm, $^{155}$Eu), can have too short half-lives ($^{99m}$Tc), can have high-energy gamma ray contamination ($^{188}$W) or the presence of other contaminants ($^{139}$Ce), or can provide calibration difficulties ($^{123m}$Te, $^{125}$Te, and $^{127m}$Te). For example, other similar radiation sources such as $^{57}$Co can likely be produced in large enough quantities for high-dose-rate brachytherapy, but at an estimated ten times the cost of $^{153}$Gd.

FIG. 53 is a flowchart illustrating an exemplary method 5300 of forming a therapeutic radiation capsule. In step 5302, a radiation source can be enclosed in a capsule. In step 5304, the capsule can be attached to a wire. The wire can be configured to guide the capsule to a target through an applicator tube. In step 5306, an applicator tube configured to guide the capsule to a target can be provided.

FIG. 54 is a flowchart illustrating an exemplary method 5400 of providing therapeutic radiation. In step 5402, a target can be identified. In step 5404, an applicator tube configured to guide a capsule proximate to the target can be provided. In an aspect, the capsule can enclose the radiation source and have a wire attached to the capsule. In step 5406, the capsule can be guided through the applicator tube proximate to the target by use of the wire.

FIG. 55 is a flowchart illustrating an exemplary method 5500 for rotating shield brachytherapy (RSBT). In step 5502, a plurality of radiation shields for RSBT can be selected. In an aspect, each one of the plurality of radiation shields having a specific radiation emission angle. In step 5504, a treatment plan can be applied by delivering radiation over a predetermined period through a specific sequence of the plurality of the plurality of radiation shields.

FIG. 56 is a flowchart illustrating an exemplary method 5600 for selecting an emission angle for use in single rotating-shield brachytherapy. In step 5602, a dose can be calculated. In step 5604, the calculated dose can be optimized. In step 5606, a first treatment plan can be generated based on the optimized dose. In step 5608, a second treatment plan can be generated. In step 5610, one of the first treatment plan or the second treatment plan can be selected.

FIG. 57 is a flowchart illustrating an exemplary method 5700 for sequencing rotating shields. In step 5702, a dose is calculated. In step 5704, the dose can be optimized. In step 5706, a treatment plan is generated based on an optimal sequence of the dose.

I-RSBT Catheter Delivery System

In an aspect, an I-RSBT catheter delivery system 6000 is shown in FIGS. 58-71, which illustrates how the intelligent use of multiple I-RSBT catheters can dramatically reduce the treatment time of S-RSBT. In general, the brachytherapy sources are inserted into multiple catheters which are then positioned at multiple positions within a targeted location within a human subject efficiently. Radiation is emitted by the sources in all directions from each dwell positions. In another aspect, the I-RSBT catheter delivery system 6000 can emit the radiation in a helical pattern, increasing the efficiency of the emission, as well as limiting the exposure for healthy tissues.

In an aspect, as shown in FIGS. 58-64 and 67-68, the I-RSBT catheter delivery system 6000 can include catheter control cartridges 6100 arranged within a cartridge magazine holder 6600 and controlled by a system controller 6700. The catheter control cartridges 6100, controlled by the system controller 6700, engage needles 6500 within a subject to deliver the I-RSBT. Given the nature of I-RSBT, the I-RSBT catheter delivery system 6000 must be able to deliver I-RSBT in numerous precise locations over a very small volume, generally only an area that is 30-100 cm$^3$.

Therefore, the catheter control cartridges 6100, which deliver the I-RSBT, can be small in size as well. While the cross sectional size of the catheter control cartridges 6100 can vary from aspect to aspect, in a preferred aspect, the catheter control cartridges 6100 can have a cross section of approximately 9.5 mm×9.5 mm.

In an aspect, as illustrated in FIGS. 59-61 and 68, a catheter control cartridge 6100 can include a RSBT catheter 6110. In an aspect, the catheter RSBT 6110 can be constructed in the multiple fashions as described above. In an example, as illustrated in FIG. 61, the RSBT catheter 6110 is configured to be inserted into a needle 6500 found within the subject. The RSBT catheter 6110 can include an outer tube/catheter 6112. The outer tube 6112 can be comprised of numerous materials, including, but not limited to, stainless steel, nitinol, titanium, and various other plastics. However, nitinol is a preferred material for use in the outer tube 6112 because of nitinol is durable, can be effectively sterilized for reuse, provides some flexibility in an orthogonal direction, but is rotationally stiff.

In an aspect, as shown in FIG. 61, the outer tube 6112 of the RSBT catheter 6110 is configured to be smaller than the interior of the needle 6500, which leads to a small space 6111 between the two once the catheter 6110 is inserted into the needle 6500. This is done because the needle 6500 is inserted into a subject, it is normally done without the catheter 6110 inserted, which can lead to the needle 6500 being compressed or bent. By configuring the RSBT catheter 6110 to be smaller than the interior of the needle 6500, a little extra space is created between the outer wall 6112 of the catheter 6110 and the inner wall of the needle 6500 to allow the RSBT catheter 6110 to be smoothly inserted into the needle 6500, and subsequently rotated.

The outer tube/catheter 6112 of the RSBT catheter 6110 retains the shield 6114. The shield 6114 can have the properties and physical dimensions of the various shields discussed in the aspects above. The shield 6114 can have a specific radiation emission angle or opening, as discussed above. The shield 6114 can be made of a variety of materials that have properties that stop the penetration of radiation. The shield 6114 can be comprised of, but not limited to, osmium, gold, silver, uranium, tungsten, lead, bismuth or platinum. In an aspect, the shield 6114 is coupled to a window 6116. The window 6116 can have the properties and physical dimensions of the various windows discussed in the various aspects above. The window 6114 can be made of a variety of materials having a lower density than the material being used in the shield 6114, allowing for the penetration of radiation through the window 6116. In an aspect, the window 6116 is comprised of a plastic. In a preferred embodiment, the window 6116, and possibly the shield 6114, would be capable of being sterilized. The window 6116 is coupled to the shield 6114 to contain the radiation source 6120. The window 6116 and the shield 6114 can be coupled to one another in various ways, including, but not limited to, a tongue-groove combination, fasteners, adhesive, or the like. In an aspect, window 6116 can rest within a cutout portion of the shield 6114 and be retained within the cutout portion through the inner surface of the catheter tube 6112, with ends of the window 6116 abutting sides of the cutout portion of the shield.

The radiation source 6120 can comprise any radioactive material that can be used to deliver radiation as desired, including, but not limited to, the materials disclosed above. The radiation source 6120 can be contained within a radiation tube/catheter 6122. The radiation tube 6122 can have the properties and physical dimensions of the various radiation tubes/catheters (e.g., catheters 320 in FIGS. 42A & C-D) discussed in the various aspects above. The radiation tube 6122 can be comprised of a variety of different materials, including, but not limited to, nitinol, stainless steel, titanium, titanium alloy, and the like. In some aspects, the shield 6114 and window 6116 of the RSBT catheter 6110 are configured to have a space 6124 between the shield/window combination and the radiation tube 6122 when the radiation source 6120 is inserted. Such a configuration allows easier placement and removal of the radiation tube 6122 between the shield 6114 and window 6116, as well as allowing for separate manufacturing of the RSBT catheter 6110 and the radiation source 6120 (i.e., the RSBT catheter 6110 can be manufactured by a different manufacturer than the radiation source). In an aspect, the shield 6114, window 6116, and radiation source 6120 are located at a distal end 6130 of the catheter 6110.

As shown in FIGS. 59-60, the RSBT catheter 6110 can be connected to a lead screw 6150, or other type of advancing mechanism, at a proximal end 6132 of the catheter. The lead screw 6150 can be made of a variety of materials, including, but not limited to aluminum, stainless steel, titanium, titanium alloy, plastic, and the like. In an aspect, the lead screw 6150 is made of a lightweight material that is not flexible. A light weight material can be desirable in order to reduce the overall weight of the RSBT catheter cartridge 6100.

The lead screw 6150 has a distal end 6152 and a proximal end 6154, with the proximal end 6132 of the RSBT catheter 6110 being coupled to the distal end 6152 of the lead screw 6150. In an aspect, RSBT catheter 6110 is configured to be removably coupled to the distal end 6152 of the lead screw 6150. In an aspect, the distal end 6152 of the lead screw 6150 can use a clamping device or other fastener means to removeably attach the RSBT catheter 6110. In other aspects, the RSBT catheter can be permanently attached to the distal end 6152 of the lead screw 6150. In an aspect, the lead screw 6150 can include an outer surface 6154 that can be threaded, discussed in more detail below.

In an aspect, the lead screw 6150 can be driven by a motor 6200. In an aspect, the motor 6200 is a stepper motor 6200 with a drive shaft 6210, a controller 6220, and a housing 6230. In an exemplary aspect, the stepper motor 6200 is a Faulhaber ADM 1220 stepper motor. However, other models of stepper motors from Faulhaber, as well as other manufacturers of stepper motors can be used to drive the lead screw 6150. The drive shaft 6210 is configured to rotate in a forward direction and a backward direction. The controller 6220 controls the activation of the motor 6200 and the rotational direction of the drive shaft 6210 as well.

The housing 6230, while protecting the inner components of the motor 6200, provides access to an exposed end of the drive shaft 6210. The exposed end of the drive shaft 6210 can protrude past the housing 6230, or the housing 6230 can provide an opening to the exposed end of the drive shaft 6210, such that the exposed end of the drive shaft 6210 can be coupled to the proximal end 6154 of the lead screw 6150. In an aspect, the proximal end 6154 of the lead screw 6150 can be removably coupled to the drive shaft 6210. Various fastening and connector means can be used to couple the proximal end 6154 of the lead screw 6150 to the drive shaft 6210. In an aspect, the fastening and connector means can include a plurality of slots found on the proximal end 6154 of the lead screw 6150 that correspond to a plurality of protrusions on the drive shaft 6210, making a male/female type connection. Clips, clamps, and the like can be used to lock the components in place.

In other aspects, the motor 6200 can include any motor capable of inserting or withdrawing the advancing mechanism 6150 into the shell 6400 in a controlled manner. In an aspect, the motor 6200 can include any motor capable of driving the lead screw 6150 in a rotational manner, pushing or pulling the lead screw 6150 into and out of the shell 6400 of the catheter cartridge 6100, discussed further below. In an aspect, a SQUIGGLE micro motor from New Scale Technologies can be used. However, it is preferred that a motor 6200 that provides precise control of the movement of the lead screw 6150 is used.

In other aspects, more than one motor 6200 can be used to drive the lead screw 6150. For example, in an aspect where it is desired that the path of the radiation emission does not rotate, a second motor can be configured to rotate the RSBT catheter 6110 to counteract the rotation to the lead screw 6150 caused by the first motor 6200.

In an aspect, as shown in FIG. 59-60, a carriage 6300 can be coupled to the housing 6230 of the motor 6200. The carriage 6300 can include a distal end 6310 and a proximal end 6320. The distal end 6310 and the proximal end 6320 of the carriage 6300 can be formed of open ended structures 6312, 6322. In an aspect, the proximal end 6320 of the carriage 6300 is connected to the housing 6230 of the motor 6200 approximate the access point of the drive shaft 6210. Various fastening means can be employed to connect the open ended structure 6322 of the proximal end 6320 of the carriage 6300 to the housing 6230 of the motor 6200. The open ended structure 6322 of the proximal end 6320 allows the lead screw 6150 to connect to the drive shaft 6210 of the motor 6200 while being housed within the carriage 6300, discussed in more detail below.

In an aspect the open ended structure 6312 of the distal end 6310 of the carriage 6300 can have a U-shaped cross section (shown in FIG. 62), allowing side access through the opened ended structure 6312. The distal and proximal ends 6310, 6320 can be connected by supporting structures 6330. In a further aspect, the carriage 6300 can be aligned to surround the lead screw 6150 in the same axial direction as the axial direction of the lead screw 6150 as it is connected to the drive shaft 6210 of the motor 6200.

As discussed in more detail below, the carriage 6300 is configured to engage with the interior of the shell 6400, and as such, the shape of the carriage 6300 can match the shape of the interior of the shell 6400 to promote the interaction between the two components 6300, 6400. In an aspect 6400, the shell 6400 has a cube shape along its length. In this aspect, as shown in FIGS. 59 and 62, the supporting structure 6330 can be comprised of 4 rods 6330 that are oriented in a parallel fashion relative to one another in order to match the shape of the interior of the shell to engage the interior of the shell 6400. The rods 6300 can be connected to the end structures 6312, 6322 of the carriage 6300. In this aspect, the rods 6300 are oriented to align within the corners of the interior of the shell 6400, preventing the carriage 6300 from rotating within the shell 6400.

In other aspects, the supporting structures 6330 can take various other forms. For example, the supporting structures 6330 can form a four full sided structure when connected. However, using rods 6330 oriented in the fashion discussed above cuts down on the overall weight of the carriage 6300 while providing stable support for the carriage 6300. In addition, by orienting the four rods 6330 in an equidistant manner, more space is provided between the lead screw 6150 and the boundaries of the carriage 6300. Given the size needs for the catheter control cartridges 6100 (i.e., multiple cartridges being used in a very small space), there is not much clearance room between the components, and therefore, any additional space can be valuable. Additionally, the use of rods 6330 allows access to the lead screw 6150 when needed. In an aspect, the carriage 6300 can be comprised of steel or other types of sturdy, durable material.

In an aspect, the carriage 6300 is configured to interact with a shell 6400, as illustrated in FIGS. 59-60, 62-64 and 67. The shell 6400 includes a hollow body 6410 with a distal end 6420 and a proximal end 6430. The ends 6420, 6430 can include openings 6422, 6432 to the interior of the hollow body 6410 of the shell 6400, with the opening 6432 of the proximal end 6430 configured to receive the carriage 6300 and the opening 6422 of the distal end 6420 configured to receive the catheter 6110. In an aspect, the distal end 6420 of the shell can include a cylinder extension 6424. The cylinder extension 6424 can be aligned with the opening 6422 of the distal end 6420, allowing the catheter 6110 to pass through its interior. In addition, the cylinder extension 6424 can be configured to engage and removably lock with components of a cartridge magazine 6600 discussed below.

The hollow body 6410 of the shell 6400, and the respective openings 6422, 6432, are configured to slidably and controllably receive the I-RSBT catheter 6100, the lead screw 6150, and the carriage 6300. In an aspect, the shape of the shell 6400 is configured to prevent the rotation of the carriage 6300 while the lead screw 6150 is being rotated by the motor 6200, discussed in detail below. In an example, as shown in FIGS. 59-60, 62-64, the shell 6400 has a rectangular shape that matches the shape of the carriage 6300. In this example, the rods 6330 of the carriage 6300 are oriented and aligned in a manner that the rods 6330, when engaging the interior of the shell 6400, are contained within the corners of the shell 6400. In other aspects, the shape of the shell 6400 can have other shapes that correspond with the shape and construction of the other components of the system 6000, including the carriage 6300 and lead screw 6150.

In an aspect, the shell 6400 can have four rectangular sides 6440, 6442, 6444, 6446, as shown in FIG. 62. In another aspect, one of the four rectangular sides 6446 can be removable in order to provide access into the interior of the shell 6400. By providing a removable side 6446, an individual can gain access to the interior of the shell 6400, as well as to components of the catheter control cartridge 6100 that are contained within the shell 6400 (e.g., the lead screw 6100, the carriage 6300, and the RSBT catheter 6110) when the system 6000 is not in use. The removable side 6446 can be secured to adjacent sides 6440, 6444 through removable set screws, clips, clamps, and other fastening means.

In an aspect, the shell 6400 can be comprised of various materials, including, but not limited to, carbon fiber, aluminum, stainless steel, sheet metal, and the like. In an aspect, while a variety of materials can be used, it is preferred that the shell material 6400 have a thickness of 0.5 mm or less. The distal end 6420 of the shell 6400 can include a radiation shield 6426. The radiation shield 6426 can be made of any material that is suitable to substantially block any radiation coming from the radiation source 6120 when the catheter 6100 is retained within the shell 6400 while not actively being used. For example, the material of the radiation shield 6426 can include, but is not limited to, stainless steel, brass, lead and the like.

The proximal end 6430 of the shell 6400 can include an advancing mechanism receiver 6450. The advancing mechanism receiver 6450 can be secured within or at the proximal end 6430 of the shell 6400. In an aspect, the advancing mechanism receiver 6450 can include a screw nut 6450. The screw nut 6450 can be utilized when the advancing mechanism 6150 is a lead screw 6150 as described above. The screw nut 6450 can secured within the proximal end 6430 approximate the opening 6432. The screw nut 6450 can include a threaded interior surface (not shown) that corresponds to the threaded exterior surface of the lead screw 6150. The screw nut 6450 is secured in a fashion to prevent any the rotation of the screw nut 6450 within the shell 6400 when interacting with threaded surface 6154 of the lead screw 6150. In an aspect, set screws can be used to secure the screw nut 6450 to the proximal end 6430 of the shell 6400. In other aspects, various other fasteners and securing means can be used to secure the screw nut 6450. In an aspect, the screw nut 6450 can be a part of a flange closing off the proximal end 6430 of the shell 6400 that only provides access through the opening of the screw nut 6540. In this aspect, the flange can include apertures that engage the support structures of the carriage 6300, preventing the carriage 6300 from rotating within the shell 6400. In other aspects, the advancing mechanism receiver 6450 can include any other receiving device or mechanism that is configured to receive the advancing mechanism 6150. In some of these aspects, the advancing mechanism receiver 6450 can be further configured to assist in controlling the movement of the advancing mechanism 6150 within the shell 6400.

In an exemplary aspect, as shown in FIGS. 59-60, the catheter control cartridge 6100 is set up to operate in the following fashion. The I-RSBT catheter 6110 is secured to the distal end 6152 of the lead screw 6150. The distal end 6310 of the carriage 6300 is received within the proximal end 6430 of the shell 6400 and the distal end 6152 of the lead screw 6150 is threaded into the screw nut 6450 of the shell 6400. When the motor 6200 is activated in the forward direction, the drive shaft 6210 rotates the lead screw 6150. The threaded surface 6154 of the lead screw 6150 and the screw nut 6450 pull the lead screw 6150, the carriage 6300, and the catheter 6110 further into the shell 6400, as shown in FIG. 60. The carriage 6300 is configured to engage the inner surfaces of the shell 6400, preventing the motor 6200 from spinning in place, but advancing the lead screw 6150. As the lead screw 6150 advances, the catheter 6110 rotates within the shell 6400 and out through the distal end 6430, as shown in FIG. 60.

In an aspect, as illustrated in FIGS. 58, 63-64, 66 and 68, the I-RSBT catheter delivery system 6000 can utilize a cartridge magazine 6600 to contain and align multiple catheter control cartridges 6100 and their I-RSBT catheters 6110 for simultaneous use. The magazine 6600 includes a distal end 6610 and a proximal end 6620. When placed within the magazine 6600, the catheter control cartridges 6100 are arranged such that the distal end 6110 of the I-RSBT catheter 6110 is aligned with the distal end 6610 of the magazine 6600, and the motor 6200 is oriented approximate the proximal end 6620 of the magazine 6600. The magazine 6600 is further configured to allow the multiple catheter control cartridges 6100 to be removed and realigned accordingly.

In an aspect, the magazine 6600 contains multiple shelves 6630 within its interior. The shelves 6630 support the catheter control cartridges 6100 when placed within the magazine 6600. In an aspect, the multiple shelves 6630 are independently adjustable within the interior of the magazine 6600. In an aspect, the interior of the side walls 6632 of the magazine 6600 include adjustable shelf retaining components that allow the height of each individual shelf 6630 to be adjusted independently.

Figure 66A:
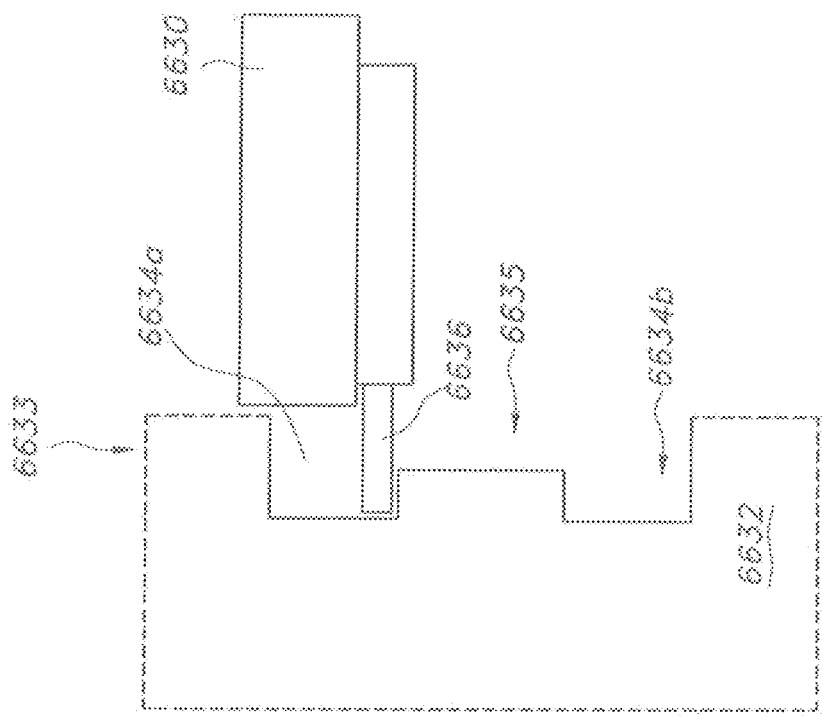

In an exemplary aspect, illustrated in FIGS. 65-66a-d, the adjustable shelf retaining components can include multiple mounts 6633 along the sides of the interior walls 6632 of the magazine 6600. The mounts 6633 should be aligned within the same plane for each shelf 6630. The mounts 6633 include bores 6634a, 6634b vertically aligned with one another that are connected by a slot 6635. The bores 6634 can have a depth greater than the depth of the connecting slot 6635. The shelves 6632 include pegs 6636 on their sides that are configured to fit within the bores 6634, as well as travel within the slot 6635. The number of pegs 6636 corresponds to the number of mounts 6633 for each shelf 6632. For example, each shelf 6630 can include two pegs 6636 on each side of the shelf 6630, with two mounts 6633 on each interior wall 6632 for each shelf 6630. The pegs 6636 can be spring loaded.

To adjust the height of the shelves 6632, the springs of the pegs 6636 are compressed (FIG. 66a-b), allowing the peg 6636 to travel within the slot 6635 (FIG. 66c) to another bore 6634b. When the peg 6636 reaches the bore 6634b, the spring releases and keeps the peg 6636 from exiting the bore 6634 into the slot 6635 (FIG. 66d). As illustrated, the mounts 6633 have two bores 6634, allowing the shelves 6632 to be adjusted between two different heights within the magazine 6600. The mounts 6633, through the positioning of the two bores 6634, allow individual shelves 6630 to be positioned at two different heights within the magazine 6600. In an exemplary aspect, the bores 6635 of each mount 6633 are separated by 5 mm, and the mounts 6633 are spaced apart vertically from one by 5 mm, making the default height between the shelves 6630 10 mm, and allowing each shelf 6630 to be adjusted 5 mm.

In another aspect, the mounts 6633 can be oriented in a different fashion along the inner walls 6632. In an example, the slots 6635 of mounts on one inner wall 6632 can be oriented at an angle between the bores 6634a-b. In an exemplary example, the slot 6635 can be oriented at 45°. The peg 6636 can be slid into the top bore 6634a, slide down the slot 6635 to the bottom bore 6634b, effectively keeping it in place. In such aspects, the pegs 6636 assigned for use with such mounts 6633 do not need to be spring loaded. With such an approach, a user can move and unlock the shelf 6630 only using two spring loaded pegs 6636, with the other non-spring loaded pegs 6636 resting in the bore 6634b, confined there by the off angled slot 6635. A user could then raise or lower the entire shelf by unlocking the two spring loaded pegs 6636, rather than four.

In an aspect, as shown in FIG. 67, the shelves 6630 can include cartridge securing means. In an aspect, the cartridge securing means are configured to prevent the cartridges 6100 from shifting from side to side on the shelves 6630. In another aspect, the cartridge securing means can assist in aligning the cartridges 6100, and more specifically the catheters 6110, with openings provided in a cartridge template 6640, discussed below. In an aspect, the cartridge securing means can include a protrusion and groove combination that the cartridges engage. In this aspect, the exterior bottom side of the shell 6400 of the cartridge 6100 can include a groove that receives a protrusion found on the shelf 6630. In an example of this aspect, the grooves found of the shelves 6630 can be uniformly distributed across the width of the shelf. In other aspects, other securing mechanisms can be used.

A cartridge template 6640 can be found at the distal end 6610 of the magazine 6600, as shown in FIGS. 64 and 68. The cartridge template 6640 can include numerous openings 6642. In an aspect, the openings 6632 are distributed uniformly across the template 6640. In an exemplary aspect, the openings 6632 are distributed in a 10 mm×10 mm grid. The openings 6642 of the template 6630 are configured to receive the I-RSBT catheters 6110 and allow them to transverse the openings 6642 in an axial direction of the catheter 6110. In an aspect, the openings 6642 can comprise a two tier opening 6642, with the first tier 6644 configured to engage cylinder extension 6424 of the shell 6400 and the second tier 6646 configured to allow the catheter 6110 to transverse the opening 6644 in the axial direction. Different securing means can be used to secure the magazine 6600 to prevent moving when it is in use. In an aspect, fasteners, clamps, vises, and the like can be used to secure the magazine 6600 in place.

In an aspect, the I-RSBT catheter 6110 of catheter control cartridge 6100 is configured to engage with a needle 6500, shown in FIGS. 69-71. The needles 6500 can include, but are not limited to, interstitial needles and intracavitary applicators. The needle 6500 has a distal end 6510 and a proximal end 6520 that both provide access into a tubular body 6530 of the needle 6500. The dimensions of the needle 6500 can vary based upon the particular application. In an aspect, the diameter of the tubular body 6530 is of sufficient size to receive the I-RSBT catheter 6110 with a small space between the outer surface of the catheter 6110 and the inner surface of the tubular body 6530 of the needle 6500. The needle 6500 can be comprised of a number of different materials. In an exemplary aspect, the needle 6500 can be made of nitinol, given that such material is ultrasound imaging, CT and MRI compatible, as well as sterilizable. Other materials, including, but not limited to, plastic, titanium, and stainless steel can be used.

The needle 6500 can be placed within the subject under ultrasound guidance, other inter-body guidance techniques, or other known guidance methods. The distal end 6510 of the needle 6500 is placed within the body of the subject, with the proximal end 6520 exposed outside the subject, providing access for the I-RSBT catheter 6110 to enter the subject. The alignment and placement of the needles 6500 is dependent on the location of the tumor being treated, and where the user believes the I-RSBT needs to be delivered. In an aspect, FIG. 68-70 show the needed position of the needles 6500 in a subject, with the proximal ends 6520 exposed outside of the body of the subject. As shown, twenty needles 6500 are being used to treat the tumor, with each needle 6500 can be assigned an identifying number (as shown, numbers 1-20). Based upon the components of the I-RSBT delivery system 6000, the catheters 6110 can be aligned with the magazine 6600 to apply the I-RSBT at the locations identified above.

In an aspect, the spacing of the needles 6500 within the subject, along with the cross sectional size of the catheter control cartridges as set up within the magazine 6600, can dictate the number of catheter control cartridges 6100, and cartridges 6100 alignment, that can be used at a single time. For example, if the cross sectional area of the cartridges 6100 is 9.5 mm×9.5 mm (with the catheter 6110 being oriented within the center of the shell 6400), and any two needles 6500 are spaced closer than 9.5 mm to one another, the I-RSBT will need to be delivered at different times for those two needles 6500.

In an aspect, FIGS. 70-71 illustrate a case of I-RSBT application in which I-RSBT is applied to the subject at two different instances. As shown in FIGS. 70-71, the needles 6500 can be positioned in different planes and at different spacing from one another. In round 1 (shown in FIG. 70), nine cartridges 6100 are aligned with nine needles 6500 to apply the I-RSBT application. As shown, the nine cartridges 6100 are positioned at various positions of the shelves 6630. FIG. 71 shows round 2 of the application of I-RSBT. In this round, ten cartridges 6100 are used with ten needles 6500 to apply the I-RSBT. As shown, the cartridges 6100 are aligned in different positions on the shelves 6630. In addition, the shelves 6630 have been aligned differently (i.e., adjustment of height of the shelves 6630 within the magazine 6600) in comparison to the shelves 6630 as shown in FIG. 70 (round 1). The height of the shelves 6300 can be adjusted in order for the cartridges 6100 to be aligned with the ten needles 6500 that were unused in round 1. In an aspect as shown in FIG. 70, the needles 6500 may not be aligned directly with the center of the cartridges 6100. In such instances, using catheters 6100 made of flexible material (e.g., nitinol) can allow the cartridges 6100 to be used.

In an aspect, the I-RSBT delivery system 6000 can employ a controller 6700 to control the application of I-RSBT. In an aspect, the controller 6700 can be configured to connect and interface with the motors 6200 of each control cartridge 6100 that is being used. In an aspect, the controller 6700 can include a driver capable of controlling each motor being used. In other aspects, the controller 6700 can include a computer 2400 as described above. Various applications associated with the computers 2400, 5101 can control the motors 6200 of the control cartridges 6100 to apply the needed doses of I-RSBT.

In an aspect, when the motors 6200 of the cartridges 6100 are activated, the drive shaft 6210 will begin to rotate, rotating the lead screw 6150. As the lead screw 6150 rotates, the threaded surface of the lead screw 6150 engages the threaded surface of the screw nut 6450. Since the cartridge 6100, by way of the shell 6400, is secured on the shelf 6630 through the securing means, the lead screw 6150, catheter 6110 and carriage 6300 advance towards the distal end 6410 of the shell 6400 and the template 6640. The catheters 6110 can then engage the openings 6642 of the template 6640, and exit into the needles 6500 at the proximal ends 6520. As the lead screw 6150 continues to rotate, the catheter 6110 rotates as well, delivering the radiation in a helical pattern. The controller 6700 can control the activation of the motor 6200 until the catheter 6100 reaches the appropriate depth and the window 6116 and shield 6614 of the catheter 6100 is positioned in the correct direction to apply the radiation to the desire location within the subject. The controller 6700 can control this operation automatically, through the use of various applications, or can be controlled manually to stop the motors 6200 based upon the user providing input based upon observations (e.g., ultrasound guidance, CT or MRI guidance).

Paddle-Based Rotating-Shield Brachytherapy (RSBT

Paddle-based rotating-shield brachytherapy (P-RSBT) is an advanced intensity modulation technique for brachytherapy treatment. P-RSBT can combine the power of S-RSBT and D-RSBT, thus utilizing the benefits of both S-RSBT and D-RSBT in the sense of balancing the treatment time and dose quality. P-RSBT is able to utilize the full angular delivery space and only one source is needed in delivery. P-RSBT model balances the plan quality and its delivery time.

In an aspect, a P-RSBT insertion device uses a set of independently operated shield paddles/paddle blades, each of which covers a sector of radiation field, to achieve intensity modulation. The shield paddles are configured to rotate around the radiation source. In an aspect, the paddle shields are configured to be rotatable about the source in a fine angular stride in order to improve dose conformity. The set of shield paddles are retractable, and can move in (close) and out (open) independently to block and to expose the source, respectively. The paddle openings form a shield aperture to azimuthally modulate the radiation dose intensity. In an aspect, the zenith emission angle is fixed in the longitudinal direction. The modulation is generated by the insertion and retraction of the shield paddles, as well as the rotation and translation of the whole applicator/insertion device.

The shield paddles of a P-RSBT system can be made of a variety of materials that have properties that stop the penetration of radiation. The shield paddles can be comprised of, but not limited to, osmium, gold, silver, uranium, tungsten, lead, bismuth or platinum. Likewise, the shield paddles can have various thicknesses as well. In an aspect, as discussed in more detail below, the shield paddles are comprised of a tungsten alloy having a thickness of approximately 0.5 mm.

FIGS. 72*a-b* and 73*a-b* illustrate a P-RSBT insertion device/applicator 7000 according to an aspect of the present invention. The P-RSBT insertion device 7000 includes a source 7010 (configured to receive a wire 7012 for guidance purposes) within a shielding catheter 7014. The source 7010 and catheter 7014 can be surrounded by a set 7015 of shield paddle blades 7020. Openings 7025 can be formed between the shield paddle blades 7020. As shown in FIG. 72*a*, a number (K) of shield paddle blades 7020 are arranged in an intracavitary catheter 7040. In an aspect, each paddle blade is uniform with one another, with each paddle blade 7020 shielding a sector of 360°/K angularly, shown in FIG. 72*b*. The set 7015 of shield paddle blades 7020 can move in (close; protract) and out (open; retract) independently to block and to expose the radiation source 7010, respectively, to form sectorial high-dose-regions which are called beams. In an aspect, the individual shield paddle blades 7020 can be contained within a sheath 7030 when placed within the catheter 7040. The sheath 7030 can include treads 7032 that match keys 7022 on the individual shield paddle blades 7020, which assist in keeping the blades 7020 in place. Matching side keys 7024 and treads 7026 can be found on the shield paddle blades 7020 as well to keep the set 7015 in correct alignment. In addition, the sheath 7030 can include an outer surface key 7034 for use with the catheter 7040, discussed below.

Shield paddle blades 7020 can be retracted, as shown in FIG. 72*a*. The paddle openings 7025 form a shield aperture to azimuthally modulate the radiation dose intensity. In the longitudinal direction, the zenith emission angle is fixed. For example, shield paddle blades 7020 of 0.5 mm thick tungsten can provide a dose transmission of less than 0.1% from an electronic brachytherapy (eBT) source 7010. The set 7015 of shield paddle blades 7020 are rotatable such that the shield paddle blades 7020 rotate about the source 7010 in a fine angular stride, further improving dose conformity. The P-RSBT source 7010 can include any of the sources discussed in more detail above, including, but not limited to a shielded 50 kV photon source (Xoft Axxent™, iCAD, Inc., Nashua, N.H., USA). FIGS. 72*b* and 73*b*—are cross-sectional views of the P-RSBT applicator 7000.

The P-RSBT applicator 7000 can be applied in a helix delivery. Referring to FIGS. 73*a-b*, in an aspect, during the P-RSBT delivery a multi-helix RSBT applicator 7000 utilizes the catheter 7040 inserted in the tumor is used. The catheter 7040 has a set of helix treads 7045 on its inner wall that matches with at least one key 7034 found on the sheath 7030, as shown in FIG. 73*b*. The set 7015 of shield paddle blades 7020 travels with the source 7010 through the catheter 7040 inserted in the tumor. The source 7010 can be configured to stop at multiple dwell positions along the central path with a spacing AX In this work, AX is set to 5 mm. At each dwell position, a number of shield apertures 7025 are formed in an optimized fashion to deliver radiation dose sequentially. The shield may rotate when necessary during the delivery. This procedure can be considered as an analogous of the multi-leaf collimation in IMRT.

In an aspect, the shield paddle blades 7020 may be indexed counter-clockwise with, initially, the k-th paddle (k=0, 1, . . . , K-1) shielding the sector from degrees k·δφ to (k+1)·δφ, where δφ is the angular size of a paddle (see FIG. 72b). In an aspect, a RSBT beamlet can be defined as $\dot{D}_{i,j,k}$ with the dose rate at the point $\vec{r}_i$ due to a shielded radiation source at dwell position $\vec{s}_j$ (j=0, . . . , J-1) with the k-th paddle open. The total dose delivered to point i is calculated as a time-weighted sum of the beamlets over all dwell positions:

$$d_i = \Sigma_{j=0}^{J-1} \Sigma_{k=0}^{K-1} \dot{D}_{i,j,k} \tau_{j,k}, \quad (33)$$

where $\tau_{j,k}$ is the emission time for which the source is located at dwell position j with the k-the paddle open. To improve the quality of the dose plan, small emission angle beamlets are used with δφ=5°. The asymmetric dose-volume optimization with smoothness control ("ADOS") method can be used for dose optimization to generate anchor plans for P-RSBT. The following objective function can be used:

$$\min \sum_{i \in VOI's} (\lambda_i^- H(\hat{d}_i - d_i) + \lambda_i^+ H(d_i - \hat{d}_i))(d_i - \hat{d}_i)^2 + \quad (34)$$

$$\beta \sum_{j \in [0, J-1]} \sum_{k \in [0, K-1]} (\tau_{j,k} - \tau_{j,(k-1)\%K})^2$$

$$\text{s.t.} \quad d_i = \sum_{j=0}^{J-1} \sum_{k=0}^{K-1} \dot{D}_{i,j,k} \cdot \tau_{j,k} \quad (34a)$$

$$\tau_{j,k} \geq 0, \forall j \in [0, J-1], k \in [0, K-1] \quad (34b)$$

In the objective function, $\hat{d}_i$ is the prescribed dose for each voxel in the volumes of interest (VOI's), and $\lambda_i^+$ and $\lambda_i^-$ are coefficients for the overdose and underdose penalties, respectively.

$$H(x) = \begin{cases} 1, & \text{if } x > 0 \\ 0, & \text{if } x \leq 0 \end{cases}$$

is a Heaviside step function. The second smoothness term in the objective function is used to reduce the complexity of the emission time sequence at each dwell position, which is important to improve the delivery efficiency with limited quality loss of the delivered plan.

This optimization model aims to achieve high quality of the output anchor plan. An optimal shield sequencing algorithm was developed to compute a deliverable plan to "best" approximate the anchor plan while subject to the delivery time constraint, by using shield paddles with a large size with the capability of rotation.

Generating P-RSBT Delivery Plans with Optimal Sequencing

The use of large-sized (i.e. larger than δφ used in anchor plan generation) paddle blades 7020 may not be able to deliver the anchor plan exactly, thus compromising the quality of the anchor plan. On the other hand, it may help improve the delivery efficiency. The rotation capability of the paddle set 7015 can help to better approximate the anchor plan with high quality, but it also prolongs the delivery time. In an aspect, the optimal shield sequencing algorithm aims to compute a deliverable P-RSBT plan from the anchor plan to balance the plan quality and the delivery time.

Assume that the size of a paddle Δφ is a multiple of the beamlet size used in the anchor plan generation, that is, Δφ=w·δφ (w>1 is an integer). Thus, the number of paddles is $$\frac{K}{w},$$

which is set to an integer. The rotation stride of the paddles 7020 can also be a multiple of δφ. In the following shield sequencing model, a rotation stride is considered to be degree δφ and the rotation is in counter-clockwise direction. The model is ready to be extended with a rotation stride of multiple δφ. As illustrated in FIG. 74, the size of a beamlet δφ equals 30°, and the paddle size Δφ equals 90° when w=3.

A P-RSBT aperture/opening 7025 can be represented by a superposition of a set of beamlets. $x_{j,m,l}$ denotes the emission time for which the source 7010 is located at dwell position j with the m-th paddle open $$\left(m = 0, 1, \ldots, \frac{K}{w} - 1\right)$$

and after a rotation of degree l·δφ (l=0, 1, . . . , w-1). Note that it is not necessary for a paddle blade 7020 to rotate a degree of larger than (w-1)·δφ. Consider the sector $s_{j,k}$ (k=0, 1, . . . , K-1) corresponding to the beamlet $b_{j,k}$ in the anchor plan. Let $$p = \left\lfloor \frac{k}{w} \right\rfloor \text{ and } q = \left(\left\lfloor \frac{k}{w} \right\rfloor - 1\right) \% \frac{K}{w},$$

where $\lfloor \cdot \rfloor$ is the floor function and % is the modulo operator. The q-th paddle, in fact, is the immediately adjacent paddle of the p-th one in the clockwise direction. The sector $s_{j,k}$ is irradiated by the beams with the p-th paddle open and l=0, . . . , k % w, and by the beams with the q-th paddle open and l=(k % w)+1, . . . , w-1. Thus, the irradiation time $t_{j,k}$ for $s_{j,k}$ is $t_{j,k} = \Sigma_{l=0}^{k \% w} x_{j,p,l} + \Sigma_{l=(k \% w)+1}^{w-1} x_{j,q,l}$. For instance, in FIGS. 74a-c, four paddle blades 7020 90° in size are shown. The size of a beamlet is =30°. Each beamlet $b_{j,k}$ covers a sector $s_{j,k}$. While opening a paddle forms a beam which can cover multiple sectors. The sector $s_{j,0}$ is covered by the beams formed with Paddle 0 open (a) and with Paddle 3 open after a rotation of degree 30° (b) and a rotation of degree 60° (c). Assume that the emission time of the beamlet $b_{j,k}$ is $\tau_{j,k}$ in the anchor plan. In an aspect, the delivery error $\varepsilon_{j,k}$, with $\varepsilon_{j,k} = t_{j,k} - \tau_{j,k}$ may then be introduced.

Given a dwell position j and a rotation configuration l, considered is the delivery time (beam-on time) for the fluence map $$M_{j,l} = \left\{ x_{j,m,l} \mid m = 0, 1, \ldots, \frac{K}{w} - 1 \right\}.$$

For the ease of the description of the delivery method, it is assumed that all non-zero entries in $M_{j,l}$ are different. The method is ready to be extended to the case that there are equal non-zero entries. To efficiently delivering $M_{j,l}$, sort $M_{j,l}$ in a non-decreasing order, and assume that the sorted non-zero entries are indexed with $m_0, m_1, \ldots, m_i$, $m_{i+1}, \ldots$ in the order. Then, the following procedure may be employed to deliver $M_{j,l}$.

Open all paddles corresponding to non-zero entries in $M_{j,l}$. After $x_{j,m_0,l}$ units of time, close Paddle $m_0$; after $x_{j,m_1,l} - x_{j,m_0,l}$ units of time, close Paddle $m_1$; so on and so forth. In general, close Paddle $m_{i+1}$ after $x_{j,m_{i+1},l} - x_{j,m_i,l}$ units of time following the close of Paddle $m_i$. In this way, the minimum delivery time for $M_{j,l}$ is $$\max_{m=0}^{\frac{K}{w}-1} \{x_{j,m,l}\}.$$

The total delivery time for all the fluence maps $M_{j,l}$'s is then $$\sum_{j=0}^{J-1} \sum_{l=0}^{w-1} \max_{m=0}^{\frac{K}{w}-1} \{x_{j,m,l}\}.$$

The shield sequencing method strives to compute a delivery plan $x_{j,m,l}$'s that "best" approximates the anchor plan subject to a given delivery time budget T. This is done in proposition to minimize the total delivery error between the anchor plan and the delivery plan.

$$\min \sum_{j=0}^{J-1} \sum_{k=0}^{K-1} (\lambda_{j,k}^- H(\tau_{j,k} - t_{j,k}) + \lambda_{j,k}^+ H(t_{j,k} - \tau_{j,k}))(t_{j,k} - \tau_{j,k})^2 \quad (35)$$

$$\text{s.t. } t_{j,k} = \sum_{l=0}^{k\%w} x_{j,p,l} + \sum_{l=(k\%w)+1}^{w-1} x_{j,q,l} t_{j,k}, \quad (35a)$$

$$p = \left\lfloor \frac{k}{w} \right\rfloor \text{ and } q = \left(\left\lfloor \frac{k}{w} \right\rfloor - 1\right) \% \frac{K}{w}$$

$$\forall j \in [0, J-1], k \in [0, K-1]$$

$$x_{j,m,l} \geq 0, \forall j \in [0, J-1], m \in \left[0, \frac{K}{w} - 1\right], l \in [0, w-1] \quad (35b)$$

$$\sum_{j=0}^{J-1} \sum_{l=0}^{w-1} \max_{m=0}^{\frac{K}{w}-1} (x_{j,m,l}) \leq T \quad (35c)$$

H(x) in Equation (35) is a Heaviside function introduced for considering the difference between overdosing and underdosing. $\lambda_{j,k}^+$ and $\lambda_{j,k}^-$ are the corresponding coefficients for overdosing and underdosing penalties. Equation (35) is formulated to a quadratic programming problem and solved by an in-house CPLEX-based optimizer.[22]

Clinical Results for P-RSBT

Five cervical cancer cases with high-risk clinical target volume (HR-CTV) larger than 40 cc were studied in this work. All cases were previously treated by MRI-guided HDR-BT. The HR-CTV and the OARs, namely the rectum, sigmoid colon, and bladder, were delineated by a radiation oncologist using the GEC-STRO recommendations.[23] For each patient, P-RSBT was simulated to be delivered through a single-channel tandem applicator without a ring or ovoids applicator. For the purpose of this study, it was assumed that the HR-CTV and OARs received a dose of 45 Gy of external beam radiation therapy (EBRT) in 25 fractions of 1.8 Gy/fraction. To each patient, it was also assumed that the same HDR-BT plan was delivered for all five treatment fractions, which is standard at the authors' institution. The HR-CTV doses [Gy] and OARs doses [Gy] were expressed as equivalent doses in 2 Gy fraction of EBRT (EQD2), using $\alpha/\beta$ values of 10 Gy and 3 Gy, respectively.

No explicit dose prescription was assumed for the HDR-BT delivery. The P-RSBT treatment goal was to escalate tumor dose without exceeding the OAR tolerances and the delivery time budgets. Specifically, the minimum dose received by 90% of the HR-CTV ($D_{90}$) was maximized under the constraint that the minimum doses to the hottest 2 cm$^3$ ($D_{2\ cc}$) of the rectum, sigmoid colon, and bladder could not exceed the tolerance doses[2, 15] of 75, 75, and 90 Gy, respectively.

For each of the 5 clinical cases, an anchor plan was generated using the ADOS method[21] with the beamlet size $\delta\varphi=5°$. The P-RSBT optimal shield sequencing was then applied to the anchor plan with a different paddle size $w \cdot \delta\varphi$ for w=1, 3, 6, 9, 12, 18 and 24. For the shield rotation stride, analysis considered $r \cdot \delta\varphi$ for r=1, 2, . . . , 6 to study the sensitivity of the P-RSBT design to different rotation strides. For the purpose of comparison, S-RSBT and D-RSBT optimal sequencing were applied to the anchor plans to generate delivery plans.

For each anchor plan, a delivery efficiency curve was computed by using each of the P-RSBT, D-RSBT and S-RSBT methods show the trade-off between the delivery time (x-axis) and the HR-CTV $D_{90}$ (y-axis) of the delivery plan. For the P-RSBT method, one delivery efficiency curve was computed for each combination of the different paddle sizes and the rotation strides considered. A delivery efficiency curve (segment) can be considered to be superior to another if it locates to the top-left of another.

Quantitative comparisons for HR-CTV $D_{90}$ with fixed delivery times (10, 15, 20, 25, 30 min/fx) also made for P-RSBT with different paddle sizes, S-RSBT and D-RSBT.

As shown by the delivery efficiency curves in FIG. 75, for all the 5 cases tested, the P-RSBT technique in general was able to achieve higher $D_{90}$'s for the output delivery plans than those achieved by S-RSBT and D-RSBT, especially when the delivery time ranges from 10 min/fx to 20 min/fx.

The data show that P-RSBT is insensitive to the paddle size when it is 60° or less. For 7 different paddle sizes tested in this study, the impact of the paddle size change to the plan quality was marginal. Taking the delivery time 15 min/fx as an example, though the $D_{90}$ of the delivery plan tended to decrease while increasing the paddle size, the average drop on $D_{90}$ for P-RSBT 30 (the number stands for the shield paddle size, measured in degrees) compared to P-RSBT 5 was 0.1 Gy. Further increase on the paddle size to 60° resulted in a 0.6 Gy drops for P-RSBT 60 compared to P-RSBT 5. The decrease was magnified to 2.5 Gy with P-RSBT 90. However, if the paddle size was increased to 120°, the $D_{90}$ drop was about 12 Gy. The detailed quantitative comparisons are shown in Table 1. For all these experimental data, the rotation stride $r \cdot \delta\varphi=50$.

Table 1, below, also demonstrates the quantitative comparisons between P-RSBT and S-RSBT/D-RSBT. For instance, comparing P-RSBT 60 to S-RSBT, the average $D_{90}$ increases over all 5 cases were 2.2 Gy, 8.3 Gy, 12.6 Gy, 11.9 Gy and 9.1Gy while setting the delivery time to be 10 min/fx, 15 min/fx, 20 min/fx, 25 min/fx and 30 min/fx, respectively; the $D_{90}$ increases against D-RSBT were 16.6 Gy, 12.9 Gy, 7.2 Gy, 3.7 Gy and 1.7 Gy, respectively.

TABLE 1

$D_{90}$ ($Gy_{10}$) comparisons between P-RSBT with different paddle sizes, S-RSBT and D-RSBT on 5 clinical cases under different delivery time limits. The rotation stride r · δφ for P-RSBT was 5°.

| Case | Delivery Time (min/fx) | P-RSBT 5 | P-RSBT 15 | P-RSBT 30 | P-RSBT 45 | P-RSBT 60 | P-RSBT 90 | P-RSBT 120 | S-RSBT | D-RSBT |
|---|---|---|---|---|---|---|---|---|---|---|
| #1 | 10 | 109.4 | 109.1 | 109.1 | 108.6 | 107.7 | 107.6 | 98.2 | 99.4 | 84.9 |
|  | 15 | 110.5 | 110.8 | 110.8 | 110.1 | 108.8 | 108.2 | 98.2 | 100.8 | 105.3 |
|  | 20 | 110.6 | 110.8 | 110.8 | 110.1 | 108.8 | 108.2 | 98.2 | 105.1 | 109.9 |
|  | 25 | 110.6 | 110.8 | 110.8 | 110.1 | 108.8 | 108.2 | 98.2 | 106.5 | 110.7 |
|  | 30 | 110.6 | 110.8 | 110.8 | 110.1 | 108.8 | 108.2 | 98.2 | 107.1 | 110.9 |
| #2 | 10 | 79.2 | 79.3 | 79.4 | 79.1 | 79.9 | 80.0 | 70.9 | 74.7 | 69.7 |
|  | 15 | 103.4 | 103.1 | 102.5 | 100.7 | 96.2 | 99.2 | 72.8 | 86.2 | 87.7 |
|  | 20 | 114.5 | 114.4 | 114.3 | 112.2 | 107.8 | 108.3 | 72.8 | 86.2 | 101.3 |
|  | 25 | 118.6 | 119.1 | 119.3 | 118.1 | 117.1 | 111.6 | 72.8 | 92.8 | 111.0 |
|  | 30 | 120.6 | 120.9 | 120.2 | 119.9 | 121.3 | 111.6 | 72.8 | 100.8 | 117.8 |
| #3 | 10 | 86.0 | 85.9 | 86.0 | 86.0 | 85.3 | 85.1 | 83.1 | 83.0 | 64.6 |
|  | 15 | 91.4 | 91.4 | 91.3 | 91.3 | 90.5 | 88.6 | 83.5 | 84.0 | 78.8 |
|  | 20 | 91.4 | 91.4 | 91.3 | 91.3 | 90.5 | 88.6 | 83.5 | 84.0 | 90.1 |
|  | 25 | 91.4 | 91.4 | 91.3 | 91.3 | 90.5 | 88.6 | 83.5 | 86.0 | 91.4 |
|  | 30 | 91.4 | 91.4 | 91.3 | 91.3 | 90.5 | 88.6 | 83.5 | 88.3 | 91.5 |
| #4 | 10 | 65.2 | 65.2 | 65.3 | 65.5 | 66.0 | 65.9 | 66.5 | 71.1 | 56.3 |
|  | 15 | 79.8 | 79.9 | 80.0 | 80.2 | 80.9 | 78.5 | 80.7 | 80.5 | 64.1 |
|  | 20 | 92.3 | 92.3 | 92.2 | 92.0 | 90.3 | 87.1 | 87.4 | 80.5 | 72.7 |
|  | 25 | 99.3 | 99.1 | 99.1 | 97.9 | 96.1 | 91.9 | 87.6 | 80.5 | 82.4 |
|  | 30 | 102.7 | 102.5 | 102.6 | 101.4 | 99.6 | 94.1 | 87.6 | 83.2 | 90.8 |
| #5 | 10 | 86.5 | 86.5 | 86.5 | 86.5 | 86.4 | 85.8 | 85.2 | 86.0 | 66.7 |
|  | 15 | 107.3 | 107.3 | 107.4 | 106.9 | 106.6 | 105.3 | 97.5 | 90.0 | 82.6 |
|  | 20 | 113.0 | 113.1 | 113.1 | 113.1 | 113.0 | 109.5 | 97.5 | 91.8 | 100.2 |
|  | 25 | 113.0 | 113.1 | 113.1 | 113.1 | 113.0 | 109.5 | 97.5 | 100.2 | 111.4 |
|  | 30 | 113.0 | 113.1 | 113.1 | 113.1 | 113.0 | 109.5 | 97.5 | 108.3 | 113.5 |
| Avg | 10 | 85.2 | 85.2 | 85.2 | 85.1 | 85.0 | 84.9 | 80.8 | 82.8 | 68.4 |
|  | 15 | 98.5 | 98.5 | 98.4 | 97.8 | 96.6 | 96.0 | 86.5 | 88.3 | 83.7 |
|  | 20 | 104.4 | 104.4 | 104.3 | 103.7 | 102.1 | 100.4 | 87.9 | 89.5 | 94.8 |
|  | 25 | 106.6 | 106.7 | 106.7 | 106.1 | 105.1 | 102.0 | 87.9 | 93.2 | 101.4 |
|  | 30 | 107.7 | 107.7 | 107.6 | 107.2 | 106.6 | 102.4 | 87.9 | 97.5 | 104.9 |

The example dose distributions are shown in FIG. 76 for Case #3 (Table 1) using with different paddle sizes of 5°, 30°, 60° and 90° for a given delivery time 15 min/fx. The corresponding dose-volume histogram (DVH)s are plotted in FIG. 77. It can be observed that the isodose contours in FIG. 76 become less conformal to the HR-CTV boundary as the paddle size increases, though the changes are marginal. The corresponding DVH curves in FIG. 77 for different paddle sizes are also observed to be similar with no significant differences. The $D_{90}$'s of those four P-RSBT delivery settings are 91.4 Gy, 91.3 Gy, 90.5 Gy and 88.6 Gy, respectively. The comparisons on dose distributions and DVH's between P-RSBT, S-RSBT and D-RSBT for Case #3 are shown in FIGS. 78 and 79, respectively.

The delivery efficiency curves for P-RSBT with respect to different rotation strides are shown in FIG. 80 for P-RSBT60 and P-RSBT90. The detailed $D_{90}$ comparisons for the delivery plans computed by P-RSBT with different combinations of the paddle size and the rotation stride are demonstrated in Table 2. In general, the increase of the rotation stride compromised the quality of the delivery plan with respect to $D_{90}$. However, the $D_{90}$ drops were marginally small. In fact, among all five cases, with the rotation stride increasing from 5° to 20°, the $D_{90}$ drops of the delivery plans by P-RSBT were within 1.5 Gy while the delivery time ranges from 10 min/fx to 30 min/fx; if the rotation stride is set to 10°, the $D_{90}$ drops were less than 0.6 Gy.

TABLE 2

$D_{90}$ ($Gy_{10}$) comparisons of the delivery plans by P-RSBT with different combinations of the paddle size and the rotation stride, the $D_{90}$'s were calculated as the mean over 5 clinical cases.

|  | delivery time (min/fx) | rotation strides | | | | | |
|---|---|---|---|---|---|---|---|
|  |  | 5° | 10° | 15° | 20° | 25° | 30° |
| P-RSBT45 | 10 | 85.1 | 85.1 | 85.1 | 84.9 | 84.9 | 84.6 |
|  | 15 | 97.8 | 97.4 | 97.2 | 96.6 | 96.6 | 96.5 |
|  | 20 | 103.7 | 103.2 | 103.0 | 102.0 | 102.0 | 101.6 |
|  | 25 | 106.1 | 105.7 | 105.4 | 104.6 | 104.4 | 103.9 |
|  | 30 | 107.2 | 106.5 | 106.2 | 105.3 | 105.1 | 104.5 |
| P-RSBT60 | 10 | 85.0 | 85.0 | 84.8 | 84.7 | 84.7 | 84.5 |
|  | 15 | 96.6 | 96.4 | 96.3 | 96.0 | 95.8 | 95.1 |
|  | 20 | 102.1 | 101.8 | 101.3 | 100.9 | 100.4 | 99.5 |
|  | 25 | 105.1 | 104.8 | 104.2 | 103.5 | 103.2 | 101.6 |
|  | 30 | 106.6 | 106.5 | 105.7 | 104.7 | 104.3 | 102.1 |
| P-RSBT90 | 10 | 84.9 | 84.9 | 84.7 | 84.7 | 84.4 | 84.4 |
|  | 15 | 96.0 | 95.8 | 95.4 | 95.2 | 94.4 | 93.8 |
|  | 20 | 100.4 | 100.0 | 99.4 | 99.1 | 98.3 | 96.8 |
|  | 25 | 102.0 | 101.6 | 101.0 | 100.4 | 99.8 | 97.8 |
|  | 30 | 102.4 | 102.0 | 101.5 | 100.7 | 100.1 | 98.1 |

P-RSBT outperforms S-RSBT in general. The delivery plan produced by P-RSBT, in an aspect, can be delivered by S-RSBT by setting the azimuthal emission angle of the shield to be the paddle size. However, S-RSBT may prolong the delivery time comparing to P-RSBT since P-RSBT can have multiple paddles open simultaneously during delivery, while S-RSBT just simulates the P-RSBT delivery with one paddles open at a time. Thus, for a given delivery time, P-RSBT is likely to achieve a higher quality delivery plan than S-RSBT. On the other hand, an S-RSBT delivery plan theoretically can be converted to a P-RSBT plan with a shorter delivery time. Experimental data generally support this analysis, with an exception of Case #4 (Table 1) while the delivery time was 10 or 15 min/fx. This is caused by the fact that the P-RSBT shield sequencing does not seek all possible paddle sizes. While with S-RSBT, the best emission angle is sought to compute a delivery plan best approximating the anchor plan. The emission angle used in the S-RSBT delivery plan for Case #4 while the delivery time was 10 min/fx (resp., 15 min/fx) is 285° (resp., 235°).

P-RSBT also performs better than D-RSBT mainly because it is able to form beam apertures with larger coverage. The maximum beam coverage used in the D-RSBT method is 180°, while it can be 360° with P-RSBT. P-RSBT does not have significant advantage over D-RSBT in forming beam apertures with fine-tuned beam coverage, thus it is not prominently better than D-RSBT with sufficiently large delivery time (~30 min/fx), which allows using more beams with small emission angles. With a given delivery time of 30 min/fx, the average $D_{90}$ of the delivery plans achieved by P-RSBT was marginally higher than that achieved by D-RSBT, which was less than 3 Gy.

Roughly speaking, for the three RSBT delivery methods—S-RSBT, D-RSBT and P-RSBT, the ability of forming small beam apertures helps on improving the dose distribution quality; while the ability of forming large beam apertures helps on reducing the delivery time. It is relatively easy to make use large beam apertures in S-RSBT and to make use small beam apertures in D-RSBT, but not the way around. P-RSBT gives a way to combine those two powers together, yet at the price of more complex apparatus design.

Reducing the paddle size theoretically improves the performance of P-RSBT, but may significantly complicate the design of the P-RSBT system. Fortunately, our experiments demonstrated that the $D_{90}$ drops of the delivery plans by P-RSBT while increasing the paddle size from 5° to 90° were marginal. As shown in Table 1, P-RSBT 60 with 6 paddles and P-RSBT 90 with 4 paddles could be considered as a good balance between the system complexity and the plan quality. Further reducing the number of paddles (e.g., P-RSBT 120) may result in significant compromise in plan quality.

The size of rotation stride $r\delta\varphi$ is another important parameter to be considered in the P-RSBT system design. While a smaller rotation stride generally provides improved dose comformity, it requires more precise control, and tends to be more vulnerable to motion uncertainty. Interestingly, our experiments shows only marginal plan quality drops while the rotation stride increase from 5° to 20° for the delivery time range between 10 min/fx and 30 min/fx. This demonstrates the feasibility of having a P-RSBT system with a small number of paddles and a large rotation stride, which may significantly simplify the complexity of a P-RSBT system design.

Experiments revealed that the smoothness of the emission times between adjacent beamlets in an anchor plan plays an important role for P-RSBT to achieve high-quality delivery plans. FIG. 81 shows the delivery efficiency curves by P-RSBT 5 and P-RSBT 60 for the anchor plans computed by two different dose optimizers: one was the ADOS method[21] in which emission time smoothness is enforced by the $L_2$-norm, and the other was based on the inverse planning by simulated annealing (IPSA) technique where no smoothness was enforced. The $D_{90}$'s of the anchor plans with ADOS and IPSA were 91.4 and 94.0 Gy, respectively. It can be observed that the $D_{90}$ drops between the delivery plans by P-RSBT 5 and P-RSBT 60 for the ADOS anchor plan were larger than those for the IPSA anchor plan. Also, the delivery efficiency curves for the ADOS anchor plan were superior to those for the IPSA anchor plan. These preliminary data justify the importance of smoothness in an anchor plan for P-RSBT to adopt large-sized paddles and large rotation strides, thus decreasing the complexity of the delivery system.

Helical RSBT

In an aspect, rotating shield brachytherapy (RSBT) can be used to overcome limitations of conventional brachytherapy. FIGS. 82a-h illustrate a comparison of conventional high-dose-rate brachytherapy (HDRB) (FIGS. 82a, c, e, and g) to RSBT (FIGS. 82b, d, f, and h). With RSBT, a radiation shield (e.g., platinum shield in FIG. 82b) is used to partially occlude the brachytherapy source (e.g., $^{153}$Gd), producing a deliberately non-radially-symmetric radiation dose distribution about the source, as shown in FIG. 82d, especially in comparison to the distribution pattern of traditional HDRB in FIG. 82c. During RSBT delivery, the radiation shield moves dynamically about the radiation source, directing radiation away from healthy sensitive tissues and into tumor tissues. RSBT can thus deliver far greater radiation doses to the tumor for a given healthy tissue dose, enabling dose escalation to the tumor and increasing tumor control probability. RSBT could also be used to deliver the same radiation doses to tumors as is delivered conventionally, while substantially reducing the radiation dose delivered to healthy tissues with the goal of reducing side effects relative to conventional brachytherapy. Computer simulations have shown the potential clinical benefits of RSBT for cervical cancer and prostate cancer. A comparison of dose distributions (0 mm and 3 mm urethral margins) in HDRB (see FIGS. 82e and g) to those of RSBT (see FIGS. 82f and h) show the improvements for treatment of cervical cancer.

In an aspect, RSBT systems and methods can be used to maintain or increase tumor dose relative to conventional techniques, but with a dramatic reduction in radiation dose to the urethra, rectum, and bladder in the treatment of prostate cancer. In an aspect, with the RSBT system, partially shielded radiation sources can be placed in the prostate away from sensitive tissues. In an exemplary aspect, partially-shielded $^{153}$Gd (240 day half-life, 60.9 keV average photon energy) radiation sources 8002 can be utilized. Conventional HDR-BT systems utilize conventional $^{192}$Ir (74 day half-life, 360 keV average energy). $^{192}$Ir emits photons with energies too high for interstitial RSBT (FIGS. 82a,c), whereas $^{153}$Gd has an appropriate photon spectrum for partial shielding. In an aspect, the $^{153}$Gd source can use Gd-3NO$_3$ (gadolinium trinitrate, a powder), which contains 3.2 TBq/g of $^{153}$Gd, and is commercial available. In an aspect, the $^{153}$Gd source can use gadolinium oxide. In an aspect, the $^{153}$Gd source can use gadolinium chloride. Other forms of $^{153}$Gd can be used (e.g., pellets or metal). In an aspect, the $^{153}$Gd source can be loaded into a capped nitinol tube with a 10 mm active length. In such aspects, the capsule can be coupled to a wire. In an exemplary aspect, the wire is a metal wire composed of a material such as nitinol. In an aspect, the combination disclosed above is configured to have a diameter of 400 μm or greater and a length of 10 mm or greater in a wire with a diameter of 600 μm or less.

Partial shielding (FIG. 82b) enables a deliberately non-symmetric dose distribution (FIG. 82d), providing the opportunity to shield healthy tissues from radiation damage. The shielded RSBT sources move dynamically inside the prostate in a manner that reduces the dose delivered to the rectum, bladder, and urethra relative to conventional HDR- BT without compromising the tumor dose (FIG. 82*e-h*). The RSBT approach thus overcomes the limitations the rectum, bladder, and urethra impose on the dose deliverable to the prostate with conventional HDR-BT.

In an aspect, as illustrated in FIGS. 83-85 illustrate various components of a RSBT system 8000, including a catheter control cartridge 8100. The catheter control cartridge 8100 can utilize a RSBT catheter 8110. In an aspect, the catheter RSBT 8110 can be constructed in the multiple fashions as described above. In an example, as illustrated in FIG. 83, the RSBT catheter 8110 is configured to be inserted into a needle (not shown) found within the subject. The RSBT catheter 8110 can include an outer tube/catheter 8112 comprised of numerous materials, including, but not limited to, nitinol. In an aspect, the RSBT catheter is configured to be smaller than the interior of the needle to allow easy insertion and rotation within the needle.

The outer tube/catheter 8112 of the RSBT catheter 8110 retains the shield 8114, as shown in FIGS. 83*a-b*. The shield 8114 can have the properties and physical dimensions of the various shields discussed in the aspects above. The shield 8114 can be made of variety of materials to stop penetration of radiation, including, but not limited to, platinum. The shield 8114 is coupled to a window 8116 to contain the radiation source 8120. The window 8116 can have the properties and physical dimensions of the various windows discussed in the various aspects above, having properties allowing penetration of radiation. In an aspect, the window 8116 is comprised of aluminum. The radiation source 8120 can be contained within a radiation tube/catheter 8122. The source 8120 can be any of the sources discussed above, including, but not limited to, $^{153}$Gd.

As shown in FIG. 84, a proximal end 1813 of the RSBT catheter 8110 can be removably connected to a distal end 8152 of a lead screw 8150, or other type of advancing mechanism of the catheter control cartridge 8100. A motor 8200 configured to drive the lead screw 8150 can be located at the proximal end 8154 of the lead screw 8150. A carriage, similar to those discussed above, can be coupled to the motor 8200. The carriage has an opening 8312 at a distal end to allow passage of the catheter 8110 in and out of the carriage, as well as an opening at the proximal end to allow access for the lead screw 8150. A shell 8400 can be placed on the carriage as discussed above, with openings 8422, 8432 at the ends 8420, 8430 to allow passage of the catheter 8110 and lead screw 8150.

The distal end 8420 of the shell 8400 can include a radiation shield 8424. In addition, a catheter monitoring camera 8426 can be mounted within the distal end 8420 of the shell 8400. The proximal end 8430 can include an advancing mechanism receiver 8450, such as a screw nut 8450, which includes a threaded interior surface (not shown) that corresponds to the threaded exterior surface of the lead screw 8150. The screw nut 8450 is secured in a fashion to prevent any the rotation of the screw nut 8450 within the shell 8400 when interacting with the lead screw 8150.

As shown in FIGS. 85-86, the RSBT delivery system 8000 can also utilize a cartridge magazine 8600, similar to that described above, for simultaneous use of multiple catheter control cartridges 8100 and their RSBT catheters 8110. The RSBT delivery system 800, with assistance from the cartridge magazine 8600, is configured to control multiple rotating sources 8110. In an exemplary aspect, each cartridge 8100 has a 9.5 mm×9.5 mm cross-section. When the motor 8150 rotates, the source/catheter 8110 moves in or out of the applicator/needle (not shown), delivering the RSBT dose. The cartridges 8100 can be arranged inside the magazine 8600, which has moveable shelves for the cartridges, to align with applicators/needles implanted within the subject.

In an aspect, the cartridge 8110 can be controlled by a control system (not shown). In an exemplary aspect, the Python programming language and the National Instruments USB-6343 Package can be used for the control system. In an aspect, the RSBT system will be configured to move the cartridge to positions in a catheter at pre-defined positions and rotation angles at the end of applicators of various lengths, ranging from 5 cm to 20 cm. FIG. 87 illustrates a standard 5 mm×5 mm template for the alignment of the implanted needles, with radiation delivered over two passes (FIG. 2*d*). The camera-based catheter monitoring and feedback control system is configured to be capable of mechanically positioning the catheters 8110 within 1 mm, 1 degree spatial accuracy in curved needles, discussed in more detail below, and capable of verifying and correcting the catheter position inside a needle to within 1 mm, 1 degree. In a further aspect, the RSBT system 8000 can be configured to position, verify, and correct multiple catheters in real time. In an aspect, the RSBT system is configured to deliver a clinical, multi-catheter prostate cancer RSBT radiation dose distribution such that the measured and predicted dose distributions agree to within 3% or 1 mm. The catheters 8110 can be retracted into the shield 8426 for safe storage quickly in the case of an emergency. Once the desired amount of radiation for the treatment has been delivered, the source is removed from the applicator, then the applicator is removed and the patient is discharged. The patient will typically receive several brachytherapy treatments, and the process is similar for each treatment.

A challenging problem with implementing RSBT is using an apparatus in which both the source position and the shield direction can be precisely controlled inside both straight and curved applicators. Curved applicators are of great importance in brachytherapy, and are commonly used to treat cervical cancer. The curvature is necessary in order to match the shape of the patient's uterus, which changes on a patient-to-patient basis and on a day-to-day basis for a given patient. In addition, interstitial applicators used to treat prostate cancer may become curved after or during implantation due to tissue motion or because of deliberate deflection by the urologist doing the implantation in order to avoid the urethra, pubic arch, or maintain a desired distance from a neighboring applicator.

Two major problems in the process of using a rotating tube approach to delivering RSBT in curved applicators. First, the shield-bearing tube must be flexible enough to bend with the applicator, which can be 30 cm long, making the use of metal (even nitinol) tubes very difficult (or impossible) for this purpose. Second, a shield-bearing tube that will bend with the applicator, such as a braided metal mesh tube or a plastic tube, creates a major problem when the tube rotates proximal in the applicator, likely twisting the applicator. Such a twist can pose a major mechanical problem, as it makes predicting the direction of the partial shield very difficult during delivery. One solution is to utilize a table of actual shield directions for all possible shield-bearing tube insertion depths and rotation angles.

As illustrated in FIGS. 88-97, the current invention is directed towards a helical RSBT (H-RSBT) apparatus 9000, which provides the clinical benefits of RSBT while overcoming the challenges associated with previous RSBT apparatus designs. With H-RSBT, the direction of a partial radiation shield is controlled using only translational motion of the radiation source. This is an advantageous property, as existing brachytherapy systems already provide accurate (±1 mm) translational motion capability, enabling such systems to be extended to accommodate RSBT delivery without the addition of rotational motors, simplifying the implementation process.

One embodiment of the H-RSBT apparatus 9000 is shown in FIGS. 88-91. The H-RSBT apparatus 9000 includes a catheter 9110 with an external shield 9150 and an applicator 9500. The H-RSBT apparatus 9000 can be utilized with already existing radiation systems, including, but not limited to, Xoft Axxent, Zeiss Intrabeam system, and $^{192}$Ir radioisotope high-dose-rate brachytherapy systems such as the Varian Varisource or the Nucletron Flexisource. Further, H-RSBT can be used for brachytherapy with other isotopes as well, such as $^{153}$Gd, $^{67}$Co, $^{169}$Yb, $^{125}$I, $^{103}$Pd, $^{131}$Cs, $^{75}$Se and the like. H-RSBT can also be done interstitially using needles and/or catheters with keyways, discussed in more detail below. In addition, the catheter 9110 can be driven by the various mechanisms, similar to those discussed above. In some aspects, a supplemental translational driving mechanism may be necessary to enable H-RSBT with existing $^{192}$Ir or other existing systems.

The catheter 9110 has a distal end 9112, a proximal end 9114, and an outer surface 9116. Similar to those catheters discussed above, the catheter 9110 is configured to contain a radiation source (not shown) within its interior at the distal end 9112. The driving mechanism (not shown) can be associated with the proximal end 9114 of the catheter 9110. A securing mechanism 9120 can be used to secure the shield 9150 to the catheter 9110. In an aspect, the securing mechanism 9120 can be an o-ring 9120 that is configured to engage the shield 9150. In other aspects, the securing mechanism 9120 can include a circumferential extrusion 9120 is configured to engage the interior of the external shield 9150.

The external shield 9150 can be configured to rotably engage the distal end 9112 of the catheter 9110, that is, where the source is located within the catheter 9110. In an aspect, the external shield 9150 is securely attached to the distal end 9112 of the catheter 9110, but is capable of rotating freely. In an aspect, the shield 9150 comprises a hollow cylindrical body 9152. The cylindrical body 9152 can be comprised of a material that blocks the radiation from the source, including, but not limited to, the shielding materials discussed above. The cylindrical body 9152 includes a distal end 9154, a middle section 9156, and a proximal end 9158. The proximal end 9158 includes an opening configured to receive the distal end 9112 of the catheter 9110. The shield 9150 includes a radiation window 9160 located along the middle section 9156. The size of the radiation window 9160 can vary based upon the desired exposure of the source.

Keys 9162 can be associated with the exterior of the shield 9150. As shown in FIGS. 89-91, the keys 9162 are oriented along the distal end 9154 of the shield 9150. In other embodiments, the keys 9162 can be located at other portions of the shield 9150, including the middle section 9156 and the proximal end 9158. As shown, the shield 9150 includes three keys 9162. The number of keys 9162 can vary in other embodiments. The keys 9162 extend outwardly from the axis for the shield 9150. As shown, the keys 9162 are aligned in the same plane perpendicular to the axis of the shield 9150. However, in other embodiments, the keys 9162 can be found in more than one plane. In addition, as shown in FIGS. 89-91, the keys 9162 are spaced equidistant from one another along the circumference of the shield 9150. In other embodiments, the keys 9162 may be placed within various distances of one another along the outer surface of the shield 9150. In an aspect, the interior surface of the shield 9150 is configured to engage the securing mechanism 9120 of the catheter 9110. The interior can include a notch configured to match the shape of the securing mechanism 9120. For example, the notch can engage an extrusion 9120 or o-ring 9210 of the catheter 9110. Other means can be used to keep the shield 9150 attached at the distal end of the catheter 9110.

The combination of the catheter 9110 and the shield 9150 are configured to engage the applicator 9500. The applicator 9500 has a hollow cylindrical body 9502 configured to receive the catheter 9110 and shield 9150. The hollow cylindrical body 9502 includes a proximal end 9504, and middle portion 9506, and a distal end 9508. The hollow cylindrical body 9502 includes an opening 9510 at the proximal end 9504 configured to receive the catheter 9110 and shield 9150. The distal end 9506 of the applicator 9500 is configured to be inserted into a body cavity or tissue mass within a subject's body. The hollow cylindrical body 9502 can be straight, or it can be curved, discussed in more detail below. The inner surface 9512 of the applicator 9500 includes keyways 9514 that extend substantially linearly along the interior of the hollow cylindrical body 9502. The keyways 9514 are configured to receive and guide the keys 9162 of the shield, discussed in more detail below. As shown, the inner surface 9512 includes a plurality of keyways 9514, specifically six keyways 9514. Other numbers of keyways 9154 can be used in other embodiments. As shown, the keyways 9514 are helical, extending along the interior of the hollow body similar to rifling. The keyways 9514 provide pathways that one or more keys 9162 protruding from the shield 9150 follow when the catheter 9110, along with the source, is translated along the applicator 9500. In an aspect, the rotating shield 9150 attaches to the end of the catheter 9110 and rotates freely about the catheter 9110 inside the applicator 9500, with the engagement of the keys 9162 within the keyways 9514 forcing the shield 9150 to rotate as the catheter 9110 moves in the axial direction of the applicator 9500. The keys 9162 of the shield 9150 occupy one or more keyways 9514 of the applicator 9500 at a given time. The position of the catheter 9110, and more specifically the radiation source, in the applicator 9500 dictates the direction of the radiation shield 9150 and window 9160 and therefore the irradiation direction. Thus, the H-RSBT apparatus 9000 only requires translational motion of the source inside the applicator for the shield to rotate.

The keyways 9512 can be cut or built into the applicator 9500 in the manufacturing process. The helical pattern of the keyways 9512 does not need to start at the proximal end 9504 of the applicator 9500. The helical pattern of the keyways 9612 can be appropriately placed at the start of a curved section of a curved applicator 9500, or, for a straight applicator 9500, at the maximum distance from the distal end 9508 at which a tumor would be expected to be present.

In an aspect, the pitch of the keyways 9512 is loose, such as 1 rotation every 6 cm, enabling a reduction in rotational uncertainty. While the keyways 9152 can be tightly wound in other embodiments, such as 1 rotation per cm or less, it is possible for the catheter 9110 to become stuck in the applicator 9500, preventing longitudinal motion from occurring. As shown in FIGS. 92 and 94, the H-RSBT applicator 9500 contains multiple loosely-wound helical keyways 9512 that are longitudinally offset from each other. Six keyways 9512 are shown, although the number of keyways 9512 could vary. Multiple keyways 9512 are preferable when they are loosely wound since using a single keyway 9512, with a winding of 1 rotation every 6 cm, would likely not provide enough emission angles (i.e., the radiation from the source of the catheter 9110 traveling through the window 9160 of the shield 9150) for the dose distribution delivered to be superior to conventional brachytherapy. Having multiple keyways 9512 increases the number of shield emission angles per cm, enabling an improvement in the deliverable dose distributions.

In an aspect, the method of use of the H-RSBT delivery apparatus 9000 discussed above proceeds as follows. The entire H-RSBT delivery can be done using one or more shields 9150, each shield 9150 with one or more protruding keys 9162 attached on its surface. In the current embodiment (FIGS. 88-93), for the first (of six) delivery segments, the shield keys #1, #2, and #3 can occupy keyways #1, #3, and #5, respectively, as shown in FIG. 93. The source travels all the way to the distal end 9508 of the applicator 9500, stopping at along the way at discrete longitudinal/angular dwell positions for preset amounts of time, or continuously moving with variable velocity at various throughout the process. After the first segment, the catheter 9110, with the source, and shield 9150 are retracted and re-inserted with the shield keys occupying a second combination of keyways, which would be keyways #2, #4, and #6, respectively. This proceeds until all of the desired combinations of keyways have been used for the delivery. FIGS. 94 and 97 illustrate how the shield motion occurs with varying translational source position.

FIG. 88 illustrates the apparatus 9000 where the applicator 9500 is an intracavitary tandem-type intravaginal that is inserted past the cervix and into the patient's uterus. The radiation source, via the catheter 9110, travels through the applicator 9500 during H-RSBT delivery, with the shield 9150 attached to the catheter 9100 but freely rotating as the catheter 9100 moves. However, the treatment of different cancers with H-RSBT needs a variety of different applicators which still can utilize the central concept of one or more helical keyways. For example, needle-type applicators can be used to treat prostate cancer with H-RSBT, as prostate cancer is treated with interstitial, rather than intracavitary, applicators. Similarly, treating breast cancer with H-RSBT can be down with an applicator that can fit inside a breast lumpectomy cavity. In an aspect, needle-type applicators for interstitial brachytherapy can be configured to be twistable, then only a single keyway may be necessary, as an external system can rotate the applicator by a pre-defined angle between source insertion/retraction operations. For example if a single keyway with ⅓ rotations per cm winding us used, then applying a 60° rotation between insertion/retraction operations provides the equivalent of six individual keyways offset from each other by 0.5 cm. In this approach a means for rotating the applicator is used, but the system can be relatively simple, as the applicator would only need to rotate to M discrete positions and by a total of (M−1)360°/M over the course of the delivery.

An additional benefit of the H-RSBT is that a shield angle monitoring system is not necessary, as shield angle is parameterized by translational position. The keyway pitch could be very loose, such as 1 rotation every 6 cm, enabling a reduction in rotational uncertainty for the paddle system relative to that achievable with a single shield.

Applications

The H-RSBT system described above can be applied to rectal, vaginal, and breast cancers without the need for a curved applicator. However, for cervical cancer (10,000 new diagnoses per year in the U.S.) and prostate cancer (200,000 new diagnoses per year), H-RSBT is delivered through curved applicators. For cervical cancer, this is because the anatomic shape of the uterus varies from patient to patient and from day-to-day. The common applicator shape for cervical cancer brachytherapy, shown in FIG. 96, has a curved central (tandem) applicator that can be substituted for tandem applicators with different curvatures depending on the patient and day. As the electronic radiation source has to be conducted into the applicator, the partially shielded cylinder attached on its tip has to rotate freely and proportionally as well. The rotation of the partially-shielded small cylinder provides precise dose coverage around that source. Hence a special applicator is required that can be solely dependent on the translational motion of the electronic source. That is, it should enable the conversion of longitudinal motion to the concurrent rotation of the shield. For the case of prostate cancer, between 14 and 20 interstitial needles (applicators) are inserted into the prostate gland, and a radiation source travels through them, delivering the radiation dose. It is desirable that the needles are flexible in order to enable the urologist placing the needles to laterally deflect them during the insertion process, enabling avoidance of structures such as the pubic arch and the urethra. Flexible needles are also desirable in order to reduce tissue trauma when the patient moves or when the tissue in the patient moves due to processes that can occur during the procedure such as peristalsis and rectal filling.

Further, the curved applicator discussed above is compatible with existing brachytherapy delivery systems. The application is compatible with a type of commercial electronic brachytherapy system called the Xoft Axxent (FIG. 97). This special eBx system uses disposable miniature X-ray radiation sources to deliver brachytherapy treatment directly to tumor beds while at the same time eliminating the need for heavily shielded environments so that it can be used in a broader range of clinical settings. It also is mounted on an arm which by means of a motor the desired longitudinal translation is provided.

Source/Shield Design

In an aspect, the shield of the system is configured to rotate about the catheter 9110, and namely the radiation source at the distal end 9112, smoothly and unimpeded during the H-RSBT procedure. In order to accomplish H-RSBT with a Xoft Axxent eBx source, a connection between the shield 9150 and the water cooling catheter 9110 surrounding the source is utilized. In an aspect, in order to ensure the shield 9150 is thick enough to provide 1% dose transmission while still rotating freely about the water cooling catheter 9110, the shield 9150 has approximately least 500 microns of clearance. This includes the shield 9150 itself and 100 microns of air surrounding the Xoft Axxent catheter 9110 to account for hygroscopic expansion of the plastic while water is flowing inside it. In this aspect, the thickness of the shield 9150 is configured to cut the dose rate down to less than 1% of its initial value. In such aspects, only 200 microns of tungsten, protactinium, rhenium, gold, osmium, platinum, iridium, thorium, or uranium is needed, leaving another 200 microns for the mechanical mechanism 9120 that connects the rotating shield 9150 to the catheter 9110 itself. In an aspect, the thickness of the plastic cooling catheter 9110 is about 200 microns. In an exemplary aspect, the cooling catheter 9110 is configured to have a protruding circumferential plastic ring 9120 that can be used to hold the shield 9150 in place in order to attach the shield 9150 to the Xoft's catheter 9110 such that it rotates, similar to that shown in FIG. 90.

In an aspect, the applicator 9500 with multi spiral keyways 9512 (as shown in FIG. 92) can be used with multiple existing brachytherapy systems, including electronic brachytherapy (Xoft, Inc., Zeiss GMBH) and isotope-based brachytherapy using $^{192}$Yr (Varian, Nucletron) or $^{169}$Yb (Oncology Systems, Inc. AccuSource). When used with electronic brachytherapy sources, H-RSBT can be delivered in procedure rooms with limited shielding, rather than in heavily-shielded high-dose-rate brachytherapy suites.

In an aspect, the applicator 9500 eliminates the need for shield angle monitoring system, as the emission direction of the shield is rigidly defined by the longitudinal insertion distance of the source. In an aspect, the H-RSBT system 9000 discussed above is compatible with paddle-based intensity-modulated brachytherapy (P-RPBT) approach discussed above in more detail.

In an aspect, as the partially shielded catheter 9110 is not curved and will remain a straight cylinder through the whole procedure, the inner diameter of the applicator 9150 can be limited in terms of the magnitude of both length and thickness of the shield 9150. FIG. 91 shows the geometrical parameters playing role in this calculation according to an aspect.

In an aspect, the maximum inner diameter of the applicator 9500 is calculated as a function of Rc, radius of the curvature, $d_x$, diameter of the catheter 9110, and x and t, length and thickness of the shield, respectively:

$$D_i = D_i(R_C, x, t) = -2R_C + \sqrt{4x^2 + (2R_C + 2t + d_x)^2} \quad (36)$$

FIG. 98 shows the plot of the inner diameter function for a specific curvature radius and two different thicknesses. As it shows the combination of the inner diameter and the length shield's length both 7 mm would be a reasonable selection for the thickness 0.5 mm, according to an aspect.

Source and Shield Trajectory Modeling

It is important to know the source direction and positioning in each dwell position precisely. An analytical equation can be used to describe the shield direction as a function of the distance along the axis. The equation models shield trajectory in treatment planning systems for RSBT in a straightforward way, and detects the shield location and direction for shield location monitoring devices. During treatment, a general computational framework can be provided to account for an arbitrary curvature in the applicators used for H-RSBT. The framework can be utilized for other applications such as prostate cancer using interstitial needles.

Based on FIG. 98, suppose: $R_C$ is radius of curvature of applicator along its axis, $R_I$ is radius of inner applicator, $\vec{f}(l)$ is applicator axis located in 3-D space at position l along the applicator, and $\theta_m(l)$ is angle of groove m at position l in the applicator. Equation (37) is a specific case of $\theta_m(l)$ distribution:

$$\theta_m(l) - \theta_{m-1}(l) = \frac{360°}{M}, \quad (37)$$

that we consider in our current geometrical design. However the whole trajectory can be modeled independent of that. In this equation M and m are the number of keyways in the applicator and the keyway index, respectively, and $\theta_0(l)$ is assumed to be 0°. This holds for all l. In the current design we assumed M is equal to 6; accordingly m=1, 2, 3, 4, 5, 6.

$\theta_m(l)$ is a general function and can be related to the number of degrees rotated per cm travelled along the applicator axis, $\beta(l)$, as follows:

$$\theta_m(l) = \theta_{m,0} \pm \int_0^l \beta(l') dl',$$

$$m = 1, \ldots, M. \quad (38)$$

where $\theta_{m,0}$ is the initial groove angle for groove m.

Moreover, suppose $\hat{n}(l)$ is the direction of source motion at applicator position, l, and can be calculated as:

$$\hat{n}(l) = \frac{\frac{d\vec{f}(l)}{dl}}{\left\| \frac{d\vec{f}(l)}{dl} \right\|}. \quad (39)$$

Thus, n(t) is a unit vector. Also, we can calculate $\hat{y}'(l)$ and $\hat{x}'(l)$ as:

$$\hat{y}'(l) = \hat{n}(l) \times \hat{x}, \quad (40)$$

$$\hat{x}'(l) = \hat{y}'(l) \times \hat{n}(l). \quad (41)$$

In general, the 3-D spatial location of the center of the entrance to the keyway to groove m at position l along the applicator is:

$$\vec{g}_m(l) = \vec{f}(l) + \vec{h}_m(l), \quad (42)$$

$$m = 1, \ldots, M,$$

where $\vec{h}_m(l)$ is defined in ($\hat{x}'$, $\hat{y}'$, $\hat{z}'$) coordinate system as:

$$\vec{h}_m(l) = \hat{x}'(l) R_I \cos[\theta_m(l)] + \hat{y}'(l) R_I \sin[\theta_m(l)]. \quad (43)$$

Let us consider the special case of $$\vec{f}(l) = 0\hat{x} + \{R_C[1 - \cos[\varphi(l)]]\}\hat{y} + \{R_C \sin[\varphi(l)]\}\hat{z}, \quad (44)$$

which translates into the Multi-helix RSB applicator trajectory on a circle, was shown in FIG. 97. As shown:

$$\varphi(l) = \frac{l}{R_C}. \quad (45)$$

Considering equations (39), (43), and (44), it is concluded that:

$$\hat{n}(l) = \sin\left(\frac{l}{R_C}\right)\hat{y} + \cos\left(\frac{l}{R_C}\right)\hat{z}. \quad (46)$$

Thus, $\hat{y}'(l)$ is calculated using the relationship:

$$\vec{u} \times \vec{v} = (u_2 v_3 - u_3 v_2)\hat{x} + (u_3 v_1 - u_1 v_3)\hat{y} + (u_1 v_2 - u_2 v_1)\hat{z}, \quad (47)$$

where $\vec{u}$ and $\vec{v}$ are equal to $\hat{n}(l)$ and $\hat{x}$ respectively. Thus:

$$\hat{y}'(l) = \cos\left(\frac{l}{R_C}\right)\hat{y} - \sin\left(\frac{l}{R_C}\right)\hat{z}. \quad (48)$$

Now:

$$\hat{x}'(l) = \hat{n}(l) \times \hat{y}'(l) =. \quad (49)$$

Putting these all together, we obtain:

$$\vec{g}_m(l) = \quad (50)$$

$$\{R_I \cos[\theta_m(l)]\}\hat{x} + \left\{ R_C\left[1 - \cos\left(\frac{l}{R_C}\right)\right] + R_I \cos\left(\frac{l}{R_C}\right)\sin[\theta_m(l)] \right\}\hat{y} +$$

$$\left\{ R_C \sin\left(\frac{l}{R_C}\right) - R_I \sin\left(\frac{l}{R_C}\right)\sin[\theta_m(l)] \right\}\hat{z},$$

$$m = 1, \ldots, M.$$

Furthermore, it is crucial to obtain $\vec{g}_m(l)$ for the case of a straight applicator. Therefore consider $R_C$ approaches to $\infty$ for all l, which would be for a straight applicator, then based on the general limit law and the L'Hôpital's rule:

$$\lim_{R_C \to \infty} \left\{ R_C \left[ 1 - \cos\left(\frac{l}{R_C}\right) \right] \right\} = 0, \quad (51)$$

$$\lim_{R_C \to \infty} \sin\left(\frac{l}{R_C}\right) = 0, \quad (52)$$

$$\lim_{R_C \to \infty} \cos\left(\frac{l}{R_C}\right) = 1, \quad (53)$$

$$\lim_{R_C \to \infty} \left[ R_C \sin\left(\frac{l}{R_C}\right) \right] = \lim_{R_C \to \infty} \left[ \frac{-\frac{1}{R_C^2} \cos\left(\frac{l}{R_C}\right) l}{-\frac{1}{R_C^2}} \right] = l, \quad (54)$$

Now we obtain:

$$\lim_{R_C \to \infty} \vec{g}_m(l) = \{R_I \cos[\theta_m(l)]\}\hat{x} + \{R_I \sin[\theta_m(l)]\}\hat{y} + l\hat{z}, \quad (55)$$

$$m = 1, \ldots, M,$$

which would be the equation for standard helix on a line.

Furthermore, in an aspect, it can be highly advantageous to provide a mathematical expression for the 3-D spatial location of the center of the entrance to the keyway to groove m and the direction of source motion at position l along the applicator axis in the cylindrical coordinate. In the case of cervical cancer treatment, for simplicity the curvature is assumed to be a segment of a circle. Suppose the desired cylindrical coordinate is defined based on FIG. 100 with its center positioned on the center of curvature. Equations (56), (57), and (58) show $\hat{R}(l)$ definition, applicator axis position vector, and position vector of the keyway respectively in the cylindrical coordinate:

$$\hat{R}(l) = -\cos[\varphi(l)]\hat{y} + \sin[\varphi(l)]\hat{z}, \quad (56)$$

$$\vec{f}(l) = R_C \hat{y} + R_C \hat{R}(l), \quad (57)$$

$$\vec{g}_m(l) = R_C \hat{y} + \{R_C - R_I \sin[\theta_m(l)]\}\hat{R}(l) + R_I \cos[\theta_m(l)]\hat{x}. \quad (58)$$

Based on the above equations the direction of radiation source is controllable at each dwell time. FIG. 99 shows the simulation for the entire system motion in three frames with the clockwise rotation of the shield. The calculated spiral notches give us the sequence of motion shown in FIG. 100.

Further, one skilled in the art will appreciate that the systems and methods disclosed herein can utilize a general-purpose computing device in the form of a computer 9600. The methods discussed above can be performed by the computer 9601. For example, the computer 1401 can perform the duties and responsibilities of the controller discussed above.

The components of the computer 9601 can comprise, but are not limited to, one or more processors or processing units 1403, a system memory 9612, and a system bus 9613 that couples various system components including the processor 9603 to the system memory 9612. In the case of multiple processing units 9603, the system can utilize parallel computing.

The system bus 9613 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 9613, and all buses specified in this description can also be implemented over a wired or wireless network connection and each of the subsystems, including the processor 9603, a mass storage device 9604, an operating system 9605, RSBT software 9606 and data 9607, both of which are configured to control and work with P-RSBT and H-RSBT systems, a network adapter 9608, system memory 9612, an Input/Output Interface 9610, a display adapter 9609, a display device 9611, and a human machine interface 9602, can be contained within one or more remote computing devices 9614a,b,c at physically separate locations, connected through buses of this form, in effect implementing a fully distributed system.

The computer 9601 typically comprises a variety of computer readable media. Exemplary readable media can be any available media that is accessible by the computer 9601 and comprises, for example and not meant to be limiting, both volatile and non-volatile media, removable and non-removable media. The system memory 9612 comprises computer readable media in the form of volatile memory, such as random access memory (RAM), and/or non-volatile memory, such as read only memory (ROM). The system memory 9612 typically contains data such as data 9607 and/or program modules such as operating system 9605 and RSBT software 9606 (i.e., controlling the various controllers, motors, etc., discussed above) that are immediately accessible to and/or are presently operated on by the processing unit 9603.

In another aspect, the computer 9601 can also comprise other removable/non-removable, volatile/non-volatile computer storage media. By way of example, FIG. 20 illustrates a mass storage device 9604, which can provide non-volatile storage of computer code, computer readable instructions, data structures, program modules, and other data for the computer 9601. For example and not meant to be limiting, a mass storage device 9604 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 9604, including by way of example, an operating system 9605 and RSBT software 9606. Each of the operating system 9605 and RSBT software 9606 (or some combination thereof) can comprise elements of the programming and the RSBT software 9606. Data 9607 can also be stored on the mass storage device 9604. Data 9607 can be stored in any of one or more databases known in the art. Examples of such databases include DB2®, Microsoft® Access, Microsoft® SQL Server, Oracle®, mySQL, PostgreSQL, and the like. The databases can be centralized or distributed across multiple systems.

In another aspect, the user can enter commands and information into the computer 9601 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 9603 via a human machine interface 9602 that is coupled to the system bus 9613, but can be connected by other interface and bus structures, such as a parallel port, game port, an IEEE 1394 Port (also known as a Firewire port), a serial port, or a universal serial bus (USB).

In yet another aspect, a display device 9611 can also be connected to the system bus 9613 via an interface, such as a display adapter 9609. It is contemplated that the computer 9601 can have more than one display adapter 9609 and the computer 9601 can have more than one display device 9611. For example, a display device can be a monitor, an LCD (Liquid Crystal Display), or a projector. In addition to the display device 9611, other output peripheral devices can comprise components such as speakers (not shown) and a printer (not shown) which can be connected to the computer 9601 via Input/Output Interface 9610. Any step and/or result of the methods can be output in any form to an output device. Such output can be any form of visual representation, including, but not limited to, textual, graphical, animation, audio, tactile, and the like.

The computer 9601 can operate in a networked environment using logical connections to one or more remote computing devices 9614*a,b,c*. By way of example, a remote computing device can be a personal computer, a laptop computer, portable computer, a server, a router, a network computer, a peer device or other common network node, and so on. Logical connections between the computer 9601 and a remote computing device 9614*a,b,c* can be made via a local area network (LAN) and a general wide area network (WAN). Such network connections can be through a network adapter 9608. A network adapter 9608 can be implemented in both wired and wireless environments. Such networking environments are conventional and commonplace in offices, enterprise-wide computer networks, intranets, and the Internet 9615.

According to an aspect, the computer 9601, via the RSBT software 9606, can control the operation of the RSBT system according to an aspect. In another aspect, the computer 9601 can comprise the controllers of the present invention For purposes of illustration, application programs and other executable program components such as the operating system 9605 are illustrated herein as discrete blocks, although it is recognized that such programs and components reside at various times in different storage components of the computing device 9601, and are executed by the data processor(s) of the computer. An implementation of RSBT software 9606 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The system and methods disclosed above are predicted to have a major impact on cancer treatment, specifically in cases of prostate cancer. Ultimately, it is thought that the RSBT system and methods discussed above will lead to a prostate cancer intervention that will provide clinicians with the unprecedented capability to reduce radiation dose to the urethra by 20-40%, rectum by 5-7%, and bladder by 5-7%, without reducing prostate dose relative to conventional systems. It has been demonstrated that reducing urethral dose reduces toxicity, and it has been shown that reducing the HDR-BT dose per fraction from 9.5 Gy per treatment fraction (2 fractions delivered) to 6 Gy per fraction (3 fractions delivered)—a 37% dose-per-fraction reduction—reduced grade ≥2 urethral stricture rates by 28.2 percentage points (31.6% vs. 3.4%). Thus RSBT provides the benefits of high-dose prostate treatments without the increased toxicity.

It is expected that the improvement in the delivered radiation dose distributions will reduce the probability of prostate cancer patients experiencing treatment-related side effects, improving quality of life. In addition RSBT systems and methods discussed above could be used to escalate prostate cancer dose without increasing dose to healthy tissues beyond conventional methods, which could improve metastasis-free tumor control in the long term, at 10+ years post-treatment.

While the systems, devices, apparatuses, protocols, processes, and methods have been described in connection with exemplary embodiments and specific illustrations, it is not intended that the scope be limited to the particular embodiments set forth, as the embodiments herein are intended in all respects to be illustrative rather than restrictive.

To the extent necessary to understand or complete the disclosure of the present invention, all publications, patents, and patent applications mentioned herein are expressly incorporated by reference to the same extent as though each were individually so incorporated.

Unless otherwise expressly stated, it is in no way intended that any protocol, procedure, process, or method set forth herein be construed as requiring that its acts or steps be performed in a specific order. Accordingly, in the subject specification, where description of a process or method does not actually recite an order to be followed by its acts or steps or it is not otherwise specifically recited in the claims or descriptions of the subject disclosure that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification or annexed drawings, or the like.

It will be apparent to those skilled in the art that various modifications and variations can be made in the subject disclosure without departing from the scope or spirit of the subject disclosure. Other embodiments of the subject disclosure will be apparent to those skilled in the art from consideration of the specification and practice of the subject disclosure as disclosed herein. It is intended that the specification and examples be considered as non-limiting illustrations only, with a true scope and spirit of the subject disclosure being indicated by the following claims.

What is claimed is:

1. A helical rotation shield brachytherapy (H-RSBT) apparatus, comprising:
   a. a radiation source;
   b. a catheter configured to retain the radiation source at a distal end;
   c. an external shield configured to engage the distal end of the catheter; and
   d. an applicator configured for insertion in a subject and to receive the catheter and rotating external shield, wherein the applicator is further configured to cause helical application of a radiation beam from the radiation source as the catheter is advanced through the applicator through interaction of the external shield and the applicator.

2. The H-RSBT apparatus of claim 1, wherein the external shield is comprised of radiation blocking material.

3. The H-RSBT apparatus of claim 2, wherein the shield further comprises a radiation window to allow the radiation beam to exit the catheter.

4. The H-RSBT apparatus of claim 1, wherein the external shield is configured to rotabably engage the distal end of the catheter, wherein the applicator is further configured to rotate the external shield.

5. The H-RSBT apparatus of claim 4, wherein the external shield comprises at least one key extending from an external surface of the external shield, and wherein the applicator comprises at least one keyway along an interior surface of the applicator, the at least one keyway configured to receive the at least one key of the external shield.

6. The H-RSBT apparatus of claim 5, wherein at least a portion of the at least one keyway is helically oriented within the interior surface of the applicator, causing the external shield to rotate, allowing the helical application of the radiation beam.

7. The H-RSBT apparatus of claim 4, wherein the external shield is configured to rotabably engage the distal end of the catheter and further comprises a plurality of keys extending from a distal end of the external shield, and wherein the applicator further comprises a plurality of keyways oriented helically within an interior surface of the applicator and configured to receive the plurality of keys of the external shield.

8. The H-RSBT apparatus of claim 7, wherein the plurality of keyways is greater in number than the plurality of keys.

9. The H-RSBT apparatus of claim 1, wherein the applicator is bent approximate at a proximal end.

10. The H-RSBT apparatus of claim 1, wherein the applicator is straight.

* * * * *